United States Patent
Dequeant et al.

(10) Patent No.: US 11,497,773 B2
(45) Date of Patent: Nov. 15, 2022

(54) GENETICALLY ENGINEERED T CELLS WITH REGNASE-1 AND/OR TGFBRII DISRUPTION HAVE IMPROVED FUNCTIONALITY AND PERSISTENCE

(71) Applicant: CRISPR Therapeutics AG, Zug (CH)

(72) Inventors: Mary-Lee Dequeant, Cambridge, MA (US); Demetrios Kalaitzidis, Cambridge, MA (US); Mohammed Ghonime, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 0 days.

(21) Appl. No.: 17/493,280

(22) Filed: Oct. 4, 2021

(65) Prior Publication Data

US 2022/0016173 A1 Jan. 20, 2022

Related U.S. Application Data

(63) Continuation of application No. 17/483,100, filed on Sep. 23, 2021.

(60) Provisional application No. 63/225,673, filed on Jul. 26, 2021, provisional application No. 63/124,429, filed on Dec. 11, 2020, provisional application No. 63/082,357, filed on Sep. 23, 2020.

(51) Int. Cl.
| | |
|---|---|
| *A61K 35/17* | (2015.01) |
| *C07K 14/705* | (2006.01) |
| *C12N 5/0783* | (2010.01) |
| *C12N 9/22* | (2006.01) |
| *C12N 15/11* | (2006.01) |
| *C07K 14/725* | (2006.01) |
| *C07K 16/28* | (2006.01) |
| *C12N 5/16* | (2006.01) |
| *C12N 15/113* | (2010.01) |
| *C12N 15/86* | (2006.01) |
| *A61K 38/00* | (2006.01) |

(52) U.S. Cl.
CPC .......... *A61K 35/17* (2013.01); *C07K 14/7051* (2013.01); *C07K 14/70521* (2013.01); *C07K 14/70575* (2013.01); *C07K 14/70578* (2013.01); *C07K 14/70596* (2013.01); *C07K 16/2803* (2013.01); *C07K 16/2875* (2013.01); *C07K 16/2878* (2013.01); *C12N 5/0636* (2013.01); *C12N 5/16* (2013.01); *C12N 9/22* (2013.01); *C12N 15/111* (2013.01); *C12N 15/113* (2013.01); *C12N 15/86* (2013.01); *A61K 38/00* (2013.01); *C07K 2317/622* (2013.01); *C12N 2310/20* (2017.05); *C12N 2310/315* (2013.01); *C12N 2310/321* (2013.01); *C12N 2510/00* (2013.01)

(58) Field of Classification Search
CPC .............. A61K 35/17; C07K 14/70575; C07K 14/70578; C07K 14/70596; C12N 5/0636; C12N 9/22; C12N 15/111; C12N 2310/20
USPC .......... 424/93.21, 184.1; 435/320.1, 325, 375
See application file for complete search history.

(56) References Cited

U.S. PATENT DOCUMENTS

| | | | |
|---|---|---|---|
| 10,166,255 B2 | 1/2019 | Moriarity et al. | |
| 10,729,725 B2 | 8/2020 | Terrett et al. | |
| 10,736,919 B2 | 8/2020 | Terrett et al. | |
| 10,857,184 B2 | 12/2020 | Terrett et al. | |
| 10,881,689 B2 | 1/2021 | Terrett et al. | |
| 11,071,755 B1 | 7/2021 | Terrett et al. | |
| 11,111,493 B2 * | 9/2021 | Benson | C07K 16/32 |
| 11,135,247 B2 | 10/2021 | Terrett et al. | |
| 11,166,985 B2 | 11/2021 | Terrett et al. | |
| 11,191,783 B2 | 12/2021 | Terrett et al. | |
| 11,421,228 B2 * | 8/2022 | Benson | C12N 9/22 |
| 2018/0112198 A1 | 4/2018 | Liu et al. | |
| 2019/0284553 A1 * | 9/2019 | Benson | A61P 35/04 |
| 2021/0139850 A1 | 5/2021 | Yu et al. | |

FOREIGN PATENT DOCUMENTS

| | | | |
|---|---|---|---|
| EP | 3854877 A1 | 7/2021 | |
| JP | 2017/002928 | 4/2018 | |
| WO | WO 2010/098429 A1 | 9/2010 | |
| WO | WO-2014153114 A1 * | 9/2014 | .......... A61K 38/177 |
| WO | WO 2019/097305 A1 | 5/2019 | |
| WO | WO-2019089884 A2 * | 5/2019 | ......... A61K 39/0011 |
| WO | WO 2019/178421 A1 | 9/2019 | |
| WO | WO 2019/215500 A1 | 11/2019 | |
| WO | WO-2019215500 A1 * | 11/2019 | ............. A61K 35/17 |

(Continued)

OTHER PUBLICATIONS

Liu et al. (2016; Cell Res. Jan. 2017; 27(1): 154-157) (Year: 2017).*

(Continued)

*Primary Examiner* — Janet L Epps-Smith
(74) *Attorney, Agent, or Firm* — McDermott Will & Emery LLP

(57) ABSTRACT

A population of genetically engineered T cells, comprising a disrupted Reg1 gene and/or a disrupted TGFBRII gene. Such genetically engineered T cells may comprise further genetic modifications, for example, a disrupted CD70 gene. The population of genetically engineered T cells exhibit one or more of (a) improved cell growth activity; (b) enhanced persistence; and (c) reduced T cell exhaustion, (d) enhanced cytotoxicity activity, (e) resistant to inhibitory effects induced by TGF-b, and (f) resistant to inhibitory effects by fibroblasts and/or inhibitory factors secreted thereby, as compared to non-engineered T cell counterparts.

20 Claims, 54 Drawing Sheets

Specification includes a Sequence Listing.

(56) References Cited

FOREIGN PATENT DOCUMENTS

| WO | WO 2019/235581 A1 | 12/2019 |
| WO | WO 2020/032160 A1 | 2/2020 |
| WO | WO 2020/095107 A1 | 5/2020 |

OTHER PUBLICATIONS

Liu et al. _Supplementary Data_(2016; Cell Res. Jan. 2017; 27(1): 154-157) (Year: 2017).*
Tang et al. (JCI Insight. 2020;5(4):e133977, pp. 1-17; Published Feb. 27, 2020) (Year: 2020).*
Wei et al. (2019, Nature, vol. 576, 19/26, pp. 471-499) (Year: 2019).*
Eyquem et al., Targeting a CAR to the TRAC locus with CRISPR/Cas9 enhances tumour rejection. Nature. Mar. 2, 2017;543(7643):113-117. Epub Feb. 22, 2017.
U.S. Appl. No. 17/483,100, filed Sep. 23, 2021, Dequeant et al.
U.S. Appl. No. 17/493,253, filed Oct. 4, 2021, Dequeant et al.
U.S. Appl. No. 17/493,271, filed Oct. 4, 2021, Dequeant et al.
Dempsey, Regnase-1 in the TME. Nat Immunol. Feb. 2020;21(2):103.
Heaton et al., Frontiers in antiviral therapy and immunotherapy. Clin Transl Immunology. Feb. 19, 2020;9(2):e1115.
Liu et al., CRISPR screen in mechanism and target discovery for cancer immunotherapy. Biochim Biophys Acta Rev Cancer, Aug. 2020;1874(1):188378(1-15). Epub May 13, 2020.
Oh et al., Monocyte chemotactic protein-induced protein-1 enhances DR5 degradation and negatively regulates DR5 activation-induced apoptosis through its deubiquitinase function. Oncogene. Jun. 2018;37(25):3415-3425, Epub Mar. 19, 2018.
Reina-Campos et al., Antitumour T cells stand the test of time. Nature. Dec. 11, 2019;576:392-3.
Roth, Editing of Endogenous Genes in Cellular Immunotherapies. Curr Hematol Malig Rep. Aug. 2020;15(4):235-240.
Wei et al., Targeting REGNASE-1 programs long-lived effector T cells for cancer therapy. Nature. Dec. 11, 2019;576(7787):471-476.
Yoshinaga et al., Post-transcriptional control of immune responses and its potential application. Clin Transl Immunology, Jun. 17, 2019;8(6):e1063(1-13).

* cited by examiner

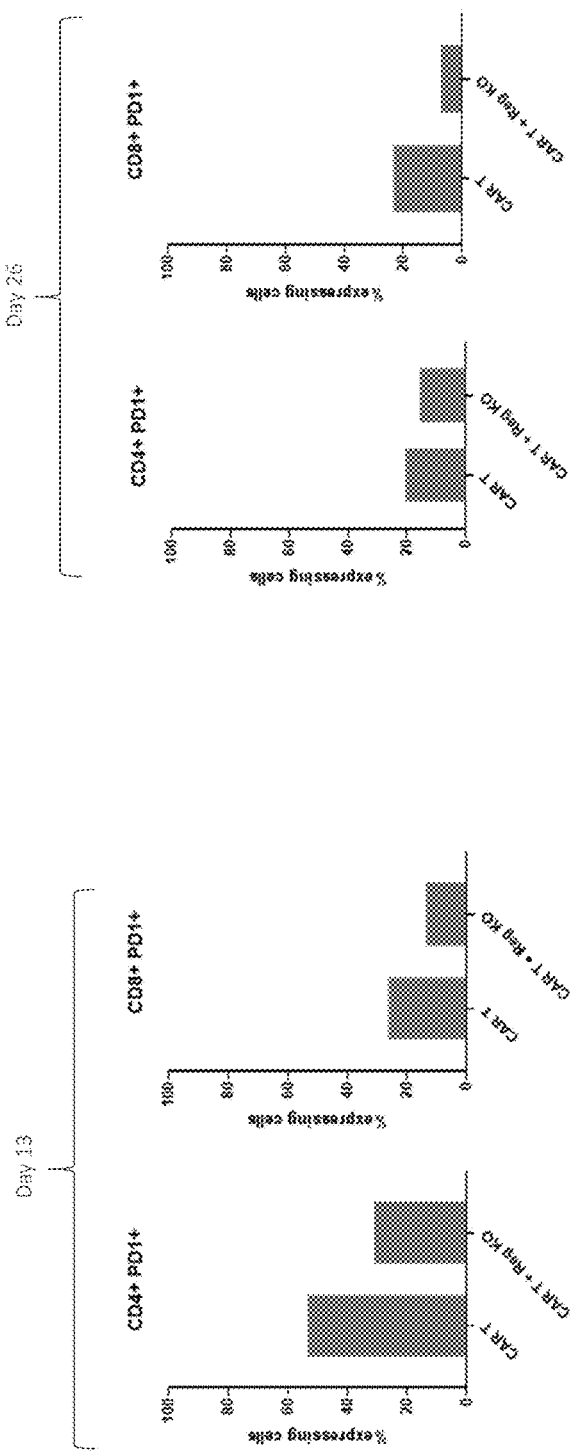
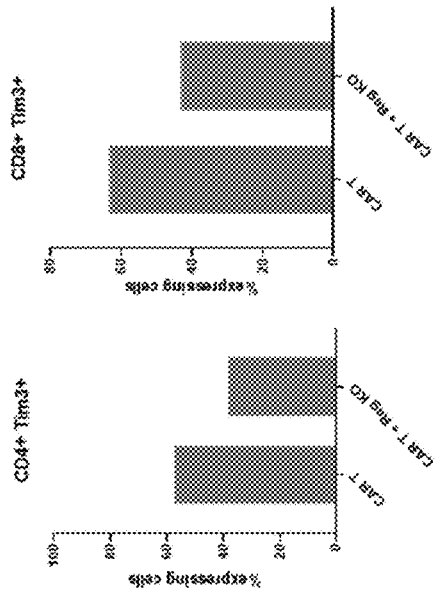
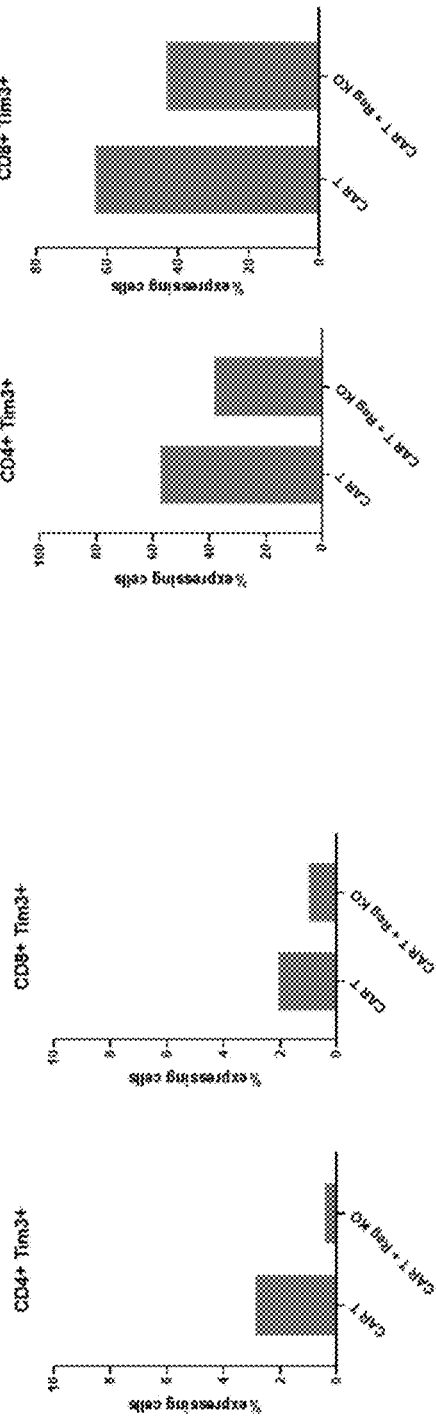
FIG. 3A, FIG. 3B, FIG. 3C, FIG. 3D

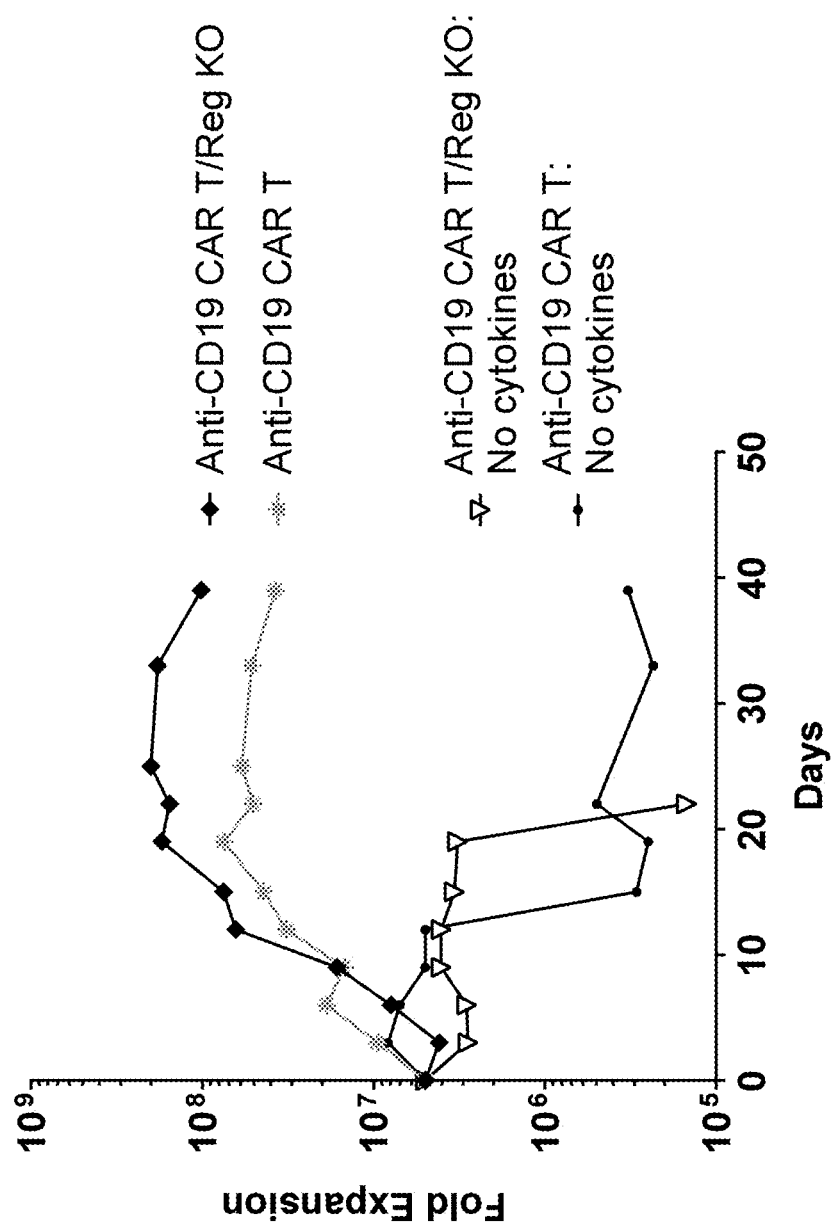

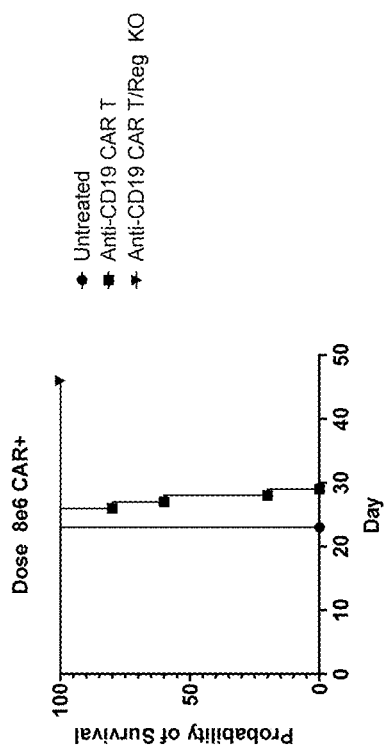
FIG. 5B
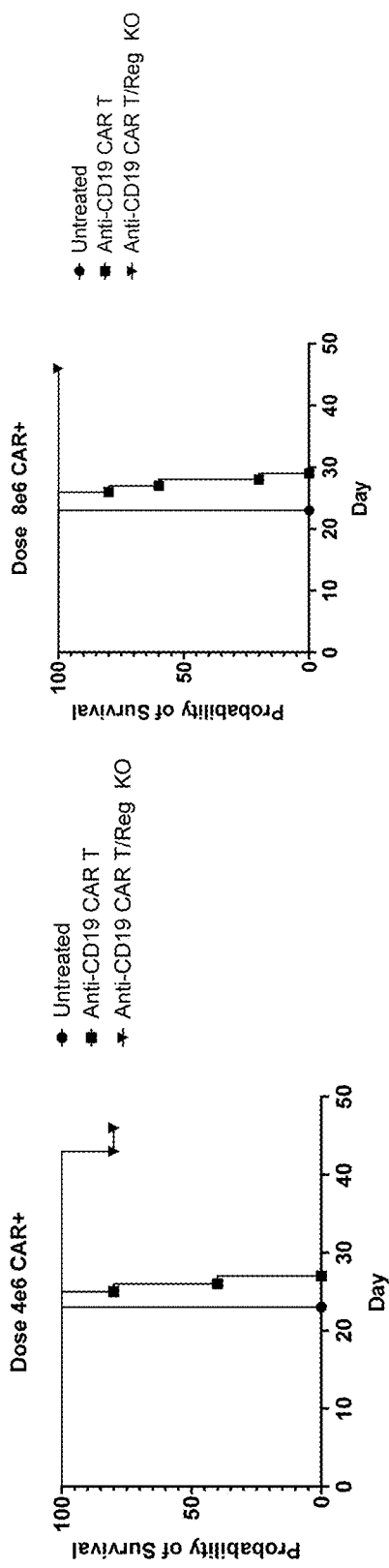
FIG. 5A
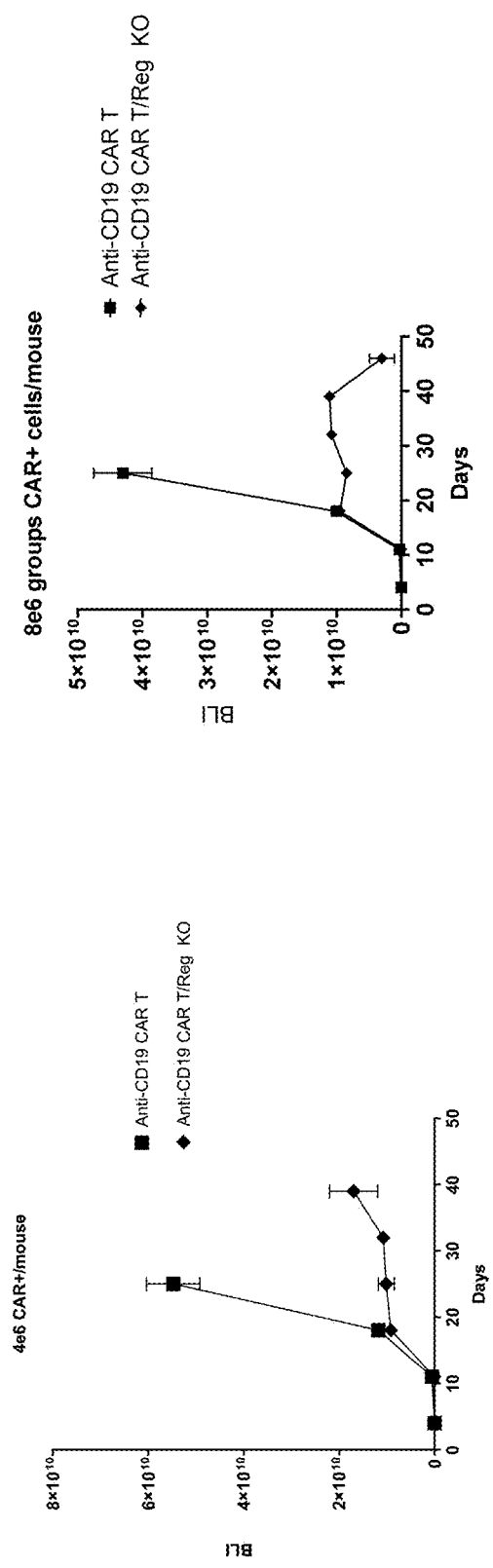
FIG. 5D
FIG. 5C

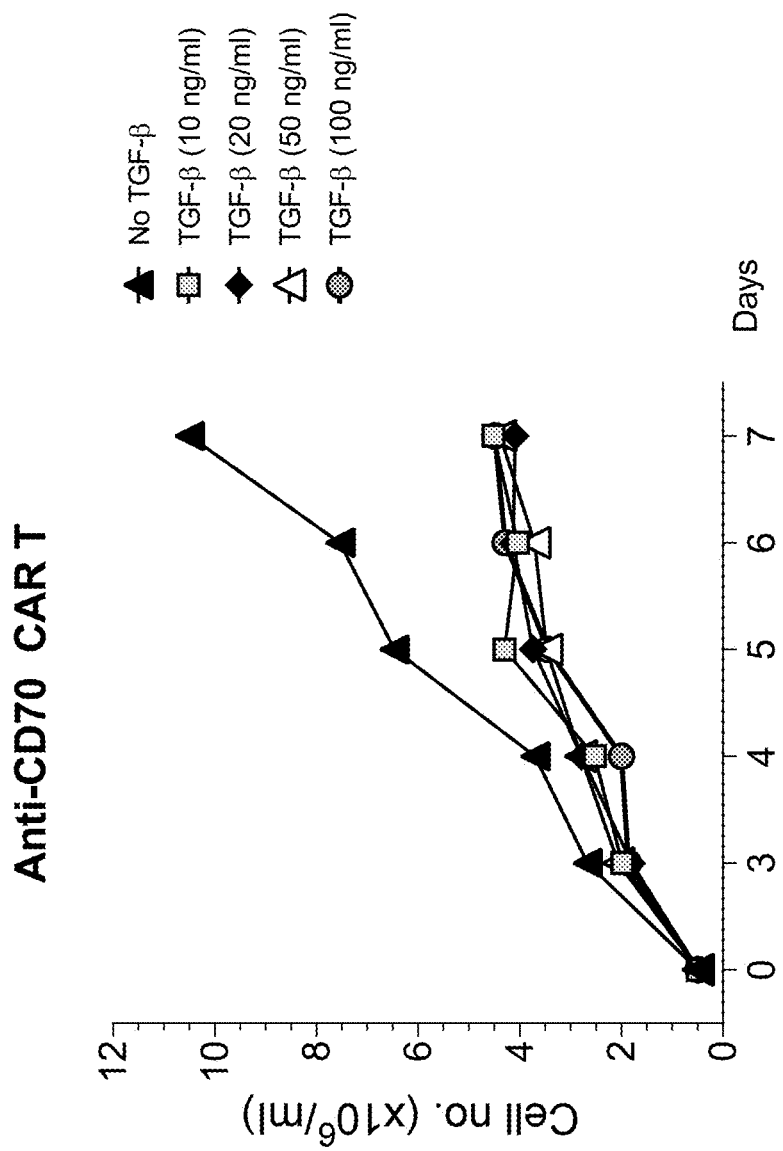

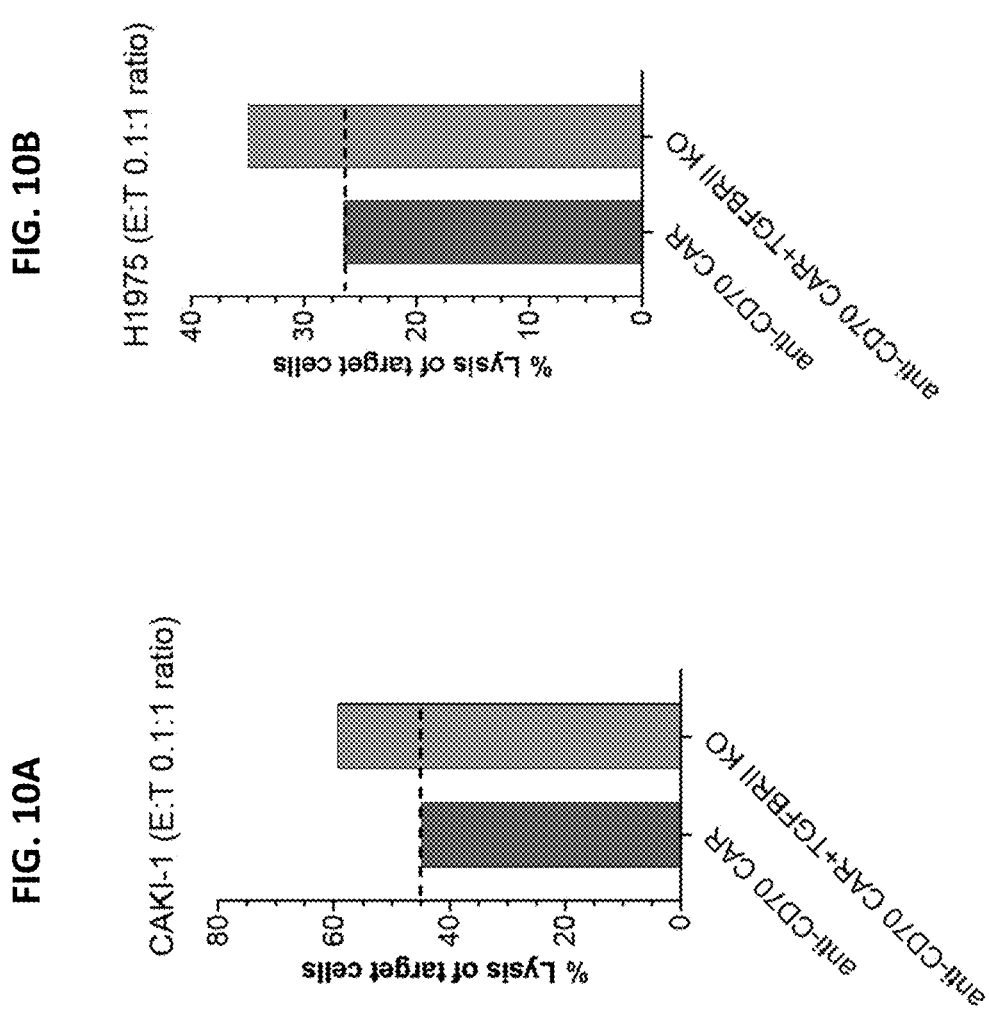

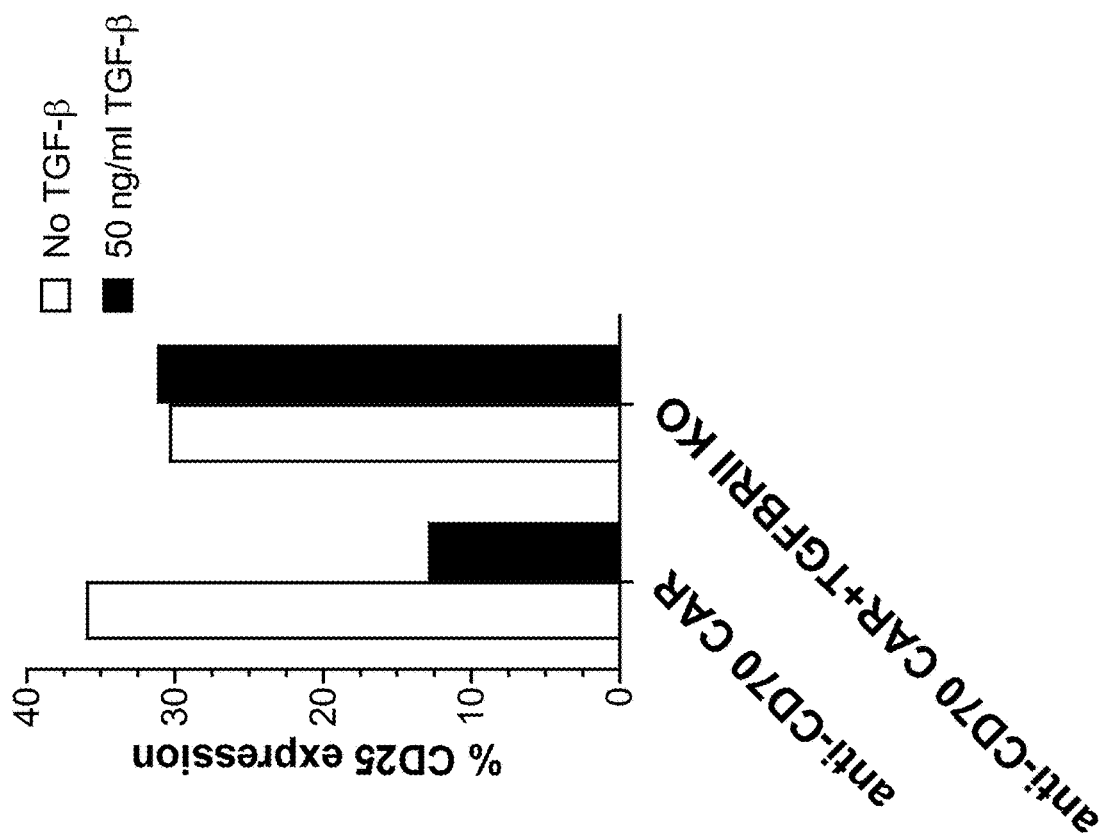

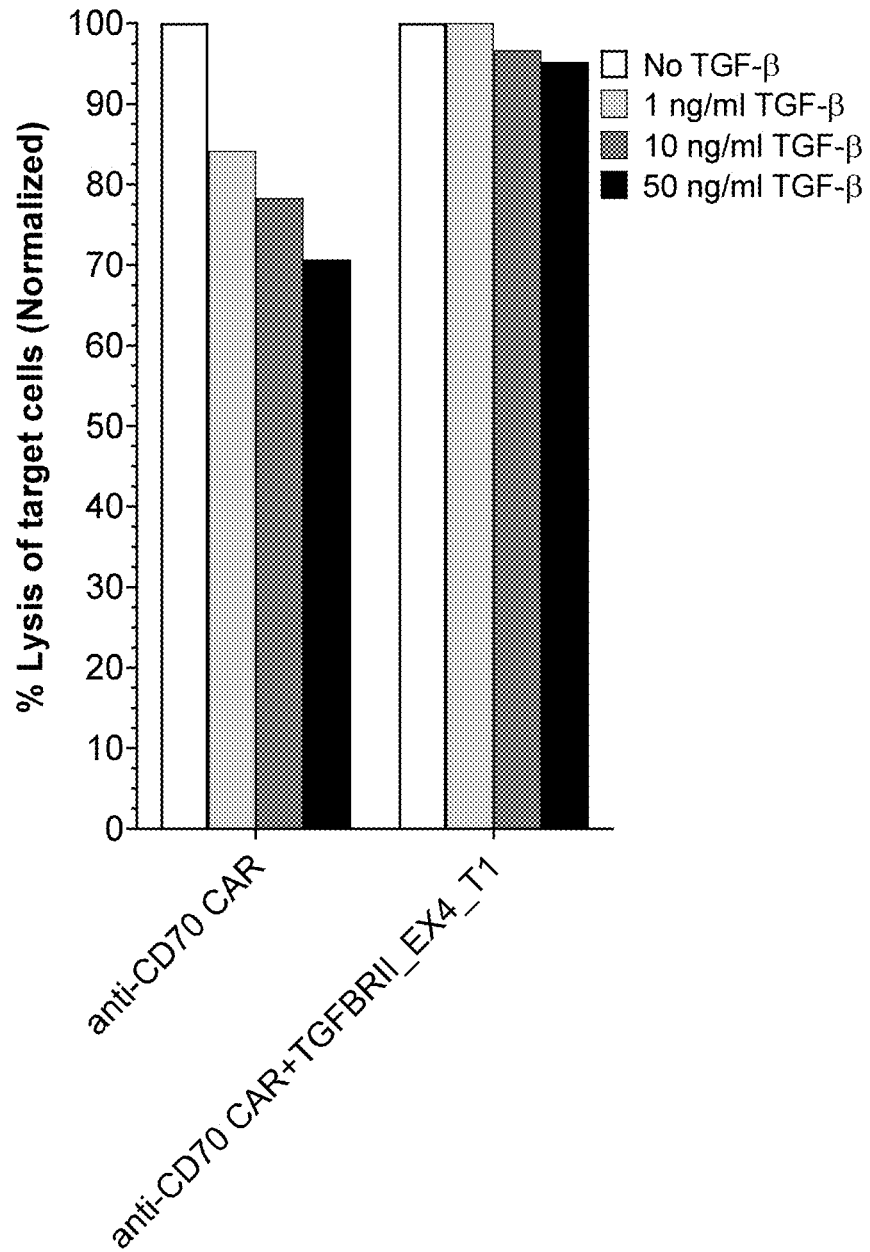

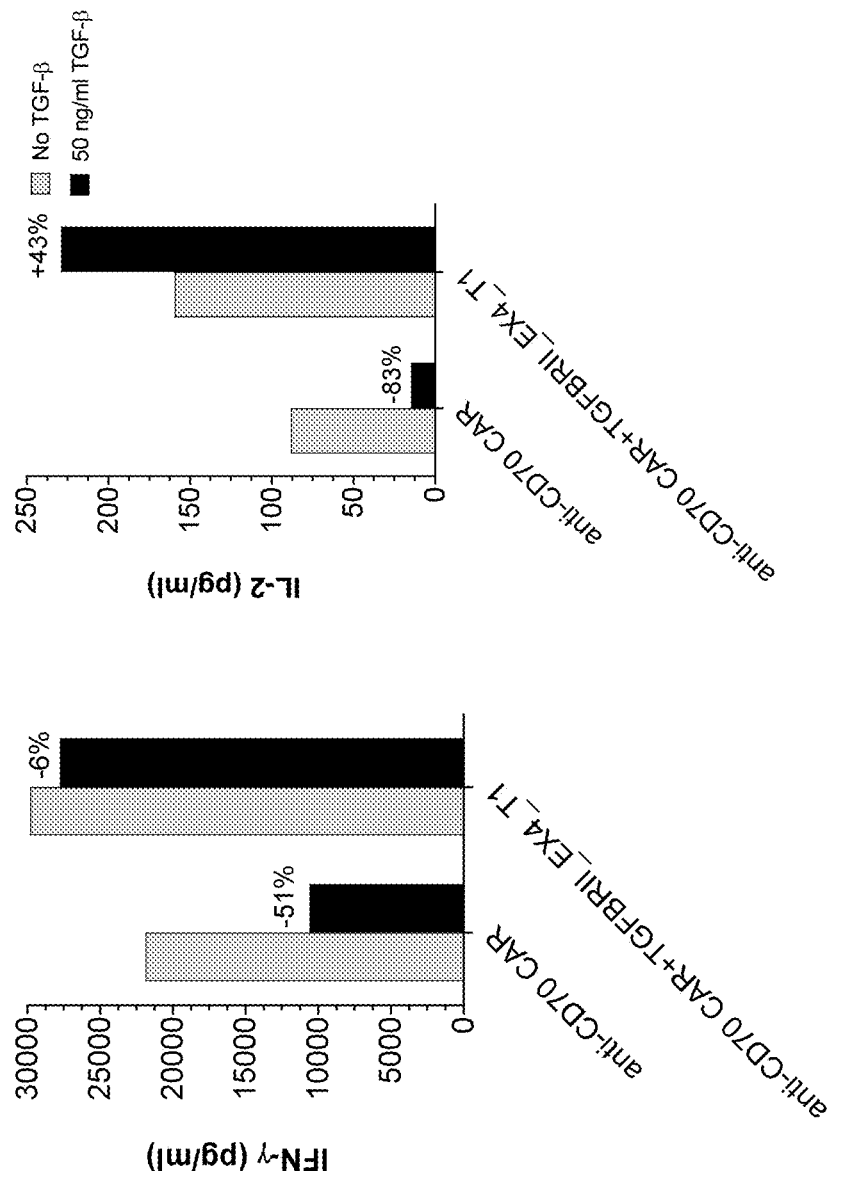

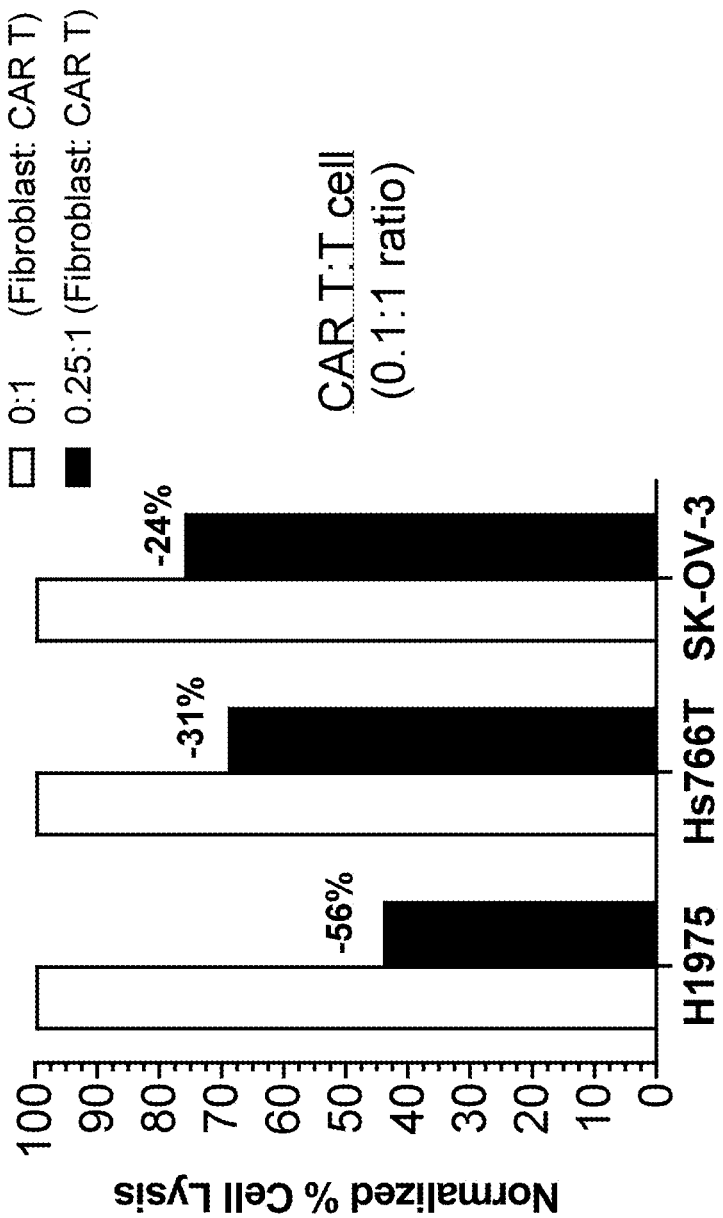

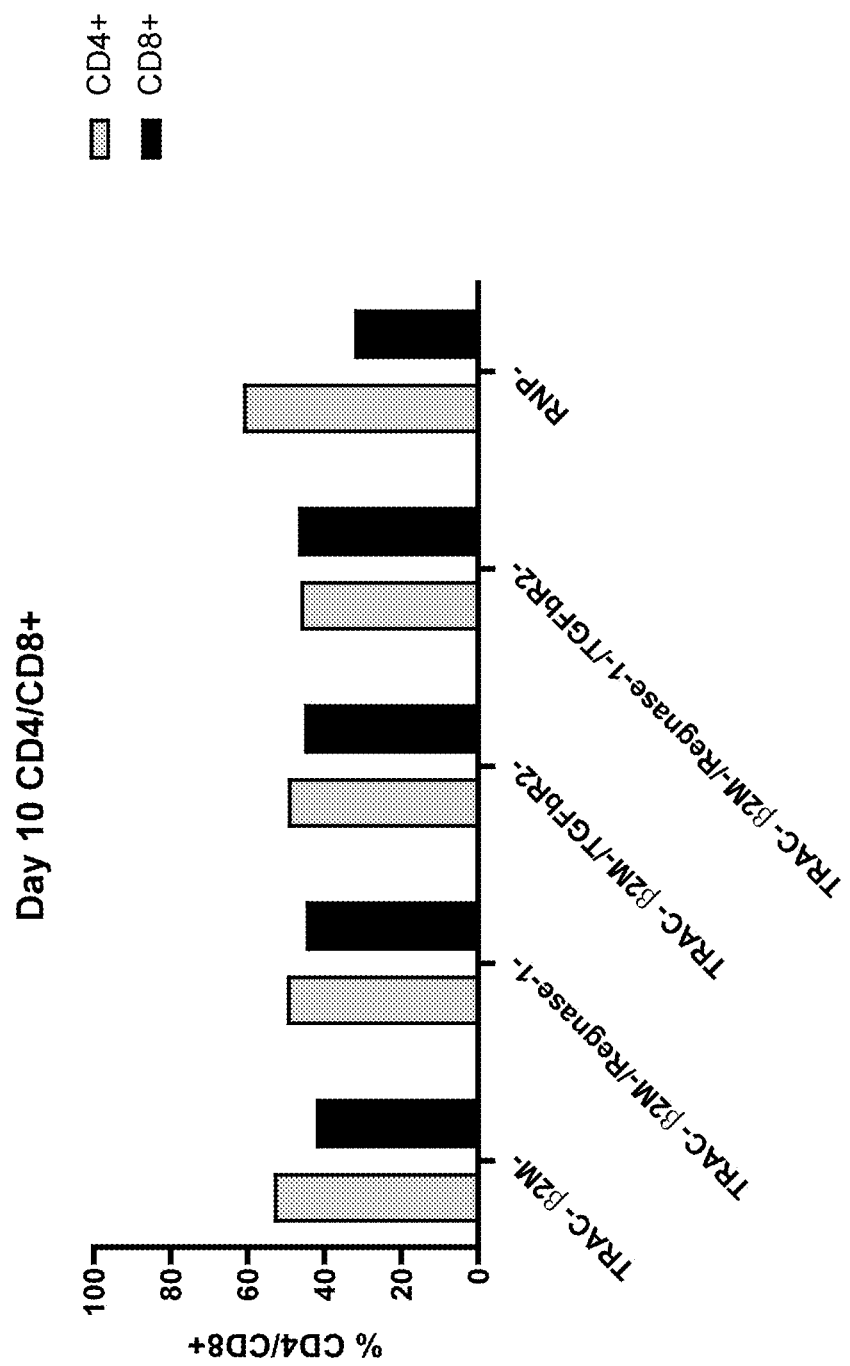

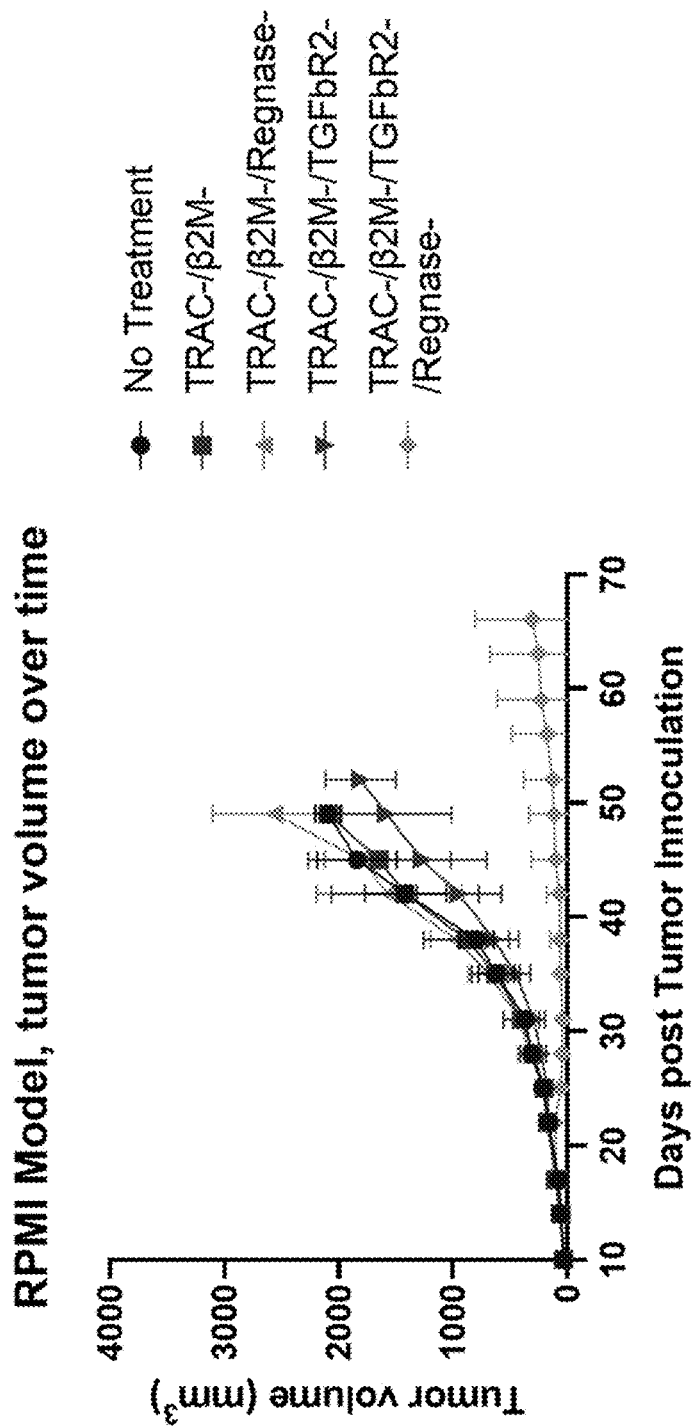

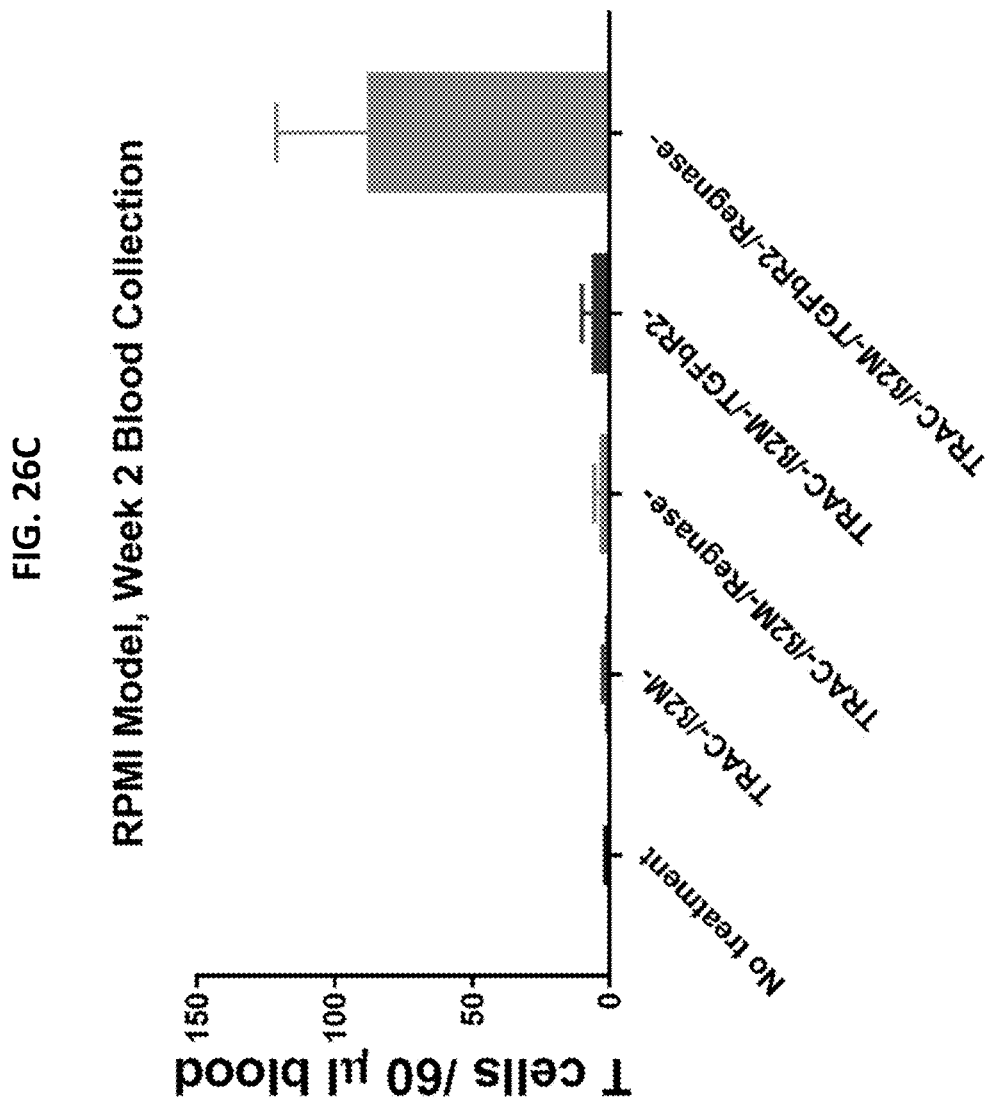

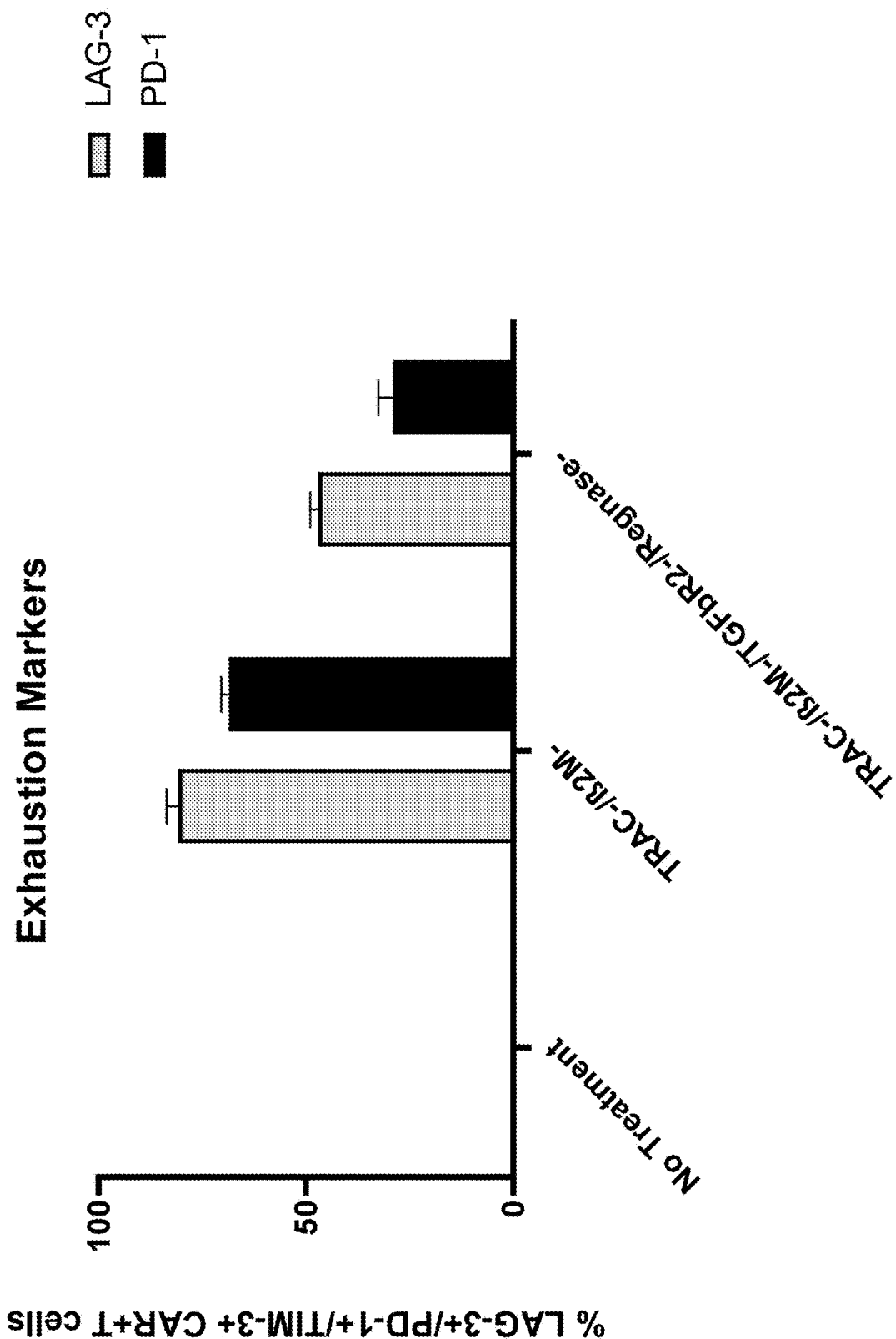

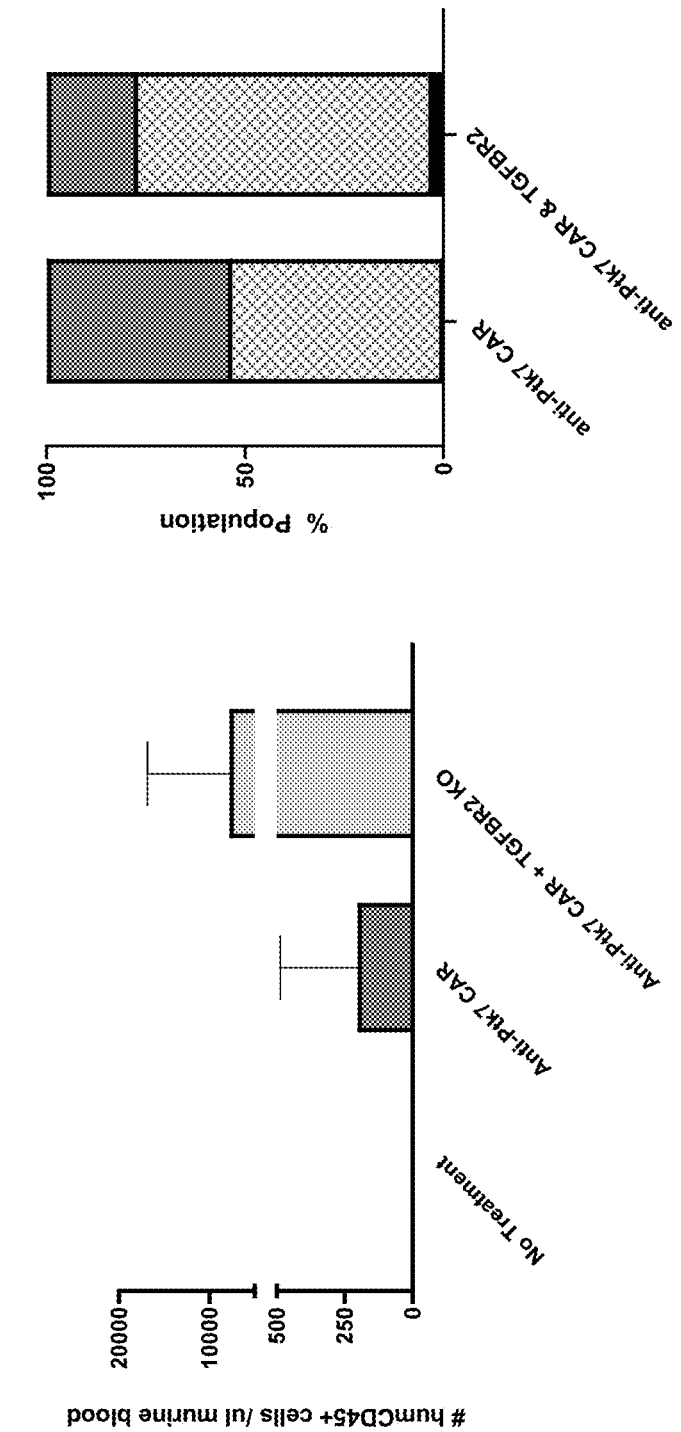

SEQUENCE LISTING

<160> NUMBER OF SEQ ID NOS: 478

<210> SEQ ID NO 1
<211> LENGTH: 1368
<212> TYPE: PRT
<213> ORGANISM: Artificial Sequence
<220> FEATURE:
<223> OTHER INFORMATION: Synthetic

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
```

```
                    355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
```

```
Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185
```

| | | | | | | | | | | | |
|---|---|---|---|---|---|---|---|---|---|---|---|
|Glu|Val|Lys|Lys|Asp|Leu|Ile|Ile|Lys|Leu|Pro|Lys|Tyr|Ser|Leu|
| |1190| | | |1195| | | |1200| | |

Phe Glu Leu Glu Asn Gly Arg Lys Arg Met Leu Ala Ser Ala Gly
  1205                1210                1215

Glu Leu Gln Lys Gly Asn Glu Leu Ala Leu Pro Ser Lys Tyr Val
  1220                1225                1230

Asn Phe Leu Tyr Leu Ala Ser His Tyr Glu Lys Leu Lys Gly Ser
  1235                1240                1245

Pro Glu Asp Asn Glu Gln Lys Gln Leu Phe Val Glu Gln His Lys
  1250                1255                1260

His Tyr Leu Asp Glu Ile Ile Glu Gln Ile Ser Glu Phe Ser Lys
  1265                1270                1275

Arg Val Ile Leu Ala Asp Ala Asn Leu Asp Lys Val Leu Ser Ala
  1280                1285                1290

Tyr Asn Lys His Arg Asp Lys Pro Ile Arg Glu Gln Ala Glu Asn
  1295                1300                1305

Ile Ile His Leu Phe Thr Leu Thr Asn Leu Gly Ala Pro Ala Ala
  1310                1315                1320

Phe Lys Tyr Phe Asp Thr Thr Ile Asp Arg Lys Arg Tyr Thr Ser
  1325                1330                1335

Thr Lys Glu Val Leu Asp Ala Thr Leu Ile His Gln Ser Ile Thr
  1340                1345                1350

Gly Leu Tyr Glu Thr Arg Ile Asp Leu Ser Gln Leu Gly Gly Asp
  1355                1360                1365

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
ccgacttctg aacgtgcggt ggg                                          23

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
tgctggcgat acgcgtccac agg                                          23

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
tcggtctatg acgagcagcg ggg                                          23

<210> SEQ ID NO 5
<211> LENGTH: 23
<212> TYPE: DNA
<213> ORGANISM: Artificial Sequence
<220> FEATURE:
<223> OTHER INFORMATION: Synthetic

```
<400> SEQUENCE: 5
atgggcagtc ctattacagc tgg                                            23

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
attgttcact tgttagcccc agg                                            23

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
gctgaagaac tgcctctata tgg                                            23

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
gcaggatttc tggttgtcac agg                                            23

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
ctccatctgt gagaagccac agg                                            23

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
cccctaccat gactttattc tgg                                            23

<210> SEQ ID NO 11
<211> LENGTH: 26
<212> TYPE: DNA
<213> ORGANISM: Artificial Sequence
<220> FEATURE:
<223> OTHER INFORMATION: Synthetic

<400> SEQUENCE: 11
ggcaccatat tcattttgca ggtgaa                                         26

<210> SEQ ID NO 12
```

```
<211> LENGTH: 25
<212> TYPE: DNA
<213> ORGANISM: Artificial Sequence
<220> FEATURE:
<223> OTHER INFORMATION: Synthetic

<400> SEQUENCE: 12
atgtgcgctc tgcccactga cgggc                                      25

<210> SEQ ID NO 13
<211> LENGTH: 29
<212> TYPE: DNA
<213> ORGANISM: Artificial Sequence
<220> FEATURE:
<223> OTHER INFORMATION: Synthetic

<400> SEQUENCE: 13
agacatgagg tctatggact tcaggctcc                                  29

<210> SEQ ID NO 14
<211> LENGTH: 100
<212> TYPE: RNA
<213> ORGANISM: Artificial Sequence
<220> FEATURE:
<223> OTHER INFORMATION: Synthetic

<400> SEQUENCE: 14
ggucaucgau gggagcaacg guuuuagagc uagaaauagc aaguuaaaau aaggcuaguc    60
cguuaucaac uugaaaaagu ggcaccgagu cggugcuuuu                        100

<210> SEQ ID NO 15
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 15
ggucaucgau gggagcaacg guuuuagagc uagaaauagc aaguuaaaau aaggcuaguc    60
cguuaucaac uugaaaaagu ggcaccgagu cggugcuuuu                        100

<210> SEQ ID NO 16
<211> LENGTH: 20
<212> TYPE: RNA
<213> ORGANISM: Artificial Sequence
<220> FEATURE:
<223> OTHER INFORMATION: Synthetic

<400> SEQUENCE: 16
ggucaucgau gggagcaacg                                             20

<210> SEQ ID NO 17
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

-continued

```
<222> LOCATION: (1)..(4)
<223> OTHER INFORMATION: modified with 2'-O-methyl phosphorothioate

<400> SEQUENCE: 17
ggucaucgau gggagcaacg                                              20

<210> SEQ ID NO 18
<211> LENGTH: 100
<212> TYPE: RNA
<213> ORGANISM: Artificial Sequence
<220> FEATURE:
<223> OTHER INFORMATION: Synthetic

<400> SEQUENCE: 18
caccaccccg cgggacuaga guuuuagagc uagaaauagc aaguuaaaau aaggcuaguc    60
cguuaucaac uugaaaaagu ggcaccgagu cggugcuuuu                        100

<210> SEQ ID NO 19
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 19
caccaccccg cgggacuaga guuuuagagc uagaaauagc aaguuaaaau aaggcuaguc    60
cguuaucaac uugaaaaagu ggcaccgagu cggugcuuuu                        100

<210> SEQ ID NO 20
<211> LENGTH: 20
<212> TYPE: RNA
<213> ORGANISM: Artificial Sequence
<220> FEATURE:
<223> OTHER INFORMATION: Synthetic

<400> SEQUENCE: 20
caccaccccg cgggacuaga                                              20

<210> SEQ ID NO 21
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 21
caccaccccg cgggacuaga                                              20

<210> SEQ ID NO 22
<211> LENGTH: 100
<212> TYPE: RNA
<213> ORGANISM: Artificial Sequence
<220> FEATURE:
<223> OTHER INFORMATION: Synthetic
```

<400> SEQUENCE: 22
ggucuggcgc ucccgcucgg guuuuagagc uagaaauagc aaguuaaaau aaggcuaguc    60
cguuaucaac uugaaaaagu ggcaccgagu cggugcuuuu                         100

<210> SEQ ID NO 23
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 23
ggucuggcgc ucccgcucgg guuuuagagc uagaaauagc aaguuaaaau aaggcuaguc    60
cguuaucaac uugaaaaagu ggcaccgagu cggugcuuuu                         100

<210> SEQ ID NO 24
<211> LENGTH: 20
<212> TYPE: RNA
<213> ORGANISM: Artificial Sequence
<220> FEATURE:
<223> OTHER INFORMATION: Synthetic

<400> SEQUENCE: 24
ggucuggcgc ucccgcucgg                                                20

<210> SEQ ID NO 25
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 25
ggucuggcgc ucccgcucgg                                                20

<210> SEQ ID NO 26
<211> LENGTH: 100
<212> TYPE: RNA
<213> ORGANISM: Artificial Sequence
<220> FEATURE:
<223> OTHER INFORMATION: Synthetic

<400> SEQUENCE: 26
uucacaccau cacgacgcgu guuuuagagc uagaaauagc aaguuaaaau aaggcuaguc    60
cguuaucaac uugaaaaagu ggcaccgagu cggugcuuuu                         100

<210> SEQ ID NO 27
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 27
uucacaccau cacgacgcgu guuuuagagc uagaaauagc aaguuaaaau aaggcuaguc      60
cguuaucaac uugaaaaagu ggcaccgagu cggugcuuuu                          100

<210> SEQ ID NO 28
<211> LENGTH: 20
<212> TYPE: RNA
<213> ORGANISM: Artificial Sequence
<220> FEATURE:
<223> OTHER INFORMATION: Synthetic

<400> SEQUENCE: 28
uucacaccau cacgacgcgu                                                 20

<210> SEQ ID NO 29
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 29
uucacaccau cacgacgcgu                                                 20

<210> SEQ ID NO 30
<211> LENGTH: 100
<212> TYPE: RNA
<213> ORGANISM: Artificial Sequence
<220> FEATURE:
<223> OTHER INFORMATION: Synthetic

<400> SEQUENCE: 30
acaccaucac gacgcguggg guuuuagagc uagaaauagc aaguuaaaau aaggcuaguc      60
cguuaucaac uugaaaaagu ggcaccgagu cggugcuuuu                          100

<210> SEQ ID NO 31
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 31
acaccaucac gacgcguggg guuuuagagc uagaaauagc aaguuaaaau aaggcuaguc      60
cguuaucaac uugaaaaagu ggcaccgagu cggugcuuuu                          100

<210> SEQ ID NO 32
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 32
acaccaucac gacgcguggg                                              20

<210> SEQ ID NO 33
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 33
acaccaucac gacgcguggg                                              20

<210> SEQ ID NO 34
<211> LENGTH: 100
<212> TYPE: RNA
<213> ORGANISM: Artificial Sequence
<220> FEATURE:
<223> OTHER INFORMATION: Synthetic

<400> SEQUENCE: 34
cuacgagucu gacgggaucg guuuuagagc uagaaauagc aaguuaaaau aaggcuaguc    60
cguuaucaac uugaaaaagu ggcaccgagu cggugcuuuu                        100

<210> SEQ ID NO 35
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 35
cuacgagucu gacgggaucg guuuuagagc uagaaauagc aaguuaaaau aaggcuaguc    60
cguuaucaac uugaaaaagu ggcaccgagu cggugcuuuu                        100

<210> SEQ ID NO 36
<211> LENGTH: 20
<212> TYPE: RNA
<213> ORGANISM: Artificial Sequence
<220> FEATURE:
<223> OTHER INFORMATION: Synthetic

<400> SEQUENCE: 36
cuacgagucu gacgggaucg                                              20

<210> SEQ ID NO 37
<211> LENGTH: 20
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 37
cuacgagucu gacgggaucg                                                20

<210> SEQ ID NO 38
<211> LENGTH: 100
<212> TYPE: RNA
<213> ORGANISM: Artificial Sequence
<220> FEATURE:
<223> OTHER INFORMATION: Synthetic

<400> SEQUENCE: 38
uugccaccca cgcgucguga guuuuagagc uagaaauagc aaguuaaaau aaggcuaguc    60
cguuaucaac uugaaaaagu ggcaccgagu cggugcuuuu                        100

<210> SEQ ID NO 39
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 39
uugccaccca cgcgucguga guuuuagagc uagaaauagc aaguuaaaau aaggcuaguc    60
cguuaucaac uugaaaaagu ggcaccgagu cggugcuuuu                        100

<210> SEQ ID NO 40
<211> LENGTH: 20
<212> TYPE: RNA
<213> ORGANISM: Artificial Sequence
<220> FEATURE:
<223> OTHER INFORMATION: Synthetic

<400> SEQUENCE: 40
uugccaccca cgcgucguga                                                20

<210> SEQ ID NO 41
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 41
uugccaccca cgcgucguga                                                20

<210> SEQ ID NO 42
<211> LENGTH: 100
<212> TYPE: RNA
```

```
<213> ORGANISM: Artificial Sequence
<220> FEATURE:
<223> OTHER INFORMATION: Synthetic

<400> SEQUENCE: 42
guucacacca ucacgacgcg guuuuagagc uagaaauagc aaguuaaaau aaggcuaguc    60
cguuaucaac uugaaaaagu ggcaccgagu cggugcuuuu                         100

<210> SEQ ID NO 43
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 43
guucacacca ucacgacgcg guuuuagagc uagaaauagc aaguuaaaau aaggcuaguc    60
cguuaucaac uugaaaaagu ggcaccgagu cggugcuuuu                         100

<210> SEQ ID NO 44
<211> LENGTH: 20
<212> TYPE: RNA
<213> ORGANISM: Artificial Sequence
<220> FEATURE:
<223> OTHER INFORMATION: Synthetic

<400> SEQUENCE: 44
guucacacca ucacgacgcg                                               20

<210> SEQ ID NO 45
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 45
guucacacca ucacgacgcg                                               20

<210> SEQ ID NO 46
<211> LENGTH: 100
<212> TYPE: RNA
<213> ORGANISM: Artificial Sequence
<220> FEATURE:
<223> OTHER INFORMATION: Synthetic

<400> SEQUENCE: 46
cacgaucccg ucagacucgu guuuuagagc uagaaauagc aaguuaaaau aaggcuaguc    60
cguuaucaac uugaaaaagu ggcaccgagu cggugcuuuu                         100

<210> SEQ ID NO 47
<211> LENGTH: 100
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 47
cacgaucccg ucagacucgu guuuuagagc uagaaauagc aaguuaaaau aaggcuaguc    60
cguuaucaac uugaaaaagu ggcaccgagu cggugcuuuu                        100

<210> SEQ ID NO 48
<211> LENGTH: 20
<212> TYPE: RNA
<213> ORGANISM: Artificial Sequence
<220> FEATURE:
<223> OTHER INFORMATION: Synthetic

<400> SEQUENCE: 48
cacgaucccg ucagacucgu                                               20

<210> SEQ ID NO 49
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 49
cacgaucccg ucagacucgu                                               20

<210> SEQ ID NO 50
<211> LENGTH: 100
<212> TYPE: RNA
<213> ORGANISM: Artificial Sequence
<220> FEATURE:
<223> OTHER INFORMATION: Synthetic

<400> SEQUENCE: 50
acgacgcgug gguggcaagc guuuuagagc uagaaauagc aaguuaaaau aaggcuaguc    60
cguuaucaac uugaaaaagu ggcaccgagu cggugcuuuu                        100

<210> SEQ ID NO 51
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 51
acgacgcgug gguggcaagc guuuuagagc uagaaauagc aaguuaaaau aaggcuaguc    60
```
cguuaucaac uugaaaaagu ggcaccgagu cggugcuuuu                          100

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
acgacgcgug ggtggcaagc                                               20

<210> SEQ ID NO 53
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 53
acgacgcgug gguggcaagc                                               20

<210> SEQ ID NO 54
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 54
gcuuuggucc cauuggucgc guuuuagagc uagaaauagc aaguuaaaau aaggcuaguc    60
cguuaucaac uugaaaaagu ggcaccgagu cggugcuuuu                          100

<210> SEQ ID NO 55
<211> LENGTH: 100
<212> TYPE: RNA
<213> ORGANISM: Artificial Sequence
<220> FEATURE:
<223> OTHER INFORMATION: Synthetic

<400> SEQUENCE: 55
gcuuuggucc cauuggucgc guuuuagagc uagaaauagc aaguuaaaau aaggcuaguc    60
cguuaucaac uugaaaaagu ggcaccgagu cggugcuuuu                          100

<210> SEQ ID NO 56
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 56

```
gcuuuggucc cauuggucgc                                              20
```

<210> SEQ ID NO 57
<211> LENGTH: 20
<212> TYPE: RNA
<213> ORGANISM: Artificial Sequence
<220> FEATURE:
<223> OTHER INFORMATION: Synthetic

<400> SEQUENCE: 57

```
gcuuuggucc cauuggucgc                                              20
```

<210> SEQ ID NO 58
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 58

```
agagcaacag ugcuguggcc guuuuagagc uagaaauagc aaguuaaaau aaggcuaguc   60
cguuaucaac uugaaaaagu ggcaccgagu cggugcuuuu                        100
```

<210> SEQ ID NO 59
<211> LENGTH: 100
<212> TYPE: RNA
<213> ORGANISM: Artificial Sequence
<220> FEATURE:
<223> OTHER INFORMATION: Synthetic

<400> SEQUENCE: 59

```
agagcaacag ugcuguggcc guuuuagagc uagaaauagc aaguuaaaau aaggcuaguc   60
cguuaucaac uugaaaaagu ggcaccgagu cggugcuuuu                        100
```

<210> SEQ ID NO 60
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 60

```
agagcaacag ugcuguggcc                                              20
```

<210> SEQ ID NO 61
<211> LENGTH: 20
<212> TYPE: RNA
<213> ORGANISM: Artificial Sequence
<220> FEATURE:
<223> OTHER INFORMATION: Synthetic

<400> SEQUENCE: 61

```
agagcaacag ugcuguggcc                                              20
```

<210> SEQ ID NO 62
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 62
gcuacucucu cuuucuggcc guuuuagagc uagaaauagc aaguuaaaau aaggcuaguc    60
cguuaucaac uugaaaaagu ggcaccgagu cggugcuuuu    100

<210> SEQ ID NO 63
<211> LENGTH: 100
<212> TYPE: RNA
<213> ORGANISM: Artificial Sequence
<220> FEATURE:
<223> OTHER INFORMATION: Synthetic

<400> SEQUENCE: 63
gcuacucucu cuuucuggcc guuuuagagc uagaaauagc aaguuaaaau aaggcuaguc    60
cguuaucaac uugaaaaagu ggcaccgagu cggugcuuuu    100

<210> SEQ ID NO 64
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 64
gcuacucucu cuuucuggcc    20

<210> SEQ ID NO 65
<211> LENGTH: 20
<212> TYPE: RNA
<213> ORGANISM: Artificial Sequence
<220> FEATURE:
<223> OTHER INFORMATION: Synthetic

<400> SEQUENCE: 65
gcuacucucu cuuucuggcc    20

<210> SEQ ID NO 66
<211> LENGTH: 23
<212> TYPE: DNA
<213> ORGANISM: Artificial Sequence
<220> FEATURE:
<223> OTHER INFORMATION: Synthetic

<400> SEQUENCE: 66
gctttggtcc cattggtcgc ggg    23

<210> SEQ ID NO 67
<211> LENGTH: 20

```
<212> TYPE: DNA
<213> ORGANISM: Artificial Sequence
<220> FEATURE:
<223> OTHER INFORMATION: Synthetic

<400> SEQUENCE: 67
gctttggtcc cattggtcgc                                          20

<210> SEQ ID NO 68
<211> LENGTH: 23
<212> TYPE: DNA
<213> ORGANISM: Artificial Sequence
<220> FEATURE:
<223> OTHER INFORMATION: Synthetic

<400> SEQUENCE: 68
agagcaacag tgctgtggcc tgg                                      23

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
agagcaacag tgctgtggcc                                          20

<210> SEQ ID NO 70
<211> LENGTH: 23
<212> TYPE: DNA
<213> ORGANISM: Artificial Sequence
<220> FEATURE:
<223> OTHER INFORMATION: Synthetic

<400> SEQUENCE: 70
gctactctct ctttctggcc tgg                                      23

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
gctactctct ctttctggcc                                          20

<210> SEQ ID NO 72
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 72
nnnnnnnnnn nnnnnnnnnn guuuuagagc uagaaauagc aaguuaaaau aaggcuaguc    60
cguuaucaac uugaaaaagu ggcaccgagu cggugcuuuu                         100

<210> SEQ ID NO 73
<211> LENGTH: 96
<212> TYPE: RNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, c, g, or u

<400> SEQUENCE: 73
nnnnnnnnnn nnnnnnnnnn guuuuagagc uagaaauagc aaguuaaaau aaggcuaguc    60
cguuaucaac uugaaaaagu ggcaccgagu cggugc                              96

<210> SEQ ID NO 74
<211> LENGTH: 114
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(30)
<223> OTHER INFORMATION: n is a, c, g, or u
<220> FEATURE:
<221> NAME/KEY: misc_feature
<222> LOCATION: (18)..(30)
<223> OTHER INFORMATION: may be absent
<220> FEATURE:
<221> NAME/KEY: misc_feature
<222> LOCATION: (108)..(114)
<223> OTHER INFORMATION: may be absent

<400> SEQUENCE: 74
nnnnnnnnnn nnnnnnnnnn nnnnnnnnnn guuuuagagc uagaaauagc aaguuaaaau    60
aaggcuaguc cguuaucaac uugaaaaagu ggcaccgagu cggugcuuuu uuuu         114

<210> SEQ ID NO 75
<211> LENGTH: 19
<212> TYPE: DNA
<213> ORGANISM: Artificial Sequence
<220> FEATURE:
<223> OTHER INFORMATION: Synthetic

<400> SEQUENCE: 75
aagagcaaca aatctgact                                                 19

<210> SEQ ID NO 76
<211> LENGTH: 39
<212> TYPE: DNA
<213> ORGANISM: Artificial Sequence
<220> FEATURE:
<223> OTHER INFORMATION: Synthetic

<400> SEQUENCE: 76
aagagcaaca gtgctgtgcc tggagcaaca aatctgact                           39

<210> SEQ ID NO 77
<211> LENGTH: 33
<212> TYPE: DNA
<213> ORGANISM: Artificial Sequence
<220> FEATURE:
<223> OTHER INFORMATION: Synthetic

<400> SEQUENCE: 77
aagagcaaca gtgctggagc aacaaatctg act                                 33

<210> SEQ ID NO 78
<211> LENGTH: 34
```

```
<212> TYPE: DNA
<213> ORGANISM: Artificial Sequence
<220> FEATURE:
<223> OTHER INFORMATION: Synthetic

<400> SEQUENCE: 78
aagagcaaca gtgcctggag caacaaatct gact                               34

<210> SEQ ID NO 79
<211> LENGTH: 19
<212> TYPE: DNA
<213> ORGANISM: Artificial Sequence
<220> FEATURE:
<223> OTHER INFORMATION: Synthetic

<400> SEQUENCE: 79
aagagcaaca gtgctgact                                               19

<210> SEQ ID NO 80
<211> LENGTH: 41
<212> TYPE: DNA
<213> ORGANISM: Artificial Sequence
<220> FEATURE:
<223> OTHER INFORMATION: Synthetic

<400> SEQUENCE: 80
aagagcaaca gtgctgtggg cctggagcaa caaatctgac t                       41

<210> SEQ ID NO 81
<211> LENGTH: 38
<212> TYPE: DNA
<213> ORGANISM: Artificial Sequence
<220> FEATURE:
<223> OTHER INFORMATION: Synthetic

<400> SEQUENCE: 81
aagagcaaca gtgctggcct ggagcaacaa atctgact                           38

<210> SEQ ID NO 82
<211> LENGTH: 41
<212> TYPE: DNA
<213> ORGANISM: Artificial Sequence
<220> FEATURE:
<223> OTHER INFORMATION: Synthetic

<400> SEQUENCE: 82
aagagcaaca gtgctgtgtg cctggagcaa caaatctgac t                       41

<210> SEQ ID NO 83
<211> LENGTH: 79
<212> TYPE: DNA
<213> ORGANISM: Artificial Sequence
<220> FEATURE:
<223> OTHER INFORMATION: Synthetic

<400> SEQUENCE: 83
cgtggcctta gctgtgctcg cgctactctc tctttctgcc tggaggctat ccagcgtgag   60
tctctcctac cctcccgct                                               79

<210> SEQ ID NO 84
<211> LENGTH: 78
<212> TYPE: DNA
<213> ORGANISM: Artificial Sequence
<220> FEATURE:
<223> OTHER INFORMATION: Synthetic
```

<400> SEQUENCE: 84
cgtggcctta gctgtgctcg cgctactctc tctttcgcct ggaggctatc cagcgtgagt    60
ctctcctacc ctcccgct                                                  78

<210> SEQ ID NO 85
<211> LENGTH: 75
<212> TYPE: DNA
<213> ORGANISM: Artificial Sequence
<220> FEATURE:
<223> OTHER INFORMATION: Synthetic

<400> SEQUENCE: 85
cgtggcctta gctgtgctcg cgctactctc tctttctgga ggctatccag cgtgagtctc    60
tcctaccctc ccgct                                                     75

<210> SEQ ID NO 86
<211> LENGTH: 84
<212> TYPE: DNA
<213> ORGANISM: Artificial Sequence
<220> FEATURE:
<223> OTHER INFORMATION: Synthetic

<400> SEQUENCE: 86
cgtggcctta gctgtgctcg cgctactctc tctttctgga tagcctggag gctatccagc    60
gtgagtctct cctaccctcc cgct                                           84

<210> SEQ ID NO 87
<211> LENGTH: 55
<212> TYPE: DNA
<213> ORGANISM: Artificial Sequence
<220> FEATURE:
<223> OTHER INFORMATION: Synthetic

<400> SEQUENCE: 87
cgtggcctta gctgtgctcg cgctatccag cgtgagtctc tcctaccctc ccgct         55

<210> SEQ ID NO 88
<211> LENGTH: 82
<212> TYPE: DNA
<213> ORGANISM: Artificial Sequence
<220> FEATURE:
<223> OTHER INFORMATION: Synthetic

<400> SEQUENCE: 88
cgtggcctta gctgtgctcg cgctactctc tctttctgtg gcctggaggc tatccagcgt    60
gagtctctcc taccctcccg ct                                             82

<210> SEQ ID NO 89
<211> LENGTH: 58
<212> TYPE: DNA
<213> ORGANISM: Artificial Sequence
<220> FEATURE:
<223> OTHER INFORMATION: Synthetic

<400> SEQUENCE: 89
cacaccacga ggcagatcac caagcccgcg caatgggacc aaagcagccc gcaggacg      58

<210> SEQ ID NO 90
<211> LENGTH: 61
<212> TYPE: DNA
<213> ORGANISM: Artificial Sequence
<220> FEATURE:
<223> OTHER INFORMATION: Synthetic

<400> SEQUENCE: 90
cacaccacga ggcagatcac caagcccgcg aaccaatggg accaaagcag cccgcaggac    60
g                                                                  61

<210> SEQ ID NO 91
<211> LENGTH: 48
<212> TYPE: DNA
<213> ORGANISM: Artificial Sequence
<220> FEATURE:
<223> OTHER INFORMATION: Synthetic

<400> SEQUENCE: 91
cacaccacga ggcagatcac caatgggacc aaagcagccc gcaggacg                48

<210> SEQ ID NO 92
<211> LENGTH: 59
<212> TYPE: DNA
<213> ORGANISM: Artificial Sequence
<220> FEATURE:
<223> OTHER INFORMATION: Synthetic

<400> SEQUENCE: 92
cacaccacga ggcagatcac caagcccgcg ccaatgggac caaagcagcc cgcaggacg    59

<210> SEQ ID NO 93
<211> LENGTH: 59
<212> TYPE: DNA
<213> ORGANISM: Artificial Sequence
<220> FEATURE:
<223> OTHER INFORMATION: Synthetic

<400> SEQUENCE: 93
cacaccacga ggcagatcac caagcccgca ccaatgggac caaagcagcc cgcaggacg    59

<210> SEQ ID NO 94
<211> LENGTH: 35
<212> TYPE: DNA
<213> ORGANISM: Artificial Sequence
<220> FEATURE:
<223> OTHER INFORMATION: Synthetic

<400> SEQUENCE: 94
cacaccacga ggcagatcac caagcccgca ggacg                             35

<210> SEQ ID NO 95
<211> LENGTH: 22
<212> TYPE: PRT
<213> ORGANISM: Artificial Sequence
<220> FEATURE:
<223> OTHER INFORMATION: Synthetic

<400> SEQUENCE: 95

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 96
<211> LENGTH: 21
<212> TYPE: PRT
<213> ORGANISM: Artificial Sequence
<220> FEATURE:
<223> OTHER INFORMATION: Synthetic

<400> SEQUENCE: 96

Met Ala Leu Pro Val Thr Ala Leu Leu Leu Pro Leu Ala Leu Leu Leu
1               5                   10                  15

His Ala Ala Arg Pro
            20

<210> SEQ ID NO 97
<211> LENGTH: 23
<212> TYPE: PRT
<213> ORGANISM: Artificial Sequence
<220> FEATURE:
<223> OTHER INFORMATION: Synthetic

<400> SEQUENCE: 97

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 98
<211> LENGTH: 126
<212> TYPE: DNA
<213> ORGANISM: Artificial Sequence
<220> FEATURE:
<223> OTHER INFORMATION: Synthetic

<400> SEQUENCE: 98
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                              126

<210> SEQ ID NO 99
<211> LENGTH: 42
<212> TYPE: PRT
<213> ORGANISM: Artificial Sequence
<220> FEATURE:
<223> OTHER INFORMATION: Synthetic

<400> SEQUENCE: 99

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 100
<211> LENGTH: 120
<212> TYPE: PRT
<213> ORGANISM: Artificial Sequence
<220> FEATURE:
<223> OTHER INFORMATION: Synthetic

<400> SEQUENCE: 100

Thr Cys Ala Ala Ala Gly Cys Gly Gly Ala Gly Thr Ala Gly Gly Thr
1               5                   10                  15

Thr Gly Thr Thr Gly Cys Ala Thr Cys Cys Gly Ala Thr Thr Ala
            20                  25                  30

Cys Ala Thr Gly Ala Ala Thr Ala Thr Gly Ala Cys Thr Cys Cys Thr
        35                  40                  45

Cys Gly Cys Cys Gly Gly Cys Cys Thr Gly Gly Gly Cys Cys Gly Ala

```
                    50                  55                  60
Cys Ala Gly Ala Ala Ala Ala Cys Ala Thr Thr Ala Cys Cys Ala
 65                  70                  75                  80

Ala Cys Cys Cys Thr Ala Thr Gly Cys Cys Cys Cys Cys Cys Ala
                 85                  90                  95

Cys Gly Ala Gly Ala Cys Thr Thr Cys Gly Cys Thr Gly Cys Gly Thr
            100                 105                 110

Ala Cys Ala Gly Gly Thr Cys Cys
        115                 120
```

<210> SEQ ID NO 101
<211> LENGTH: 40
<212> TYPE: PRT
<213> ORGANISM: Artificial Sequence
<220> FEATURE:
<223> OTHER INFORMATION: Synthetic

<400> SEQUENCE: 101

```
Ser Lys Arg Ser Arg Leu Leu His Ser Asp Tyr Met Asn Met Thr Pro
 1               5                  10                  15

Arg Arg Pro Gly Pro Thr Arg Lys His Tyr Gln Pro Tyr Ala Pro Pro
             20                  25                  30

Arg Asp Phe Ala Ala Tyr Arg Ser
         35                  40
```

<210> SEQ ID NO 102
<211> LENGTH: 336
<212> TYPE: DNA
<213> ORGANISM: Artificial Sequence
<220> FEATURE:
<223> OTHER INFORMATION: Synthetic

<400> SEQUENCE: 102

```
cgagtgaagt tttcccgaag cgcagacgct ccggcatatc agcaaggaca gaatcagctg      60
tataacgaac tgaatttggg acgccgcgag gagtatgacg tgcttgataa acgccggggg     120
agagacccgg aaatgggggg taaaccccga agaaagaatc cccaagaagg actctacaat     180
gaactccaga aggataagat ggcggaggcc tactcagaaa taggtatgaa gggcgaacga     240
cgacggggaa aggtcacga tggcctctac caagggttga gtacggcaac caagatacg     300
tacgatgcac tgcatatgca ggccctgcct cccaga                               336
```

<210> SEQ ID NO 103
<211> LENGTH: 112
<212> TYPE: PRT
<213> ORGANISM: Artificial Sequence
<220> FEATURE:
<223> OTHER INFORMATION: Synthetic

<400> SEQUENCE: 103

```
Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
 65                  70                  75                  80
```

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
gatgggagca acgtggccat                                                   20

<210> SEQ ID NO 105
<211> LENGTH: 11
<212> TYPE: PRT
<213> ORGANISM: Artificial Sequence
<220> FEATURE:
<223> OTHER INFORMATION: Synthetic

<400> SEQUENCE: 105

Arg Ala Ser Gln Asp Ile Ser Lys Tyr Leu Asn
1               5                   10

<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

His Thr Ser Arg Leu His Ser
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Gln Gln Gly Asn Thr Leu Pro Tyr Thr
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic

<400> SEQUENCE: 108

Asp Tyr Gly Val Ser
1               5

<210> SEQ ID NO 109
<211> LENGTH: 16
<212> TYPE: PRT
<213> ORGANISM: Artificial Sequence
<220> FEATURE:
<223> OTHER INFORMATION: Synthetic

```
<400> SEQUENCE: 109

Val Ile Trp Gly Ser Glu Thr Thr Tyr Tyr Asn Ser Ala Leu Lys Ser
1               5                   10                  15

<210> SEQ ID NO 110
<211> LENGTH: 12
<212> TYPE: PRT
<213> ORGANISM: Artificial Sequence
<220> FEATURE:
<223> OTHER INFORMATION: Synthetic

<400> SEQUENCE: 110

His Tyr Tyr Tyr Gly Gly Ser Tyr Ala Met Asp Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic

<400> SEQUENCE: 111

Arg Ala Ser Gln Asp Ile Ser Lys Tyr Leu Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Synthetic

<400> SEQUENCE: 112

His Thr Ser Arg Leu His Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic

<400> SEQUENCE: 113

Gln Gln Gly Asn Thr Leu Pro Tyr Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic

<400> SEQUENCE: 114

Gly Val Ser Leu Pro Asp Tyr
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic

<400> SEQUENCE: 115
```

```
Trp Gly Ser Glu Thr
1               5
```

<210> SEQ ID NO 116
<211> LENGTH: 12
<212> TYPE: PRT
<213> ORGANISM: Artificial Sequence
<220> FEATURE:
<223> OTHER INFORMATION: Synthetic

<400> SEQUENCE: 116

```
His Tyr Tyr Tyr Gly Gly Ser Tyr Ala Met Asp Tyr
1               5                   10
```

<210> SEQ ID NO 117
<211> LENGTH: 1518
<212> TYPE: DNA
<213> ORGANISM: Artificial Sequence
<220> FEATURE:
<223> OTHER INFORMATION: Synthetic

<400> SEQUENCE: 117

| | | | | | |
|---|---|---|---|---|---|
| atgcttcttt | tggttacgtc | tctgttgctt | tgcgaacttc | ctcatccagc | gttcttgctg | 60 |
| atccccgata | ttcagatgac | tcagaccacc | agtagcttgt | ctgcctcact | gggagaccga | 120 |
| gtaacaatct | cctgcagggc | aagtcaagac | attagcaaat | acctcaattg | gtaccagcag | 180 |
| aagcccgacg | gaacggtaaa | actcctcatc | tatcatacgt | caaggttgca | ttccggagta | 240 |
| ccgtcacgat | tttcaggttc | tgggagcgga | actgactatt | ccttgactat | ttcaaacctc | 300 |
| gagcaggagg | acattgcgac | atattttgt | caacaaggta | taccctccc | ttacactttc | 360 |
| ggaggaggaa | ccaaactcga | aattaccggg | tccaccagtg | gctctgggaa | gcctggcagt | 420 |
| ggagaaggtt | ccactaaagg | cgaggtgaag | ctccaggaga | gcggcccgg | tctcgttgcc | 480 |
| cccagtcaaa | gcctctctgt | aacgtgcaca | gtgagtggtg | tatcattgcc | tgattatggc | 540 |
| gtctcctgga | taaggcagcc | cccgcgaaag | ggtcttgaat | ggcttggggt | aatatggggc | 600 |
| tcagagacaa | cgtattataa | ctccgctctc | aaaagtcgct | tgacgataat | aaaagataac | 660 |
| tccaagagtc | aagttttcct | taaaatgaac | agtttgcaga | ctgacgatac | cgctatatat | 720 |
| tattgtgcta | acattatta | ctacggcggt | agttacgcga | tggattattg | ggggcagggg | 780 |
| acttctgtca | cagtcagtag | tgctgctgcc | tttgtcccgg | tatttctccc | agccaaaccg | 840 |
| accacgactc | ccgccccgcg | ccctccgaca | cccgctccca | ccatcgcctc | tcaacctctt | 900 |
| agtcttcgcc | ccgaggcatg | ccgacccgcc | gccggggtg | ctgttcatac | gaggggcttg | 960 |
| gacttcgctt | gtgatattta | catttgggct | ccgttggcgg | gtacgtgcgg | cgtccttttg | 1020 |
| ttgtcactcg | ttattacttt | gtattgtaat | cacaggaatc | gctcaaagcg | gagtaggttg | 1080 |
| ttgcattccg | attacatgaa | tatgactcct | cgccggcctg | ggccgacaag | aaaacattac | 1140 |
| caaccctatg | ccccccacg | agacttcgct | gcgtacaggt | cccgagtgaa | gttttcccga | 1200 |
| agcgcagacg | ctccggcata | tcagcaagga | cagaatcagc | tgtataacga | actgaatttg | 1260 |
| ggacgccgcg | aggagtatga | cgtgcttgat | aaacgccggg | ggagagaccc | ggaaatgggg | 1320 |
| ggtaaacccc | gaagaaagaa | tcccaagaa | ggactctaca | atgaactcca | gaaggataag | 1380 |
| atggcggagg | cctactcaga | aataggtatg | aagggcgaac | gacgacgggg | aaaaggtcac | 1440 |
| gatggcctct | accaagggtt | gagtacggca | accaaagata | cgtacgatgc | actgcatatg | 1500 |
| caggccctgc | ctcccaga | | | | | 1518 |

<210> SEQ ID NO 118
<211> LENGTH: 506
<212> TYPE: PRT
<213> ORGANISM: Artificial Sequence
<220> FEATURE:
<223> OTHER INFORMATION: Synthetic

<400> SEQUENCE: 118

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270

Pro Val Phe Leu Pro Ala Lys Pro Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
            340                 345                 350

Asn Arg Ser Lys Arg Ser Arg Leu Leu His Ser Asp Tyr Met Asn Met
        355                 360                 365
```

Thr Pro Arg Arg Pro Gly Pro Thr Arg Lys His Tyr Gln Pro Tyr Ala
370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
                420                 425                 430

Arg Gly Arg Asp Pro Glu Met Gly Gly Lys Pro Arg Lys Asn Pro
            435                 440                 445

Gln Glu Gly Leu Tyr Asn Glu Leu Gln Lys Asp Lys Met Ala Glu Ala
        450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
            500                 505

<210> SEQ ID NO 119
<211> LENGTH: 735
<212> TYPE: DNA
<213> ORGANISM: Artificial Sequence
<220> FEATURE:
<223> OTHER INFORMATION: Synthetic

<400> SEQUENCE: 119
gatattcaga tgactcagac caccagtagc ttgtctgcct cactgggaga ccgagtaaca      60
atctcctgca gggcaagtca agacattagc aaatacctca attggtacca gcagaagccc     120
gacggaacgg taaaactcct catctatcat acgtcaaggt tgcattccgg agtaccgtca     180
cgattttcag gttctgggag cggaactgac tattccttga ctatttcaaa cctcgagcag     240
gaggacattg cgacatattt ttgtcaacaa ggtaataccc tcccttacac tttcggagga     300
ggaaccaaac tcgaaattac cgggtccacc agtggctctg gaagcctgg cagtggagaa      360 ggttccacta aaggcgaggt gaagctccag gagagcggcc ccggtctcgt tgcccccagt     420
caaagcctct ctgtaacgtg cacagtgagt ggtgtatcat tgcctgatta tggcgtctcc     480
tggataaggc agcccccgcg aaagggtctt gaatggcttg gggtaatatg gggctcagag     540
acaacgtatt ataactccgc tctcaaaagt cgcttgacga taataaaaga taactccaag     600
agtcaagttt tccttaaaat gaacagtttg cagactgacg ataccgctat atattattgt     660
gctaaacatt attactacgg cggtagttac gcgatggatt attgggggca ggggacttct     720
gtcacagtca gtagt                                                      735

<210> SEQ ID NO 120
<211> LENGTH: 245
<212> TYPE: PRT
<213> ORGANISM: Artificial Sequence
<220> FEATURE:
<223> OTHER INFORMATION: Synthetic

<400> SEQUENCE: 120

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Ser Thr Ser Gly
             100                 105                 110

Ser Gly Lys Pro Gly Ser Gly Glu Gly Ser Thr Lys Gly Glu Val Lys
         115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                 165                 170                 175

Trp Gly Ser Glu Thr Thr Tyr Tyr Asn Ser Ala Leu Lys Ser Arg Leu
             180                 185                 190

Thr Ile Ile Lys Asp Asn Ser Lys Ser Gln Val Phe Leu Lys Met Asn
         195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245

<210> SEQ ID NO 121
<211> LENGTH: 261
<212> TYPE: DNA
<213> ORGANISM: Artificial Sequence
<220> FEATURE:
<223> OTHER INFORMATION: Synthetic

<400> SEQUENCE: 121
gctgctgcct tgtcccggt atttctccca gccaaaccga ccacgactcc cgccccgcgc    60
cctccgacac ccgctcccac catcgcctct caacctctta gtcttcgccc cgaggcatgc   120
cgacccgccg ccgggggtgc tgttcatacg aggggcttgg acttcgcttg tgatatttac   180
atttgggctc cgttggcggg tacgtgcggc gtccttttgt tgtcactcgt tattactttg   240
tattgtaatc acaggaatcg c                                            261

<210> SEQ ID NO 122
<211> LENGTH: 252
<212> TYPE: DNA
<213> ORGANISM: Artificial Sequence
<220> FEATURE:
<223> OTHER INFORMATION: Synthetic

<400> SEQUENCE: 122
tttgtcccgg tatttctccc agccaaaccg accacgactc cgccccgcg ccctccgaca    60 cccgctccca ccatcgcctc tcaacctctt agtcttcgcc cgaggcatg ccgacccgcc   120 gccgggggtg ctgttcatac gaggggcttg gacttcgctt gtgatattta catttgggct   180
ccgttggcgg gtacgtgcgg cgtccttttg ttgtcactcg ttattacttt gtattgtaat   240
cacaggaatc gc                                                       252

<210> SEQ ID NO 123
<211> LENGTH: 84
<212> TYPE: PRT
<213> ORGANISM: Artificial Sequence
<220> FEATURE:
<223> OTHER INFORMATION: Synthetic

<400> SEQUENCE: 123

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 124
<211> LENGTH: 120
<212> TYPE: PRT
<213> ORGANISM: Artificial Sequence
<220> FEATURE:
<223> OTHER INFORMATION: Synthetic

<400> SEQUENCE: 124

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 125
<211> LENGTH: 107
<212> TYPE: PRT
<213> ORGANISM: Artificial Sequence
<220> FEATURE:
<223> OTHER INFORMATION: Synthetic

<400> SEQUENCE: 125

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                 70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
                100                 105

<210> SEQ ID NO 126
<211> LENGTH: 18
<212> TYPE: PRT
<213> ORGANISM: Artificial Sequence
<220> FEATURE:
<223> OTHER INFORMATION: Synthetic

<400> SEQUENCE: 126

Gly Ser Thr Gly Ser Gly Lys Pro Gly Ser Gly Glu Gly Ser Thr
 1               5                   10                  15

Lys Gly

<210> SEQ ID NO 127
<211> LENGTH: 15
<212> TYPE: PRT
<213> ORGANISM: Artificial Sequence
<220> FEATURE:
<223> OTHER INFORMATION: Synthetic

<400> SEQUENCE: 127

Arg Ala Ser Lys Ser Val Ser Thr Ser Gly Tyr Ser Phe Met His
 1               5                   10                  15

<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Ser Lys Ser Val Ser Thr Ser Gly Tyr Ser Phe
 1               5                   10

<210> SEQ ID NO 129
<211> LENGTH: 7
<212> TYPE: PRT
<213> ORGANISM: Artificial Sequence
<220> FEATURE:
<223> OTHER INFORMATION: Synthetic

<400> SEQUENCE: 129

Leu Ala Ser Asn Leu Glu Ser
 1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic

<400> SEQUENCE: 130

```
<210> SEQ ID NO 131
<211> LENGTH: 6
<212> TYPE: PRT
<213> ORGANISM: Artificial Sequence
<220> FEATURE:
<223> OTHER INFORMATION: Synthetic

<400> SEQUENCE: 131

Ser Arg Glu Val Pro Trp
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic

<400> SEQUENCE: 132

Asn Tyr Gly Met Asn
1               5

<210> SEQ ID NO 133
<211> LENGTH: 10
<212> TYPE: PRT
<213> ORGANISM: Artificial Sequence
<220> FEATURE:
<223> OTHER INFORMATION: Synthetic

<400> SEQUENCE: 133

Gly Tyr Thr Phe Thr Asn Tyr Gly Met Asn
1               5                   10

<210> SEQ ID NO 134
<211> LENGTH: 17
<212> TYPE: PRT
<213> ORGANISM: Artificial Sequence
<220> FEATURE:
<223> OTHER INFORMATION: Synthetic

<400> SEQUENCE: 134

Trp Ile Asn Thr Tyr Thr Gly Glu Pro Thr Tyr Ala Asp Ala Phe Lys
1               5                   10                  15

Gly

<210> SEQ ID NO 135
<211> LENGTH: 6
<212> TYPE: PRT
<213> ORGANISM: Artificial Sequence
<220> FEATURE:
<223> OTHER INFORMATION: Synthetic

<400> SEQUENCE: 135

Asn Thr Tyr Thr Gly Glu
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic
```

Gln His Ser Arg Glu Val Pro Trp Thr
1               5

<400> SEQUENCE: 136

Asp Tyr Gly Asp Tyr Gly Met Asp Tyr
1               5

<210> SEQ ID NO 137
<211> LENGTH: 14
<212> TYPE: PRT
<213> ORGANISM: Artificial Sequence
<220> FEATURE:
<223> OTHER INFORMATION: Synthetic

<400> SEQUENCE: 137

Cys Ala Arg Asp Tyr Gly Asp Tyr Gly Met Asp Tyr Trp Gly
1               5                   10

<210> SEQ ID NO 138
<211> LENGTH: 508
<212> TYPE: PRT
<213> ORGANISM: Artificial Sequence
<220> FEATURE:
<223> OTHER INFORMATION: Synthetic

<400> SEQUENCE: 138

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Asn Tyr Gly Met Asn Trp Val Arg Gln Ala Pro Gly Gln
    50                  55                  60

Gly Leu Lys Trp Met Gly Trp Ile Asn Thr Tyr Thr Gly Glu Pro Thr
65                  70                  75                  80

Tyr Ala Asp Ala Phe Lys Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Asp Tyr Gly Asp Tyr Gly Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Gly Asp Ile Val Met Thr
145                 150                 155                 160

Gln Ser Pro Asp Ser Leu Ala Val Ser Leu Gly Glu Arg Ala Thr Ile
                165                 170                 175

Asn Cys Arg Ala Ser Lys Ser Val Ser Thr Ser Gly Tyr Ser Phe Met
            180                 185                 190

His Trp Tyr Gln Gln Lys Pro Gly Gln Pro Pro Lys Leu Leu Ile Tyr
        195                 200                 205

Leu Ala Ser Asn Leu Glu Ser Gly Val Pro Asp Arg Phe Ser Gly Ser
    210                 215                 220

Gly Ser Gly Thr Asp Phe Thr Leu Thr Ile Ser Ser Leu Gln Ala Glu
225                 230                 235                 240

Asp Val Ala Val Tyr Tyr Cys Gln His Ser Arg Glu Val Pro Trp Thr
                245                 250                 255

Phe Gly Gln Gly Thr Lys Val Glu Ile Lys Ser Ala Ala Ala Phe Val
            260                 265                 270

Pro Val Phe Leu Pro Ala Lys Pro Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
                340                 345                 350

Asn Arg Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
        420                 425                 430

Lys Arg Arg Gly Arg Asp Pro Glu Met Gly Gly Lys Pro Arg Arg Lys
    435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
        500                 505

<210> SEQ ID NO 139
<211> LENGTH: 735
<212> TYPE: DNA
<213> ORGANISM: Artificial Sequence
<220> FEATURE:
<223> OTHER INFORMATION: Synthetic

<400> SEQUENCE: 139
gatatagtta tgacccaatc acccgatagt cttgcggtaa gcctggggga gcgagcaaca      60
ataaactgtc gggcatcaaa atccgtcagt acaagcgggt attcattcat gcactggtat     120
caacagaaac ccggtcagcc acccaagctc ctgatttatc ttgcgtctaa tcttgagtcc     180
ggcgtcccag accggttttc cggctccggg agcggcacgg atttactctt actatttct     240 agccttcagg ccgaagatgt ggcggtatac tactgccagc attcaaggga agttccttgg     300
acgttcggtc agggcacgaa agtggaaatt aaaggcgggg gggatccggc ggggggaggg     360
tctggaggag gtggcagtgg tcaggtccaa ctggtgcagt ccggggcaga ggtaaaaaaa     420
cccggcgcgt ctgttaaggt ttcatgcaag gccagtggat atactttcac caattacgga     480
atgaactggg tgaggcaggc ccctggtcaa ggcctgaaat ggatgggatg gataaacacg     540
tacaccggtg aacctaccta tgccgatgcc tttaagggtc gggttacgat acgagagac      600 acctccatat caacagccta catggagctc agcagattga ggagtgacga tacgcagtc     660 tattactgtg caagagacta cggcgattat ggcatggatt actggggcca ggcactaca     720 gtaaccgttt ccagc                                                    735

<210> SEQ ID NO 140
<211> LENGTH: 245
<212> TYPE: PRT
<213> ORGANISM: Artificial Sequence
<220> FEATURE:
<223> OTHER INFORMATION: Synthetic

<400> SEQUENCE: 140

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Gly
            100                 105                 110

Gly Gly Gly Ser Gly Gly Gly Gly Ser Gly Gly Gly Gly Ser Gly Gln
        115                 120                 125

Val Gln Leu Val Gln Ser Gly Ala Glu Val Lys Lys Pro Gly Ala Ser
130                 135                 140

Val Lys Val Ser Cys Lys Ala Ser Gly Tyr Thr Phe Thr Asn Tyr Gly
145                 150                 155                 160

Met Asn Trp Val Arg Gln Ala Pro Gly Gln Gly Leu Lys Trp Met Gly
                165                 170                 175

Trp Ile Asn Thr Tyr Thr Gly Glu Pro Thr Tyr Ala Asp Ala Phe Lys
            180                 185                 190

Gly Arg Val Thr Met Thr Arg Asp Thr Ser Ile Ser Thr Ala Tyr Met
        195                 200                 205

Glu Leu Ser Arg Leu Arg Ser Asp Asp Thr Ala Val Tyr Tyr Cys Ala
    210                 215                 220

Arg Asp Tyr Gly Asp Tyr Gly Met Asp Tyr Trp Gly Gln Gly Thr Thr
225                 230                 235                 240

Val Thr Val Ser Ser
                245

<210> SEQ ID NO 141
<211> LENGTH: 735
<212> TYPE: DNA
<213> ORGANISM: Artificial Sequence
<220> FEATURE:
<223> OTHER INFORMATION: Synthetic

<400> SEQUENCE: 141
caggtccagt tggtgcaaag cggggcggag gtgaaaaaac ccggcgcttc cgtgaaggtg      60
tcctgtaagg cgtccggtta tacgttcacg aactacggga tgaattgggt tcgccaagcg    120
ccggggcagg gactgaaatg gatgggggtgg ataaatacct acaccggcga acctacatac    180
gccgacgctt ttaaagggcg agtcactatg acgcgcgata ccagcatatc caccgcatac    240
atggagctgt cccgactccg gtcagacgac acggctgtct actattgtgc tcgggactat    300

```
ggcgattatg gcatggacta ctggggtcag ggtacgactg taacagttag tagtggtgga    360
ggcggcagtg gcggggggg aagcggagga ggggttctg gtgacatagt tatgacccaa     420
tccccagata gtttggcggt ttctctgggc gagagggcaa cgattaattg tcgcgcatca    480
aagagcgttt caacgagcgg atattctttt atgcattggt accagcaaaa acccggacaa    540
ccgccgaagc tgctgatcta cttggcttca atcttgagt ctggggtgcc ggaccgattt     600
tctggtagtg gaagcggaac tgactttacg ctcacgatca gttcactgca ggctgaggat    660
gtagcggtct attattgcca gcacagtaga gaagtcccct ggaccttcgg tcaaggcacg    720
aaagtagaaa ttaaa                                                     735
```

<210> SEQ ID NO 142
<211> LENGTH: 245
<212> TYPE: PRT
<213> ORGANISM: Artificial Sequence
<220> FEATURE:
<223> OTHER INFORMATION: Synthetic

<400> SEQUENCE: 142

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Asp Ile Val Met Thr Gln Ser Pro Asp Ser
    130                 135                 140

Leu Ala Val Ser Leu Gly Glu Arg Ala Thr Ile Asn Cys Arg Ala Ser
145                 150                 155                 160

Lys Ser Val Ser Thr Ser Gly Tyr Ser Phe Met His Trp Tyr Gln Gln
                165                 170                 175

Lys Pro Gly Gln Pro Pro Lys Leu Leu Ile Tyr Leu Ala Ser Asn Leu
            180                 185                 190

Glu Ser Gly Val Pro Asp Arg Phe Ser Gly Ser Gly Ser Gly Thr Asp
        195                 200                 205

Phe Thr Leu Thr Ile Ser Ser Leu Gln Ala Glu Asp Val Ala Val Tyr
    210                 215                 220

Tyr Cys Gln His Ser Arg Glu Val Pro Trp Thr Phe Gly Gln Gly Thr
225                 230                 235                 240

Lys Val Glu Ile Lys
                245
```

<210> SEQ ID NO 143
<211> LENGTH: 118
<212> TYPE: PRT

<213> ORGANISM: Artificial Sequence
<220> FEATURE:
<223> OTHER INFORMATION: Synthetic

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 144
<211> LENGTH: 111
<212> TYPE: PRT
<213> ORGANISM: Artificial Sequence
<220> FEATURE:
<223> OTHER INFORMATION: Synthetic

<400> SEQUENCE: 144

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys
            100                 105                 110

<210> SEQ ID NO 145
<211> LENGTH: 1524
<212> TYPE: DNA
<213> ORGANISM: Artificial Sequence
<220> FEATURE:
<223> OTHER INFORMATION: Synthetic

<400> SEQUENCE: 145
atggcgcttc cggtgacagc actgctcctc cccttggcgc tgttgctcca cgcagcaagg      60
ccgcaggtgc agctggtgca gagcggagcc gagctcaaga agcccggagc ctccgtgaag     120
gtgagctgca aggccagcgg caacaccctg accaactacg tgatccactg ggtgagacaa     180
gcccccggcc aaaggctgga gtggatgggc tacatcctgc cctacaacga cctgaccaag     240

```
tacagccaga agttccaggg cagggtgacc atcaccaggg ataagagcgc ctccaccgcc    300
tatatggagc tgagcagcct gaggagcgag gacaccgctg tgtactactg tacaaggtgg    360
gactgggacg gcttctttga ccctgggc cagggcacaa cagtgaccgt cagcagcggc      420
```
```
ggcggaggca gcggcggcgg cggcagcggc ggaggcggaa gcgaaatcgt gatgacccag    480
agccccgcca cactgagcgt gagccctggc gagagggcca gcatctcctg cagggctagc    540
caaagcctgg tgcacagcaa cggcaacacc cacctgcact ggtaccagca gagacccgga    600
caggctccca ggctgctgat ctacagcgtg agcaacaggt tctccgaggt gcctgccagg    660
tttagcggca gcggaagcgg caccgacttt accctgacca tcagcagcgt ggagtccgag    720
gacttcgccg tgtattactg cagccagacc agccacatcc cttacacctt cggcggcggc    780
accaagctgg agatcaaaag tgctgctgcc tttgtcccgg tatttctccc agccaaaccg    840
accacgactc ccgccccgcg ccctccgaca cccgctccca ccatcgcctc tcaacctctt    900
agtcttcgcc ccgaggcatg ccgacccgcc gccggggtg ctgttcatac gagggcttg      960
```
```
gacttcgctt gtgatattta catttgggct ccgttggcgg gtacgtgcgg cgtccttttg   1020
ttgtcactcg ttattacttt gtattgtaat cacaggaatc gcaacgggg cagaaagaaa    1080
ctcctgtata tattcaaaca accatttatg agaccagtac aaaactactca agaggaagat  1140
```
```
ggctgtagct gccgatttcc agaagaagaa gaaggaggat gtgaactgcg agtgaagttt   1200
tcccgaagcg cagacgctcc ggcatatcag caaggacaga atcagctgta taacgaactg   1260
aatttgggac gccgcgagga gtatgacgtg cttgataaac gccggggag agacccggaa    1320
atggggggta aaccccgaag aaagaatccc caagaaggac tctacaatga actccagaag   1380
gataagatgg cggaggccta ctcagaaata ggtatgaagg gcgaacgacg acggggaaaa   1440
ggtcacgatg gcctctacca agggttgagt acggcaacca agatacgta cgatgcactg    1500
catatgcagg ccctgcctcc caga                                          1524

<210> SEQ ID NO 146
<211> LENGTH: 508
<212> TYPE: PRT
<213> ORGANISM: Artificial Sequence
<220> FEATURE:
<223> OTHER INFORMATION: Synthetic

<400> SEQUENCE: 146

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Leu
            20                  25                  30

Lys Lys Pro Gly Ala Ser Val Lys Val Ser Cys Lys Ala Ser Gly Asn
        35                  40                  45

Thr Leu Thr Asn Tyr Val Ile His Trp Val Arg Gln Ala Pro Gly Gln
    50                  55                  60

Arg Leu Glu Trp Met Gly Tyr Ile Leu Pro Tyr Asn Asp Leu Thr Lys
65                  70                  75                  80

Tyr Ser Gln Lys Phe Gln Gly Arg Val Thr Ile Thr Arg Asp Lys Ser
                85                  90                  95

Ala Ser Thr Ala Tyr Met Glu Leu Ser Ser Leu Arg Ser Glu Asp Thr
            100                 105                 110

Ala Val Tyr Tyr Cys Thr Arg Trp Asp Trp Asp Gly Phe Phe Asp Pro
        115                 120                 125

Trp Gly Gln Gly Thr Thr Val Thr Val Ser Ser Gly Gly Gly Gly Ser
```

```
                130                 135                 140
Gly Gly Gly Gly Ser Gly Gly Gly Ser Glu Ile Val Met Thr Gln
145                 150                 155                 160

Ser Pro Ala Thr Leu Ser Val Ser Pro Gly Glu Arg Ala Ser Ile Ser
                165                 170                 175

Cys Arg Ala Ser Gln Ser Leu Val His Ser Asn Gly Asn Thr His Leu
                180                 185                 190

His Trp Tyr Gln Gln Arg Pro Gly Gln Ala Pro Arg Leu Leu Ile Tyr
            195                 200                 205

Ser Val Ser Asn Arg Phe Ser Glu Val Pro Ala Arg Phe Ser Gly Ser
        210                 215                 220

Gly Ser Gly Thr Asp Phe Thr Leu Thr Ile Ser Ser Val Glu Ser Glu
225                 230                 235                 240

Asp Phe Ala Val Tyr Tyr Cys Ser Gln Thr Ser His Ile Pro Tyr Thr
                245                 250                 255

Phe Gly Gly Gly Thr Lys Leu Glu Ile Lys Ser Ala Ala Ala Phe Val
                260                 265                 270

Pro Val Phe Leu Pro Ala Lys Pro Thr Thr Thr Pro Ala Pro Arg Pro
            275                 280                 285

Pro Thr Pro Ala Pro Thr Ile Ala Ser Gln Pro Leu Ser Leu Arg Pro
        290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
                340                 345                 350

Asn Arg Lys Arg Gly Arg Lys Lys Leu Leu Tyr Ile Phe Lys Gln Pro
            355                 360                 365

Phe Met Arg Pro Val Gln Thr Thr Gln Glu Glu Asp Gly Cys Ser Cys
        370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
                420                 425                 430

Lys Arg Arg Gly Arg Asp Pro Glu Met Gly Gly Lys Pro Arg Arg Lys
            435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
                500                 505

<210> SEQ ID NO 147
<211> LENGTH: 735
<212> TYPE: DNA
<213> ORGANISM: Artificial Sequence
<220> FEATURE:
<223> OTHER INFORMATION: Synthetic
```

<400> SEQUENCE: 147

```
caggtgcagc tggtgcagag cggagccgag ctcaagaagc ccggagcctc cgtgaaggtg    60
agctgcaagg ccagcggcaa caccctgacc aactacgtga tccactgggt gagacaagcc   120
cccggccaaa ggctggagtg gatgggctac atcctgccct acaacgacct gaccaagtac   180
agccagaagt tccagggcag ggtgaccatc accagggata gagcgcctc caccgcctat    240
atggagctga gcagcctgag gagcgaggac accgctgtgt actactgtac aaggtgggac   300
tgggacggct tctttgaccc ctggggccag ggcacaacag tgaccgtcag cagcggcggc   360
ggaggcagcg gcggcggcgg cagcggcgga ggcggaagcg aaatcgtgat gacccagagc   420
cccgccacac tgagcgtgag ccctggcgag agggccagca tctcctgcag ggctagccaa   480
agcctggtgc acagcaacgg caacacccac ctgcactggt accagcagag acccggacag   540
gctcccaggc tgctgatcta cagcgtgagc aacaggttct ccgaggtgcc tgccaggttt   600
agcggcagcg gaagcggcac cgactttacc ctgaccatca gcagcgtgga gtccgaggac   660
ttcgccgtgt attactgcag ccagaccagc cacatccctt acaccttcgg cggcggcacc   720
aagctggaga tcaaa                                                    735
```

<210> SEQ ID NO 148
<211> LENGTH: 245
<212> TYPE: PRT
<213> ORGANISM: Artificial Sequence
<220> FEATURE:
<223> OTHER INFORMATION: Synthetic

<400> SEQUENCE: 148

```
Gln Val Gln Leu Val Gln Ser Gly Ala Glu Leu Lys Lys Pro Gly Ala
1               5                   10                  15

Ser Val Lys Val Ser Cys Lys Ala Ser Gly Asn Thr Leu Thr Asn Tyr
            20                  25                  30

Val Ile His Trp Val Arg Gln Ala Pro Gly Gln Arg Leu Glu Trp Met
        35                  40                  45

Gly Tyr Ile Leu Pro Tyr Asn Asp Leu Thr Lys Tyr Ser Gln Lys Phe
    50                  55                  60

Gln Gly Arg Val Thr Ile Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Asp Trp Asp Gly Phe Phe Asp Pro Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Ala Ser Ile Ser Cys Arg Ala Ser Gln
145                 150                 155                 160

Ser Leu Val His Ser Asn Gly Asn Thr His Leu His Trp Tyr Gln Gln
                165                 170                 175

Arg Pro Gly Gln Ala Pro Arg Leu Leu Ile Tyr Ser Val Ser Asn Arg
            180                 185                 190

Phe Ser Glu Val Pro Ala Arg Phe Ser Gly Ser Gly Ser Gly Thr Asp
        195                 200                 205

Phe Thr Leu Thr Ile Ser Ser Val Glu Ser Glu Asp Phe Ala Val Tyr
    210                 215                 220
```

Tyr Cys Ser Gln Thr Ser His Ile Pro Tyr Thr Phe Gly Gly Gly Thr
225                 230                 235                 240

Lys Leu Glu Ile Lys
            245

<210> SEQ ID NO 149
<211> LENGTH: 118
<212> TYPE: PRT
<213> ORGANISM: Artificial Sequence
<220> FEATURE:
<223> OTHER INFORMATION: Synthetic

<400> SEQUENCE: 149

Gln Val Gln Leu Val Gln Ser Gly Ala Glu Leu Lys Lys Pro Gly Ala
1               5                   10                  15

Ser Val Lys Val Ser Cys Lys Ala Ser Gly Asn Thr Leu Thr Asn Tyr
            20                  25                  30

Val Ile His Trp Val Arg Gln Ala Pro Gly Gln Arg Leu Glu Trp Met
        35                  40                  45

Gly Tyr Ile Leu Pro Tyr Asn Asp Leu Thr Lys Tyr Ser Gln Lys Phe
    50                  55                  60

Gln Gly Arg Val Thr Ile Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Asp Trp Asp Gly Phe Phe Asp Pro Trp Gly Gln Gly Thr
            100                 105                 110

Thr Val Thr Val Ser Ser
        115

<210> SEQ ID NO 150
<211> LENGTH: 112
<212> TYPE: PRT
<213> ORGANISM: Artificial Sequence
<220> FEATURE:
<223> OTHER INFORMATION: Synthetic

<400> SEQUENCE: 150

Glu Ile Val Met Thr Gln Ser Pro Ala Thr Leu Ser Val Ser Pro Gly
1               5                   10                  15

Glu Arg Ala Ser Ile Ser Cys Arg Ala Ser Gln Ser Leu Val His Ser
            20                  25                  30

Asn Gly Asn Thr His Leu His Trp Tyr Gln Gln Arg Pro Gly Gln Ala
        35                  40                  45

Pro Arg Leu Leu Ile Tyr Ser Val Ser Asn Arg Phe Ser Glu Val Pro
    50                  55                  60

Ala Arg Phe Ser Gly Ser Gly Ser Gly Thr Asp Phe Thr Leu Thr Ile
65                  70                  75                  80

Ser Ser Val Glu Ser Glu Asp Phe Ala Val Tyr Tyr Cys Ser Gln Thr
                85                  90                  95

Ser His Ile Pro Tyr Thr Phe Gly Gly Gly Thr Lys Leu Glu Ile Lys
            100                 105                 110

<210> SEQ ID NO 151
<211> LENGTH: 16
<212> TYPE: PRT
<213> ORGANISM: Artificial Sequence
<220> FEATURE:
<223> OTHER INFORMATION: Synthetic

```
<400> SEQUENCE: 151

Arg Ala Ser Gln Ser Leu Val His Ser Asn Gly Asn Thr His Leu His
1               5                   10                  15

<210> SEQ ID NO 152
<211> LENGTH: 7
<212> TYPE: PRT
<213> ORGANISM: Artificial Sequence
<220> FEATURE:
<223> OTHER INFORMATION: Synthetic

<400> SEQUENCE: 152

Ser Val Ser Asn Arg Phe Ser
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Ser Gln Thr Ser His Ile Pro Tyr Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Ser Gln Thr Ser His Ile Pro Tyr Thr
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic

<400> SEQUENCE: 155

Asn Tyr Val Ile His
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic

<400> SEQUENCE: 156

Gly Asn Thr Leu Thr Asn Tyr
1               5

<210> SEQ ID NO 157
<211> LENGTH: 17
<212> TYPE: PRT
<213> ORGANISM: Artificial Sequence
<220> FEATURE:
<223> OTHER INFORMATION: Synthetic
```

<400> SEQUENCE: 157

Tyr Ile Leu Pro Tyr Asn Asp Leu Thr Lys Tyr Ser Gln Lys Phe Gln
1               5                   10                  15
Gly

<210> SEQ ID NO 158
<211> LENGTH: 6
<212> TYPE: PRT
<213> ORGANISM: Artificial Sequence
<220> FEATURE:
<223> OTHER INFORMATION: Synthetic

<400> SEQUENCE: 158

Leu Pro Tyr Asn Asp Leu
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Trp Asp Trp Asp Gly Phe Phe Asp Pro
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Trp Asp Trp Asp Gly Phe Phe Asp Pro
1               5

<210> SEQ ID NO 161
<211> LENGTH: 145
<212> TYPE: DNA
<213> ORGANISM: Artificial Sequence
<220> FEATURE:
<223> OTHER INFORMATION: Synthetic

<400> SEQUENCE: 161
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                           145

<210> SEQ ID NO 162
<211> LENGTH: 130
<212> TYPE: DNA
<213> ORGANISM: Artificial Sequence
<220> FEATURE:
<223> OTHER INFORMATION: Synthetic

<400> SEQUENCE: 162
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

```
<210> SEQ ID NO 163
<211> LENGTH: 145
<212> TYPE: DNA
<213> ORGANISM: Artificial Sequence
<220> FEATURE:
<223> OTHER INFORMATION: Synthetic

<400> SEQUENCE: 163
aggaacccct agtgatggag ttggccactc cctctctgcg cgctcgctcg ctcactgagg    60
ccgcccgggc aaagcccggg cgtcgggcga cctttggtcg cccggcctca gtgagcgagc   120
gagcgcgcag agagggagtg gccaa                                         145

<210> SEQ ID NO 164
<211> LENGTH: 141
<212> TYPE: DNA
<213> ORGANISM: Artificial Sequence
<220> FEATURE:
<223> OTHER INFORMATION: Synthetic

<400> SEQUENCE: 164
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag ctgcctgcag g                                             141

<210> SEQ ID NO 165
<211> LENGTH: 800
<212> TYPE: DNA
<213> ORGANISM: Artificial Sequence
<220> FEATURE:
<223> OTHER INFORMATION: Synthetic

<400> SEQUENCE: 165
gagatgtaag gagctgctgt gacttgctca aggccttata tcgagtaaac ggtagtgctg    60
gggcttagac gcaggtgttc tgatttatag ttcaaaacct ctatcaatga gagagcaatc   120
tcctggtaat gtgatagatt tcccaactta atgccaacat accataaacc tcccattctg   180
ctaatgccca gcctaagttg gggagaccac tccagattcc aagatgtaca gtttgctttg   240
ctgggccttt tcccatgcc tgcctttact ctgccagagt tatattgctg gggttttgaa   300
gaagatccta ttaaataaaa gaataagcag tattattaag tagccctgca tttcaggttt   360
ccttgagtgg caggccaggc ctggccgtga acgttcactg aaatcatggc ctcttggcca   420
agattgatag cttgtgcctg tccctgagtc ccagtccatc acgagcagct ggtttctaag   480
atgctatttc ccgtataaag catgagaccg tgacttgcca gccccacaga gccccgccct   540
tgtccatcac tggcatctgg actccagcct gggttggggc aaagagggaa atgagatcat   600
gtcctaaccc tgatcctctt gtcccacaga tatccgaaac cctgaccctg ccgtgtacca   660
gctgagagac tctaaatcca gtgacaagtc tgtctgccta ttcaccgatt tgattctca   720 aacaaatgtg tcacaaagta aggattctga tgtgtatatc acagacaaaa ctgtgctaga   780
catgaggtct atggacttca                                               800

<210> SEQ ID NO 166
<211> LENGTH: 804
<212> TYPE: DNA
<213> ORGANISM: Artificial Sequence
<220> FEATURE:
<223> OTHER INFORMATION: Synthetic

<400> SEQUENCE: 166
```

| | |
|---|---|
| tggagcaaca aatctgactt tgcatgtgca aacgccttca acaacagcat tattccagaa | 60 |
| gacaccttct tccccagccc aggtaagggc agctttggtg ccttcgcagg ctgtttcctt | 120 |
| gcttcaggaa tggccaggtt ctgcccagag ctctggtcaa tgatgtctaa aactcctctg | 180 |
| attggtggtc tcggccttat ccattgccac caaaaccctc ttttactaa gaaacagtga | 240 |
| gccttgttct ggcagtccag agaatgacac gggaaaaaag cagatgaaga gaaggtggca | 300 |
| ggagagggca cgtggcccag cctcagtctc tccaactgag ttcctgcctg cctgcctttg | 360 |
| ctcagactgt ttgccccctta ctgctcttct aggcctcatt ctaagcccct ctccaagtt | 420 |
| gcctctcctt atttctccct gtctgccaaa aaatctttcc cagctcacta agtcagtctc | 480 |
| acgcagtcac tcattaaccc accaatcact gattgtgccg gcacatgaat gcaccaggtg | 540 |
| ttgaagtgga ggaattaaaa agtcagatga ggggtgtgcc cagaggaagc accattctag | 600 |
| ttgggggagc ccatctgtca gctgggaaaa gtccaaataa cttcagattg gaatgtgttt | 660 |
| taactcaggg ttgagaaaac agctaccttc aggacaaaag tcagggaagg gctctctgaa | 720 |
| gaaatgctac ttgaagatac cagccctacc aagggcaggg agaggaccct atagaggcct | 780 |
| gggacaggag ctcaatgaga aagg | 804 |

<210> SEQ ID NO 167
<211> LENGTH: 1178
<212> TYPE: DNA
<213> ORGANISM: Artificial Sequence
<220> FEATURE:
<223> OTHER INFORMATION: Synthetic

<400> SEQUENCE: 167

| | |
|---|---|
| ggctccggtg cccgtcagtg ggcagagcgc acatcgccca cagtccccga gaagttgggg | 60 |
| ggaggggtcg gcaattgaac cggtgcctag agaaggtggc gcggggtaaa ctgggaaagt | 120 |
| gatgtcgtgt actggctccg ccttttttccc gagggtgggg gagaaccgta tataagtgca | 180 |
| gtagtcgccg tgaacgttct ttttcgcaac gggtttgccg ccagaacaca ggtaagtgcc | 240 |
| gtgtgtggtt cccgcgggcc tggcctcttt acgggttatg gcccttgcgt gccttgaatt | 300 |
| acttccactg gctgcagtac gtgattcttg atcccgagct tcgggttgga agtgggtggg | 360 |
| agagttcgag gccttgcgct taaggagccc cttcgcctcg tgcttgagtt gaggcctggc | 420 |
| ctgggcgctg gggccgccgc gtgcgaatct ggtggcacct tcgcgcctgt ctcgctgctt | 480 |
| tcgataagtc tctagccatt taaaatttt gatgacctgc tgcgacgctt ttttttctggc | 540 |
| aagatagtct tgtaaatgcg ggccaagatc tgcacactgg tatttcggtt tttggggccg | 600 |
| cgggcggcga cggggcccgt gcgtcccagc gcacatgttc ggcgaggcgg ggcctgcgag | 660 |
| cgcggccacc gagaatcgga cggggtagt ctcaagctgg ccggcctgct ctggtgcctg | 720 |
| gcctcgcgcc gccgtgtatc gccccgccct gggcggcaag gctggcccgg tcggcaccag | 780 |
| ttgcgtgagc ggaaagatgg ccgcttcccg gccctgctgc agggagctca aaatggagga | 840 |
| cgcggcgctc gggagagcgg gcgggtgagt cacccacaca aaggaaaagg gccttttccgt | 900 |
| cctcagccgt cgcttcatgt gactccacgg agtaccgggc gccgtccagg cacctcgatt | 960 |
| agttctcgag ctttttggagt acgtcgtctt taggttgggg ggagggggttt tatgcgatgg | 1020 |
| agtttccccca cactgagtgg gtggagactg aagttaggcc agcttggcac ttgatgtaat | 1080 |
| tctccttgga atttgccctt tttgagtttg gatcttggtt cattctcaag cctcagacag | 1140 |
| tggttcaaag ttttttttcttt ccatttcagg tgtcgtga | 1178 |

<210> SEQ ID NO 168
<211> LENGTH: 4358
<212> TYPE: DNA
<213> ORGANISM: Artificial Sequence
<220> FEATURE:
<223> OTHER INFORMATION: Synthetic

<400> SEQUENCE: 168

| | | | | | | |
|---|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | gggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggtttctaag | 480 |
| atgctatttc | ccgtataaag | catgagaccg | tgacttgcca | gccccacaga | gccccgccct | 540 |
| tgtccatcac | tggcatctgg | actccagcct | gggttgggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | ggctccggtg | cccgtcagtg | ggcagagcgc | acatcgccca | 840 |
| cagtccccga | gaagttgggg | ggaggggtcg | gcaattgaac | cggtgcctag | agaaggtggc | 900 |
| gcggggtaaa | ctgggaaagt | gatgtcgtgt | actggctccg | ccttttccc | gagggtgggg | 960 |
| gagaaccgta | tataagtgca | gtagtcgccg | tgaacgttct | ttttcgcaac | gggtttgccg | 1020 |
| ccagaacaca | ggtaagtgcc | gtgtgtggtt | cccgcgggcc | tggcctcttt | acgggttatg | 1080 |
| gcccttgcgt | gccttgaatt | acttccactg | gctgcagtac | gtgattcttg | atcccgagct | 1140 |
| tcgggttgga | agtgggtggg | agagttcgag | gccttgcgct | taaggagccc | cttcgcctcg | 1200 |
| tgcttgagtt | gaggcctggc | ctgggcgctg | gggccgccgc | gtgcgaatct | ggtggcacct | 1260 |
| tcgcgcctgt | ctcgctgctt | tcgataagtc | tctagccatt | taaaattttt | gatgacctgc | 1320 |
| tgcgacgctt | ttttttctggc | aagatagtct | tgtaaatgcg | ggccaagatc | tgcacactgg | 1380 |
| tatttcggtt | tttggggccg | cgggcggcga | cggggcccgt | gcgtcccagc | gcacatgttc | 1440 |
| ggcgaggcgg | ggcctgcgag | cgcggccacc | gagaatcgga | cggggggtagt | ctcaagctgg | 1500 |
| ccggcctgct | ctggtgcctg | gcctcgcgcc | gccgtgtatc | gccccgccct | gggcggcaag | 1560 |
| gctggcccgg | tcgcaccag | ttgcgtgagc | ggaaagatgg | ccgcttcccg | gccctgctgc | 1620 |
| agggagctca | aaatggagga | cgcggcgctc | gggagagcgg | gcgggtgagt | cacccacaca | 1680 |
| aaggaaaagg | gcctttccgt | cctcagccgt | cgcttcatgt | gactccacgg | agtaccgggc | 1740 |
| gccgtccagg | cacctcgatt | agttctcgag | cttttggagt | acgtcgtctt | taggttgggg | 1800 |
| ggaggggttt | tatgcgatgg | agtttcccca | cactgagtgg | gtggagactg | aagttaggcc | 1860 |
| agcttggcac | ttgatgtaat | tctccttgga | atttgccctt | tttgagtttg | gatcttggtt | 1920 |
| cattctcaag | cctcagacag | tggttcaaag | ttttttttctt | ccatttcagg | tgtcgtgacc | 1980 |
| accatgcttc | ttttggttac | gtctctgttg | ctttgcgaac | ttcctcatcc | agcgttcttg | 2040 |
| ctgatccccg | atattcagat | gactcagacc | accagtagct | tgtctgcctc | actgggagac | 2100 |

```
cgagtaacaa tctcctgcag ggcaagtcaa gacattagca aatacctcaa ttggtaccag    2160
cagaagcccg acggaacggt aaaactcctc atctatcata cgtcaaggtt gcattccgga    2220
gtaccgtcac gatttttcagg ttctgggagc ggaactgact attccttgac tatttcaaac   2280
ctcgagcagg aggacattgc gacatatttt tgtcaacaag gtaatacccct cccttacact   2340
ttcggaggag gaaccaaact cgaaattacc gggtccacca gtggctctgg gaagcctggc    2400
agtggagaag gttccactaa aggcgaggtg aagctccagg agagcggccc cggtctcgtt    2460
gcccccagtc aaagcctctc tgtaacgtgc acagtgagtg gtgtatcatt gcctgattat    2520
ggcgtctcct ggataaggca gccccgcgca aagggtcttg aatggcttgg ggtaatatgg    2580
ggctcagaga caacgtatta taactccgct ctcaaaagtc gcttgacgat aataaaagat    2640
aactccaaga gtcaagtttt ccttaaaatg aacagtttgc agactgacga taccgctata    2700
tattattgtg ctaaacatta ttactacggc ggtagttacg cgatggatta ttgggggcag    2760
gggacttctg tcacagtcag tagtgctgct gcctttgtcc cggtatttct cccagccaaa    2820
ccgaccacga ctcccgcccc gcgccctccg acacccgctc ccaccatcgc ctctcaacct    2880
cttagtcttc gccccgaggc atgccgaccc gccgccgggg gtgctgttca tacgaggggc    2940
ttggacttcg cttgtgatat ttacatttgg gctccgttgg cgggtacgtg cggcgtcctt    3000
ttgttgtcac tcgttattac tttgtattgt aatcacagga atcgctcaaa gcggagtagg    3060
ttgttgcatt ccgattacat gaatatgact cctcgccggc ctgggccgac aagaaaacat    3120
taccaaccct atgcccccccc acgagacttc gctgcgtaca ggtcccgagt gaagttttcc    3180
cgaagcgcag acgctccggc atatcagcaa ggacagaatc agctgtataa cgaactgaat    3240
ttgggacgcc gcgaggagta tgacgtgctt gataaacgcc gggggagaga cccggaaatg    3300
gggggtaaac cccgaagaaa gaatcccccaa gaaggactct acaatgaact ccagaaggat    3360
aagatggcgg aggcctactc agaaataggt atgaagggcg aacgacgacg gggaaaaggt    3420
cacgatggcc tctaccaagg gttgagtacg gcaaccaaag atacgtacga tgcactgcat    3480
atgcaggccc tgcctcccag ataataataa aatcgctatc catcgaagat ggatgtgtgt    3540
tggtttttg tgtgtggagc aacaaatctg actttgcatg tgcaaacgcc ttcaacaaca    3600
gcattattcc agaagacacc ttcttcccca gcccaggtaa gggcagcttt ggtgccttcg    3660
caggctgttt ccttgcttca ggaatggcca ggttctgccc agagctctgg tcaatgatgt    3720
ctaaaactcc tctgattggt ggtctcggcc ttatccattg ccaccaaaac cctcttttta    3780
ctaagaaaca gtgagccttg ttctggcagt ccagagaatg acacgggaaa aaagcagatg    3840
aagagaaggt ggcaggagag ggcacgtggc ccagcctcag tctctccaac tgagttcctg    3900
cctgcctgcc tttgctcaga ctgtttgccc cttactgctc ttctaggcct cattctaagc    3960
ccctctccca agttgcctct ccttatttct ccctgtctgc caaaaaatct ttcccagctc    4020
actaagtcag tctcacgcag tcactcatta acccaccaat cactgattgt gccggcacat    4080
gaatgcacca ggtgttgaag tggaggaatt aaaaagtcag atgaggggtg tgcccagagg    4140
aagcaccatt ctagttgggg gagcccatct gtcagctggg aaaagtccaa ataacttcag    4200
attggaatgt gttttaactc agggttgaga aaacagctac cttcaggaca aaagtcaggg    4260
aagggctctc tgaagaaatg ctacttgaag ataccagccc taccaagggc agggagagga    4320
ccctatagag gcctgggaca ggagctcaat gagaaagg                            4358
```

<210> SEQ ID NO 169
<211> LENGTH: 4364

<212> TYPE: DNA
<213> ORGANISM: Artificial Sequence
<220> FEATURE:
<223> OTHER INFORMATION: Synthetic

<400> SEQUENCE: 169

| | | | | | |
|---|---|---|---|---|---|
| gagatgtaag | gagctgctgt | gacttgctca | aggccttata | tcgagtaaac | ggtagtgctg | 60 |
| gggcttagac | gcaggtgttc | tgatttatag | ttcaaaacct | ctatcaatga | gagagcaatc | 120 |
| tcctggtaat | gtgatagatt | tcccaactta | atgccaacat | accataaacc | tcccattctg | 180 |
| ctaatgccca | gcctaagttg | gggagaccac | tccagattcc | aagatgtaca | gtttgctttg | 240 |
| ctgggccttt | ttcccatgcc | tgcctttact | ctgccagagt | tatattgctg | ggttttgaa | 300 |
| gaagatccta | ttaaataaaa | gaataagcag | tattattaag | tagccctgca | tttcaggttt | 360 |
| ccttgagtgg | caggccaggc | ctggccgtga | acgttcactg | aaatcatggc | ctcttggcca | 420 |
| agattgatag | cttgtgcctg | tccctgagtc | ccagtccatc | acgagcagct | ggtttctaag | 480 |
| atgctatttc | ccgtataaag | catgagaccg | tgacttgcca | gccccacaga | gccccgccct | 540 |
| tgtccatcac | tggcatctgg | actccagcct | gggttggggc | aaagagggaa | atgagatcat | 600 |
| gtcctaaccc | tgatcctctt | gtcccacaga | tatccagaac | cctgaccctg | ccgtgtacca | 660 |
| gctgagagac | tctaaatcca | gtgacaagtc | tgtctgccta | ttcaccgatt | ttgattctca | 720 |
| aacaaatgtg | tcacaaagta | aggattctga | tgtgtatatc | acagacaaaa | ctgtgctaga | 780 |
| catgaggtct | atggacttca | ggctccggtg | cccgtcagtg | ggcagagcgc | acatcgccca | 840 |
| cagtccccga | gaagttgggg | ggaggggtcg | gcaattgaac | cggtgcctag | agaaggtggc | 900 |
| gcggggtaaa | ctgggaaagt | gatgtcgtgt | actggctccg | ccttttcc | gagggtgggg | 960 |
| gagaaccgta | tataagtgca | gtagtcgccg | tgaacgttct | ttttcgcaac | gggtttgccg | 1020 |
| ccagaacaca | ggtaagtgcc | gtgtgtggtt | cccgcgggcc | tggcctcttt | acgggttatg | 1080 |
| gcccttgcgt | gccttgaatt | acttccactg | gctgcagtac | gtgattcttg | atcccgagct | 1140 |
| tcgggttgga | agtgggtggg | agagttcgag | gccttgcgct | taaggagccc | cttcgcctcg | 1200 |
| tgcttgagtt | gaggcctggc | ctgggcgctg | gggccgccgc | gtgcgaatct | ggtggcacct | 1260 |
| tcgcgcctgt | ctcgctgctt | tcgataagtc | tctagccatt | taaaattttt | gatgacctgc | 1320 |
| tgcgacgctt | ttttctggc | aagatagtct | tgtaaatgcg | ggccaagatc | tgcacactgg | 1380 |
| tatttcggtt | tttggggccg | cgggcggcga | cggggcccgt | gcgtcccagc | gcacatgttc | 1440 |
| ggcgaggcgg | ggcctgcgag | cgcggccacc | gagaatcgga | cggggtagt | ctcaagctgg | 1500 |
| ccggcctgct | ctggtgcctg | gcctcgcgcc | gccgtgtatc | gccccgccct | gggcggcaag | 1560 |
| gctggcccgg | tcggcaccag | ttgcgtgagc | ggaaagatgg | ccgcttccg | gccctgctgc | 1620 |
| agggagctca | aaatggagga | cgcggcgctc | gggagagcgg | gcgggtgagt | cacccacaca | 1680 |
| aaggaaaagg | gcctttccgt | cctcagccgt | cgcttcatgt | gactccacgg | agtaccgggc | 1740 |
| gccgtccagg | cacctcgatt | agttctcgag | cttttggagt | acgtcgtctt | taggttgggg | 1800 |
| ggaggggttt | tatgcgatgg | agtttcccca | cactgagtgg | gtggagactg | aagttaggcc | 1860 |
| agcttggcac | ttgatgtaat | tctccttgga | atttgccctt | tttgagtttg | gatcttggtt | 1920 |
| cattctcaag | cctcagacag | tggttcaaag | ttttttcct | ccatttcagg | tgtcgtgacc | 1980 |
| accatggcgc | ttccggtgac | agcactgctc | ctcccttgg | cgctgttgct | ccacgcagca | 2040 |
| aggccgcagg | tccagttggt | gcaaagcggg | gcggaggtga | aaaaccggg | cgcttccgtg | 2100 |
| aaggtgtcct | gtaaggcgtc | cggttatacg | ttcacgaact | acgggatgaa | ttgggttcgc | 2160 |

-continued

```
caagcgccgg ggcagggact gaaatggatg gggtggataa ataccdacac cggcgaacct    2220
acatacgccg acgcttttaa agggcgagtc actatgacgc gcgataccag catatccacc    2280
gcatacatgg agctgtcccg actccggtca gacgacacgg ctgtctacta ttgtgctcgg    2340
gactatggcg attatggcat ggactactgg ggtcagggta cgactgtaac agttagtagt    2400
ggtggaggcg gcagtggcgg ggggggaagc ggaggagggg gttctggtga catagttatg    2460
acccaatccc cagatagttt ggcggttttct ctgggcgaga gggcaacgat taattgtcgc    2520
gcatcaaaga gcgtttcaac gagcggatat tcttttatgc attggtacca gcaaaaaccc    2580
ggacaaccgc cgaagctgct gatctacttg gcttcaaatc ttgagtctgg ggtgccggac    2640
cgattttctg gtagtggaag cggaactgac tttacgctca cgatcagttc actgcaggct    2700
gaggatgtag cggtctatta ttgccagcac agtagagaag tcccctggac cttcggtcaa    2760
ggcacgaaag tagaaattaa aagtgctgct gcctttgtcc cggtatttct cccagccaaa    2820
ccgaccacga ctcccgcccc gcgccctccg acacccgctc ccaccatcgc ctctcaacct    2880
cttagtcttc gccccgaggc atgccgaccc gccgccgggg gtgctgttca tacgaggggc    2940
ttggacttcg cttgtgatat ttacatttgg gctccgttgg cgggtacgtg cggcgtcctt    3000
ttgttgtcac tcgttattac tttgtattgt aatcacagga atcgcaaacg gggcagaaag    3060
aaactcctgt atatattcaa acaaccattt atgagaccag tacaaactac tcaagaggaa    3120
gatggctgta gctgccgatt tccagaagaa gaagaaggag gatgtgaact gcgagtgaag    3180
ttttcccgaa gcgcagacgc tccggcatat cagcaaggac agaatcagct gtataacgaa    3240
ctgaatttgg gacgccgcga ggagtatgac gtgcttgata aacgccgggg gagagacccg    3300
gaaatggggg gtaaaccccg aagaaagaat ccccaagaag gactctacaa tgaactccag    3360
aaggataaga tggcggaggc ctactcagaa ataggtatga agggcaacg acgacgggga    3420
aaaggtcacg atggcctcta ccaagggttg agtacggcaa ccaaagatac gtacgatgca    3480
ctgcatatgc aggccctgcc tcccagataa taataaaatc gctatccatc gaagatggat    3540
gtgtgttggt ttttgtgtg tggagcaaca aatctgactt tgcatgtgca aacgccttca    3600
acaacagcat tattccagaa gacaccttct tccccagccc aggtaagggc agctttggtg    3660
ccttcgcagg ctgtttcctt gcttcaggaa tggccaggtt ctgcccagag ctctggtcaa    3720
tgatgtctaa aactcctctg attggtggtc tcggccttat ccattgccac caaaaccctc    3780
tttttactaa gaaacagtga gccttgttct ggcagtccag agaatgacac gggaaaaaag    3840
cagatgaaga gaaggtggca ggagagggca cgtggcccag cctcagtctc tccaactgag    3900
ttcctgcctg cctgcctttg ctcagactgt ttgccccta ctgctcttct aggcctcatt    3960
ctaagcccct tctccaagtt gcctctcctt atttctccct gtctgccaaa aaatctttcc    4020
cagctcacta agtcagtctc acgcagtcac tcattaaccc accaatcact gattgtgccg    4080
gcacatgaat gcaccaggtg ttgaagtgga ggaattaaaa agtcagatga ggggtgtgcc    4140
cagaggaagc accattctag ttgggggagc ccatctgtca gctgggaaaa gtccaaataa    4200
cttcagattg gaatgtgttt taactcaggg ttgagaaaac agctacccttc aggacaaaag    4260
tcagggaagg gctctctgaa gaaatgctac ttgaagatac cagccctacc aagggcaggg    4320
agaggaccct atagaggcct gggacaggag ctcaatgaga aagg                    4364
```

<210> SEQ ID NO 170
<211> LENGTH: 4364
<212> TYPE: DNA
<213> ORGANISM: Artificial Sequence
<220> FEATURE:
<223> OTHER INFORMATION: Synthetic

<400> SEQUENCE: 170

```
gagatgtaag gagctgctgt gacttgctca aggccttata tcgagtaaac ggtagtgctg      60
gggcttagac gcaggtgttc tgatttatag ttcaaaacct ctatcaatga gagagcaatc     120
tcctggtaat gtgatagatt tcccaactta atgccaacat accataaacc tcccattctg     180
ctaatgccca gcctaagttg gggagaccac tccagattcc aagatgtaca gtttgctttg     240
ctgggccttt ttcccatgcc tgcctttact ctgccagagt tatattgctg gggttttgaa     300
gaagatccta ttaaataaaa gaataagcag tattattaag tagccctgca tttcaggttt     360
ccttgagtgg caggccaggc ctggccgtga acgttcactg aaatcatggc ctcttggcca     420
agattgatag cttgtgcctg tccctgagtc ccagtccatc acgagcagct ggtttctaag     480
atgctatttc ccgtataaag catgagaccg tgacttgcca gccccacaga gccccgccct     540
tgtccatcac tggcatctgg actccagcct gggttgggc aaagagggaa atgagatcat      600
gtcctaaccc tgatcctctt gtcccacaga tatccagaac cctgaccctg ccgtgtacca     660
gctgagagac tctaaatcca gtgacaagtc tgtctgccta ttcaccgatt ttgattctca     720
aacaaatgtg tcacaaagta aggattctga tgtgtatatc acagacaaaa ctgtgctaga     780
catgaggtct atggacttca ggctccggtg cccgtcagtg ggcagagcgc acatcgccca     840
cagtccccga aagttggggg gaggggtcg gcaattgaac cggtgcctag agaaggtggc      900
gcggggtaaa ctgggaaagt gatgtcgtgt actggctccg cctttttccc gagggtgggg     960
gagaaccgta tataagtgca gtagtcgccg tgaacgttct ttttcgcaac gggtttgccg    1020
ccagaacaca ggtaagtgcc gtgtgtggtt cccgcgggcc tggcctcttt acgggttatg    1080
gcccttgcgt gccttgaatt acttccactg gctgcagtac gtgattcttg atcccgagct    1140
tcgggttgga agtgggtggg agagttcgag gccttgcgct taaggagccc cttcgcctcg    1200
tgcttgagtt gaggcctggc ctgggcgctg gggccgccgc gtgcgaatct ggtggcacct    1260
tcgcgcctgt ctcgctgctt tcgataagtc tctagccatt taaaatttt gatgacctgc     1320
tgcgacgctt tttttctggc aagatagtct tgtaaatgcg ggccaagatc tgcacactgg    1380
tatttcggtt tttggggccg cgggcggcga cggggcccgt gcgtcccagc gcacatgttc    1440
ggcgaggcgg ggcctgcgag cgcggccacc gagaatcgga cggggggtagt ctcaagctgg   1500
ccggcctgct ctggtgcctg gcctcgcgcc gccgtgtatc gccccgccct gggcggcaag    1560
gctggcccgg tcgcaccag ttgcgtgagc ggaaagatgg ccgcttcccg gccctgctgc     1620
agggagctca aaatggagga cgcggcgctc gggagagcgg gcgggtgagt cacccacaca    1680
aaggaaaagg gcctttccgt cctcagccgt cgcttcatgt gactccacgg agtaccgggc    1740
gccgtccagg cacctcgatt agttctcgag cttttggagt acgtcgtctt taggttgggg    1800
ggagggggttt tatgcgatgg agtttcccca cactgagtgg gtggagactg aagttaggcc    1860
agcttggcac ttgatgtaat tctccttgga atttgccctt tttgagtttg gatcttggtt    1920
cattctcaag cctcagacag tggttcaaag ttttttttctt ccatttcagg tgtcgtgacc    1980
accatggcgc ttcggtgac agcactgctc ctcccttgg cgctgttgct ccacgcagca      2040
aggccgcagg tgcagctggt gcagagcgga gccgagctca agaagcccgg agcctccgtg    2100
aaggtgagct gcaaggccag cggcaacacc ctgaccaact acgtgatcca ctgggtgaga    2160
caagccccg gccaaaggct ggagtggatg ggctacatcc tgccctacaa cgacctgacc     2220
```

-continued

```
aagtacagcc agaagttcca gggcagggtg accatcacca gggataagag cgcctccacc    2280
gcctatatgg agctgagcag cctgaggagc gaggacaccg ctgtgtacta ctgtacaagg    2340
tgggactggg acggcttctt tgacccctgg ggccagggca acagtgac cgtcagcagc      2400
ggcggcggag gcagcggcgg cggcggcagc ggcggaggcg gaagcgaaat cgtgatgacc    2460
cagagccccg ccacactgag cgtgagccct ggcgagaggg ccagcatctc ctgcagggct    2520
agccaaagcc tggtgcacag caacggcaac acccacctgc actggtacca gcagagaccc    2580
ggacaggctc ccaggctgct gatctacagc gtgagcaaca ggttctccga ggtgcctgcc    2640
aggtttagcg gcagcggaag cggcaccgac tttacccctga ccatcagcag cgtggagtcc    2700
gaggacttcg ccgtgtatta ctgcagccag accagccaca tcccttacac cttcggcggc    2760
ggcaccaagc tggagatcaa aagtgctgct gcctttgtcc cggtatttct cccagccaaa    2820
ccgaccacga ctcccgcccc cgcgcctccg cacccgctc ccaccatcgc ctctcaacct     2880
cttagtcttc gccccgaggc atgccgaccc gccgccgggg gtgctgttca tacgaggggc    2940
ttggacttcg cttgtgatat ttacatttgg gctccgttgg cgggtacgtg cggcgtcctt    3000
ttgttgtcac tcgttattac tttgtattgt aatcacagga atcgcaaacg gggcagaaag    3060
aaactcctgt atatattcaa acaaccattt atgagaccag tacaaactac tcaagaggaa    3120
gatggctgta gctgccgatt ccagaagaa gaagaaggag gatgtgaact gcgagtgaag    3180
ttttcccgaa gcgcagacgc tccggcatat cagcaaggac agaatcagct gtataacgaa    3240
ctgaatttgg gacgccgcga ggagtatgac gtgcttgata acgccgggg gagagacccg    3300
gaaatggggg gtaaaccccg aagaaagaat ccccaagaag gactctacaa tgaactccag    3360
aaggataaga tggcggaggc ctactcagaa ataggtatga agggcgaacg acgacgggga    3420
aaaggtcacg atggcctcta ccaagggttg agtacggcaa ccaaagatac gtacgatgca    3480
ctgcatatgc aggccctgcc tcccagataa taataaaatc gctatccatc gaagatggat    3540
gtgtgttggt tttttgtgtg tggagcaaca aatctgactt tgcatgtgca aacgccttca    3600
acaacagcat tattccagaa gacaccttct tccccagccc aggtaagggc agctttggtg    3660
ccttcgcagg ctgtttcctt gcttcaggaa tggccaggtt ctgcccagag ctctggtcaa    3720
tgatgtctaa aactcctctg attggtggtc tcggccttat ccattgccac caaaaccctc    3780
ttttactaa gaaacagtga gccttgttct ggcagtccag agaatgacac gggaaaaaag    3840
cagatgaaga gaaggtggca ggagagggca cgtggcccag cctcagtctc tccaactgag    3900
ttcctgcctg cctgccttg ctcagactgt ttgcccctta ctgctcttct aggcctcatt      3960
ctaagcccct tctccaagtt gcctctcctt atttctccct gtctgccaaa aaatctttcc    4020
cagctcacta agtcagtctc acgcagtcac tcattaaccc accaatcact gattgtgccg    4080
gcacatgaat gcaccaggtg ttgaagtgga ggaattaaaa agtcagatga ggggtgtgcc    4140
cagaggaagc accattctag ttgggggagc ccatctgtca gctgggaaaa gtccaaataa    4200
cttcagattg gaatgtgttt taactcaggg ttgagaaaac agctaccttc aggacaaaag    4260
tcagggaagg gctctctgaa gaaatgctac ttgaagatac cagccctacc aagggcaggg    4320
agaggaccct atagaggcct gggacaggag ctcaatgaga aagg                     4364
```

<210> SEQ ID NO 171
<211> LENGTH: 23
<212> TYPE: DNA
<213> ORGANISM: Artificial Sequence
<220> FEATURE:
<223> OTHER INFORMATION: Synthetic

```
<400> SEQUENCE: 171
ggtcatcgat gggagcaacg tgg                                               23

<210> SEQ ID NO 172
<211> LENGTH: 23
<212> TYPE: DNA
<213> ORGANISM: Artificial Sequence
<220> FEATURE:
<223> OTHER INFORMATION: Synthetic

<400> SEQUENCE: 172
caccaccccg cgggactaga ggg                                               23

<210> SEQ ID NO 173
<211> LENGTH: 23
<212> TYPE: DNA
<213> ORGANISM: Artificial Sequence
<220> FEATURE:
<223> OTHER INFORMATION: Synthetic

<400> SEQUENCE: 173
ggtctggcgc tcccgctcgg tgg                                               23

<210> SEQ ID NO 174
<211> LENGTH: 23
<212> TYPE: DNA
<213> ORGANISM: Artificial Sequence
<220> FEATURE:
<223> OTHER INFORMATION: Synthetic

<400> SEQUENCE: 174
ttcacaccat cacgacgcgt ggg                                               23

<210> SEQ ID NO 175
<211> LENGTH: 23
<212> TYPE: DNA
<213> ORGANISM: Artificial Sequence
<220> FEATURE:
<223> OTHER INFORMATION: Synthetic

<400> SEQUENCE: 175
acaccatcac gacgcgtggg tgg                                               23

<210> SEQ ID NO 176
<211> LENGTH: 23
<212> TYPE: DNA
<213> ORGANISM: Artificial Sequence
<220> FEATURE:
<223> OTHER INFORMATION: Synthetic

<400> SEQUENCE: 176
ctacgagtct gacgggatcg tgg                                               23

<210> SEQ ID NO 177
<211> LENGTH: 23
<212> TYPE: DNA
<213> ORGANISM: Artificial Sequence
<220> FEATURE:
<223> OTHER INFORMATION: Synthetic

<400> SEQUENCE: 177
ttgccaccca cgcgtcgtga tgg                                               23

<210> SEQ ID NO 178
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 178
gttcacacca tcacgacgcg tgg                                              23

<210> SEQ ID NO 179
<211> LENGTH: 23
<212> TYPE: DNA
<213> ORGANISM: Artificial Sequence
<220> FEATURE:
<223> OTHER INFORMATION: Synthetic

<400> SEQUENCE: 179
cacgatcccg tcagactcgt agg                                              23

<210> SEQ ID NO 180
<211> LENGTH: 23
<212> TYPE: DNA
<213> ORGANISM: Artificial Sequence
<220> FEATURE:
<223> OTHER INFORMATION: Synthetic

<400> SEQUENCE: 180
acgacgcgtg ggtggcaagc ggg                                              23

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
gatgggagca aacgtggcca t                                                21

<210> SEQ ID NO 182
<211> LENGTH: 19
<212> TYPE: DNA
<213> ORGANISM: Artificial Sequence
<220> FEATURE:
<223> OTHER INFORMATION: Synthetic

<400> SEQUENCE: 182
gatgggagca cgtggccat                                                   19

<210> SEQ ID NO 183
<211> LENGTH: 17
<212> TYPE: DNA
<213> ORGANISM: Artificial Sequence
<220> FEATURE:
<223> OTHER INFORMATION: Synthetic

<400> SEQUENCE: 183
gatgggaacg tggccat                                                     17

<210> SEQ ID NO 184
<211> LENGTH: 12
<212> TYPE: DNA
<213> ORGANISM: Artificial Sequence
<220> FEATURE:
<223> OTHER INFORMATION: Synthetic

<400> SEQUENCE: 184
```
gatgggagcc at                                        12

<210> SEQ ID NO 185
<211> LENGTH: 10
<212> TYPE: DNA
<213> ORGANISM: Artificial Sequence
<220> FEATURE:
<223> OTHER INFORMATION: Synthetic

<400> SEQUENCE: 185
gatgggccat                                           10

<210> SEQ ID NO 186
<211> LENGTH: 10
<212> TYPE: DNA
<213> ORGANISM: Artificial Sequence
<220> FEATURE:
<223> OTHER INFORMATION: Synthetic

<400> SEQUENCE: 186
acgtggccat                                           10

<210> SEQ ID NO 187
<211> LENGTH: 21
<212> TYPE: DNA
<213> ORGANISM: Artificial Sequence
<220> FEATURE:
<223> OTHER INFORMATION: Synthetic

<400> SEQUENCE: 187
ccgcgggact tagagggagc t                              21

<210> SEQ ID NO 188
<211> LENGTH: 11
<212> TYPE: DNA
<213> ORGANISM: Artificial Sequence
<220> FEATURE:
<223> OTHER INFORMATION: Synthetic

<400> SEQUENCE: 188
ccgcgggagc t                                         11

<210> SEQ ID NO 189
<211> LENGTH: 19
<212> TYPE: DNA
<213> ORGANISM: Artificial Sequence
<220> FEATURE:
<223> OTHER INFORMATION: Synthetic

<400> SEQUENCE: 189
ccgcgggata gagggagct                                 19

<210> SEQ ID NO 190
<211> LENGTH: 10
<212> TYPE: DNA
<213> ORGANISM: Artificial Sequence
<220> FEATURE:
<223> OTHER INFORMATION: Synthetic

<400> SEQUENCE: 190
ccgcgggact                                           10

<210> SEQ ID NO 191
<211> LENGTH: 18
<212> TYPE: DNA

```
<213> ORGANISM: Artificial Sequence
<220> FEATURE:
<223> OTHER INFORMATION: Synthetic

<400> SEQUENCE: 191
ccgcgggtag agggagct                                              18

<210> SEQ ID NO 192
<211> LENGTH: 12
<212> TYPE: DNA
<213> ORGANISM: Artificial Sequence
<220> FEATURE:
<223> OTHER INFORMATION: Synthetic

<400> SEQUENCE: 192 ccgcgggag ct                                                     12

<210> SEQ ID NO 193
<211> LENGTH: 19
<212> TYPE: DNA
<213> ORGANISM: Artificial Sequence
<220> FEATURE:
<223> OTHER INFORMATION: Synthetic

<400> SEQUENCE: 193
ccgcgggaca gagggagct                                             19

<210> SEQ ID NO 194
<211> LENGTH: 19
<212> TYPE: DNA
<213> ORGANISM: Artificial Sequence
<220> FEATURE:
<223> OTHER INFORMATION: Synthetic

<400> SEQUENCE: 194
ccgcgggact gagggagct                                             19

<210> SEQ ID NO 195
<211> LENGTH: 11
<212> TYPE: DNA
<213> ORGANISM: Artificial Sequence
<220> FEATURE:
<223> OTHER INFORMATION: Synthetic

<400> SEQUENCE: 195
ccgagggagc t                                                     11

<210> SEQ ID NO 196
<211> LENGTH: 15
<212> TYPE: DNA
<213> ORGANISM: Artificial Sequence
<220> FEATURE:
<223> OTHER INFORMATION: Synthetic

<400> SEQUENCE: 196
ccgcgggagg gagct                                                 15

<210> SEQ ID NO 197
<211> LENGTH: 14
<212> TYPE: DNA
<213> ORGANISM: Artificial Sequence
<220> FEATURE:
<223> OTHER INFORMATION: Synthetic

<400> SEQUENCE: 197
ccgtagaggg agct                                                  14
```

<210> SEQ ID NO 198
<211> LENGTH: 21
<212> TYPE: DNA
<213> ORGANISM: Artificial Sequence
<220> FEATURE:
<223> OTHER INFORMATION: Synthetic

<400> SEQUENCE: 198
cgctcccgct tcggtggctg t                                      21

<210> SEQ ID NO 199
<211> LENGTH: 19
<212> TYPE: DNA
<213> ORGANISM: Artificial Sequence
<220> FEATURE:
<223> OTHER INFORMATION: Synthetic

<400> SEQUENCE: 199
cgctcccgcc ggtggctgt                                         19

<210> SEQ ID NO 200
<211> LENGTH: 19
<212> TYPE: DNA
<213> ORGANISM: Artificial Sequence
<220> FEATURE:
<223> OTHER INFORMATION: Synthetic

<400> SEQUENCE: 200
cgctcccgtc ggtggctgt                                         19

<210> SEQ ID NO 201
<211> LENGTH: 18
<212> TYPE: DNA
<213> ORGANISM: Artificial Sequence
<220> FEATURE:
<223> OTHER INFORMATION: Synthetic

<400> SEQUENCE: 201
cgctcccgcg gtggctgt                                          18

<210> SEQ ID NO 202
<211> LENGTH: 19
<212> TYPE: DNA
<213> ORGANISM: Artificial Sequence
<220> FEATURE:
<223> OTHER INFORMATION: Synthetic

<400> SEQUENCE: 202
cgctcccgct ggtggctgt                                         19

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cgctccctcg gtggctgt                                          18

<210> SEQ ID NO 204
<211> LENGTH: 22
<212> TYPE: DNA
<213> ORGANISM: Artificial Sequence
<220> FEATURE:

<223> OTHER INFORMATION: Synthetic

<400> SEQUENCE: 204
cgctcccgct ttcggtggct gt                                               22

<210> SEQ ID NO 205
<211> LENGTH: 16
<212> TYPE: DNA
<213> ORGANISM: Artificial Sequence
<220> FEATURE:
<223> OTHER INFORMATION: Synthetic

<400> SEQUENCE: 205
cgctcccggt ggctgt                                                      16

<210> SEQ ID NO 206
<211> LENGTH: 18
<212> TYPE: DNA
<213> ORGANISM: Artificial Sequence
<220> FEATURE:
<223> OTHER INFORMATION: Synthetic

<400> SEQUENCE: 206
catcacgacg tgggtggc                                                    18

<210> SEQ ID NO 207
<211> LENGTH: 15
<212> TYPE: DNA
<213> ORGANISM: Artificial Sequence
<220> FEATURE:
<223> OTHER INFORMATION: Synthetic

<400> SEQUENCE: 207
catcacgtgg gtggc                                                       15

<210> SEQ ID NO 208
<211> LENGTH: 21
<212> TYPE: DNA
<213> ORGANISM: Artificial Sequence
<220> FEATURE:
<223> OTHER INFORMATION: Synthetic

<400> SEQUENCE: 208
catcacgacg ccgtgggtgg c                                                21

<210> SEQ ID NO 209
<211> LENGTH: 14
<212> TYPE: DNA
<213> ORGANISM: Artificial Sequence
<220> FEATURE:
<223> OTHER INFORMATION: Synthetic

<400> SEQUENCE: 209
catcacgacg tggc                                                        14

<210> SEQ ID NO 210
<211> LENGTH: 21
<212> TYPE: DNA
<213> ORGANISM: Artificial Sequence
<220> FEATURE:
<223> OTHER INFORMATION: Synthetic

<400> SEQUENCE: 210
catcacgacg gcgtgggtgg c                                                21

```
<210> SEQ ID NO 211
<211> LENGTH: 10
<212> TYPE: DNA
<213> ORGANISM: Artificial Sequence
<220> FEATURE:
<223> OTHER INFORMATION: Synthetic

<400> SEQUENCE: 211
cgtgggtggc                                                             10

<210> SEQ ID NO 212
<211> LENGTH: 17
<212> TYPE: DNA
<213> ORGANISM: Artificial Sequence
<220> FEATURE:
<223> OTHER INFORMATION: Synthetic

<400> SEQUENCE: 212
catcacgacg tggtggc                                                     17

<210> SEQ ID NO 213
<211> LENGTH: 21
<212> TYPE: DNA
<213> ORGANISM: Artificial Sequence
<220> FEATURE:
<223> OTHER INFORMATION: Synthetic

<400> SEQUENCE: 213
catcacgacg tcgtgggtgg c                                                21

<210> SEQ ID NO 214
<211> LENGTH: 16
<212> TYPE: DNA
<213> ORGANISM: Artificial Sequence
<220> FEATURE:
<223> OTHER INFORMATION: Synthetic

<400> SEQUENCE: 214
catcacgacg ggtggc                                                      16

<210> SEQ ID NO 215
<211> LENGTH: 15
<212> TYPE: DNA
<213> ORGANISM: Artificial Sequence
<220> FEATURE:
<223> OTHER INFORMATION: Synthetic

<400> SEQUENCE: 215
catcacgacg gtggc                                                       15

<210> SEQ ID NO 216
<211> LENGTH: 21
<212> TYPE: DNA
<213> ORGANISM: Artificial Sequence
<220> FEATURE:
<223> OTHER INFORMATION: Synthetic

<400> SEQUENCE: 216
cacgacgcgt tgggtggcaa g                                                21

<210> SEQ ID NO 217
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 217
cacgacgcgg gtggcaag                                                18

<210> SEQ ID NO 218
<211> LENGTH: 11
<212> TYPE: DNA
<213> ORGANISM: Artificial Sequence
<220> FEATURE:
<223> OTHER INFORMATION: Synthetic

<400> SEQUENCE: 218
cacgacgcaa g                                                       11

<210> SEQ ID NO 219
<211> LENGTH: 16
<212> TYPE: DNA
<213> ORGANISM: Artificial Sequence
<220> FEATURE:
<223> OTHER INFORMATION: Synthetic

<400> SEQUENCE: 219
cacgacgcgt ggcaag                                                  16

<210> SEQ ID NO 220
<211> LENGTH: 19
<212> TYPE: DNA
<213> ORGANISM: Artificial Sequence
<220> FEATURE:
<223> OTHER INFORMATION: Synthetic

<400> SEQUENCE: 220
cacgacgcgg ggtggcaag                                               19

<210> SEQ ID NO 221
<211> LENGTH: 21
<212> TYPE: DNA
<213> ORGANISM: Artificial Sequence
<220> FEATURE:
<223> OTHER INFORMATION: Synthetic

<400> SEQUENCE: 221
tctgacggga atcgtggttt c                                            21

<210> SEQ ID NO 222
<211> LENGTH: 13
<212> TYPE: DNA
<213> ORGANISM: Artificial Sequence
<220> FEATURE:
<223> OTHER INFORMATION: Synthetic

<400> SEQUENCE: 222
tctgacgggt ttc                                                     13

<210> SEQ ID NO 223
<211> LENGTH: 14
<212> TYPE: DNA
<213> ORGANISM: Artificial Sequence
<220> FEATURE:
<223> OTHER INFORMATION: Synthetic

<400> SEQUENCE: 223
tctgacgtgg tttc                                                    14

<210> SEQ ID NO 224
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 224
tctgacggga ttcgtggttt c                                              21

<210> SEQ ID NO 225
<211> LENGTH: 19
<212> TYPE: DNA
<213> ORGANISM: Artificial Sequence
<220> FEATURE:
<223> OTHER INFORMATION: Synthetic

<400> SEQUENCE: 225
tctgacggga cgtggtttc                                                 19

<210> SEQ ID NO 226
<211> LENGTH: 14
<212> TYPE: DNA
<213> ORGANISM: Artificial Sequence
<220> FEATURE:
<223> OTHER INFORMATION: Synthetic

<400> SEQUENCE: 226
tctgtcgtgg tttc                                                      14

<210> SEQ ID NO 227
<211> LENGTH: 12
<212> TYPE: DNA
<213> ORGANISM: Artificial Sequence
<220> FEATURE:
<223> OTHER INFORMATION: Synthetic

<400> SEQUENCE: 227
tctgacggtt tc                                                        12

<210> SEQ ID NO 228
<211> LENGTH: 19
<212> TYPE: DNA
<213> ORGANISM: Artificial Sequence
<220> FEATURE:
<223> OTHER INFORMATION: Synthetic

<400> SEQUENCE: 228
tctgacgggt cgtggtttc                                                 19

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229
tctgacggga gtcgtggttt c                                              21

<210> SEQ ID NO 230
<211> LENGTH: 21
<212> TYPE: DNA
<213> ORGANISM: Artificial Sequence
<220> FEATURE:
<223> OTHER INFORMATION: Synthetic

<400> SEQUENCE: 230
```

```
tctgacggga ctcgtggttt c                                              21
```

<210> SEQ ID NO 231
<211> LENGTH: 10
<212> TYPE: DNA
<213> ORGANISM: Artificial Sequence
<220> FEATURE:
<223> OTHER INFORMATION: Synthetic

<400> SEQUENCE: 231

```
tcgtggtttc                                                           10
```

<210> SEQ ID NO 232
<211> LENGTH: 18
<212> TYPE: DNA
<213> ORGANISM: Artificial Sequence
<220> FEATURE:
<223> OTHER INFORMATION: Synthetic

<400> SEQUENCE: 232

```
tctgacggtc gtggtttc                                                  18
```

<210> SEQ ID NO 233
<211> LENGTH: 18
<212> TYPE: DNA
<213> ORGANISM: Artificial Sequence
<220> FEATURE:
<223> OTHER INFORMATION: Synthetic

<400> SEQUENCE: 233

```
tctgacggga gtggtttc                                                  18
```

<210> SEQ ID NO 234
<211> LENGTH: 21
<212> TYPE: DNA
<213> ORGANISM: Artificial Sequence
<220> FEATURE:
<223> OTHER INFORMATION: Synthetic

<400> SEQUENCE: 234

```
ccacgcgtcg gtgatggtgt g                                              21
```

<210> SEQ ID NO 235
<211> LENGTH: 21
<212> TYPE: DNA
<213> ORGANISM: Artificial Sequence
<220> FEATURE:
<223> OTHER INFORMATION: Synthetic

<400> SEQUENCE: 235

```
ccacgcgtcg ttgatggtgt g                                              21
```

<210> SEQ ID NO 236
<211> LENGTH: 11
<212> TYPE: DNA
<213> ORGANISM: Artificial Sequence
<220> FEATURE:
<223> OTHER INFORMATION: Synthetic

<400> SEQUENCE: 236

```
ccacgcgtgt g                                                         11
```

<210> SEQ ID NO 237
<211> LENGTH: 21
<212> TYPE: DNA
<213> ORGANISM: Artificial Sequence

```
<220> FEATURE:
<223> OTHER INFORMATION: Synthetic

<400> SEQUENCE: 237
ccacgcgtcg atgatggtgt g                                      21

<210> SEQ ID NO 238
<211> LENGTH: 18
<212> TYPE: DNA
<213> ORGANISM: Artificial Sequence
<220> FEATURE:
<223> OTHER INFORMATION: Synthetic

<400> SEQUENCE: 238
ccacgcgtcg atggtgtg                                          18

<210> SEQ ID NO 239
<211> LENGTH: 19
<212> TYPE: DNA
<213> ORGANISM: Artificial Sequence
<220> FEATURE:
<223> OTHER INFORMATION: Synthetic

<400> SEQUENCE: 239
ccacgcgtct gatggtgtg                                         19

<210> SEQ ID NO 240
<211> LENGTH: 21
<212> TYPE: DNA
<213> ORGANISM: Artificial Sequence
<220> FEATURE:
<223> OTHER INFORMATION: Synthetic

<400> SEQUENCE: 240
ccacgcgtcg ctgatggtgt g                                      21

<210> SEQ ID NO 241
<211> LENGTH: 10
<212> TYPE: DNA
<213> ORGANISM: Artificial Sequence
<220> FEATURE:
<223> OTHER INFORMATION: Synthetic

<400> SEQUENCE: 241
ccacgcgtcg                                                   10

<210> SEQ ID NO 242
<211> LENGTH: 15
<212> TYPE: DNA
<213> ORGANISM: Artificial Sequence
<220> FEATURE:
<223> OTHER INFORMATION: Synthetic

<400> SEQUENCE: 242
ccacgcgtcg gtgtg                                             15

<210> SEQ ID NO 243
<211> LENGTH: 15
<212> TYPE: DNA
<213> ORGANISM: Artificial Sequence
<220> FEATURE:
<223> OTHER INFORMATION: Synthetic

<400> SEQUENCE: 243
ccacgcgtgg gtgtg                                             15
```

<210> SEQ ID NO 244
<211> LENGTH: 17
<212> TYPE: DNA
<213> ORGANISM: Artificial Sequence
<220> FEATURE:
<223> OTHER INFORMATION: Synthetic

<400> SEQUENCE: 244
ccacgcgtga tggtgtg                                                17

<210> SEQ ID NO 245
<211> LENGTH: 14
<212> TYPE: DNA
<213> ORGANISM: Artificial Sequence
<220> FEATURE:
<223> OTHER INFORMATION: Synthetic

<400> SEQUENCE: 245
ccacgcgtcg tgtg                                                   14

<210> SEQ ID NO 246
<211> LENGTH: 13
<212> TYPE: DNA
<213> ORGANISM: Artificial Sequence
<220> FEATURE:
<223> OTHER INFORMATION: Synthetic

<400> SEQUENCE: 246
ccacgcgtcg tga                                                    13

<210> SEQ ID NO 247
<211> LENGTH: 13
<212> TYPE: DNA
<213> ORGANISM: Artificial Sequence
<220> FEATURE:
<223> OTHER INFORMATION: Synthetic

<400> SEQUENCE: 247
ccacgcgtgg gtg                                                    13

<210> SEQ ID NO 248
<211> LENGTH: 21
<212> TYPE: DNA
<213> ORGANISM: Artificial Sequence
<220> FEATURE:
<223> OTHER INFORMATION: Synthetic

<400> SEQUENCE: 248
ccatcacgac cgcgtgggtg g                                           21

<210> SEQ ID NO 249
<211> LENGTH: 15
<212> TYPE: DNA
<213> ORGANISM: Artificial Sequence
<220> FEATURE:
<223> OTHER INFORMATION: Synthetic

<400> SEQUENCE: 249
ccatcacgtg ggtgg                                                  15

<210> SEQ ID NO 250
<211> LENGTH: 17
<212> TYPE: DNA
<213> ORGANISM: Artificial Sequence
<220> FEATURE:
<223> OTHER INFORMATION: Synthetic

```
<400> SEQUENCE: 250
ccatcacgcg tgggtgg                                                      17

<210> SEQ ID NO 251
<211> LENGTH: 21
<212> TYPE: DNA
<213> ORGANISM: Artificial Sequence
<220> FEATURE:
<223> OTHER INFORMATION: Synthetic

<400> SEQUENCE: 251
ccatcacgac agcgtgggtg g                                                 21

<210> SEQ ID NO 252
<211> LENGTH: 21
<212> TYPE: DNA
<213> ORGANISM: Artificial Sequence
<220> FEATURE:
<223> OTHER INFORMATION: Synthetic

<400> SEQUENCE: 252
ccgtcagact tcgtaggcca g                                                 21

<210> SEQ ID NO 253
<211> LENGTH: 11
<212> TYPE: DNA
<213> ORGANISM: Artificial Sequence
<220> FEATURE:
<223> OTHER INFORMATION: Synthetic

<400> SEQUENCE: 253
ccgtaggcca g                                                            11

<210> SEQ ID NO 254
<211> LENGTH: 10
<212> TYPE: DNA
<213> ORGANISM: Artificial Sequence
<220> FEATURE:
<223> OTHER INFORMATION: Synthetic

<400> SEQUENCE: 254
ccgtcagact                                                              10

<210> SEQ ID NO 255
<211> LENGTH: 12
<212> TYPE: DNA
<213> ORGANISM: Artificial Sequence
<220> FEATURE:
<223> OTHER INFORMATION: Synthetic

<400> SEQUENCE: 255
ccgtcagacc ag                                                           12

<210> SEQ ID NO 256
<211> LENGTH: 18
<212> TYPE: DNA
<213> ORGANISM: Artificial Sequence
<220> FEATURE:
<223> OTHER INFORMATION: Synthetic

<400> SEQUENCE: 256
ccgtcagacg taggccag                                                     18

<210> SEQ ID NO 257
```

<211> LENGTH: 12
<212> TYPE: DNA
<213> ORGANISM: Artificial Sequence
<220> FEATURE:
<223> OTHER INFORMATION: Synthetic

<400> SEQUENCE: 257
ccgtcaggcc ag                                                         12

<210> SEQ ID NO 258
<211> LENGTH: 19
<212> TYPE: DNA
<213> ORGANISM: Artificial Sequence
<220> FEATURE:
<223> OTHER INFORMATION: Synthetic

<400> SEQUENCE: 258
ccgtcagacc gtaggccag                                                  19

<210> SEQ ID NO 259
<211> LENGTH: 19
<212> TYPE: DNA
<213> ORGANISM: Artificial Sequence
<220> FEATURE:
<223> OTHER INFORMATION: Synthetic

<400> SEQUENCE: 259
ccgtcagact gtaggccag                                                  19

<210> SEQ ID NO 260
<211> LENGTH: 21
<212> TYPE: DNA
<213> ORGANISM: Artificial Sequence
<220> FEATURE:
<223> OTHER INFORMATION: Synthetic

<400> SEQUENCE: 260
gtgggtggca aagcgggtgg t                                               21

<210> SEQ ID NO 261
<211> LENGTH: 19
<212> TYPE: DNA
<213> ORGANISM: Artificial Sequence
<220> FEATURE:
<223> OTHER INFORMATION: Synthetic

<400> SEQUENCE: 261
gtgggtggca gcgggtggt                                                  19

<210> SEQ ID NO 262
<211> LENGTH: 21
<212> TYPE: DNA
<213> ORGANISM: Artificial Sequence
<220> FEATURE:
<223> OTHER INFORMATION: Synthetic

<400> SEQUENCE: 262
gtgggtggca tagcgggtgg t                                               21

<210> SEQ ID NO 263
<211> LENGTH: 18
<212> TYPE: DNA
<213> ORGANISM: Artificial Sequence
<220> FEATURE:
<223> OTHER INFORMATION: Synthetic

<400> SEQUENCE: 263

<210> SEQ ID NO 264
<211> LENGTH: 101
<212> TYPE: RNA
<213> ORGANISM: Artificial Sequence
<220> FEATURE:
<223> OTHER INFORMATION: Synthetic

<400> SEQUENCE: 264
ccgacuucug aacgugcggu guuuuagagc uagaaauagc aaguuaaaau aaggcuaguc    60
cguuaucaac uugaaaaagu ggcaccgagu cggugcmuuu u                      101

<210> SEQ ID NO 265
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (100)..(103)
<223> OTHER INFORMATION: modified with 2'-O-methyl phosphorothioate

<400> SEQUENCE: 265
ccgacuucug aacgugcggu gggguuuuag agcuagaaau agcaaguuaa aauaaggcua    60
guccguuauc aacuugaaaa aguggcaccg agucggugcu uuu                    103

<210> SEQ ID NO 266
<211> LENGTH: 20
<212> TYPE: RNA
<213> ORGANISM: Artificial Sequence
<220> FEATURE:
<223> OTHER INFORMATION: Synthetic

<400> SEQUENCE: 266
ccgacuucug aacgugcggu                                                20

<210> SEQ ID NO 267
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 267
cccgacuucu gaacgugcgg u                                              21

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
ccgcgggact agagggagct                                                20

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
ccgacttctg aacgtgcggt                                              20

<210> SEQ ID NO 270
<211> LENGTH: 101
<212> TYPE: RNA
<213> ORGANISM: Artificial Sequence
<220> FEATURE:
<223> OTHER INFORMATION: Synthetic

<400> SEQUENCE: 270
ugcuggcgau acgcguccac guuuuagagc uagaaauagc aaguuaaaau aaggcuaguc    60
cguuaucaac uugaaaaagu ggcaccgagu cggugcmuuu u                      101

<210> SEQ ID NO 271
<211> LENGTH: 101
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (98)..(101)
<223> OTHER INFORMATION: modified with 2'-O-methyl phosphorothioate

<400> SEQUENCE: 271
ugcuggcgau acgcguccac guuuuagagc uagaaauagc aaguuaaaau aaggcuaguc    60
cguuaucaac uugaaaaagu ggcaccgagu cggugcmuuu u                      101

<210> SEQ ID NO 272
<211> LENGTH: 20
<212> TYPE: RNA
<213> ORGANISM: Artificial Sequence
<220> FEATURE:
<223> OTHER INFORMATION: Synthetic

<400> SEQUENCE: 272
ugcuggcgau acgcguccac                                              20

<210> SEQ ID NO 273
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 273
ugcuggcgau acgcguccac                                              20

<210> SEQ ID NO 274
<211> LENGTH: 20

```
<212> TYPE: DNA
<213> ORGANISM: Artificial Sequence
<220> FEATURE:
<223> OTHER INFORMATION: Synthetic

<400> SEQUENCE: 274
cgctcccgct cggtggctgt                                               20

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275
tgctggcgat acgcgtccac                                               20

<210> SEQ ID NO 276
<211> LENGTH: 100
<212> TYPE: RNA
<213> ORGANISM: Artificial Sequence
<220> FEATURE:
<223> OTHER INFORMATION: Synthetic

<400> SEQUENCE: 276
ucggucuaug acgagcagcg guuuuagagc uagaaauagc aaguuaaaau aaggcuaguc   60
cguuaucaac uugaaaaagu ggcaccgagu cggugcuuuu                        100

<210> SEQ ID NO 277
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 277
ucggucuaug acgagcagcg guuuuagagc uagaaauagc aaguuaaaau aaggcuaguc   60
cguuaucaac uugaaaaagu ggcaccgagu cggugcuuuu                        100

<210> SEQ ID NO 278
<211> LENGTH: 20
<212> TYPE: RNA
<213> ORGANISM: Artificial Sequence
<220> FEATURE:
<223> OTHER INFORMATION: Synthetic

<400> SEQUENCE: 278
ucggucuaug acgagcagcg                                               20

<210> SEQ ID NO 279
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
```

<223> OTHER INFORMATION: modified with 2'-O-methyl phosphorothioate

<400> SEQUENCE: 279
ucggucuaug acgagcagcg                                           20

<210> SEQ ID NO 280
<211> LENGTH: 20
<212> TYPE: DNA
<213> ORGANISM: Artificial Sequence
<220> FEATURE:
<223> OTHER INFORMATION: Synthetic

<400> SEQUENCE: 280
catcacgacg cgtgggtggc                                           20

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
tcggtctatg acgagcagcg                                           20

<210> SEQ ID NO 282
<211> LENGTH: 101
<212> TYPE: RNA
<213> ORGANISM: Artificial Sequence
<220> FEATURE:
<223> OTHER INFORMATION: Synthetic

<400> SEQUENCE: 282
augggcaguc cuauuacagc guuuuagagc uagaaauagc aaguuaaaau aaggcuaguc    60
cguuaucaac uugaaaaagu ggcaccgagu cggugcmuuu u                      101

<210> SEQ ID NO 283
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 283
augggcaguc cuauuacagc guuuuagagc uagaaauagc aaguuaaaau aaggcuaguc    60
cguuaucaac uugaaaaagu ggcaccgagu cggugcuuuu                        100

<210> SEQ ID NO 284
<211> LENGTH: 20
<212> TYPE: RNA
<213> ORGANISM: Artificial Sequence
<220> FEATURE:
<223> OTHER INFORMATION: Synthetic

<400> SEQUENCE: 284
augggcaguc cuauuacagc                                           20

```
<210> SEQ ID NO 285
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 285
augggcaguc cuauuacagc                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
cacgacgcgt gggtggcaag                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
atgggcagtc ctattacagc                                              20

<210> SEQ ID NO 288
<211> LENGTH: 100
<212> TYPE: RNA
<213> ORGANISM: Artificial Sequence
<220> FEATURE:
<223> OTHER INFORMATION: Synthetic

<400> SEQUENCE: 288
auuguucacu uguuagcccc guuuuagagc uagaaauagc aaguuaaaau aaggcuaguc    60
cguuaucaac uugaaaaagu ggcaccgagu cggugcuuuu                        100

<210> SEQ ID NO 289
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (100)..(103)
<223> OTHER INFORMATION: modified with 2'-O-methyl phosphorothioate

<400> SEQUENCE: 289
auuguucacu uguuagcccc aggguuuuag agcuagaaau agcaaguuaa aauaaggcua    60
guccguuauc aacuugaaaa aguggcaccg agucggugcu uuu                    103

<210> SEQ ID NO 290
<211> LENGTH: 20
<212> TYPE: RNA
```

```
<213> ORGANISM: Artificial Sequence
<220> FEATURE:
<223> OTHER INFORMATION: Synthetic

<400> SEQUENCE: 290
auuguucacu uguuagcccc                                              20

<210> SEQ ID NO 291
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 291
auuguucacu uguuagcccc                                              20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
tctgacggga tcgtggtttc                                              20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
attgttcact tgttagcccc                                              20

<210> SEQ ID NO 294
<211> LENGTH: 100
<212> TYPE: RNA
<213> ORGANISM: Artificial Sequence
<220> FEATURE:
<223> OTHER INFORMATION: Synthetic

<400> SEQUENCE: 294
gcugaagaac ugccucuaua guuuuagagc uagaaauagc aaguuaaaau aaggcuaguc    60
cguuaucaac uugaaaaagu ggcaccgagu cggugcuuuu                        100

<210> SEQ ID NO 295
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 295
```

```
gcugaagaac ugccucuaua guuuuagagc uagaaauagc aaguuaaaau aaggcuaguc    60
cguuaucaac uugaaaaagu ggcaccgagu cggugcuuuu                        100

<210> SEQ ID NO 296
<211> LENGTH: 20
<212> TYPE: RNA
<213> ORGANISM: Artificial Sequence
<220> FEATURE:
<223> OTHER INFORMATION: Synthetic

<400> SEQUENCE: 296
gcugaagaac ugccucuaua                                               20

<210> SEQ ID NO 297
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 297
gcugaagaac ugccucuaua                                               20

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
ccacgcgtcg tgatggtgtg                                               20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
gctgaagaac tgcctctata                                               20

<210> SEQ ID NO 300
<211> LENGTH: 100
<212> TYPE: RNA
<213> ORGANISM: Artificial Sequence
<220> FEATURE:
<223> OTHER INFORMATION: Synthetic

<400> SEQUENCE: 300
gcaggauuuc ugguugucac guuuuagagc uagaaauagc aaguuaaaau aaggcuaguc    60
cguuaucaac uugaaaaagu ggcaccgagu cggugcuuuu                        100

<210> SEQ ID NO 301
<211> LENGTH: 100
<212> TYPE: RNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 301
gcaggauuuc ugguugucac guuuuagagc uagaaauagc aaguuaaaau aaggcuaguc     60
cguuaucaac uugaaaaagu ggcaccgagu cggugcuuuu                         100

<210> SEQ ID NO 302
<211> LENGTH: 20
<212> TYPE: RNA
<213> ORGANISM: Artificial Sequence
<220> FEATURE:
<223> OTHER INFORMATION: Synthetic

<400> SEQUENCE: 302
gcaggauuuc ugguugucac                                                20

<210> SEQ ID NO 303
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 303
gcaggauuuc ugguugucac                                                20

<210> SEQ ID NO 304
<211> LENGTH: 20
<212> TYPE: DNA
<213> ORGANISM: Artificial Sequence
<220> FEATURE:
<223> OTHER INFORMATION: Synthetic

<400> SEQUENCE: 304
ccatcacgac gcgtgggtgg                                                20

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
gcaggatttc tggttgtcac                                                20

<210> SEQ ID NO 306
<211> LENGTH: 100
<212> TYPE: RNA
<213> ORGANISM: Artificial Sequence
<220> FEATURE:
<223> OTHER INFORMATION: Synthetic

<400> SEQUENCE: 306
cuccaucugu gagaagccac guuuuagagc uagaaauagc aaguuaaaau aaggcuaguc     60
cguuaucaac uugaaaaagu ggcaccgagu cggugcuuuu                         100
```

<210> SEQ ID NO 307
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 307
cuccaucugu gagaagccac guuuuagagc uagaaauagc aaguuaaaau aaggcuaguc        60
cguuaucaac uugaaaaagu ggcaccgagu cggugcuuuu        100

<210> SEQ ID NO 308
<211> LENGTH: 20
<212> TYPE: RNA
<213> ORGANISM: Artificial Sequence
<220> FEATURE:
<223> OTHER INFORMATION: Synthetic

<400> SEQUENCE: 308
cuccaucugu gagaagccac        20

<210> SEQ ID NO 309
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 309
cuccaucugu gagaagccac        20

<210> SEQ ID NO 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
ccgtcagact cgtaggccag        20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
ctccatctgt gagaagccac        20

<210> SEQ ID NO 312
<211> LENGTH: 100
<212> TYPE: RNA

```
<213> ORGANISM: Artificial Sequence
<220> FEATURE:
<223> OTHER INFORMATION: Synthetic

<400> SEQUENCE: 312
ccccuaccau gacuuuauuc guuuuagagc uagaaauagc aaguuaaaau aaggcuaguc    60
cguuaucaac uugaaaaagu ggcaccgagu cggugcuuuu                         100

<210> SEQ ID NO 313
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate
<220> FEATURE:
<221> NAME/KEY: misc_feature
<222> LOCATION: (97)..(100)
<223> OTHER INFORMATION: modified with 2'-O-methyl phosphorothioate

<400> SEQUENCE: 313
ccccuaccau gacuuuauuc guuuuagagc uagaaauagc aaguuaaaau aaggcuaguc    60
cguuaucaac uugaaaaagu ggcaccgagu cggugcuuuu                         100

<210> SEQ ID NO 314
<211> LENGTH: 20
<212> TYPE: RNA
<213> ORGANISM: Artificial Sequence
<220> FEATURE:
<223> OTHER INFORMATION: Synthetic

<400> SEQUENCE: 314
ccccuaccau gacuuuauuc                                                20

<210> SEQ ID NO 315
<211> LENGTH: 20
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with 2'-O-methyl phosphorothioate

<400> SEQUENCE: 315
ccccuaccau gacuuuauuc                                                20

<210> SEQ ID NO 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
gtgggtggca agcgggtggt                                                20

<210> SEQ ID NO 317
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 317
cccctaccat gactttattc                                              20

<210> SEQ ID NO 318
<211> LENGTH: 20
<212> TYPE: DNA
<213> ORGANISM: Artificial Sequence
<220> FEATURE:
<223> OTHER INFORMATION: Synthetic

<400> SEQUENCE: 318
ggtcatcgat gggagcaacg                                              20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
caccaccccg cgggactaga                                              20

<210> SEQ ID NO 320
<211> LENGTH: 20
<212> TYPE: DNA
<213> ORGANISM: Artificial Sequence
<220> FEATURE:
<223> OTHER INFORMATION: Synthetic

<400> SEQUENCE: 320
ggtctggcgc tcccgctcgg                                              20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
ttcacaccat cacgacgcgt                                              20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
acaccatcac gacgcgtggg                                              20

<210> SEQ ID NO 323
<211> LENGTH: 20
<212> TYPE: DNA
<213> ORGANISM: Artificial Sequence
<220> FEATURE:
<223> OTHER INFORMATION: Synthetic

<400> SEQUENCE: 323
ctacgagtct gacgggatcg                                              20

<210> SEQ ID NO 324
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 324
ttgccaccca cgcgtcgtga                                          20

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
gttcacacca tcacgacgcg                                          20

<210> SEQ ID NO 326
<211> LENGTH: 20
<212> TYPE: DNA
<213> ORGANISM: Artificial Sequence
<220> FEATURE:
<223> OTHER INFORMATION: Synthetic

<400> SEQUENCE: 326
cacgatcccg tcagactcgt                                          20

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
acgacgcgtg ggtggcaagc                                          20

<210> SEQ ID NO 328
<211> LENGTH: 5
<212> TYPE: PRT
<213> ORGANISM: Artificial Sequence
<220> FEATURE:
<223> OTHER INFORMATION: Synthetic

<400> SEQUENCE: 328

Ser Tyr Tyr Ile His
1               5

<210> SEQ ID NO 329
<211> LENGTH: 17
<212> TYPE: PRT
<213> ORGANISM: Artificial Sequence
<220> FEATURE:
<223> OTHER INFORMATION: Synthetic

<400> SEQUENCE: 329

Val Ile Tyr Pro Gly Asn Asp Asp Ile Ser Tyr Asn Gln Lys Phe Gln
1               5                   10                  15

Gly

<210> SEQ ID NO 330
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 330

Glu Val Arg Leu Arg Tyr Phe Asp Val
1               5

<210> SEQ ID NO 331
<211> LENGTH: 17
<212> TYPE: PRT
<213> ORGANISM: Artificial Sequence
<220> FEATURE:
<223> OTHER INFORMATION: Synthetic

<400> SEQUENCE: 331

Lys Ser Ser Gln Ser Val Phe Phe Ser Ser Gln Lys Asn Tyr Leu
1               5                   10                  15

Ala

<210> SEQ ID NO 332
<211> LENGTH: 7
<212> TYPE: PRT
<213> ORGANISM: Artificial Sequence
<220> FEATURE:
<223> OTHER INFORMATION: Synthetic

<400> SEQUENCE: 332

Trp Ala Ser Thr Arg Glu Ser
1               5

<210> SEQ ID NO 333
<211> LENGTH: 8
<212> TYPE: PRT
<213> ORGANISM: Artificial Sequence
<220> FEATURE:
<223> OTHER INFORMATION: Synthetic

<400> SEQUENCE: 333

His Gln Tyr Leu Ser Ser Arg Thr
1               5

<210> SEQ ID NO 334
<211> LENGTH: 118
<212> TYPE: PRT
<213> ORGANISM: Artificial Sequence
<220> FEATURE:
<223> OTHER INFORMATION: Synthetic

<400> SEQUENCE: 334

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
            100                 105                 110
```

Thr Val Thr Val Ser Ser
        115

<210> SEQ ID NO 335
<211> LENGTH: 112
<212> TYPE: PRT
<213> ORGANISM: Artificial Sequence
<220> FEATURE:
<223> OTHER INFORMATION: Synthetic

<400> SEQUENCE: 335

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

<210> SEQ ID NO 336
<211> LENGTH: 246
<212> TYPE: PRT
<213> ORGANISM: Artificial Sequence
<220> FEATURE:
<223> OTHER INFORMATION: Synthetic

<400> SEQUENCE: 336

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Gly Gly Gly Gly Gly Ser Gly Gly Gly Ser Gly Gly Gly Gly Gly Ser
        115                 120                 125

Gln Val Gln Leu Gln Gln Pro Gly Ala Glu Val Val Lys Pro Gly Ala
    130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe 180                 185                 190
Gln Gly Lys Ala Thr Leu Thr Ala Asp Lys Ser Ser Thr Thr Ala Tyr
                195                 200                 205

Met Gln Leu Ser Ser Leu Thr Ser Glu Asp Ser Ala Val Tyr Tyr Cys
            210                 215                 220

Ala Arg Glu Val Arg Leu Arg Tyr Phe Asp Val Trp Gly Gln Gly Thr
225                 230                 235                 240

Thr Val Thr Val Ser Ser
                245

<210> SEQ ID NO 337
<211> LENGTH: 738
<212> TYPE: DNA
<213> ORGANISM: Artificial Sequence
<220> FEATURE:
<223> OTHER INFORMATION: Synthetic

<400> SEQUENCE: 337
gaaatcgtcc tcacacaatc cccggggagc ctcgcagtca gtcctgggga acgagtcact      60
atgagctgca atccagtca gagtgttttt ttctcaagta gccagaagaa ctacctcgca     120
tggtaccaac aaataccggg gcaatctccc cgcttgctta tactgggc aagtacccgc      180 gaatccggcg taccggatcg attcacggga tctgggtcag gtactgattt cactttgact     240
atcagctctg ttcagcctga agatttggca atttactact gtcaccaata cttgagtagc     300
cgaactttcg ccagggcac gaagctcgaa atcaagggcg agggggagg ttctggtggg      360 ggcggttctg gcggtggagg aagccaagta cagttgcaac agccagggc ggaggtcgta      420 aaacctgggg cgtctgtcaa gatgagctgt aaagcaagtg gatacacctt cacctcctac     480
tatatacatt ggattaagca aactccgggt caggggctgg aatgggttgg cgttatatac     540
cccgggaacg atgatatatc atacaaccaa aaatttcaag gcaaggcgac tctgactgcc     600
gataagagta gcacaacagc ttacatgcag ctttcttccc tgaccagcga agattcagca     660
gtttactact gcgctcggga agtgcgcctg cgatactttg atgtctgggg tcaaggaact     720
acagttactg tatcaagc                                                   738

<210> SEQ ID NO 338
<211> LENGTH: 507
<212> TYPE: PRT
<213> ORGANISM: Artificial Sequence
<220> FEATURE:
<223> OTHER INFORMATION: Synthetic

<400> SEQUENCE: 338

Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Ser Leu
            20                  25                  30

Ala Val Ser Pro Gly Glu Arg Val Thr Met Ser Cys Lys Ser Ser Gln
        35                  40                  45

Ser Val Phe Phe Ser Ser Gln Lys Asn Tyr Leu Ala Trp Tyr Gln
    50                  55                  60

Gln Ile Pro Gly Gln Ser Pro Arg Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Pro Glu Asp Leu Ala Ile

```
                100              105              110
Tyr Tyr Cys His Gln Tyr Leu Ser Ser Arg Thr Phe Gly Gln Gly Thr
            115              120              125
Lys Leu Glu Ile Lys Gly Gly Gly Gly Ser Gly Gly Gly Gly Ser
130              135              140
Gly Gly Gly Ser Gln Val Gln Leu Gln Pro Gly Ala Glu Val
145              150              155              160
Val Lys Pro Gly Ala Ser Val Lys Met Ser Cys Lys Ala Ser Gly Tyr
            165              170              175
Thr Phe Thr Ser Tyr Tyr Ile His Trp Ile Lys Gln Thr Pro Gly Gln
            180              185              190
Gly Leu Glu Trp Val Gly Val Ile Tyr Pro Gly Asn Asp Asp Ile Ser
            195              200              205
Tyr Asn Gln Lys Phe Gln Gly Lys Ala Thr Leu Thr Ala Asp Lys Ser
210              215              220
Ser Thr Thr Ala Tyr Met Gln Leu Ser Ser Leu Thr Ser Glu Asp Ser
225              230              235              240
Ala Val Tyr Tyr Cys Ala Arg Glu Val Arg Leu Arg Tyr Phe Asp Val
            245              250              255
Trp Gly Gln Gly Thr Thr Val Thr Val Ser Ser Ala Ala Ala Phe
            260              265              270
Val Pro Val Phe Leu Pro Ala Lys Pro Thr Thr Thr Pro Ala Pro Arg
            275              280              285
Pro Pro Thr Pro Ala Pro Thr Ile Ala Ser Gln Pro Leu Ser Leu Arg
            290              295              300
Pro Glu Ala Cys Arg Pro Ala Ala Gly Gly Ala Val His Thr Arg Gly
305              310              315              320
Leu Asp Phe Ala Cys Asp Ile Tyr Ile Trp Ala Pro Leu Ala Gly Thr
            325              330              335
Cys Gly Val Leu Leu Leu Ser Leu Val Ile Thr Leu Tyr Cys Asn His
            340              345              350
Arg Asn Arg Ser Lys Arg Ser Arg Leu Leu His Ser Asp Tyr Met Asn
            355              360              365
Met Thr Pro Arg Arg Pro Gly Pro Thr Arg Lys His Tyr Gln Pro Tyr
370              375              380
Ala Pro Pro Arg Asp Phe Ala Ala Tyr Arg Ser Arg Val Lys Phe Ser
385              390              395              400
Arg Ser Ala Asp Ala Pro Ala Tyr Gln Gln Gly Gln Asn Gln Leu Tyr
            405              410              415
Asn Glu Leu Asn Leu Gly Arg Arg Glu Glu Tyr Asp Val Leu Asp Lys
            420              425              430
Arg Arg Gly Arg Asp Pro Glu Met Gly Gly Lys Pro Arg Arg Lys Asn
            435              440              445
Pro Gln Glu Gly Leu Tyr Asn Glu Leu Gln Lys Asp Lys Met Ala Glu
            450              455              460
Ala Tyr Ser Glu Ile Gly Met Lys Gly Glu Arg Arg Arg Gly Lys Gly
465              470              475              480
His Asp Gly Leu Tyr Gln Gly Leu Ser Thr Ala Thr Lys Asp Thr Tyr
            485              490              495
Asp Ala Leu His Met Gln Ala Leu Pro Pro Arg
            500              505

<210> SEQ ID NO 339
```

<211> LENGTH: 509
<212> TYPE: PRT
<213> ORGANISM: Artificial Sequence
<220> FEATURE:
<223> OTHER INFORMATION: Synthetic

<400> SEQUENCE: 339

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Gly Ser Leu
            20                  25                  30

Ala Val Ser Pro Gly Glu Arg Val Thr Met Ser Cys Lys Ser Ser Gln
        35                  40                  45

Ser Val Phe Phe Ser Ser Gln Lys Asn Tyr Leu Ala Trp Tyr Gln
    50                  55                  60

Gln Ile Pro Gly Gln Ser Pro Arg Leu Leu Ile Tyr Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Pro Glu Asp Leu Ala Ile
            100                 105                 110

Tyr Tyr Cys His Gln Tyr Leu Ser Ser Arg Thr Phe Gly Gln Gly Thr
        115                 120                 125

Lys Leu Glu Ile Lys Gly Gly Gly Gly Ser Gly Gly Gly Gly Ser
130                 135                 140

Gly Gly Gly Gly Ser Gln Val Gln Leu Gln Pro Gly Ala Glu Val
145                 150                 155                 160

Val Lys Pro Gly Ala Ser Val Lys Met Ser Cys Lys Ala Ser Gly Tyr
                165                 170                 175

Thr Phe Thr Ser Tyr Tyr Ile His Trp Ile Lys Gln Thr Pro Gly Gln
            180                 185                 190

Gly Leu Glu Trp Val Gly Val Ile Tyr Pro Gly Asn Asp Asp Ile Ser
        195                 200                 205

Tyr Asn Gln Lys Phe Gln Gly Lys Ala Thr Leu Thr Ala Asp Lys Ser
210                 215                 220

Ser Thr Thr Ala Tyr Met Gln Leu Ser Ser Leu Thr Ser Glu Asp Ser
225                 230                 235                 240

Ala Val Tyr Tyr Cys Ala Arg Glu Val Arg Leu Arg Tyr Phe Asp Val
                245                 250                 255

Trp Gly Gln Gly Thr Thr Val Thr Val Ser Ser Ala Ala Ala Phe
            260                 265                 270

Val Pro Val Phe Leu Pro Ala Lys Pro Thr Thr Thr Pro Ala Pro Arg
        275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn His
            340                 345                 350

Arg Asn Arg Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
370                 375                 380
```

Cys Arg Phe Pro Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
            405                 410                 415

Leu Tyr Asn Glu Leu Asn Leu Gly Arg Arg Glu Glu Tyr Asp Val Leu
        420                 425                 430

Asp Lys Arg Arg Gly Arg Asp Pro Glu Met Gly Gly Lys Pro Arg Arg
    435                 440                 445

Lys Asn Pro Gln Glu Gly Leu Tyr Asn Glu Leu Gln Lys Asp Lys Met
450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 340
<211> LENGTH: 5
<212> TYPE: PRT
<213> ORGANISM: Artificial Sequence
<220> FEATURE:
<223> OTHER INFORMATION: Synthetic

<400> SEQUENCE: 340

Ser Tyr Gly Met His
1               5

<210> SEQ ID NO 341
<211> LENGTH: 17
<212> TYPE: PRT
<213> ORGANISM: Artificial Sequence
<220> FEATURE:
<223> OTHER INFORMATION: Synthetic

<400> SEQUENCE: 341

Val Ile Trp Asp Asp Gly Ser Asn Lys Tyr Tyr Val Asp Ser Val Lys
1               5                   10                  15

Gly

<210> SEQ ID NO 342
<211> LENGTH: 17
<212> TYPE: PRT
<213> ORGANISM: Artificial Sequence
<220> FEATURE:
<223> OTHER INFORMATION: Synthetic

<400> SEQUENCE: 342

Asp Asp Tyr Tyr Gly Ser Gly Ser Phe Asn Ser Tyr Tyr Gly Thr Asp
1               5                   10                  15

Val

<210> SEQ ID NO 343
<211> LENGTH: 11
<212> TYPE: PRT
<213> ORGANISM: Artificial Sequence
<220> FEATURE:
<223> OTHER INFORMATION: Synthetic

<400> SEQUENCE: 343

Arg Ala Ser Gln Ser Val Ser Ile Tyr Leu Ala

<210> SEQ ID NO 344
<211> LENGTH: 7
<212> TYPE: PRT
<213> ORGANISM: Artificial Sequence
<220> FEATURE:
<223> OTHER INFORMATION: Synthetic

<400> SEQUENCE: 344

Asp Ala Ser Asn Arg Ala Thr
1               5

<210> SEQ ID NO 345
<211> LENGTH: 10
<212> TYPE: PRT
<213> ORGANISM: Artificial Sequence
<220> FEATURE:
<223> OTHER INFORMATION: Synthetic

<400> SEQUENCE: 345

Gln Gln Arg Ser Asn Trp Pro Pro Phe Thr
1               5                   10

<210> SEQ ID NO 346
<211> LENGTH: 126
<212> TYPE: PRT
<213> ORGANISM: Artificial Sequence
<220> FEATURE:
<223> OTHER INFORMATION: Synthetic

<400> SEQUENCE: 346

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser
        115                 120                 125

<210> SEQ ID NO 347
<211> LENGTH: 108
<212> TYPE: PRT
<213> ORGANISM: Artificial Sequence
<220> FEATURE:
<223> OTHER INFORMATION: Synthetic

<400> SEQUENCE: 347

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Tyr
            20                  25                  30

Leu Ala Trp Tyr Gln Gln Lys Pro Gly Gln Ala Pro Arg Leu Leu Ile

```
              35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys
            100                 105
```

<210> SEQ ID NO 348
<211> LENGTH: 249
<212> TYPE: PRT
<213> ORGANISM: Artificial Sequence
<220> FEATURE:
<223> OTHER INFORMATION: Synthetic

<400> SEQUENCE: 348

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Ile Trp Asp Asp Gly Ser Asn Lys Tyr Tyr Val Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
         115                 120                 125

Gly Gly Ser Gly Gly Gly Gly Ser Gly Gly Gly Gly Ser Glu Ile Val
130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
         195                 200                 205

Gly Thr Asp Phe Thr Leu Thr Ile Ser Ser Leu Glu Pro Glu Asp Phe
210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys
            245
```

<210> SEQ ID NO 349
<211> LENGTH: 510
<212> TYPE: PRT
<213> ORGANISM: Artificial Sequence
<220> FEATURE:
<223> OTHER INFORMATION: Synthetic

<400> SEQUENCE: 349

Met Ala Leu Pro Val Thr Ala Leu Leu Pro Leu Ala Leu Leu Leu
1               5                   10                  15

His Ala Ala Arg Pro Gln Val Gln Leu Val Glu Ser Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Tyr Gly Ser Gly Ser Phe
        115                 120                 125

Asn Ser Tyr Tyr Gly Thr Asp Val Trp Gly Gln Gly Thr Thr Val Thr
130                 135                 140

Val Ser Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190

Ile Tyr Leu Ala Trp Tyr Gln Gln Lys Pro Gly Gln Ala Pro Arg Leu
        195                 200                 205

Leu Ile Tyr Asp Ala Ser Asn Arg Ala Thr Gly Ile Pro Ala Arg Phe
210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
            260                 265                 270

Ala Ala Phe Val Pro Val Phe Leu Pro Ala Lys Pro Thr Thr Thr Pro
        275                 280                 285

Ala Pro Arg Pro Pro Thr Pro Ala Pro Thr Ile Ala Ser Gln Pro Leu
        290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Asn His Arg Asn Arg Ser Lys Arg Ser Arg Leu Leu His Ser Asp
        355                 360                 365

Tyr Met Asn Met Thr Pro Arg Arg Pro Gly Pro Thr Arg Lys His Tyr
        370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn

```
            405                 410                 415
Gln Leu Tyr Asn Glu Leu Asn Leu Gly Arg Arg Glu Tyr Asp Val
        420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 350
<211> LENGTH: 512
<212> TYPE: PRT
<213> ORGANISM: Artificial Sequence
<220> FEATURE:
<223> OTHER INFORMATION: Synthetic

<400> SEQUENCE: 350

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Trp Asp Asp Gly Ser Asn Lys Tyr
65                  70                  75                  80

Tyr Val Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Asp Tyr Tyr Gly Ser Gly Ser Phe
        115                 120                 125

Asn Ser Tyr Tyr Gly Thr Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Glu Ile Val Leu Thr Gln Ser Pro Ala Thr Leu Ser Leu Ser
                165                 170                 175

Pro Gly Glu Arg Ala Thr Leu Ser Cys Arg Ala Ser Gln Ser Val Ser
            180                 185                 190

Ile Tyr Leu Ala Trp Tyr Gln Gln Lys Pro Gly Gln Ala Pro Arg Leu
        195                 200                 205

Leu Ile Tyr Asp Ala Ser Asn Arg Ala Thr Gly Ile Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Val Tyr Tyr Cys Gln Gln Arg Ser Asn Trp
                245                 250                 255

Pro Pro Phe Thr Phe Gly Pro Gly Thr Lys Val Asp Ile Lys Ser Ala
```

```
                260             265             270
Ala Ala Phe Val Pro Val Phe Leu Pro Ala Lys Pro Thr Thr Thr Pro
            275                 280                 285
Ala Pro Arg Pro Pro Thr Pro Ala Pro Thr Ile Ala Ser Gln Pro Leu
        290                 295                 300
Ser Leu Arg Pro Glu Ala Cys Arg Pro Ala Ala Gly Gly Ala Val His
305                 310                 315                 320
Thr Arg Gly Leu Asp Phe Ala Cys Asp Ile Tyr Ile Trp Ala Pro Leu
                325                 330                 335
Ala Gly Thr Cys Gly Val Leu Leu Leu Ser Leu Val Ile Thr Leu Tyr
            340                 345                 350
Cys Asn His Arg Asn Arg Lys Arg Gly Arg Lys Lys Leu Leu Tyr Ile
            355                 360                 365
Phe Lys Gln Pro Phe Met Arg Pro Val Gln Thr Thr Gln Glu Glu Asp
        370                 375                 380
Gly Cys Ser Cys Arg Phe Pro Glu Glu Glu Glu Gly Gly Cys Glu Leu
385                 390                 395                 400
Arg Val Lys Phe Ser Arg Ser Ala Asp Ala Pro Ala Tyr Gln Gln Gly
                405                 410                 415
Gln Asn Gln Leu Tyr Asn Glu Leu Asn Leu Gly Arg Arg Glu Glu Tyr
            420                 425                 430
Asp Val Leu Asp Lys Arg Arg Gly Arg Asp Pro Glu Met Gly Gly Lys
        435                 440                 445
Pro Arg Arg Lys Asn Pro Gln Glu Gly Leu Tyr Asn Glu Leu Gln Lys
    450                 455                 460
Asp Lys Met Ala Glu Ala Tyr Ser Glu Ile Gly Met Lys Gly Glu Arg
465                 470                 475                 480
Arg Arg Gly Lys Gly His Asp Gly Leu Tyr Gln Gly Leu Ser Thr Ala
                485                 490                 495
Thr Lys Asp Thr Tyr Asp Ala Leu His Met Gln Ala Leu Pro Pro Arg
            500                 505                 510

<210> SEQ ID NO 351
<211> LENGTH: 4361
<212> TYPE: DNA
<213> ORGANISM: Artificial Sequence
<220> FEATURE:
<223> OTHER INFORMATION: Synthetic

<400> SEQUENCE: 351
gagatgtaag gagctgctgt gacttgctca aggccttata tcgagtaaac ggtagtgctg    60
gggcttagac gcaggtgttc tgatttatag ttcaaaacct ctatcaatga gagagcaatc   120
tcctggtaat gtgatagatt tcccaactta atgccaacat accataaacc tcccattctg   180
ctaatgccca gcctaagttg gggagaccac tccagattcc aagatgtaca gtttgctttg   240
ctgggccttt ttcccatgcc tgcctttact ctgccagagt tatattgctg ggttttgaa    300 gaagatccta ttaaataaaa gaataagcag tattattaag tagccctgca tttcaggttt   360
ccttgagtgg caggccaggc ctggccgtga acgttcactg aaatcatggc ctcttggcca   420
agattgatag cttgtgcctg tccctgagtc ccagtccatc acgagcagct ggtttctaag   480
atgctatttc ccgtataaag catgagaccg tgacttgcca gccccacaga gccccgccct   540
tgtccatcac tggcatctgg actccagcct gggttgggggc aaagagggaa atgagatcat   600
gtcctaaccc tgatcctctt gtcccacaga tatccagaac cctgaccctg ccgtgtacca   660
```

-continued

| | |
|---|---|
| gctgagagac tctaaatcca gtgacaagtc tgtctgccta ttcaccgatt ttgattctca | 720 |
| aacaaatgtg tcacaaagta aggattctga tgtgtatatc acagacaaaa ctgtgctaga | 780 |
| catgaggtct atggacttca ggctccggtg cccgtcagtg ggcagagcgc acatcgccca | 840 |
| cagtccccga gaagttgggg ggaggggtcg gcaattgaac cggtgcctag agaaggtggc | 900 |
| gcggggtaaa ctgggaaagt gatgtcgtgt actggctccg ccttttcc gagggtgggg | 960 |
| gagaaccgta tataagtgca gtagtcgccg tgaacgttct ttttcgcaac gggtttgccg | 1020 |
| ccagaacaca ggtaagtgcc gtgtgtggtt cccgcgggcc tggcctcttt acgggttatg | 1080 |
| gcccttgcgt gccttgaatt acttccactg gctgcagtac gtgattcttg atcccgagct | 1140 |
| tcgggttgga agtgggtggg agagttcgag gccttgcgct taaggagccc cttcgcctcg | 1200 |
| tgcttgagtt gaggcctggc ctgggcgctg gggccgccgc gtgcgaatct ggtggcacct | 1260 |
| tcgcgcctgt ctcgctgctt tcgataagtc tctagccatt taaaattttt gatgacctgc | 1320 |
| tgcgacgctt ttttctggc aagatagtct tgtaaatgcg ggccaagatc tgcacactgg | 1380 |
| tatttcggtt tttggggccg cggcggcga cggggcccgt gcgtcccagc gcacatgttc | 1440 |
| ggcgaggcgg ggcctgcgag cgcggccacc gagaatcgga cggggtagt ctcaagctgg | 1500 |
| ccggcctgct ctggtgcctg gcctcgcgcc gccgtgtatc gccccgccct gggcggcaag | 1560 |
| gctggcccgg tcggcaccag ttgcgtgagc ggaaagatgg ccgcttccg gccctgctgc | 1620 |
| agggagctca aaatggagga gcggcgctc gggagagcgg gcgggtgagt cacccacaca | 1680 |
| aaggaaaagg gccttccgt cctcagccgt cgcttcatgt gactccacgg agtaccgggc | 1740 |
| gccgtccagg cacctcgatt agttctcgag cttttggagt acgtcgtctt taggttgggg | 1800 |
| ggaggggttt tatgcgatgg agtttccca cactgagtgg gtggagactg aagttaggcc | 1860 |
| agcttggcac ttgatgtaat tctccttgga atttgccctt tttgagtttg gatcttggtt | 1920 |
| cattctcaag cctcagacag tggttcaaag ttttttctt ccatttcagg tgtcgtgacc | 1980 |
| accatggcgc ttccggtgac agcactgctc ctcccttgg cgctgttgct ccacgcagca | 2040 |
| aggccggaaa tcgtcctcac acaatccccg gggagcctcg cagtcagtcc tggggaacga | 2100 |
| gtcactatga gctgcaaatc cagtcagagt gttttttct caagtagcca gaagaactac | 2160 |
| ctcgcatggt accaacaaat accggggcaa tctccccgct tgcttatata ctgggcaagt | 2220 |
| acccgcgaat ccgcgtacc ggatcgattc acgggatctg ggtcaggtac tgatttcact | 2280 |
| ttgactatca gctctgttca gcctgaagat ttggcaattt actactgtca ccaatacttg | 2340 |
| agtagccgaa ctttcggcca gggcacgaag ctcgaaatca agggcggagg gggaggttct | 2400 |
| ggtgggggcg gttctggcgg tggaggaagc caagtacagt tgcaacagcc aggggcggag | 2460 |
| gtcgtaaaac ctgggcgtc tgtcaagatg agctgtaaag caagtggata caccttcacc | 2520 |
| tcctactata tacattggat taagcaaact ccgggtcagg gctggaatg ggttggcgtt | 2580 |
| atataccccg ggaacgatga tatatcatac aaccaaaaat ttcaaggcaa ggcgactctg | 2640 |
| actgccgata agagtagcac aacagcttac atgcagcttt cttccctgac cagcgaagat | 2700 |
| tcagcagttt actactgcgc tcgggaagtg cgcctgcgat actttgatgt ctggggtcaa | 2760 |
| ggaactacag ttactgtatc aagcagtgct gctgcctttg tcccggtatt tctcccagcc | 2820 |
| aaaccgacca cgactcccgc cccgcgccct ccgacacccg ctcccaccat cgcctctcaa | 2880 |
| cctcttagtc ttcgccccga ggcatgccga cccgccgccg ggggtgctgt tcatacgagg | 2940 |
| ggcttggact tcgcttgtga tatttacatt tgggctccgt tggcgggtac gtgcggcgtc | 3000 |
| cttttgttgt cactcgttat tactttgtat tgtaatcaca ggaatcgctc aaagcggagt | 3060 |

| | |
|---|---|
| aggttgttgc attccgatta catgaatatg actcctcgcc ggcctgggcc gacaagaaaa | 3120 |
| cattaccaac cctatgcccc cccacgagac ttcgctgcgt acaggtcccg agtgaagttt | 3180 |
| tcccgaagcg cagacgctcc ggcatatcag caaggacaga atcagctgta taacgaactg | 3240 |
| aatttgggac gccgcgagga gtatgacgtg cttgataaac gccgggggag agacccggaa | 3300 |
| atggggggta aaccccgaag aaagaatccc caagaaggac tctacaatga actccagaag | 3360 |
| gataagatgg cggaggccta ctcagaaata ggtatgaagg cgaacgacg acggggaaaa | 3420 |
| ggtcacgatg gcctctacca agggttgagt acggcaacca agatacgta cgatgcactg | 3480 |
| catatgcagg ccctgcctcc cagataataa taaaatcgct atccatcgaa gatggatgtg | 3540 |
| tgttggtttt ttgtgtgtgg agcaacaaat ctgactttgc atgtgcaaac gccttcaaca | 3600 |
| acagcattat tccagaagac accttcttcc ccagcccagg taagggcagc tttggtgcct | 3660 |
| tcgcaggctg tttccttgct tcaggaatgg ccaggttctg cccagagctc tggtcaatga | 3720 |
| tgtctaaaac tcctctgatt ggtggtctcg gccttatcca ttgccaccaa aaccctcttt | 3780 |
| ttactaagaa acagtgagcc ttgttctggc agtccagaga atgacacggg aaaaaagcag | 3840 |
| atgaagagaa ggtggcagga gagggcacgt ggcccagcct cagtctctcc aactgagttc | 3900 |
| ctgcctgcct gcctttgctc agactgtttg ccccttactg ctcttctagg cctcattcta | 3960 |
| agcccttct ccaagttgcc tctccttatt tctccctgtc tgccaaaaaa tctttcccag | 4020 |
| ctcactaagt cagtctcacg cagtcactca ttaacccacc aatcactgat tgtgccggca | 4080 |
| catgaatgca ccaggtgttg aagtggagga attaaaaagt cagatgaggg gtgtgcccag | 4140 |
| aggaagcacc attctagttg ggggagccca tctgtcagct gggaaaagtc caaataactt | 4200 |
| cagattggaa tgtgttttaa ctcagggttg agaaaacagc taccttcagg acaaaagtca | 4260 |
| gggaagggct ctctgaagaa atgctacttg aagataccag ccctaccaag ggcagggaga | 4320 |
| ggaccctata gaggcctggg acaggagctc aatgagaaag g | 4361 |

<210> SEQ ID NO 352
<211> LENGTH: 4367
<212> TYPE: DNA
<213> ORGANISM: Artificial Sequence
<220> FEATURE:
<223> OTHER INFORMATION: Synthetic

<400> SEQUENCE: 352

| | |
|---|---|
| gagatgtaag gagctgctgt gacttgctca aggccttata tcgagtaaac ggtagtgctg | 60 |
| gggcttagac gcaggtgttc tgatttatag ttcaaaacct ctatcaatga gagagcaatc | 120 |
| tcctggtaat gtgatagatt tcccaactta atgccaacat accataaacc tcccattctg | 180 |
| ctaatgccca gcctaagttg gggagaccac tccagattcc aagatgtaca gtttgctttg | 240 |
| ctgggccttt ttcccatgcc tgcctttact ctgccagagt tatattgctg ggttttgaa | 300 |
| gaagatccta ttaaataaaa gaataagcag tattattaag tagccctgca tttcaggttt | 360 |
| ccttgagtgg caggccaggc ctggccgtga cgttcactg aaatcatggc ctcttggcca | 420 |
| agattgatag cttgtgcctg tccctgagtc ccagtccatc acgagcagct ggtttctaag | 480 |
| atgctatttc ccgtataaag catgagaccg tgacttgcca gccccacaga gccccgccct | 540 |
| tgtccatcac tggcatctgg actccagcct gggttgggc aaagagggaa atgagatcat | 600 |
| gtcctaaccc tgatcctctt gtcccacaga tatccagaac cctgaccctg ccgtgtacca | 660 |
| gctgagagac tctaaatcca gtgacaagtc tgtctgccta ttcaccgatt ttgattctca | 720 |

```
aacaaatgtg tcacaaagta aggattctga tgtgtatatc acagacaaaa ctgtgctaga    780
catgaggtct atggacttca ggctccggtg cccgtcagtg ggcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg ccttttccc gagggtgggg    960
gagaaccgta tataagtgca gtagtcgccg tgaacgttct ttttcgcaac gggtttgccg   1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggttgga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaattttt gatgacctgc   1320
tgcgacgctt ttttctggc aagatagtct tgtaaatgcg ggccaagatc tgcacactgg   1380
tatttcggtt tttggggccg cgggcggcga cggggcccgt gcgtcccagc gcacatgttc   1440
ggcgaggcgg ggcctgcgag cgcggccacc gagaatcgga cggggtagt ctcaagctgg   1500
ccggcctgct ctggtgcctg gcctcgcgcc gccgtgtatc gccccgccct gggcggcaag   1560
gctgcccgt cggcaccag ttgcgtgagc ggaaagatgg ccgcttcccg gccctgctgc    1620
agggagctca aaatggagga gcggcgcgctc gggagagcgg gcgggtgagt cacccacaca   1680
aaggaaaagg gcctttccgt cctcagccgt cgcttcatgt gactccacgg agtaccgggc   1740
gccgtccagg cacctcgatt agttctcgag cttttggagt acgtcgtctt taggttgggg   1800
ggagggttt tatgcgatgg agtttcccca cactgagtgg gtggagactg aagttaggcc   1860
agcttggcac ttgatgtaat tctccttgga atttgcccttt tttgagtttg gatcttggtt   1920
cattctcaag cctcagacag tggttcaaag ttttttcctt ccatttcagg tgtcgtgacc   1980
accatggcgc ttccggtgac agcactgctc ctccccttgg cgctgttgct ccacgcagca   2040
aggccggaaa tcgtcctcac acaatccccg gggagcctcg cagtcagtcc tggggaacga   2100
gtcactatga gctgcaaatc cagtcagagt gtttttttct caagtagcca aagaactac    2160
ctcgcatgg accaacaaat accggggcaa tctccccgct tgcttatata ctgggcaagt   2220
acccgcgaat ccggcgtacc ggatcgattc acgggatctg ggtcaggtac tgatttcact   2280
ttgactatca gctctgttca gcctgaagat ttggcaattt actactgtca ccaatacttg   2340
agtagccgaa cttccggcca gggcacgaag ctcgaaatca agggcggagg gggaggttct   2400
ggtggggcg ttctggcgg tggaggaagc caagtacagt tgcaacagcc aggggcggag    2460
gtcgtaaaac ctggggcgtc tgtcaagatg agctgtaaag caagtggata caccttcacc   2520
tcctactata tacattggat taagcaaact ccgggtcagg ggctggaatg ggttggcgtt   2580
ataccccccg ggaacgatga tatatcatac aaccaaaaat ttcaaggcaa ggcgactctg   2640
actgccgata agagtagcac aacagcttac atgcagcttt cttccctgac cagcgaagat   2700
tcagcagttt actactgcgc tcgggaagtg cgcctgcgat actttgatgt ctggggtcaa   2760
ggaactacag ttactgtatc aagcagtgct gctgcctttg tcccggtatt tctcccagcc   2820
aaaccgacca cgactcccgc cccgcgccct ccgacacccg ctcccaccat cgcctctcaa   2880
cctcttagtc ttcgccccga ggcatgccga cccgccgccg ggggtgctgt tcatacgagg   2940
ggcttggact tcgcttgtga tatttacatt tgggctccgt tggcgggtac gtgcggcgtc   3000
cttttgttgt cactcgttat tactttgtat tgtaatcaca ggaatcgcaa acggggcaga   3060
aagaaactcc tgtatatatt caaacaacca tttatgagac cagtacaaac tactcaagag   3120
```

```
gaagatggct gtagctgccg atttccagaa gaagaagaag gaggatgtga actgcgagtg   3180
aagttttccc gaagcgcaga cgctccggca tatcagcaag acagaatca gctgtataac    3240 gaactgaatt tgggacgccg cgaggagtat gacgtgcttg ataaacgccg ggggagagac   3300
ccggaaatgg ggggtaaacc ccgaagaaag aatccccaag aaggactcta caatgaactc   3360
cagaaggata agatggcgga ggcctactca gaaataggta tgaagggcga acgacgacgg   3420
ggaaaaggtc acgatggcct ctaccaaggg ttgagtacgg caaccaaaga tacgtacgat   3480
gcactgcata tgcaggccct gcctcccaga taataataaa atcgctatcc atcgaagatg   3540
gatgtgtgtt ggttttttgt gtgtggagca acaaatctga cttttgcatgt gcaaacgcct   3600 tcaacaacag cattattcca gaagacacct tcttccccag cccaggtaag ggcagctttg   3660
gtgccttcgc aggctgtttc cttgcttcag gaatggccag gttctgccca gagctctggt   3720
caatgatgtc taaaactcct ctgattggtg gtctcggcct tatccattgc caccaaaacc   3780 ctcttttac taagaaacag tgagcctttgt tctggcagtc cagagaatga cacgggaaaa   3840
aagcagatga agagaaggtg gcaggagagg gcacgtggcc cagcctcagt ctctccaact   3900
gagttcctgc ctgcctgcct ttgctcagac tgtttgcccc ttactgctct tctaggcctc   3960
attctaagcc ccttctccaa gttgcctctc cttatttctc cctgtctgcc aaaaaatctt   4020
tcccagctca ctaagtcagt ctcacgcagt cactcattaa cccaccaatc actgattgtg   4080
ccggcacatg aatgcaccag gtgttgaagt ggaggaatta aaaagtcaga tgagggtgt    4140 gcccagagga agcaccattc tagttggggg agcccatctg tcagctggga aaagtccaaa   4200
taacttcaga ttggaatgtg ttttaactca gggttgagaa aacagctacc ttcaggacaa   4260 aagtcagga agggctctct gaagaaatgc tacttgaaga taccagcccct accaagggca   4320 gggagaggac cctatagagg cctgggacag gagctcaatg agaaagg                 4367
```

<210> SEQ ID NO 353
<211> LENGTH: 484
<212> TYPE: PRT
<213> ORGANISM: Artificial Sequence
<220> FEATURE:
<223> OTHER INFORMATION: Synthetic

<400> SEQUENCE: 353

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140
```

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
            165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
            210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ala Phe Val Pro Val Phe Leu Pro Ala
            245                 250                 255

Lys Pro Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
            275                 280                 285

Ala Gly Gly Ala Val His Thr Arg Gly Leu Asp Phe Ala Cys Asp Ile
            290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Asn His Arg Asn Arg Ser Lys Arg Ser
            325                 330                 335

Arg Leu Leu His Ser Asp Tyr Met Asn Met Thr Pro Arg Arg Pro Gly
            340                 345                 350

Pro Thr Arg Lys His Tyr Gln Pro Tyr Ala Pro Pro Arg Asp Phe Ala
            355                 360                 365

Ala Tyr Arg Ser Arg Val Lys Phe Ser Arg Ser Ala Asp Ala Pro Ala
            370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
            405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
            450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 354
<211> LENGTH: 487
<212> TYPE: PRT
<213> ORGANISM: Artificial Sequence
<220> FEATURE:
<223> OTHER INFORMATION: Synthetic

<400> SEQUENCE: 354

Gln Val Gln Leu Val Gln Ser Gly Ala Glu Val Lys Lys Pro Gly Ala
1               5                   10                  15

-continued

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
            35                  40                  45

Gly Trp Ile Asn Thr Tyr Thr Gly Glu Pro Thr Tyr Ala Asp Ala Phe
            50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Asp Tyr Gly Asp Tyr Gly Met Asp Tyr Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Gly Asp Ile Val Met Thr Gln Ser Pro Asp Ser
            130                 135                 140

Leu Ala Val Ser Leu Gly Glu Arg Ala Thr Ile Asn Cys Arg Ala Ser
145                 150                 155                 160

Lys Ser Val Ser Thr Ser Gly Tyr Ser Phe Met His Trp Tyr Gln Gln
            165                 170                 175

Lys Pro Gly Gln Pro Pro Lys Leu Leu Ile Tyr Leu Ala Ser Asn Leu
            180                 185                 190

Glu Ser Gly Val Pro Asp Arg Phe Ser Gly Ser Gly Ser Gly Thr Asp
            195                 200                 205

Phe Thr Leu Thr Ile Ser Ser Leu Gln Ala Glu Asp Val Ala Val Tyr
            210                 215                 220

Tyr Cys Gln His Ser Arg Glu Val Pro Trp Thr Phe Gly Gln Gly Thr
225                 230                 235                 240

Lys Val Glu Ile Lys Ser Ala Ala Phe Val Pro Val Phe Leu Pro
            245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
            290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Asn His Arg Asn Arg Lys Arg Gly
            325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu

```
                435                 440                 445
Ile Gly Met Lys Gly Glu Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 355
<211> LENGTH: 487
<212> TYPE: PRT
<213> ORGANISM: Artificial Sequence
<220> FEATURE:
<223> OTHER INFORMATION: Synthetic

<400> SEQUENCE: 355

Gln Val Gln Leu Val Gln Ser Gly Ala Glu Leu Lys Lys Pro Gly Ala
1               5                   10                  15

Ser Val Lys Val Ser Cys Lys Ala Ser Gly Asn Thr Leu Thr Asn Tyr
            20                  25                  30

Val Ile His Trp Val Arg Gln Ala Pro Gly Gln Arg Leu Glu Trp Met
        35                  40                  45

Gly Tyr Ile Leu Pro Tyr Asn Asp Leu Thr Lys Tyr Ser Gln Lys Phe
    50                  55                  60

Gln Gly Arg Val Thr Ile Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Asp Trp Asp Gly Phe Phe Asp Pro Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Glu Ile Val Met Thr Gln Ser Pro Ala Thr Leu
    130                 135                 140

Ser Val Ser Pro Gly Glu Arg Ala Ser Ile Ser Cys Arg Ala Ser Gln
145                 150                 155                 160

Ser Leu Val His Ser Asn Gly Asn Thr His Leu His Trp Tyr Gln Gln
                165                 170                 175

Arg Pro Gly Gln Ala Pro Arg Leu Leu Ile Tyr Ser Val Ser Asn Arg
            180                 185                 190

Phe Ser Glu Val Pro Ala Arg Phe Ser Gly Ser Gly Ser Gly Thr Asp
        195                 200                 205

Phe Thr Leu Thr Ile Ser Ser Val Glu Ser Glu Asp Phe Ala Val Tyr
    210                 215                 220

Tyr Cys Ser Gln Thr Ser His Ile Pro Tyr Thr Phe Gly Gly Gly Thr
225                 230                 235                 240

Lys Leu Glu Ile Lys Ser Ala Ala Ala Phe Val Pro Val Phe Leu Pro
                245                 250                 255

Ala Lys Pro Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
```

```
305                 310                 315                 320
Ser Leu Val Ile Thr Leu Tyr Cys Asn His Arg Asn Arg Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
                450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 356
<211> LENGTH: 486
<212> TYPE: PRT
<213> ORGANISM: Artificial Sequence
<220> FEATURE:
<223> OTHER INFORMATION: Synthetic

<400> SEQUENCE: 356

```
Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
                20                  25                  30

Ser Ser Gln Lys Asn Tyr Leu Ala Trp Tyr Gln Gln Ile Pro Gly Gln
                35                  40                  45

Ser Pro Arg Leu Leu Ile Tyr Trp Ala Ser Thr Arg Glu Ser Gly Val
                50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
                100                 105                 110

Gly Gly Gly Gly Ser Gly Gly Gly Gly Ser Gly Gly Gly Gly Ser
                115                 120                 125

Gln Val Gln Leu Gln Gln Pro Gly Ala Glu Val Val Lys Pro Gly Ala
                130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
```

Gln Gly Lys Ala Thr Leu Thr Ala Asp Lys Ser Ser Thr Ala Tyr
            180                 185                 190

Met Gln Leu Ser Ser Leu Thr Ser Glu Asp Ser Ala Val Tyr Tyr Cys
        195                 200                 205

Ala Arg Glu Val Arg Leu Arg Tyr Phe Asp Val Trp Gly Gln Gly Thr
    210                 215                 220

Ala Arg Glu Val Arg Leu Arg Tyr Phe Asp Val Trp Gly Gln Gly Thr
225                 230                 235                 240

Thr Val Thr Val Ser Ser Ala Ala Ala Phe Val Pro Val Phe Leu
            245                 250                 255

Pro Ala Lys Pro Thr Thr Thr Pro Ala Pro Arg Pro Pro Thr Pro Ala
        260                 265                 270

Pro Thr Ile Ala Ser Gln Pro Leu Ser Leu Arg Pro Glu Ala Cys Arg
    275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Asn His Arg Asn Arg Ser Lys
            325                 330                 335

Arg Ser Arg Leu Leu His Ser Asp Tyr Met Asn Met Thr Pro Arg Arg
        340                 345                 350

Pro Gly Pro Thr Arg Lys His Tyr Gln Pro Tyr Ala Pro Pro Arg Asp
    355                 360                 365

Phe Ala Ala Tyr Arg Ser Arg Val Lys Phe Ser Arg Ser Ala Asp Ala
        370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
        420                 425                 430

Tyr Asn Glu Leu Gln Lys Asp Lys Met Ala Glu Ala Tyr Ser Glu Ile
    435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 357
<211> LENGTH: 488
<212> TYPE: PRT
<213> ORGANISM: Artificial Sequence
<220> FEATURE:
<223> OTHER INFORMATION: Synthetic

<400> SEQUENCE: 357

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val

-continued

```
            50                  55                  60
Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
                100                 105                 110

Gly Gly Gly Gly Gly Ser Gly Gly Gly Ser Gly Gly Gly Gly Ser
                115                 120                 125

Gln Val Gln Leu Gln Gln Pro Gly Ala Glu Val Val Lys Pro Gly Ala
    130                 135                 140

Ser Val Lys Met Ser Cys Lys Ala Ser Gly Tyr Thr Phe Thr Ser Tyr
145                 150                 155                 160

Tyr Ile His Trp Ile Lys Gln Thr Pro Gly Gln Gly Leu Glu Trp Val
                165                 170                 175

Gly Val Ile Tyr Pro Gly Asn Asp Asp Ile Ser Tyr Asn Gln Lys Phe
                180                 185                 190

Gln Gly Lys Ala Thr Leu Thr Ala Asp Lys Ser Ser Thr Thr Ala Tyr
                195                 200                 205

Met Gln Leu Ser Ser Leu Thr Ser Glu Asp Ser Ala Val Tyr Tyr Cys
    210                 215                 220

Ala Arg Glu Val Arg Leu Arg Tyr Phe Asp Val Trp Gly Gln Gly Thr
225                 230                 235                 240

Thr Val Thr Val Ser Ser Ala Ala Ala Phe Val Pro Val Phe Leu
                245                 250                 255

Pro Ala Lys Pro Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
                275                 280                 285

Pro Ala Ala Gly Gly Ala Val His Thr Arg Gly Leu Asp Phe Ala Cys
                290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Asn His Arg Asn Arg Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
                370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460

Leu Tyr Gln Gly Leu Ser Thr Ala Thr Lys Asp Thr Tyr Asp Ala Leu
465                 470                 475                 480
```

His Met Gln Ala Leu Pro Pro Arg
                485

<210> SEQ ID NO 358
<211> LENGTH: 489
<212> TYPE: PRT
<213> ORGANISM: Artificial Sequence
<220> FEATURE:
<223> OTHER INFORMATION: Synthetic

<400> SEQUENCE: 358

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
    210                 215                 220

Ala Val Tyr Tyr Cys Gln Gln Arg Ser Asn Trp Pro Pro Phe Thr Phe
225                 230                 235                 240

Gly Pro Gly Thr Lys Val Asp Ile Lys Ser Ala Ala Ala Phe Val Pro
                245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Ser Lys Arg Ser Arg Leu Leu His Ser Asp Tyr Met Asn Met Thr
            340                 345                 350

```
Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
        370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
            450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 359
<211> LENGTH: 491
<212> TYPE: PRT
<213> ORGANISM: Artificial Sequence
<220> FEATURE:
<223> OTHER INFORMATION: Synthetic

<400> SEQUENCE: 359

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Asp Asp Gly Ser Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Gly Ser Gly Ser Phe Asn Ser Tyr Tyr Gly
            100                 105                 110

Thr Asp Val Trp Gly Gln Gly Thr Thr Val Thr Val Ser Ser Gly Gly
        115                 120                 125

Gly Gly Ser Gly Gly Gly Ser Gly Gly Gly Gly Ser Glu Ile Val
        130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ile Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205

Gly Thr Asp Phe Thr Leu Thr Ile Ser Ser Leu Glu Pro Glu Asp Phe
210                 215                 220
```

Ala Val Tyr Tyr Cys Gln Gln Arg Ser Asn Trp Pro Pro Phe Thr Phe
225                 230                 235                 240

Gly Pro Gly Thr Lys Val Asp Ile Lys Ser Ala Ala Phe Val Pro
            245                 250                 255

Val Phe Leu Pro Ala Lys Pro Thr Thr Thr Pro Ala Pro Arg Pro Pro
        260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
            325                 330                 335

Arg Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
            450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 360
<211> LENGTH: 20
<212> TYPE: DNA
<213> ORGANISM: Artificial Sequence
<220> FEATURE:
<223> OTHER INFORMATION: Synthetic

<400> SEQUENCE: 360
ctgaacgtgc ggtgggatcg                                            20

<210> SEQ ID NO 361
<211> LENGTH: 10
<212> TYPE: DNA
<213> ORGANISM: Artificial Sequence
<220> FEATURE:
<223> OTHER INFORMATION: Synthetic

<400> SEQUENCE: 361
ctgaacgtgc                                                       10

<210> SEQ ID NO 362
<211> LENGTH: 15

```
<212> TYPE: DNA
<213> ORGANISM: Artificial Sequence
<220> FEATURE:
<223> OTHER INFORMATION: Synthetic

<400> SEQUENCE: 362
ctgaacgtgg gatcg                                                   15

<210> SEQ ID NO 363
<211> LENGTH: 21
<212> TYPE: DNA
<213> ORGANISM: Artificial Sequence
<220> FEATURE:
<223> OTHER INFORMATION: Synthetic

<400> SEQUENCE: 363
ctgaacgtgc cggtgggatc g                                            21

<210> SEQ ID NO 364
<211> LENGTH: 19
<212> TYPE: DNA
<213> ORGANISM: Artificial Sequence
<220> FEATURE:
<223> OTHER INFORMATION: Synthetic

<400> SEQUENCE: 364
ctgaacgtgg gtgggatcg                                               19

<210> SEQ ID NO 365
<211> LENGTH: 10
<212> TYPE: DNA
<213> ORGANISM: Artificial Sequence
<220> FEATURE:
<223> OTHER INFORMATION: Synthetic

<400> SEQUENCE: 365
ggtgggatcg                                                         10

<210> SEQ ID NO 366
<211> LENGTH: 18
<212> TYPE: DNA
<213> ORGANISM: Artificial Sequence
<220> FEATURE:
<223> OTHER INFORMATION: Synthetic

<400> SEQUENCE: 366
ctgaacgtgg tgggatcg                                                18

<210> SEQ ID NO 367
<211> LENGTH: 16
<212> TYPE: DNA
<213> ORGANISM: Artificial Sequence
<220> FEATURE:
<223> OTHER INFORMATION: Synthetic

<400> SEQUENCE: 367
ctgaacggtg ggatcg                                                  16

<210> SEQ ID NO 368
<211> LENGTH: 12
<212> TYPE: DNA
<213> ORGANISM: Artificial Sequence
<220> FEATURE:
<223> OTHER INFORMATION: Synthetic

<400> SEQUENCE: 368
```
ctggtgggat cg                                                              12

<210> SEQ ID NO 369
<211> LENGTH: 21
<212> TYPE: DNA
<213> ORGANISM: Artificial Sequence
<220> FEATURE:
<223> OTHER INFORMATION: Synthetic

<400> SEQUENCE: 369
ctgaacgtgc aggtgggatc g                                                    21

<210> SEQ ID NO 370
<211> LENGTH: 18
<212> TYPE: DNA
<213> ORGANISM: Artificial Sequence
<220> FEATURE:
<223> OTHER INFORMATION: Synthetic

<400> SEQUENCE: 370
ctgaacgtgc gtggatcg                                                        18

<210> SEQ ID NO 371
<211> LENGTH: 20
<212> TYPE: DNA
<213> ORGANISM: Artificial Sequence
<220> FEATURE:
<223> OTHER INFORMATION: Synthetic

<400> SEQUENCE: 371
gatacgcgtc cacaggacga                                                      20

<210> SEQ ID NO 372
<211> LENGTH: 19
<212> TYPE: DNA
<213> ORGANISM: Artificial Sequence
<220> FEATURE:
<223> OTHER INFORMATION: Synthetic

<400> SEQUENCE: 372
gatacgcgtc acaggacga                                                       19

<210> SEQ ID NO 373
<211> LENGTH: 21
<212> TYPE: DNA
<213> ORGANISM: Artificial Sequence
<220> FEATURE:
<223> OTHER INFORMATION: Synthetic

<400> SEQUENCE: 373
gatacgcgtc ccacaggacg a                                                    21

<210> SEQ ID NO 374
<211> LENGTH: 18
<212> TYPE: DNA
<213> ORGANISM: Artificial Sequence
<220> FEATURE:
<223> OTHER INFORMATION: Synthetic

<400> SEQUENCE: 374
gatacgcgtc caggacga                                                        18

<210> SEQ ID NO 375
<211> LENGTH: 16
<212> TYPE: DNA
<213> ORGANISM: Artificial Sequence

```
<220> FEATURE:
<223> OTHER INFORMATION: Synthetic

<400> SEQUENCE: 375
gatacgcaca ggacga                                                     16

<210> SEQ ID NO 376
<211> LENGTH: 14
<212> TYPE: DNA
<213> ORGANISM: Artificial Sequence
<220> FEATURE:
<223> OTHER INFORMATION: Synthetic

<400> SEQUENCE: 376
gatacacagg acga                                                       14

<210> SEQ ID NO 377
<211> LENGTH: 13
<212> TYPE: DNA
<213> ORGANISM: Artificial Sequence
<220> FEATURE:
<223> OTHER INFORMATION: Synthetic

<400> SEQUENCE: 377
gatacgcgtc cga                                                        13

<210> SEQ ID NO 378
<211> LENGTH: 12
<212> TYPE: DNA
<213> ORGANISM: Artificial Sequence
<220> FEATURE:
<223> OTHER INFORMATION: Synthetic

<400> SEQUENCE: 378
gatacgcgtc ga                                                         12

<210> SEQ ID NO 379
<211> LENGTH: 17
<212> TYPE: DNA
<213> ORGANISM: Artificial Sequence
<220> FEATURE:
<223> OTHER INFORMATION: Synthetic

<400> SEQUENCE: 379
gatacgcgtc aggacga                                                    17

<210> SEQ ID NO 380
<211> LENGTH: 12
<212> TYPE: DNA
<213> ORGANISM: Artificial Sequence
<220> FEATURE:
<223> OTHER INFORMATION: Synthetic

<400> SEQUENCE: 380
gatacaggac ga                                                         12

<210> SEQ ID NO 381
<211> LENGTH: 17
<212> TYPE: DNA
<213> ORGANISM: Artificial Sequence
<220> FEATURE:
<223> OTHER INFORMATION: Synthetic

<400> SEQUENCE: 381
gatacgccac aggacga                                                    17
```

<210> SEQ ID NO 382
<211> LENGTH: 10
<212> TYPE: DNA
<213> ORGANISM: Artificial Sequence
<220> FEATURE:
<223> OTHER INFORMATION: Synthetic

<400> SEQUENCE: 382
gatacgcgtc                                                              10

<210> SEQ ID NO 383
<211> LENGTH: 21
<212> TYPE: DNA
<213> ORGANISM: Artificial Sequence
<220> FEATURE:
<223> OTHER INFORMATION: Synthetic

<400> SEQUENCE: 383
gatacgcgtc acacaggacg a                                                 21

<210> SEQ ID NO 384
<211> LENGTH: 19
<212> TYPE: DNA
<213> ORGANISM: Artificial Sequence
<220> FEATURE:
<223> OTHER INFORMATION: Synthetic

<400> SEQUENCE: 384
gatacgctgc acaggacga                                                    19

<210> SEQ ID NO 385
<211> LENGTH: 14
<212> TYPE: DNA
<213> ORGANISM: Artificial Sequence
<220> FEATURE:
<223> OTHER INFORMATION: Synthetic

<400> SEQUENCE: 385
gatacgcagg acga                                                         14

<210> SEQ ID NO 386
<211> LENGTH: 13
<212> TYPE: DNA
<213> ORGANISM: Artificial Sequence
<220> FEATURE:
<223> OTHER INFORMATION: Synthetic

<400> SEQUENCE: 386
acgcacagga cga                                                          13

<210> SEQ ID NO 387
<211> LENGTH: 20
<212> TYPE: DNA
<213> ORGANISM: Artificial Sequence
<220> FEATURE:
<223> OTHER INFORMATION: Synthetic

<400> SEQUENCE: 387
atgacgagca gcggggtctg                                                   20

<210> SEQ ID NO 388
<211> LENGTH: 21
<212> TYPE: DNA
<213> ORGANISM: Artificial Sequence
<220> FEATURE:
<223> OTHER INFORMATION: Synthetic

<400> SEQUENCE: 388
atgacgagca agcggggtct g                                              21

<210> SEQ ID NO 389
<211> LENGTH: 17
<212> TYPE: DNA
<213> ORGANISM: Artificial Sequence
<220> FEATURE:
<223> OTHER INFORMATION: Synthetic

<400> SEQUENCE: 389
atgacgagcg gggtctg                                                   17

<210> SEQ ID NO 390
<211> LENGTH: 18
<212> TYPE: DNA
<213> ORGANISM: Artificial Sequence
<220> FEATURE:
<223> OTHER INFORMATION: Synthetic

<400> SEQUENCE: 390
atgacgaagc ggggtctg                                                  18

<210> SEQ ID NO 391
<211> LENGTH: 14
<212> TYPE: DNA
<213> ORGANISM: Artificial Sequence
<220> FEATURE:
<223> OTHER INFORMATION: Synthetic

<400> SEQUENCE: 391
atgagcgggg tctg                                                      14

<210> SEQ ID NO 392
<211> LENGTH: 22
<212> TYPE: DNA
<213> ORGANISM: Artificial Sequence
<220> FEATURE:
<223> OTHER INFORMATION: Synthetic

<400> SEQUENCE: 392
atgacgagca aagcggggtc tg                                             22

<210> SEQ ID NO 393
<211> LENGTH: 13
<212> TYPE: DNA
<213> ORGANISM: Artificial Sequence
<220> FEATURE:
<223> OTHER INFORMATION: Synthetic

<400> SEQUENCE: 393
atgacggggt ctg                                                       13

<210> SEQ ID NO 394
<211> LENGTH: 20
<212> TYPE: DNA
<213> ORGANISM: Artificial Sequence
<220> FEATURE:
<223> OTHER INFORMATION: Synthetic

<400> SEQUENCE: 394
catgacttta ttctggaaga                                                20

<210> SEQ ID NO 395

```
<211> LENGTH: 13
<212> TYPE: DNA
<213> ORGANISM: Artificial Sequence
<220> FEATURE:
<223> OTHER INFORMATION: Synthetic

<400> SEQUENCE: 395
catgactgga aga                                                              13

<210> SEQ ID NO 396
<211> LENGTH: 16
<212> TYPE: DNA
<213> ORGANISM: Artificial Sequence
<220> FEATURE:
<223> OTHER INFORMATION: Synthetic

<400> SEQUENCE: 396
catgacttct ggaaga                                                           16

<210> SEQ ID NO 397
<211> LENGTH: 17
<212> TYPE: DNA
<213> ORGANISM: Artificial Sequence
<220> FEATURE:
<223> OTHER INFORMATION: Synthetic

<400> SEQUENCE: 397
catgactttc tggaaga                                                          17

<210> SEQ ID NO 398
<211> LENGTH: 21
<212> TYPE: DNA
<213> ORGANISM: Artificial Sequence
<220> FEATURE:
<223> OTHER INFORMATION: Synthetic

<400> SEQUENCE: 398
catgacttta tttctggaag a                                                     21

<210> SEQ ID NO 399
<211> LENGTH: 21
<212> TYPE: DNA
<213> ORGANISM: Artificial Sequence
<220> FEATURE:
<223> OTHER INFORMATION: Synthetic

<400> SEQUENCE: 399
catgacttta attctggaag a                                                     21

<210> SEQ ID NO 400
<211> LENGTH: 18
<212> TYPE: DNA
<213> ORGANISM: Artificial Sequence
<220> FEATURE:
<223> OTHER INFORMATION: Synthetic

<400> SEQUENCE: 400
catgactttt ctggaaga                                                         18

<210> SEQ ID NO 401
<211> LENGTH: 11
<212> TYPE: DNA
<213> ORGANISM: Artificial Sequence
<220> FEATURE:
<223> OTHER INFORMATION: Synthetic

<400> SEQUENCE: 401
```
catctggaag a                                                                          11

<210> SEQ ID NO 402
<211> LENGTH: 19
<212> TYPE: DNA
<213> ORGANISM: Artificial Sequence
<220> FEATURE:
<223> OTHER INFORMATION: Synthetic

<400> SEQUENCE: 402
catgactttt tctggaaga                                                                  19

<210> SEQ ID NO 403
<211> LENGTH: 19
<212> TYPE: DNA
<213> ORGANISM: Artificial Sequence
<220> FEATURE:
<223> OTHER INFORMATION: Synthetic

<400> SEQUENCE: 403
catgacttta tctggaaga                                                                  19

<210> SEQ ID NO 404
<211> LENGTH: 13
<212> TYPE: DNA
<213> ORGANISM: Artificial Sequence
<220> FEATURE:
<223> OTHER INFORMATION: Synthetic

<400> SEQUENCE: 404
catgacttta aga                                                                        13

<210> SEQ ID NO 405
<211> LENGTH: 10
<212> TYPE: DNA
<213> ORGANISM: Artificial Sequence
<220> FEATURE:
<223> OTHER INFORMATION: Synthetic

<400> SEQUENCE: 405
ttctggaaga                                                                            10

<210> SEQ ID NO 406
<211> LENGTH: 18
<212> TYPE: DNA
<213> ORGANISM: Artificial Sequence
<220> FEATURE:
<223> OTHER INFORMATION: Synthetic

<400> SEQUENCE: 406
catgacttta ctggaaga                                                                   18

<210> SEQ ID NO 407
<211> LENGTH: 20
<212> TYPE: DNA
<213> ORGANISM: Artificial Sequence
<220> FEATURE:
<223> OTHER INFORMATION: Synthetic

<400> SEQUENCE: 407
gtcctattac agctggggca                                                                 20

<210> SEQ ID NO 408
<211> LENGTH: 18
<212> TYPE: DNA

```
<213> ORGANISM: Artificial Sequence
<220> FEATURE:
<223> OTHER INFORMATION: Synthetic

<400> SEQUENCE: 408
gtcctattag ctggggca                                                 18

<210> SEQ ID NO 409
<211> LENGTH: 19
<212> TYPE: DNA
<213> ORGANISM: Artificial Sequence
<220> FEATURE:
<223> OTHER INFORMATION: Synthetic

<400> SEQUENCE: 409
gtcctattaa gctggggca                                                19

<210> SEQ ID NO 410
<211> LENGTH: 17
<212> TYPE: DNA
<213> ORGANISM: Artificial Sequence
<220> FEATURE:
<223> OTHER INFORMATION: Synthetic

<400> SEQUENCE: 410
gtcctatagc tggggca                                                  17

<210> SEQ ID NO 411
<211> LENGTH: 16
<212> TYPE: DNA
<213> ORGANISM: Artificial Sequence
<220> FEATURE:
<223> OTHER INFORMATION: Synthetic

<400> SEQUENCE: 411
gtcctaagct ggggca                                                   16

<210> SEQ ID NO 412
<211> LENGTH: 15
<212> TYPE: DNA
<213> ORGANISM: Artificial Sequence
<220> FEATURE:
<223> OTHER INFORMATION: Synthetic

<400> SEQUENCE: 412
gtcctagctg gggca                                                    15

<210> SEQ ID NO 413
<211> LENGTH: 17
<212> TYPE: DNA
<213> ORGANISM: Artificial Sequence
<220> FEATURE:
<223> OTHER INFORMATION: Synthetic

<400> SEQUENCE: 413
gtcctattac tggggca                                                  17

<210> SEQ ID NO 414
<211> LENGTH: 14
<212> TYPE: DNA
<213> ORGANISM: Artificial Sequence
<220> FEATURE:
<223> OTHER INFORMATION: Synthetic

<400> SEQUENCE: 414
gtccagctgg ggca                                                     14
```

<210> SEQ ID NO 415
<211> LENGTH: 21
<212> TYPE: DNA
<213> ORGANISM: Artificial Sequence
<220> FEATURE:
<223> OTHER INFORMATION: Synthetic

<400> SEQUENCE: 415
gtcctattac cagctggggc a                                              21

<210> SEQ ID NO 416
<211> LENGTH: 17
<212> TYPE: DNA
<213> ORGANISM: Artificial Sequence
<220> FEATURE:
<223> OTHER INFORMATION: Synthetic

<400> SEQUENCE: 416
gtcctattgc tggggca                                                   17

<210> SEQ ID NO 417
<211> LENGTH: 19
<212> TYPE: DNA
<213> ORGANISM: Artificial Sequence
<220> FEATURE:
<223> OTHER INFORMATION: Synthetic

<400> SEQUENCE: 417
gtcctattac gctggggca                                                 19

<210> SEQ ID NO 418
<211> LENGTH: 11
<212> TYPE: DNA
<213> ORGANISM: Artificial Sequence
<220> FEATURE:
<223> OTHER INFORMATION: Synthetic

<400> SEQUENCE: 418
gtcctggggc a                                                         11

<210> SEQ ID NO 419
<211> LENGTH: 20
<212> TYPE: DNA
<213> ORGANISM: Artificial Sequence
<220> FEATURE:
<223> OTHER INFORMATION: Synthetic

<400> SEQUENCE: 419
acttgttagc cccagggcca                                                20

<210> SEQ ID NO 420
<211> LENGTH: 18
<212> TYPE: DNA
<213> ORGANISM: Artificial Sequence
<220> FEATURE:
<223> OTHER INFORMATION: Synthetic

<400> SEQUENCE: 420
acttgttagc cagggcca                                                  18

<210> SEQ ID NO 421
<211> LENGTH: 19
<212> TYPE: DNA
<213> ORGANISM: Artificial Sequence
<220> FEATURE:

<223> OTHER INFORMATION: Synthetic

<400> SEQUENCE: 421
acttgttagc ccagggcca                                            19

<210> SEQ ID NO 422
<211> LENGTH: 17
<212> TYPE: DNA
<213> ORGANISM: Artificial Sequence
<220> FEATURE:
<223> OTHER INFORMATION: Synthetic

<400> SEQUENCE: 422
acttgttagc agggcca                                              17

<210> SEQ ID NO 423
<211> LENGTH: 12
<212> TYPE: DNA
<213> ORGANISM: Artificial Sequence
<220> FEATURE:
<223> OTHER INFORMATION: Synthetic

<400> SEQUENCE: 423
acttgttagc ca                                                   12

<210> SEQ ID NO 424
<211> LENGTH: 14
<212> TYPE: DNA
<213> ORGANISM: Artificial Sequence
<220> FEATURE:
<223> OTHER INFORMATION: Synthetic

<400> SEQUENCE: 424
acttgttagg gcca                                                 14

<210> SEQ ID NO 425
<211> LENGTH: 21
<212> TYPE: DNA
<213> ORGANISM: Artificial Sequence
<220> FEATURE:
<223> OTHER INFORMATION: Synthetic

<400> SEQUENCE: 425
acttgttagc ccccagggcc a                                         21

<210> SEQ ID NO 426
<211> LENGTH: 17
<212> TYPE: DNA
<213> ORGANISM: Artificial Sequence
<220> FEATURE:
<223> OTHER INFORMATION: Synthetic

<400> SEQUENCE: 426
acttgttccc agggcca                                              17

<210> SEQ ID NO 427
<211> LENGTH: 10
<212> TYPE: DNA
<213> ORGANISM: Artificial Sequence
<220> FEATURE:
<223> OTHER INFORMATION: Synthetic

<400> SEQUENCE: 427
cccagggcca                                                      10

```
<210> SEQ ID NO 428
<211> LENGTH: 18
<212> TYPE: DNA
<213> ORGANISM: Artificial Sequence
<220> FEATURE:
<223> OTHER INFORMATION: Synthetic

<400> SEQUENCE: 428
acttgttacc cagggcca                                                 18

<210> SEQ ID NO 429
<211> LENGTH: 15
<212> TYPE: DNA
<213> ORGANISM: Artificial Sequence
<220> FEATURE:
<223> OTHER INFORMATION: Synthetic

<400> SEQUENCE: 429
acttgcccag ggcca                                                    15

<210> SEQ ID NO 430
<211> LENGTH: 16
<212> TYPE: DNA
<213> ORGANISM: Artificial Sequence
<220> FEATURE:
<223> OTHER INFORMATION: Synthetic

<400> SEQUENCE: 430
acttgtccca gggcca                                                   16

<210> SEQ ID NO 431
<211> LENGTH: 10
<212> TYPE: DNA
<213> ORGANISM: Artificial Sequence
<220> FEATURE:
<223> OTHER INFORMATION: Synthetic

<400> SEQUENCE: 431
accagggcca                                                          10

<210> SEQ ID NO 432
<211> LENGTH: 13
<212> TYPE: DNA
<213> ORGANISM: Artificial Sequence
<220> FEATURE:
<223> OTHER INFORMATION: Synthetic

<400> SEQUENCE: 432
acttgcaggg cca                                                      13

<210> SEQ ID NO 433
<211> LENGTH: 13
<212> TYPE: DNA
<213> ORGANISM: Artificial Sequence
<220> FEATURE:
<223> OTHER INFORMATION: Synthetic

<400> SEQUENCE: 433
acttgttagc cca                                                      13

<210> SEQ ID NO 434
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 434
aactgcctct atatggtgtg                                            20

<210> SEQ ID NO 435
<211> LENGTH: 21
<212> TYPE: DNA
<213> ORGANISM: Artificial Sequence
<220> FEATURE:
<223> OTHER INFORMATION: Synthetic

<400> SEQUENCE: 435
aactgcctct tatatggtgt g                                          21

<210> SEQ ID NO 436
<211> LENGTH: 18
<212> TYPE: DNA
<213> ORGANISM: Artificial Sequence
<220> FEATURE:
<223> OTHER INFORMATION: Synthetic

<400> SEQUENCE: 436
aactgcctat atggtgtg                                              18

<210> SEQ ID NO 437
<211> LENGTH: 18
<212> TYPE: DNA
<213> ORGANISM: Artificial Sequence
<220> FEATURE:
<223> OTHER INFORMATION: Synthetic

<400> SEQUENCE: 437
aactgcctct atggtgtg                                              18

<210> SEQ ID NO 438
<211> LENGTH: 19
<212> TYPE: DNA
<213> ORGANISM: Artificial Sequence
<220> FEATURE:
<223> OTHER INFORMATION: Synthetic

<400> SEQUENCE: 438
aactgcctca tatggtgtg                                             19

<210> SEQ ID NO 439
<211> LENGTH: 16
<212> TYPE: DNA
<213> ORGANISM: Artificial Sequence
<220> FEATURE:
<223> OTHER INFORMATION: Synthetic

<400> SEQUENCE: 439
aactgtatat ggtgtg                                                16

<210> SEQ ID NO 440
<211> LENGTH: 17
<212> TYPE: DNA
<213> ORGANISM: Artificial Sequence
<220> FEATURE:
<223> OTHER INFORMATION: Synthetic

<400> SEQUENCE: 440
aactgctata tggtgtg                                               17

<210> SEQ ID NO 441
<211> LENGTH: 14
```

```
<212> TYPE: DNA
<213> ORGANISM: Artificial Sequence
<220> FEATURE:
<223> OTHER INFORMATION: Synthetic

<400> SEQUENCE: 441
aactatatgg tgtg                                                      14

<210> SEQ ID NO 442
<211> LENGTH: 19
<212> TYPE: DNA
<213> ORGANISM: Artificial Sequence
<220> FEATURE:
<223> OTHER INFORMATION: Synthetic

<400> SEQUENCE: 442
aactgcctta tatggtgtg                                                 19

<210> SEQ ID NO 443
<211> LENGTH: 10
<212> TYPE: DNA
<213> ORGANISM: Artificial Sequence
<220> FEATURE:
<223> OTHER INFORMATION: Synthetic

<400> SEQUENCE: 443
aactgcctct                                                           10

<210> SEQ ID NO 444
<211> LENGTH: 11
<212> TYPE: DNA
<213> ORGANISM: Artificial Sequence
<220> FEATURE:
<223> OTHER INFORMATION: Synthetic

<400> SEQUENCE: 444
tatatggtgt g                                                         11

<210> SEQ ID NO 445
<211> LENGTH: 11
<212> TYPE: DNA
<213> ORGANISM: Artificial Sequence
<220> FEATURE:
<223> OTHER INFORMATION: Synthetic

<400> SEQUENCE: 445
aactgcctct a                                                         11

<210> SEQ ID NO 446
<211> LENGTH: 19
<212> TYPE: DNA
<213> ORGANISM: Artificial Sequence
<220> FEATURE:
<223> OTHER INFORMATION: Synthetic

<400> SEQUENCE: 446
aactgcctct tatggtgtg                                                 19

<210> SEQ ID NO 447
<211> LENGTH: 10
<212> TYPE: DNA
<213> ORGANISM: Artificial Sequence
<220> FEATURE:
<223> OTHER INFORMATION: Synthetic

<400> SEQUENCE: 447
```
aactggtgtg 10

<210> SEQ ID NO 448
<211> LENGTH: 20
<212> TYPE: DNA
<213> ORGANISM: Artificial Sequence
<220> FEATURE:
<223> OTHER INFORMATION: Synthetic

<400> SEQUENCE: 448
ttctggttgt cacaggtgga 20

<210> SEQ ID NO 449
<211> LENGTH: 21
<212> TYPE: DNA
<213> ORGANISM: Artificial Sequence
<220> FEATURE:
<223> OTHER INFORMATION: Synthetic

<400> SEQUENCE: 449
ttctggttgt tcacaggtgg a 21

<210> SEQ ID NO 450
<211> LENGTH: 10
<212> TYPE: DNA
<213> ORGANISM: Artificial Sequence
<220> FEATURE:
<223> OTHER INFORMATION: Synthetic

<400> SEQUENCE: 450
ttctggtgga 10

<210> SEQ ID NO 451
<211> LENGTH: 10
<212> TYPE: DNA
<213> ORGANISM: Artificial Sequence
<220> FEATURE:
<223> OTHER INFORMATION: Synthetic

<400> SEQUENCE: 451
ttcaggtgga 10

<210> SEQ ID NO 452
<211> LENGTH: 18
<212> TYPE: DNA
<213> ORGANISM: Artificial Sequence
<220> FEATURE:
<223> OTHER INFORMATION: Synthetic

<400> SEQUENCE: 452
ttctggttca caggtgga 18

<210> SEQ ID NO 453
<211> LENGTH: 22
<212> TYPE: DNA
<213> ORGANISM: Artificial Sequence
<220> FEATURE:
<223> OTHER INFORMATION: Synthetic

<400> SEQUENCE: 453
ttctggttgt ttcacaggtg ga 22

<210> SEQ ID NO 454
<211> LENGTH: 11
<212> TYPE: DNA
<213> ORGANISM: Artificial Sequence -continued

```
<220> FEATURE:
<223> OTHER INFORMATION: Synthetic

<400> SEQUENCE: 454
ttctggttgg a                                                              11

<210> SEQ ID NO 455
<211> LENGTH: 21
<212> TYPE: DNA
<213> ORGANISM: Artificial Sequence
<220> FEATURE:
<223> OTHER INFORMATION: Synthetic

<400> SEQUENCE: 455
ttctggttgt ccacaggtgg a                                                   21

<210> SEQ ID NO 456
<211> LENGTH: 13
<212> TYPE: DNA
<213> ORGANISM: Artificial Sequence
<220> FEATURE:
<223> OTHER INFORMATION: Synthetic

<400> SEQUENCE: 456
ttccacaggt gga                                                            13

<210> SEQ ID NO 457
<211> LENGTH: 19
<212> TYPE: DNA
<213> ORGANISM: Artificial Sequence
<220> FEATURE:
<223> OTHER INFORMATION: Synthetic

<400> SEQUENCE: 457
ttctggtttc acaggtgga                                                      19

<210> SEQ ID NO 458
<211> LENGTH: 19
<212> TYPE: DNA
<213> ORGANISM: Artificial Sequence
<220> FEATURE:
<223> OTHER INFORMATION: Synthetic

<400> SEQUENCE: 458
ttctggttgc acaggtgga                                                      19

<210> SEQ ID NO 459
<211> LENGTH: 21
<212> TYPE: DNA
<213> ORGANISM: Artificial Sequence
<220> FEATURE:
<223> OTHER INFORMATION: Synthetic

<400> SEQUENCE: 459
ttctggttgt acacaggtgg a                                                   21

<210> SEQ ID NO 460
<211> LENGTH: 10
<212> TYPE: DNA
<213> ORGANISM: Artificial Sequence
<220> FEATURE:
<223> OTHER INFORMATION: Synthetic

<400> SEQUENCE: 460
ttctggttga                                                                10
```

```
<210> SEQ ID NO 461
<211> LENGTH: 19
<212> TYPE: DNA
<213> ORGANISM: Artificial Sequence
<220> FEATURE:
<223> OTHER INFORMATION: Synthetic

<400> SEQUENCE: 461
ttctggttgt acaggtgga                                                 19

<210> SEQ ID NO 462
<211> LENGTH: 20
<212> TYPE: DNA
<213> ORGANISM: Artificial Sequence
<220> FEATURE:
<223> OTHER INFORMATION: Synthetic

<400> SEQUENCE: 462
tgtgagaagc cacaggaagt                                                20

<210> SEQ ID NO 463
<211> LENGTH: 10
<212> TYPE: DNA
<213> ORGANISM: Artificial Sequence
<220> FEATURE:
<223> OTHER INFORMATION: Synthetic

<400> SEQUENCE: 463
tgtgagaagt                                                           10

<210> SEQ ID NO 464
<211> LENGTH: 19
<212> TYPE: DNA
<213> ORGANISM: Artificial Sequence
<220> FEATURE:
<223> OTHER INFORMATION: Synthetic

<400> SEQUENCE: 464
tgtgagaagc acaggaagt                                                 19

<210> SEQ ID NO 465
<211> LENGTH: 21
<212> TYPE: DNA
<213> ORGANISM: Artificial Sequence
<220> FEATURE:
<223> OTHER INFORMATION: Synthetic

<400> SEQUENCE: 465
tgtgagaagc ccacaggaag t                                              21

<210> SEQ ID NO 466
<211> LENGTH: 11
<212> TYPE: DNA
<213> ORGANISM: Artificial Sequence
<220> FEATURE:
<223> OTHER INFORMATION: Synthetic

<400> SEQUENCE: 466
tgtgaggaag t                                                         11

<210> SEQ ID NO 467
<211> LENGTH: 18
<212> TYPE: DNA
<213> ORGANISM: Artificial Sequence
<220> FEATURE:
<223> OTHER INFORMATION: Synthetic
```

<400> SEQUENCE: 467
tgtgagaagc caggaagt                                                18

<210> SEQ ID NO 468
<211> LENGTH: 14
<212> TYPE: DNA
<213> ORGANISM: Artificial Sequence
<220> FEATURE:
<223> OTHER INFORMATION: Synthetic

<400> SEQUENCE: 468
tgtgagaagg aagt                                                    14

<210> SEQ ID NO 469
<211> LENGTH: 10
<212> TYPE: DNA
<213> ORGANISM: Artificial Sequence
<220> FEATURE:
<223> OTHER INFORMATION: Synthetic

<400> SEQUENCE: 469
cacaggaagt                                                         10

<210> SEQ ID NO 470
<211> LENGTH: 21
<212> TYPE: DNA
<213> ORGANISM: Artificial Sequence
<220> FEATURE:
<223> OTHER INFORMATION: Synthetic

<400> SEQUENCE: 470
tgtgagaagc acacaggaag t                                            21

<210> SEQ ID NO 471
<211> LENGTH: 17
<212> TYPE: DNA
<213> ORGANISM: Artificial Sequence
<220> FEATURE:
<223> OTHER INFORMATION: Synthetic

<400> SEQUENCE: 471
tgtgagaagc aggaagt                                                 17

<210> SEQ ID NO 472
<211> LENGTH: 14
<212> TYPE: DNA
<213> ORGANISM: Artificial Sequence
<220> FEATURE:
<223> OTHER INFORMATION: Synthetic

<400> SEQUENCE: 472
tgtgcacagg aagt                                                    14

<210> SEQ ID NO 473
<211> LENGTH: 11
<212> TYPE: DNA
<213> ORGANISM: Artificial Sequence
<220> FEATURE:
<223> OTHER INFORMATION: Synthetic

<400> SEQUENCE: 473
ccacaggaag t                                                       11

<210> SEQ ID NO 474

```
<211> LENGTH: 17
<212> TYPE: DNA
<213> ORGANISM: Artificial Sequence
<220> FEATURE:
<223> OTHER INFORMATION: Synthetic

<400> SEQUENCE: 474
tgtgagacac aggaagt                                              17

<210> SEQ ID NO 475
<211> LENGTH: 15
<212> TYPE: DNA
<213> ORGANISM: Artificial Sequence
<220> FEATURE:
<223> OTHER INFORMATION: Synthetic

<400> SEQUENCE: 475
tgtgagacag gaagt                                                15

<210> SEQ ID NO 476
<211> LENGTH: 18
<212> TYPE: DNA
<213> ORGANISM: Artificial Sequence
<220> FEATURE:
<223> OTHER INFORMATION: Synthetic

<400> SEQUENCE: 476
tgtgagaaca caggaagt                                             18

<210> SEQ ID NO 477
<211> LENGTH: 10
<212> TYPE: DNA
<213> ORGANISM: Artificial Sequence
<220> FEATURE:
<223> OTHER INFORMATION: Synthetic

<400> SEQUENCE: 477
tgtgagaagc                                                      10

<210> SEQ ID NO 478
<211> LENGTH: 22
<212> TYPE: DNA
<213> ORGANISM: Artificial Sequence
<220> FEATURE:
<223> OTHER INFORMATION: Synthetic

<400> SEQUENCE: 478
tgtgagaagc cacacaggaa gt                                        22
```

GENETICALLY ENGINEERED T CELLS WITH REGNASE-1 AND/OR TGFBRII DISRUPTION HAVE IMPROVED FUNCTIONALITY AND PERSISTENCE

CROSS REFERENCE TO RELATED APPLICATIONS

This application is a continuation of, and claims the benefit of and priority to, U.S. patent application Ser. No. 17/483,100 filed Sep. 23, 2021, which claims the benefit of the filing dates of U.S. Provisional Application No. 63/082,357, filed Sep. 23, 2020, U.S. Provisional Application No. 63/124,429, filed Dec. 11, 2020, and U.S. Provisional Application No. 63/225,673, filed Jul. 26, 2021. The entire contents of each of the prior applications are incorporated by reference herein.

REFERENCE TO SEQUENCE LISTING

The instant application contains a substitute Sequence Listing that has been filed electronically in the form of a text file, created Nov. 16, 2021, and named "095136-0379-026USCON3_SUBSEQ.TXT" (236,352 bytes), the contents of which are incorporated by reference herein in their entirety.

BACKGROUND OF THE INVENTION

Chimeric antigen receptor (CAR) T-cell therapy uses genetically modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

T cells having improved persistence in culture are desired in CAR T therapy. Such T cells live longer in both in vitro and in vivo, thereby conferring benefits in CAR T cell manufacturing and clinical applications. However, it remains challenging to improve persistence of T cells in culture.

SUMMARY OF THE INVENTION

The present disclosure is based, at least in part, on the development of genetically edited T cells carrying a disrupted Regnase 1 (Reg1) gene (e.g., "Reg1 Knockout T cells"), a disrupted TGFBRII gene (e.g., "TGFBRII Knockout T cells", or genetically edited T cells carrying both a disrupted Reg1 gene and a disrupted TGFBRII gene, and effective methods of producing such genetically edited T cells via CRISPR/Cas-mediated gene editing using guide RNAs, for example, those targeting specific sites within the Reg1 gene with high on-target editing efficiency and low off-target editing efficiency, and/or those targeting specific sites within the TGFBRII gene with high on-target editing efficiency and low off-target editing efficiency.

Such genetically engineered T cells exhibits at least one of the following advantageous features: (a) improved cell growth activity; (b) enhanced persistence; (c) reduced T cell exhaustion; (d) resistant to inhibitory effects induced by TGF-β; (e) enhanced cell killing capacity; and (f) resistant to inhibitory effects by fibroblasts and/or inhibitory factors secreted thereby.

The Reg1 disrupted T cells, the TGFBRII disrupted T cells, or the Reg1/TGFBRII double disrupted T cells disclosed herein can further be genetically engineered to express a chimeric antigen receptor (CAR) targeting an antigen of interest, e.g., an antigen associated with an undesired cell such as a cancer cell, and to comprise one or more additional disrupted genes, for example, TRAC, β2M, CD70, or a combination thereof. The resultant CAR-expressing, Reg1 disrupted T cells exhibit enhanced cytotoxic activity against target cells and anti-tumor activity as compared with CAR-T cells having a wild-type Reg1 gene.

In some aspects, the current disclosure is related to the development of genetically engineered CAR T cells that comprise a disrupted Reg1 gene. The genetically engineered CAR T cells, in certain aspects, are further genetically engineered to comprise a disrupted cluster of differentiation 70 (CD70) gene. In some aspects, the CAR T cells described herein may express anti-CD70 CAR, anti-cluster of differentiation 19 (CD19) CAR or anti-B-cell maturation antigen (anti-BCMA) CAR.

The genetically edited T cells disclosed herein showed enhanced cell expansion, longevity and proliferation capacity in culture, enhanced potency (e.g., enhanced cytotoxicity), and enhanced CAR-T efficacy in animal models (via, e.g., longer persistence). Further, the genetically edited T cells showed cytokine-dependent growth, indicating safety. In addition, disrupting both the Reg1 and TGFBRII genes exhibited synergistic effects in anti-tumor activity and CAR-T cell expansion and persistence as observed in animal models.

Accordingly, the present disclosure provides, in some aspects, a population of genetically engineered T cells, comprising: (i) a disrupted Regnase-1 (Reg1) gene; and/or (ii) a disrupted Transforming Growth Factor Beta Receptor II (TGFBRII) gene. In some embodiments, the population of genetically engineered T cells comprises (i). In some embodiments, population of genetically engineered T cells comprises (ii). In other embodiments, the population of genetically engineered T cells comprises both (i) and (ii). Any of the genetically engineered T cells may be further engineered to express a chimeric antigen receptor (CAR).

The population of genetically engineered T cells disclosed herein, as compared to non-engineered T cell counterparts, has one or more of the following features: (a) improved cell growth activity; (b) enhanced persistence; (c) reduced T cell exhaustion; (d) resistant to inhibitory effects induced by TGF-β; (e) enhanced cell killing capacity; and (f) resistant to inhibitory effects by fibroblasts and/or inhibitory factors secreted thereby.

In some embodiments, the disrupted Reg1 gene is genetically edited in exon 1, exone 2, exon 3, or exon 4. In some examples, the disrupted Reg1 gene is genetically edited in exon 2 and/or exon 4. Alternatively or in addition, the disrupted TGFBRII gene is genetically edited in exon 1, exon 2, exon 3, exon 4, or exon 5. In some examples, the disrupted TGFBRII gene is genetically edited in exon 4. In other examples, the disrupted TGFBRII gene is genetically edited in exon 5. The disrupted Reg1 gene, the disrupted TGFBRII gene, or both can be genetically edited by a CRISPR/Cas-mediated gene editing system.

In some instances, the CRISPR/Cas-mediated gene editing comprises a guide RNA (gRNA) targeting a site in the Reg1 gene that comprises a nucleotide sequence listed in Table 22 (with or without PAM) (e.g., SEQ ID NO: 320, 322, 323, or 327, or the corresponding ones with PAM). For example, the gRNA targeting the Reg1 gene comprises a spacer that comprises the nucleotide sequence of listed in Table 22 (e.g., SEQ ID NO: 24, 32, 36, or 52). In some examples, the disrupted Reg1 gene comprises a nucleotide sequence selected from those listed in Tables 29-38 (e.g., Table 31, 33, 34, or 38).

In some instances, the CRISPR/Cas-mediated gene editing system comprises a guide RNA (gRNA) targeting a site in the TGFBRII gene that comprises a nucleotide sequence listed in Table 39 (with or without PAM). For example, the gRNA targeting the TGFBRII gene comprises a spacer listed in Table 39, for example, having a nucleotide sequence of any one of SEQ ID NOs: 270, 302, 308, and 312. In some examples, the disrupted TGFBRII gene may comprise a nucleotide sequence selected from those listed in Tables 40-48 (e.g., Table 43).

Any of the gRNAs disclosed herein may further comprise a scaffold sequence. For example, the gRNA targeting the Reg1 gene comprises any of the nucleotide sequences listed in Table 22. Examples include 22, 23, 30, 31, 34, 35, 50, and 51. Alternatively or in addition, the gRNA targeting the TGFBRII gene may comprise any of the nucleotide sequences provided in Table 39. Examples include SEQ ID NOs: 270, 271, 300, 301, 306, 307, 312, and 313.

Any of the populations of genetically engineered T cells disclosed herein may further comprise: (iii) a disrupted T cell receptor alpha chain constant region (TRAC) gene, (iv) a disrupted beta-2-microglobulin (β2M) gene, (v) a disrupted CD70 gene, or (vi) a combination of any of (iii)-(v). In some embodiments, the T cells comprise a disrupted T cell receptor alpha chain constant region (TRAC) gene. Alternatively or in addition, the T cells comprise a disrupted beta-2-microglobulin (β2M) gene. Any of the T cells disclosed herein may also comprise a disrupted CD70 gene. In some examples, the disrupted TRAC gene, the disrupted β2M gene, and/or the disrupted CD70 gene is genetically edited by one or more CRISPR/Cas-mediated gene editing system In some embodiments, the genetically engineered T cells may comprise a nucleic acid encoding the CAR, and wherein the nucleic acid is inserted in the genome of the T cells. In some instances, the nucleic acid encoding the CAR is inserted in the disrupted Reg1 gene, the disrupted TGFBRII gene, the disrupted TRAC gene, the disrupted β2M, or the disrupted CD70 gene. In some examples, the nucleic acid encoding the CAR is inserted in the disrupted TRAC gene. In specific examples, the nucleic acid encoding the CAR may replace the deleted fragment comprising SEQ ID NO: 69 in the TRAC gene. In some examples, the disrupted Reg1 gene may comprise a nucleotide sequence listed in Tables 29-38 (e.g., Table 31, 33, 34, or 38). In some examples, the disrupted TGFBRII gene may comprise a nucleotide sequence selected from those listed in Tables 40-48 (e.g., Table 43). In some examples, the disrupted TRAC gene may comprise a nucleotide sequence of any one of SEQ ID NOs: 75-82 (see Table 24). In some examples, the disrupted β2M may comprise a nucleotide sequence of any one of SEQ ID NOs: 83-88 (see Table 25). In some examples, the disrupted CD70 gene may comprise a nucleotide sequence of any one of SEQ ID NOs: 89-94 (see Table 26).

Any of the CAR constructs disclosed herein may comprise an extracellular antigen binding domain specific to a tumor antigen, a co-stimulatory signaling domain of 4-1BB or CD28, and a cytoplasmic signaling domain of CD3c. In some examples, the tumor antigen is CD19. In some examples, the tumor antigen is BCMA. In some examples, the tumor antigen is CD70. In some examples, the tumor antigen is CD33. In some examples, the tumor antigen is PTK7.

In some embodiments, the CAR binds CD19 (anti-CD19 CAR). The extracellular antigen binding domain in the anti-CD19 CAR can be a single chain variable fragment (scFv) that binds CD19 (anti-CD19 scFv). In some instances, the anti-CD19 scFv may comprise (i) a heavy chain variable region ($V_H$) that comprises the same heavy chain complementary determining regions (CDRs) as those in SEQ ID NO: 124; and (ii) a light chain variable region ($V_L$) that comprises the same light chain CDRs as those in SEQ ID NO: 125. In some examples, the $V_H$ comprises the amino acid sequence of SEQ ID NO: 124 and the $V_L$ comprises the amino acid sequence of SEQ ID NO: 125. In one example, the anti-CD19 scFv comprises the amino acid sequence of SEQ ID NO: 120. In one specific example, the anti-CD19 CAR comprises the amino acid sequence of SEQ ID NO: 118 (with an N-terminal signal peptide) or SEQ ID NO:353 (without N-terminal signal peptide).

In some embodiments, the CAR binds CD70 (anti-CD70 CAR). The extracellular antigen binding domain in the anti-CD70 CAR can be a single chain variable fragment (scFv) that binds CD70 (anti-CD70 scFv). In some instances, the anti-CD70 scFv comprises (i) a heavy chain variable region ($V_H$) that comprises the same heavy chain complementary determining regions (CDRs) as those in SEQ ID NO: 143; and (ii) a light chain variable region ($V_L$) that comprises the same light chain CDRs as those in SEQ ID NO: 144. In some examples, the $V_H$ comprises the amino acid sequence of SEQ ID NO: 143 and the $V_L$ comprises the amino acid sequence of SEQ ID NO: 144. In one example, the anti-CD70 scFv comprises the amino acid sequence of SEQ ID NO: 140 or 142. In one specific example, the anti-CD70 CAR comprises the amino acid sequence of SEQ ID NO: 138 (with an N-terminal signal peptide) or SEQ ID NO:354 (without N-terminal signal peptide).

In some embodiments, the CAR binds BCMA (anti-BCMA CAR). The extracellular antigen binding domain in the anti-BCMA CAR can be a single chain variable fragment (scFv) that binds BCMA (anti-BCMA CAR). In some instances, the anti-BCMA scFv comprises (i) a heavy chain variable region ($V_H$) that comprises the same heavy chain complementary determining regions (CDRs) as those in SEQ ID NO: 149; and (ii) a light chain variable region ($V_L$) that comprises the same light chain CDRs as those in SEQ ID NO: 150. In some examples, the $V_H$ comprises the amino acid sequence of SEQ ID NO: 149 and the $V_L$ comprises the amino acid sequence of SEQ ID NO: 150. In one example, the anti-BCMA scFv comprises the amino acid sequence of SEQ ID NO: 148. In one specific example, the anti-BCMA CAR comprises the amino acid sequence of SEQ ID NO: 146 (with an N-terminal signal peptide) or SEQ ID NO:355 (without N-terminal signal peptide).

The genetically engineered T cells disclosed herein may be derived from primary T cells of one or more human donors. In some instances, the genetically engineered T cells show cytokine-dependent growth.

In other aspects, the present disclosure provides a method for preparing any of the populations of genetically engineered T cells disclosed herein. In some instances, the method may comprise: (a) providing a plurality of cells, which are T cells or precursor cells thereof; (b) genetically editing the Reg1 gene and/or the TGFBRII gene; and (c) producing the population of genetically engineered T cells having disrupted Reg1 gene and/or the TGFBRII gene. In some examples, the T cells of step (a) are derived from primary T cells of one or more human donors. In some examples, step (b) comprises genetically editing the Reg1 gene. In some examples, step (b) comprises genetically editing the TGFBRII gene. In some examples, step (b) comprises genetically editing both the Reg1 gene and the TGFBRII gene.

In some embodiments, step (b) is performed by one or more CRISPR/Cas-mediated gene editing systems. For example, step (b) can be performed by delivering to the plurality of cells an RNA-guided nuclease and a gRNA targeting the Reg1 gene. In some instances, the gRNA targeting the Reg1 gene may be specific to an exon of the Reg1 gene, e.g., exon 2 or exon 4. In some examples, the gRNA targeting the Reg1 gene comprises a spacer that comprises a nucleotide sequence listed in Table 22 (e.g., SEQ ID NO: 24, 32, 36, or 52).

Alternatively or in addition, step (b) can be performed, inter alia, by delivering to the plurality of cells an RNA-guided nuclease and a gRNA targeting the TGFBRII gene. For example, the gRNA targeting the TGFBRII gene may be specific to an exon of the TGFBRII gene, e.g., exon 1, exon 2, exon 3, exon 4, and exon 5. In one example, the gRNA targeting the TGFBRII gene is specific to exon 4. In another example, the gRNA targeting the TGFBRII gene is specific to exon 5. In some instances, the gRNA targeting the TGFBRII gene comprises a spacer listed in Table 39. Examples include SEQ ID NOs: 272, 302, 308, and 314.

Any of the gRNAs disclosed herein may further comprise a scaffold sequence. For example, the gRNA targeting the Reg1 gene may comprise any of the nucleotide sequences listed in Table 22. Examples include SEQ ID NO: 22, 23, 30, 31, 34, 35, 50, and 51. Alternatively or in addition, the gRNA targeting the TGFBRII gene may comprise any of the nucleotide sequences provided in Table 39. Examples include SEQ ID NOs: 270, 271, 300, 301, 306, 307, 312, and 313.

In any of the methods disclosed herein, the plurality of T cells in step (a) comprises one or more of the following genetic modifications: (i) engineered to express a chimeric antigen receptor (CAR); (ii) has a disrupted T cell receptor alpha chain constant region (TRAC) gene; (iii) has a disrupted β2M gene; and (iv) has a disrupted CD70 gene.

Alternatively, any of the methods disclosed herein may further comprise:
(i) delivering to the T cells a nucleic acid encoding a chimeric antigen receptor (CAR);
(ii) genetically editing a TRAC gene to disrupt its expression;
(iii) genetically editing a β2M gene to disrupt its expression;
(iv) genetically editing a CD70 gene to disrupt its expression; or
(v) a combination thereof.

In some embodiments, one or more of (i)-(iv) are performed by one or more CRISPR/Cas-mediated gene editing system comprising one or more RNA-guided nucleases and one or more gRNAs targeting the TRAC gene, the β2M gene, and/or the CD70 gene. In some examples, the gRNA targeting the TRAC gene comprises a spacer that comprises the nucleotide sequence of SEQ ID NO: 61. In some examples, the gRNA targeting the β2M gene comprises a spacer that comprises the nucleotide sequence of SEQ ID NO: 65. In some examples, the gRNA targeting the CD70 gene comprises a spacer that comprises the nucleotide sequence of SEQ ID NO: 57. See Table 23.

In some embodiments, the method disclosed herein may comprise delivering to the T cells one or more ribonucleoprotein particles (RNP), which may comprise the RNA-guided nuclease, one or more of the gRNAs, and the nucleic acid encoding the CAR. In some examples, the RNA-guided nuclease is a Cas9 nuclease, for example, a S. pyogenes Cas9 nuclease.

In some embodiments, the nucleic acid encoding the CAR is in an AAV vector. In some instances, the nucleic acid encoding the CAR comprises a left homology arm and a right homology arm flanking the nucleotide sequence encoding the CAR. The left homology arm and the right homology arm are homologous to a genomic locus in the T cells, allowing for insertion of the nucleic acid into the genomic locus. In some examples, the genomic locus is in the Reg1 gene. In some examples, the genomic locus is in the TGFBRII gene. In some examples, the genomic locus is in the TRAC gene. In some examples, the genomic locus is in the β2M gene. In some examples, the genomic locus is in the CD70 gene.

In some examples, the method comprising disrupting the TRAC gene by a CRISPR/Cas-mediated gene editing system comprising a gRNA comprising the nucleotide sequence of SEQ ID NO: 59 and the nucleic acid encoding the CAR is inserted at the site targeted by the gRNA. Alternatively or in addition, the method may comprise delivering to the T cells a nucleic acid encoding a CAR, which is specific to CD70, and genetically editing the CD70 gene to disrupt its expression.

Any population of the genetically engineered T cells prepared by a method disclosed herein is also within the scope of the present disclosure.

Further, the present disclosure provides a method for eliminating undesired cells in a subject, the method comprising administering to a subject in need thereof any of the populations of genetically engineered T cells disclosed herein. In some embodiments, the undesired cells are cancer cells, for example, hematopoietic cancer cells or solid tumor cells. In some embodiments, the undesired cells are $CD19^+$. In some embodiments, the undesired cells are $BCMA^+$. In some embodiments, the undesired cells are $CD70^+$. In some embodiments, the undesired cells are $CD33^+$. In some embodiments, the undesired cells are $PTK7^+$.

In yet other aspects, provided herein is a guide RNA (gRNA) targeting a Reg1 gene, comprising a nucleotide sequence specific to a fragment in exon 2 or exon 4 of the Reg1 gene. In some embodiments, the gRNA comprises a spacer listed in Table 22 (e.g., SEQ ID NO: 24, 32, 36 or 52). Such a gRNA may further comprise a scaffold sequence. Alternatively or in addition, the gRNA comprises one or more modified nucleotides. For example, the gRNA comprises one or more 2'-O-methyl phosphorothioate residues at the 5' and/or 3' terminus of the gRNA. Examples of gRNAs targeting Reg1 include any of those listed in Table 22 (e.g., SEQ ID NO: 22, 23, 30, 31, 34, 35, 50, or 51; see also disclosures herein).

In still other aspects, provided herein is a guide RNA (gRNA) targeting a TGFBRII gene, comprising a nucleotide sequence specific to a fragment in exon 1, exon 2, exon 3, exon 4, or exon5 of the TGFBRII gene. In some examples, the gRNA comprises a nucleotide sequence specific to exon 4 of the TGFBRII gene. In other examples, the gRNA comprises a nucleotide sequence specific to exon 5 of the TGFBRII gene. In some instances, the gRNA comprises a spacer having the nucleotide sequence listed in Table 39 (e.g., SEQ ID NOs: 272, 302, 308, and 314). Such a gRNA may further comprise a scaffold sequence. Alternatively or in addition, the gRNA comprises one or more modified nucleotides. For example, the gRNA comprises one or more 2'-O-methyl phosphorothioate residues at the 5' and/or 3' terminus of the gRNA. Examples of gRNAs targeting the TGFBRII gene include any of those listed in Table 39 (e.g., SEQ ID NOs: 270, 271, 300, 301, 306, 307, 312, and 313).

Also within the scope of the present disclosure are any of the genetically engineered T cells, gRNAs targeting Reg1, or gRNAs targeting TGFBRII for use in treating a target disease as disclosed herein (e.g., cancer such as those disclosed herein), or uses of such for manufacturing a medicament for the intended therapeutic purposes The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1A: Proliferation of anti-CD70 CAR T cells (CAR T) with Reg1 KO using one of the 10 guides (Z01-Z10) targeting Reg1 as indicated. CAR T indicates anti-CD70 CAR T cells with an unedited (wild-type) Reg1 gene. FIG. 1B: Proliferation of anti-CD70 CAR T cells with Reg1 KO using guide REG1-Z10 (Z10) up to 52 days post HDR. Anti-CD70 CAR T cells with an unedited Reg1 gene are also shown (CAR T). (A) and (B) refer to duplicative assays.

FIG. 2A: Cell lysis of ACHN cells by anti-CD70 CAR T cells with Reg1 KO, using Regnase guides Z03 or Z10, relative to CAR T cells with an unedited (wild-type) Reg1 gene (CAR T). Cell lysis was measured after 24 h co-culture at day 12 post HDR. FIG. 2B: Cell lysis of ACHN cells by anti-CD70 CAR T cells with Regnase 1 KO using Regnase guides Z05 or Z06 relative to CAR T cells with an unedited Reg1 gene. Cell lysis was measured after 24 h co-culture at day 12 post HDR. FIG. 2C: Cell lysis of ACHN cells by anti-CD70 CAR T cells with Regnase 1 KO, using Regnase guides Z03, Z05, Z06 or Z10 relative to CAR T cells with an unedited Reg1 gene. Cell lysis was measured after 24 h co-culture at day 27 post HDR. FIG. 2D: Cell lysis of caki-1 cells by anti-CD70 CAR T cells with Regnase 1 KO using Regnase guides Z03, Z05, Z06 or Z10 relative to CAR T cells with an unedited Reg1 gene. Cell lysis was measured after 24 h co-culture at day 27 post HDR. FIG. 2E: Cell lysis of 769P cells by anti-CD70 CAR T cells with Regnase 1 KO using Regnase guides Z03, Z05, Z06 or Z10 relative to CAR T cells with an unedited Reg1 gene. Cell lysis was measured after 24 h co-culture at day 27 post HDR.

FIGS. 3A-3D include diagrams showing that exemplary CAR T cells (anti-CD70 CAR T cells) with Reg1 KO (CAR T+Reg KO, using Z10 guide as an example) express lower levels of T cell exhaustion markers in vitro relative to Reg1 wild-type counterparts (CAR T). FIG. 3A: Day 13 post HDR PD1 expression in CD4+ and CD8+ anti-CD70 CAR T cells with Reg1 KO (+Reg KO) relative to wild-type counterparts. FIG. 3B: Day 26 post HDR PD1 expression in CD4+ and CD8+ anti-CD70 CAR T cells with Reg1 KO (+Reg KO) relative to wild-type counterparts. FIG. 3C: Day 13 post HDR Tim3 expression in CD4+ and CD8+ anti-CD70 CAR T cells with Reg1 KO (+Reg KO) relative to wild-type counterparts. FIG. 3D: Day 26 post HDR Tim3 expression in CD4+ and CD8+ anti-CD70 CAR T cells with Reg1 KO (+Reg KO) relative to wild-type counterparts.

FIG. 4 is a diagram showing that exemplary CAR T cells (anti-CD19 CAR T cells) with Reg1 KO showed enhanced expansion in the presence of cytokines in vitro and continue to depend on cytokines for in vitro expansion. Anti-CD19 CAR T cells with a Reg1 KO (Anti-CD19 CAR T/Reg KO) and anti-CD19 CAR T cells with a wild-type Reg1 gene (Anti-CD19 CAR T) were cultured in the presence and absence (No cytokines) of cytokines for 40 days.

FIGS. 5A-5D include diagrams showing that exemplary CAR T cells (anti-CD19 CAR T cells) with Reg1 KO (Anti-CD19 CAR T/Reg KO) provide superior in vivo survival and decreased tumor burden relative to Reg1 wild-type counterparts (Anti-CD19 CAR T) in the intravenous disseminated Nalm-6 human acute lymphoblastic leukemia tumor xenograft mouse model. FIG. 5A: Probability of survival of untreated mice, mice dosed with 4e6 anti-CD19 CAR T cells, and 4e6 anti-CD19 CAR T/Reg KO cells. FIG. 5B: Probability of survival of untreated mice, mice dosed with 8e6 anti-CD19 CAR T cells, and 8e6 anti-CD19 CAR T/Reg KO cells. FIG. 5C: Bioluminescence signal from bioluminescent model leukemia cells in mice treated with 4e6 anti-CD19 CAR T cells or 4e6 anti-CD19 CAR T/Reg KO cells. FIG. 5D: Bioluminescence signal from bioluminescent model leukemia cells in mice treated with 8e6 anti-CD19 CAR T cells or 8e6 anti-CD19 CAR T/Reg KO cells.

FIG. 6A: Cell lysis of ACHN cells by anti-CD70 CAR T cells with Reg1 KO using guide REG1-Z10 (CAR T+Reg KO) relative to Reg1 wild-type counterparts (CAR T). Cell lysis was measured after 24 h co-culture at day 19 and 26 post HDR. FIG. 6B: Cell lysis of caki-1 cells by anti-CD70 CAR T cells with Reg1 KO using guide REG1-Z10 (CAR T+Reg KO) relative to Reg1 wild-type counterparts (CAR T). Cell lysis was measured after 24 h co-culture at day 13, 19 and 26 post HDR.

FIG. 7A: Indel rates of edited TGFBRII gene by eight gRNAs that target different TGFBRII gene exon5 as indicated. From left to right, EX1_T1, EX1_T3, EX2_T1, EX3_T1, EX3_T2, EX4_T1, EX4_T2, and EX5_T1, the nucleotide sequence of each of which is provided in Table 32. FIG. 7B: immunoblot of TGFBRII expression in gene-edited T cells. GAPDH was used as a loading control. The mock sample is unedited T cells with wild-type TGFBRII.

FIGS. 8A-8K include diagrams showing the effect of TGF-β on CAR T cell expansion. Anti-CD70 CAR T cells were exposed to different concentrations of recombinant human TGF-β (10, 20, 50, 100 ng/ml) and cell number was recorded at different time points (FIG. 8A). T cells with or without TGFBRII knock-out, generated using different TGFBRII gRNAs as indicated, were incubated with 0 or 50 ng/ml of TGFB-β and cell expansion was recorded over time (FIGS. 8B-8K).

FIGS. 10A-10E include diagrams showing the effect of TGFBRII KO on CAR T cell kill ability against multiple tumor cell lines. The cell kill capacity of anti-CD70 CAR T cells was compared to anti-CD70 CAR T cells with TGFBRII KO. Cell killing activity of the CAR T cells was assessed against CAM-1 (FIG. 10A) H1975 (FIG. 10B), Hs-766T (FIG. 10C), 786-O (FIG. 10D) and SK-OV3 (FIG. 10E). TGFBRII KO improves cytotoxicity of CAR-T cells.

FIG. 11 is a graph showing the effect of TGFBRII KO on CAR T cell phenotype. Anti-CD70 CAR T cells with or without TGFBRII KO were exposed to 50 ng/ml recombinant human TGF-β and the expression of CD25 was assessed by flow cytometry. TGFBRII KO protects CAR T from TGF-β inhibitory effect on cell phenotype.

FIG. 12 is a graph showing that TGFBRII KO protects CAR T cells against TGF-β inhibitory effect on cytotoxicity. Anti-CD70 CAR T cells was co-cultured with target tumor cells (A498) in the presences or absence of TGF-β (0, 1, 10, 50 ng/ml) The ability of anti-CD70 CAR T cells with unedited TGFBRII to kill target cells, were compared to anti-CD70 CAR T with TGFBRII KO using an exemplary guide RNA as indicated.

FIGS. 13A-13C include diagrams showing that TGFBRII KO anti-CD70 CAR T cells are resistant to TGF-β inhibitory effects on effector function. Anti-CD70 CAR T cells were co-cultured with target cells (A498) with TGF-β (50 ng/ml) or without TGF-β and compared to anti-CD70 CAR T with TGFBRII KO (e.g.: anti-CD70 CAR+TGFBRII_EX4_T1) in their ability to kill target cells. T cell proliferation (FIG. 13A) and effector cytokine secretion was assessed by Luminx (FIGS. 13B and 13C).

FIG. 14 is a graph showing fibroblasts reduce CAR-T cell cytolytic activity. Anti-CD70 CAR T was co-cultured with target cells (A498) with or without fibroblast (CCL-190) placed in a transwell plate at 0.25:1, fibroblast: anti-CD70 CAR T.

FIG. 16A: improved potency. FIG. 16B: improved CAR expansion.

FIG. 17A: CAKI-1 renal cell carcinoma xenograph model with anti-CD70 CAR T cells. FIG. 17B: H1975 lung cancer xenograph model with anti-CD70 CAR T cells.

FIG. 18A: reduction in RCC (A498) tumor size. FIG. 18B: inhibition of RCC tumor cell growth following rechallenge with ACHN cells.

FIG. 19A: CAR-T cell differentiation. FIG. 19B: CAR-T cell expansion.

FIG. 20A: reduction in tumor size. FIG. 20B: Survival rates.

FIG. 22A shows CAR T cell expansion in the Jeko-1 xenograph model. FIG. 22B shows CAR T cell expansion in the nalm-6 xenograph model.

FIGS. 23A-23D include diagrams showing consistent rates of CRISPR/Cas editing in anti-BCMA CAR-T cells with Reg-1 and/or TGFBRII disruption as determined by flowcytometry. FIG. 23A: levels of $TCR^-$ cells. FIG. 23B: levels of $β2M^-$ cells. FIG. 23C: levels of CAR' cells. FIG. 23D: ratio of $CD4^+/CD8^+$ cells.

FIG. 24A: TGFBRII disruption efficiency. FIG. 24B: Reg-1 disruption efficiency.

FIGS. 25A-25B: cytotoxicity against MM1s (multiple myeloma cell line) cells (25A) relative to K562 cells (25B). FIGS. 25C-25D: cytotoxicity against JeKo-1 cells (mantle cell lymphoma cell line) (25C) relative to K562 cells (25D).

FIGS. 26A-26C include diagrams showing that the combined disruption of Regnase-1 and TGFBRII improved anti-BCMA CAR-T activity against murine multiple myeloma in an animal model. FIG. 26A: tumor volume reduction. FIG. 26B: survival rate. FIG. 26C: CAR-T cell expansion in peripheral blood.

FIGS. 27A-27F include diagrams showing that the combined disruption of Regnase and TGFBRII improves anti-BCMA CAR-T activity against murine mantle lymphoma in an animal model. FIG. 27A: tumor volume reduction. FIG. 27B: survival rate. FIG. 27C: CAR-T cell expansion in peripheral blood. FIG. 27D: PD-1 and LAG-3 levels in CAR T cells. FIG. 27E: levels of circulating T cells at three weeks post CAR-T injection. FIG. 27F: levels of exhaustion markers (LAG-3 and PD-1) on circulating T cells at three weeks post CAR-T injection.

FIG. 29A: TGFBRII disruption alone improves anti-PTK7 CAR T-cell potency in a long-term in vitro rechallenge assay. FIG. 29B: TGFBRII disruption improves anti-PTK7 CAR T-cell persistence and expansion in a long-term in vitro rechallenge assay as measured by humCD45+ cells. FIG. 29C: TGFBRII disruption enhances cytotoxic CD8+ T cells expressing the anti-PTK7 CAR. FIG. 29D: CD4+ cells expressing the anti-PTK7 CAR remains consistent regardless of TGFBRII disruption.

FIG. 30A: effect of treatment on tumor volume. FIG. 30B: effect of treatment on body weight. •Group 1: no treatment. ○: Group 2: anti-PTK7 CAR-T cells, $5×10^6$ cells/mouse (iv) Day 1. □: Group 3: anti-PTK7 CAR/TGFBRII KO T cells, $5×10^6$ cells/mouse (iv) Day 1. UTA chow was administered 9 days prior to CAR-T cell treatment to applicable groups.

FIGS. 31A-31B include diagrams showing T cell fractions in a pancreatic cell carcinoma (Hs766T) tumor xenograft animal model treated with anti-PTK7 CAR T cells with or without TGFBRII disruption. FIG. 31A: number of humCD45+ cells/ul in murine blood at Day 47 post dose. FIG. 31B: CAR-T cell differentiation at Day 47 post dose.

DETAILED DESCRIPTION OF THE INVENTION

Figure 1A:
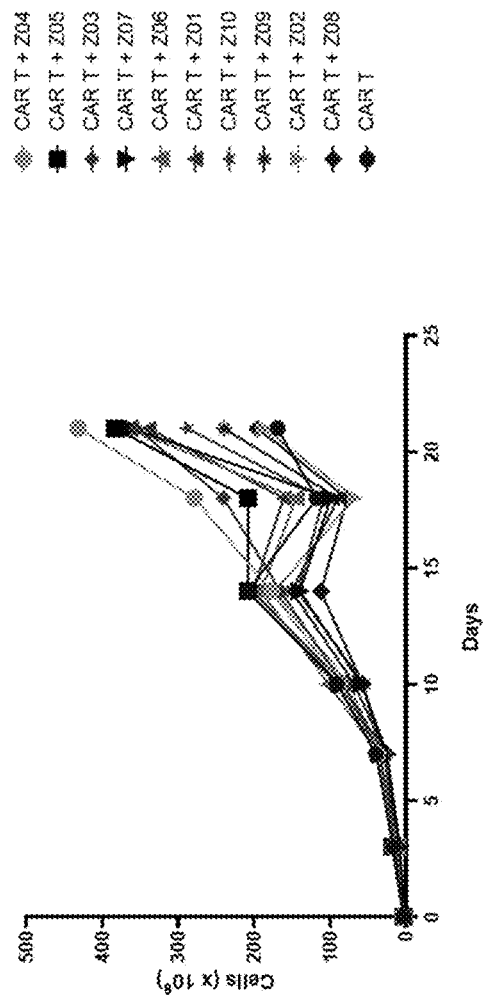
FIGS. 1A and 1B include diagrams showing that exemplary CAR T cells (anti-CD70 CAR T cells) with Reg1 KO exhibit superior in vitro expansion

The present disclosure aims at establishing genetically engineered T cells having improved growth activity, persistence, reduced T cell exhaustion, and enhanced potency, a long-felt need in CAR-T therapy. Such a T cell may use bona fide T cells as the starting material, for example, non-transformed T cells, terminally differentiated T cells, T cells having stable genome, and/or T cells that depend on cytokines and growth factors for proliferation and expansion. Alternatively, such a T cell may use T cells generated from precursor cells such as hematopoietic stem cells (e.g., iPSCs), e.g., in vitro culture. The T cells disclosed herein may confer one or more benefits in both CAR-T cell manufacturing and clinical applications.

Conventional allogenic CAR T cells are produced wherein a single donor leukopak is edited in most cases so that the cells can avoid components of the patient immune system and thus do not cause GvHD. The process of expanding these CAR T cells can yield 10s to 100s of vialed drug product. Patients may receive a single dose or multiple doses. During the manufacturing process, these CAR T cells lose potential due to various mechanisms, for example, apoptosis, exhaustion, replicative senescence, and other processes where the cells become less fit.

The genetically engineered T cells having a disrupted TGFBRII gene, a disrupted Reg1 gene, or a combination thereof, and optionally one or more additional genetic edits, for example, a disrupted TRAC gene, a disrupted β2M gene, a disrupted CD70 gene, and/or an inserted nucleic acid coding for a chimeric antigen receptor (CAR), or a combination thereof.

Unexpectedly, the present disclosure reports that knocking out Reg1 in T cells led to various advantageous features in T cell-mediated cell therapy such as CAR-T therapy. Examples include, but are not limited to: improved cell culture growth and in vitro expansion including faster expansion, longer viability, faster proliferation and/or increased resistance to apoptosis, which are beneficial for manufacturing and production of therapeutic T-cell based products such as CAR-T cells; T cell potency advantages related to maintaining therapeutic T cells (e.g., CAR-T cells) in vitro and in vivo potency and activity (target cell killing) for a more effective and persistent T-cell based therapeutic products; production and/or retention of more central memory cells; lower expression of T cell exhaustion markers (such as, PD-1, Tim-3); improved efficacy of T cell therapeutics in vivo, related to decreasing tumor burden and increasing survival of CAR T treated subjects.

Further, unexpectedly, T cells having a disrupted TGFBRII gene showed advantageous features, including improved cell growth and expansion, enhanced cytotoxicity activity, resistant to the inhibitory effect mediated by TGFβ, and/or mediated by fibroblasts. Given such advantageous features, the genetically engineered T cells (e.g., CAR-T cells) disclosed herein, having a disrupted TGFBRII gene and optionally other genetic edits as disclosed herein, would be expected to exhibit superior therapeutic effects, for example, superior anti-tumor effects, e.g., in TME of a solid tumor.

Moreover, CAR-T cells having both a disrupted Reg1 gene and a disrupted TGFBRII gene showed much higher anti-tumor activities, as well as CAR-T cell expansion in animal models as relative to CAR-T cells having a disrupted Reg1 gene or a disrupted TGFBRII gene.

Other unlimited advantageous features of the T cells provided herein include:

(a) Improved quality and consistency of CAR-T cell-based therapeutics.

(b) Greater potency and longer-lived potency of CAR-T cells produced from the T cells in human patients.

(c) Reduced dosage requirement. Because the T cells disclosed herein have enhanced proliferation and expansion capacities, they can live longer in vivo. As such, a lower dose relative to standard CAR-T therapy may be used to achieve substantially similar therapeutic effects relative to a high dose of conventional CAR-T cell therapy.

(d) Increased efficacy resulting from enhanced proliferation and expansion of the CAR-T cells disclosed herein, enhanced cytotoxicity, and prolonged persistence in vivo. Further, the T cells would provide the benefit of titratable dosing in patients to optimize safety and efficacy as noted above.

(e) Extended therapeutic effects due to reduced exhaustion and/or replicative senescence and prolonged persistence of the T cells both in vitro and in vivo.

(f) Enhanced anti-tumor activity, e.g., reduction of tumor size and/or elongated survival rates.

Accordingly, provided herein are T cells having improved persistence in culture, methods of producing such T cells, and methods of using such T cells for producing therapeutic T cells such as CAR-T cells. Components and processes (e.g., the CRISPR approach for gene editing and components used therein) for making the T cells disclosed herein are also within the scope of the present disclosure.

I. Genetically Engineered T Cells Having Enhanced Features

The T cells disclosed herein comprises genetically engineered T cells having enhanced persistence in culture. Such genetically engineered T cells may have genetic editing of the Reg1 gene or genetic editing of the TGFBRII gene. In some instances, such genetically engineered T cells may have genetic editing of both the Reg1 gene and the TGFBRII gene.

In some embodiments, the genetically engineered T cells may have genetic editing in one or more additional genes involved in T cell exhaustion, such as CD70. As shown by the studies disclosed herein, such genetically engineered T cells show one or more of the following superior features as relative to the T cell counterparts having a wild-type Regnase 1 gene: enhanced expansion capacity in culture (e.g., expandable in culture for at least 4 weeks, e.g., at least 6 weeks; and/or at least 10-fold expandable, for example, at least 15-fold expandable, relative to the non-edited counterpart), enhanced longevity, enhanced proliferation capacity, greater T cell activation, enhanced potency, enhanced expression of central memory T cell markers, and reduced expression of T cell exhaustion markers.

The genetically engineered T cells may be derived from parent T cells (e.g., non-edited wild-type T cells) obtained from a suitable source, for example, one or more mammal donors. In some examples, the parent T cells are primary T cells (e.g., non-transformed and terminally differentiated T cells) obtained from one or more human donors. Alternatively, the parent T cells may be differentiated from precursor T cells obtained from one or more suitable donor or stem cells such as hematopoietic stem cells or inducible pluripotent stem cells (iPSC), which may be cultured in vitro.

In some embodiments, the genetically engineered T cells carry a disrupted Reg1 gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7).

In some embodiments, the genetically engineered T cells carry a disrupted TGFBRII gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7). In some examples, the genetically engineered T cells may express an anti-PTK7 CAR such as those disclosed herein. In some instances, such genetically engineered T cells may have a wild-type endogenous Reg-1 gene.

In some embodiments, the genetically engineered T cells carry a disrupted Reg1 gene and a disrupted TGFBRII gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7).

Any of the genetically engineered T cells may be generated via gene editing (including genomic editing), a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When a sequence of an endogenous gene is edited, for example by deletion, insertion or substitution of nucleotide(s)/nucleic acid(s), the endogenous gene comprising the affected sequence may be knocked-out due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

(a) Genetically Edited Genes

In some aspects, the present disclosure provides genetically engineered T cells that may comprise a disrupted Reg1 gene, a disrupted TGFBRII gene, or a combination thereof. In some embodiments, the genetically engineered T cells provided herein comprise both a disrupted Reg1 gene and a disrupted TGFBRII gene. In some instances, the genetically engineered T cells disclosed herein may further comprise a disrupted CD70 gene, a disrupted β2M gene, a disrupted TRAC gene, or a combination thereof.

As used herein, a "disrupted gene" refers to a gene comprising an insertion, deletion or substitution relative to an endogenous gene such that expression of a functional protein from the endogenous gene is reduced or inhibited. As used herein, "disrupting a gene" refers to a method of inserting, deleting or substituting at least one nucleotide/nucleic acid in an endogenous gene such that expression of a functional protein from the endogenous gene is reduced or inhibited. Methods of disrupting a gene are known to those of skill in the art and described herein.

In some embodiments, a cell that comprises a disrupted gene does not express (e.g., at the cell surface) a detectable level (e.g., in an immune assay using an antibody binding to the encoded protein or by flow cytometry) of the protein encoded by the gene. A cell that does not express a detectable level of the protein may be referred to as a knockout cell.

Reg1 Gene Editing

In some embodiments, the genetically engineered T cells may comprise a disrupted gene involved in mRNA decay. Such a gene may be Reg1. Reg1 contains a zinc finger motif, binds RNA and exhibits ribonuclease activity. Reg1 plays roles in both immune and non-immune cells and its expression can be rapidly induced under diverse conditions including microbial infections, treatment with inflammatory cytokines and chemical or mechanical stimulation. Human Reg1 gene is located on chromosome 1p34.3. Additional information can be found in GenBank under Gene ID: 80149.

In some examples, the genetically engineered T cells may comprise a disrupted Reg1 gene such that the expression of Reg1 in the T cells is substantially reduced or eliminated completely. The disrupted Reg1 gene may comprise one or more genetic edits at one or more suitable target sites (e.g., in coding regions or in non-coding regulatory regions such as promoter regions) that disrupt expression of the Reg1 gene. Such target sites may be identified based on the gene editing approach for use in making the genetically engineered T cells. Exemplary target sites for the genetic edits may include exon 1, exon 2, exon 3, exon 4, exon 5, exon 6, or a combination thereof. In some examples, one or more genetic editing may occur in exon 2 or exon 4. Such genetic editing may be induced by the CRISPR/Cas technology using a suitable guide RNA, for example, those listed in Table 22. The resultant edited Reg1 gene using a gRNA listed in Table 22 may comprise one or more edited sequences provided in Tables 29-38 below.

TGFBRII Gene Editing

In some embodiments, the genetically engineered T cells may comprise a disrupted TGFBRII gene, which encodes Transforming Growth Factor Receptor Type II (TGFBRII). TGFBRII receptors are a family of serine/threonine kinase receptors involved in the TGFβ signaling pathway. These receptors bind growth factor and cytokine signaling proteins in the TGFβ family, for example, TGFβs (TGFβ1, TGFβ2, and TGFβ3), bone morphogenetic proteins (BMPs), growth differentiation factors (GDFs), activin and inhibin, myostatin, anti-Müllerian hormone (AMH), and NODAL.

In some examples, the genetically engineered T cells may comprise a disrupted TGFBRII gene such that the expression of TGFBRII in the T cells is substantially reduced or eliminated completely. The disrupted TGFBRII gene may comprise one or more genetic edits at one or more suitable target sites (e.g., in coding regions or in non-coding regulatory regions such as promoter regions) that disrupt expression of the TGFBRII gene. Such target sites may be identified based on the gene editing approach for use in making the genetically engineered T cells. Exemplary target sites for the genetic edits may include exon 1, exon 2, exon 3, exon 4, exon 5, or a combination thereof. In some examples, one or more genetic editing may occur in exon 4 and/or exon 5. Such genetic editing may be induced by a gene editing technology, (e.g., the CRISPR/Cas technology) using a suitable guide RNA, for example, those listed in Table 39. The resultant edited TGFBRII gene using a gRNA listed in Table 39 may comprise one or more edited sequences provided in Tables 40-48 below.

CD70 Gene Editing

T cell exhaustion is a process of stepwise and progressive loss of T cell functions, which may be induced by prolonged antigen stimulation or other factors. Genes involved in T cell exhaustion refer to those that either positively regulate or negatively regulate this biological process. The genetically engineered T cells disclosed herein may comprise genetic editing of a gene that positively regulates T cell exhaustion to disrupt its expression. Alternatively or in addition, the genetically engineered T cells may comprise genetic editing of a gene that negatively regulates T cell exhaustion to enhance its expression and/or biologic activity of the gene product.

In some embodiments, the genetically engineered T cells may comprise an edited gene involved in T cell exhaustion, e.g., disruption of a gene that positively regulates T cell exhaustion. Such a gene may be a Cluster of Differentiation 70 (CD70) gene. CD70 is a member of the tumor necrosis factor superfamily and its expression is restricted to activated T and B lymphocytes and mature dendritic cells. CD70 is implicated in tumor cell and regulatory T cell survival through interaction with its ligand, CD27. CD70 and its receptor CD27 have multiple roles in immune function in multiple cell types including T cells (activated and $T_{reg}$ cells), and B cells.

It was also found that disrupting the CD70 gene in immune cells engineered to express an antigen targeting moiety enhanced anti-tumor efficacy against large tumors and induced a durable anti-cancer memory response. Specifically, the anti-cancer memory response prevented tumor growth upon re-challenge. Further, it has been demonstrated disrupting the CD70 gene results in enhanced cytotoxicity of immune cells engineered to express an antigen targeting moiety at lower ratios of engineered immune cells to target cells, indicating the potential efficacy of low doses of engineered immune cells. See, e.g., WO2019/215500, the relevant disclosures of which are incorporated by reference for the purpose and subject matter referenced herein.

Structures of CD70 genes are known in the art. For example, human CD70 gene is located on chromosome 19p13.3. The gene contains four protein encoding exon5. Additional information can be found in GenBank under Gene ID: 970.

In some examples, the genetically engineered T cells may comprise a disrupted CD70 gene such that the expression of CD70 in the T cells is substantially reduced or eliminated completely. The disrupted CD70 gene may comprise one or more genetic edits at one or more suitable target sites (e.g., in coding regions or in non-coding regulatory regions such as promoter regions) that disrupt expression of the CD70 gene. Such target sites may be identified based on the gene editing approach for use in making the genetically engineered T cells. Exemplary target sites for the genetic edits may include exon 1, exon 2, exon 3, exon 4, or a combination thereof. See also WO2019/215500, the relevant disclosures of which are incorporated by reference for the purpose and subject matter referenced herein.

In some embodiments, the gRNA targeting CD70 listed in Table 23 (CD70-7) may be used for disrupting the CD70 gene via CRISPR/Cas9 gene editing. In some examples, an edited CD70 gene may comprise a nucleotide sequence selected from the following sequences in Table 26.

β2M Gene Edit

In some embodiments, the genetically engineered T cells disclosed herein may further comprise a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

In some embodiments, an edited β2M gene may comprise a nucleotide sequence selected from the following sequences in Table 25. It is known to those skilled in the art that different nucleotide sequences in an edited gene such as an edited β2M gene (e.g., those in Table 25) may be generated by a single gRNA such as the one listed in Table 23 (β2M-1). See also WO2019097305, the relevant disclosures of which are incorporated by reference for the subject matter and purpose referenced herein.

The genetically engineered T cells disclosed herein may further comprise one or more additional gene edits (e.g., gene knock-in or knock-out) to improve T cell function. Examples include knock-in or knock-out genes to improve target cell lysis, knock-in or knock-out genes to enhance performance of therapeutic T cells such as CAR-T cells prepared from the genetically engineered T cells.

TRAC Gene Edit

In some embodiments, the genetically engineered T cells as disclosed herein may further comprise a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. See also WO2019097305, the relevant disclosures of which are incorporated by reference herein for the purpose and subject matter referenced herein.

In some embodiments, an edited TRAC gene may comprise a nucleotide sequence selected from the following sequences in Table 24. It is known to those skilled in the art that different nucleotide sequences in an edited gene such as an edited TRAC gene (e.g., those in Table 24) may be generated by a single gRNA such as the one listed in Table 23 (TA-1).

It should be understood that more than one suitable target site/gRNA can be used for each target gene disclosed herein, for example, those known in the art or disclosed herein. Additional examples can be found in, e.g., WO2019097305, the relevant disclosures of which are incorporated by reference herein for the purpose and subject matter referenced herein.

(b) Exemplary Improved Features of Genetically Engineered T Cells Disclosed Herein Any of the genetically engineered T cell having a disrupted Reg1 gene, and optionally one or more additional genetic edits, for example, a disrupted CD70 gene, a disrupted TRAC gene, a disrupted β2M gene, a CAR-coding nucleic acid insertion, or a combination thereof, may be expandable in culture for greater than 4 weeks, for example, greater than 5 weeks, greater than 6 weeks, greater than 8 weeks, and greater than 10 weeks. In some examples, the genetically engineered T cells comprise a disrupted Reg1 (optionally, disruptions in CD70) and are expandable after 6 weeks (e.g., after 7 weeks, after 8 weeks, after 9 weeks, or after 10 weeks) in culture. Such genetically engineered T cells may maintain the ability to be activated after 6 weeks (e.g., after 7 weeks, after 8 weeks, after 9 weeks, or after 10 weeks) in culture. Further, such genetically engineered T cells have an increased expansion capacity, which can be at least 10-fold (e.g., at least 15-fold) higher than the non-engineered counterparts, i.e., T cells having the same genetic background as the engineered T cells disclosed herein except that the counterpart T cells have a wild-type Reg1 gene.

Further, the genetically engineered T cells disclosed herein may exhibit enhanced T cell persistence. "T cell persistence" as used herein refers to the tendency of T cells to continue to grow, proliferate, self-renew, expand, and maintain healthy activity in culture. In some instances, T cell persistence can be represented by the longevity that T cells can grow and expand in vitro, which can be measured by conventional methods and/or assays described herein. In other instances, T cell persistence can be represented by the reduction of cell death (e.g., apoptosis) or reduction in cell states characterized by exhaustion or replicative senescence. In yet other instances, T cell persistence can be presented by the maintenance of T cell activation capacity in culture.

Alternatively or in addition, the genetically engineered T cells disclosed may grow faster and longer than the non-engineered T cells, for example, as observed in vitro cell culture. In some instances, the genetically engineered T cells may grow at least 50% (e.g., at least 1-fold, at least 2-fold, at least 5-fold, or more) than the non-engineered T cells in a conventional in vitro T cell culture (e.g., as described in Examples below). In other instances, the genetically engineered T cells may maintain a high growth rate (e.g., having substantially the same growth rate or with only a slight reduction) in vitro for at least 20 days (e.g., at least 25 days, at least 30 days, at least 35 days, at least 40 days, at least 45 days, at least 50 days, or longer).

In addition, the genetically engineered T cells may exhibit a reduced level of cell exhaustion as relative to the non-engineered T cell counterpart. In some instances, a reduced level of cell exhaustion is reflected by a higher level of central memory T cells in the whole T cell population. The population of genetically engineered T cells disclosed may comprise a higher number of central memory T cells as compared to non-engineered T cell counterparts. For example, in some instances the population of genetically engineered T cells include a higher number of central memory T cells that are characterized by enhanced expression of CD27 and/or CD45RO as compared to non-engineered T cell counterparts. In some instances, the population of genetically engineered T cells disclosed exhibit reduced T cell exhaustion, which is characterized, for example, by reduced expression of PD-1 and/or TIM3 as compared to non-engineered T cell counterparts.

Any of the genetically engineered T cell having a disrupted TGFBRII gene, and optionally one or more additional genetic edits, for example, a disrupted CD70 gene, a disrupted TRAC gene, a disrupted β2M gene, a CAR-coding nucleic acid insertion, or a combination thereof, may have improved growth and expansion activities, both in vitro and in vivo, as compared with the non-engineered counterpart, which refers to T cells having the same genetic background except for an undisrupted TGFBRII gene. Further, such genetically engineered T cells (e.g., CAR-T cells) may exhibit enhanced cytotoxicity activity, for example, against undesired cells (e.g., tumor cells) expressing an antigen targeted by the CAR expressed in the CAR-T cells, as compared with the non-engineered counterpart. Such genetically engineered T cells (e.g., CAR-T cells) may also be resistant to inhibitory effects mediated by the TGFβ signaling and/or by fibroblast (e.g., in TME). For example, the genetically engineered T cells with a disrupted TGFBRII gene may be resistant to inhibitory factors secreted by fibroblasts.

In some embodiments, the genetically engineered T cells may further comprise one or more disrupted genes (e.g., CD70, Reg1, or a combination thereof) to improve T cell persistency. "T cell persistence" as used herein refers to the tendency of T cells to continue to grow, proliferate, self-renew, expand, and maintain healthy activity in culture. In some instances, T cell persistence can be represented by the longevity that T cells can grow and expand in vitro, which can be measured by conventional methods and/or assays described herein. In other instances, T cell persistence can be represented by the reduction of cell death (e.g., apoptosis) or reduction in cell states characterized by exhaustion or replicative senescence. In yet other instances, T cell persistence can be presented by the maintenance of T cell activation capacity in culture.

For example, such genetically engineered T cells may be expandable in culture for greater than 4 weeks, for example, greater than 5 weeks, greater than 6 weeks, greater than 8 weeks, and greater than 10 weeks. In some examples, the genetically engineered T cells comprise a disrupted TGFBRII gene, and a disrupted CD70 gene, Reg1 gene, or both may be expandable after 6 weeks (e.g., after 7 weeks, after 8 weeks, after 9 weeks, or after 10 weeks) in culture. Such genetically engineered T cells may maintain the ability to be activated after 6 weeks (e.g., after 7 weeks, after 8 weeks, after 9 weeks, or after 10 weeks) in culture. Such genetically engineered T cells may exhibit more improved growth and expansion capacity relative to the T cells having the same genetic background except for an undisrupted TGFBRII gene, and an undisrupted CD70 gene and/or Reg1 gene.

In addition, any of the genetically engineered T cell having a disrupted TGFBRII gene and a disrupted Reg1 gene, and optionally one or more additional genetic edits, for example, a disrupted CD70 gene, a disrupted TRAC gene, a disrupted β2M gene, a CAR-coding nucleic acid insertion, or a combination thereof, may have expansion advantage (e.g., in vivo) over counterpart T cells, i.e., having the disrupted TGFBRII gene or the disrupted Reg1 gene (but not both), as well as the other additional genetic edits. CAR-T cells having disruptions of both the TGFBRII gene and the Reg1 gene were found to be more potent in cancer treatment than the counterpart T cells as observed in xenograft mouse models. Accordingly, CAR-T cells having disruptions of both the TGFBRII gene and the Reg1 gene would be expected to show superior cancer treatment efficacy.

(c) Methods of Making Genetically Engineered T Cells

The genetically engineered T cells disclosed herein can be prepared by genetic editing of parent T cells or precursor cells thereof via a conventional gene editing method or those described herein.

(a) T Cells

In some embodiments, T cells can be derived from one or more suitable mammals, for example, one or more human donors. T cells can be obtained from a number of sources, including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some examples, T cells can be isolated from a mixture of immune cells (e.g., those described herein) to produce an isolated T cell population. For example, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, subpopulations of T cells may be isolated by positive or negative selection prior to genetic engineering and/or post genetic engineering.

An isolated population of T cells may express one or more of the T cell markers, including, but not limited to a CD3+, CD4+, CD8+, or a combination thereof. In some embodiments, the T cells are isolated from a donor, or subject, and first activated and stimulated to proliferate in vitro prior to undergoing gene editing.

In some instances, the T cell population comprises primary T cells isolated from one or more human donors. Such T cells are terminally differentiated, not transformed, depend on cytokines and/or growth factors for growth, and/or have stable genomes.

Alternatively, the T cells may be derived from stem cells (e.g., HSCs or iPSCs) via in vitro differentiation.

T cells from a suitable source can be subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells can be activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells. In some embodiments, T cells are activated at the same time that genome editing compositions are introduced into the T cells. In some instances, the T cell population can be expanded and/or activated after the genetic editing as disclosed herein. T cell populations or isolated T cells generated by any of the gene editing methods described herein are also within the scope of the present disclosure.

(b) Gene Editing Methods

Any of the genetically engineered T cells can be prepared using conventional gene editing methods or those described herein to edit one or more of the target genes disclosed herein (targeted editing). Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

In some embodiments, gene disruption may occur by deletion of a genomic sequence using two guide RNAs. Methods of using CRISPR-Cas gene editing technology to create a genomic deletion in a cell (e.g., to knock out a gene in a cell) are known (Bauer D E et al. Vis. Exp. 2015; 95:e52118).

Available endonucleases capable of introducing specific and targeted DSBs include, but not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration. Some exemplary approaches are disclosed in detail below.

CRISPR-Cas9 Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

tracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

Endonuclease for Use in CRISPR

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 may be substituted with another RNA-guided endonuclease, such as Cpf1 (of a class II CRISPR/Cas system).

In some embodiments, the CRISPR/Cas system comprises components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease is from a Type-II CRISPR/Cas system (e.g., a Cas9 protein from a CRISPR/Cas9 system). In some embodiments, the Cas nuclease is from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

In some embodiments, a Cas nuclease may comprise more than one nuclease domain. For example, a Cas9 nuclease may comprise at least one RuvC-like nuclease domain (e.g., Cpf1) and at least one HNH-like nuclease domain (e.g., Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease).

```
Amino acid sequence of Cas9 nuclease (SEQ ID NO:
1):
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLIP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNEDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK
```

-continued

```
YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

In some embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

Guide RNAs (gRNAs)

The CRISPR technology involves the use of a genome-targeting nucleic acid that can direct the endonuclease to a specific target sequence within a target gene for gene editing at the specific target sequence. The genome-targeting nucleic acid can be a RNA. A genome-targeting RNA is referred to as a "guide RNA" or "gRNA" herein. A guide RNA comprises at least a spacer sequence that hybridizes to a target nucleic acid sequence within a target gene for editing, and a CRISPR repeat sequence.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

A spacer sequence in a gRNA is a sequence (e.g., a 20 nucleotide sequence) that defines the target sequence (e.g., a DNA target sequences, such as a genomic target sequence) of a target gene of interest. In some embodiments, the spacer sequence range from 15 to 30 nucleotides. For example, the spacer sequence may contain 15, 16, 17, 18, 19, 29, 21, 22, 23, 24, 25, 26, 27, 28, 29, or 30 nucleotides. In some embodiments, a spacer sequence contains 20 nucleotides.

The "target sequence" is in a target gene that is adjacent to a PAM sequence and is the sequence to be modified by an RNA-guided nuclease (e.g., Cas9). The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 69), then the gRNA spacer sequence is 5'-AGAGCAACAGUGCUGUGGCC-3' (SEQ ID NO: 61). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNN<u>NRG</u>-3', the target nucleic acid can be the sequence that corresponds to the Ns, wherein N can be any nucleotide, and the underlined NRG sequence is the S. pyogenes PAM.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be an sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 23 below. In these exemplary sequences, the fragment of "n" refers to the spacer sequence at the 5' end.

In some embodiments, the sgRNA comprises comprise no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

In some embodiments, the gRNAs disclosed herein target a Reg1 gene, for example, target a site within exon 1, exon 2, exon 3, exon 4, exon 5, or exon 6 of the Reg1 gene. Such a gRNA may comprise a spacer sequence complementary (complete or partially) to the target sequences in exon 2 or exon 4 of a Reg1 gene, or a fragment thereof. Exemplary target sequences of Reg1 and exemplary gRNA sequences are provided in Table 22 below.

In some embodiments, the gRNAs disclosed herein target a TGFBRII gene, for example, target a site within exon 1, exon 2, exon 3, exon 4, exon 5, or exon 6 of the TGFBRII gene. Such a gRNA may comprise a spacer sequence complementary (complete or partially) to the target sequences in exon 4 or exon 5 of a TGFBRII gene, or a fragment thereof. Exemplary target sequences of TGFBRII and exemplary gRNA sequences are provided in Table 39 below.

In some embodiments, the gRNAs disclosed herein target a CD70 gene, for example, target a site within exon 1 or exon 3 of a CD70 gene. Such a gRNA may comprise a spacer sequence complementary (complete or partially) to the target sequences in exon 1 or exon 3 of a CD70 gene, or a fragment thereof. Exemplary target sequences in a CD70 gene and exemplary gRNAs specific to the CD70 gene are provided in Table 23 below.

In some embodiments, the gRNAs disclosed herein target a β2M gene, for example, target a suitable site within a β2M gene. See also WO2019097305, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In some embodiments, the gRNAs disclosed herein target a TRAC gene. See also WO2019097305, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and RNA-guided nuclease create breaks in the TRAC genomic region resulting Indels in the TRAC gene disrupting expression of the mRNA or protein.

Exemplary spacer sequences and gRNAs targeting a β2M gene or TRAC gene are provided in Table 23 below.

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some examples, the gRNAs of the present disclosure can be are produced in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in WO2013/151666. Accordingly, the present disclosure also includes polynucleotides, e.g., DNA, constructs and vectors are used to in vitro transcribe a gRNA described herein.

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art. In some embodiments, non-natural modified nucleobases can be introduced into any of the gRNAs disclosed herein during synthesis or post-synthesis. In certain embodiments, modifications are on internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, enzymatic or chemical ligation methods can be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

In some embodiments of the present disclosure, a CRISPR/Cas nuclease system for use in genetically editing any of the target genes disclosed here may include at least one guide RNA. In some examples, the CRISPR/Cas nuclease system may contain multiple gRNAs, for example, 2, 3, or 4 gRNAs. Such multiple gRNAs may target different sites in a same target gene. Alternatively, the multiple gRNAs may target different genes. In some embodiments, the guide RNA(s) and the Cas protein may form a ribonucleoprotein (RNP), e.g., a CRISPR/Cas complex. The guide RNA(s) may guide the Cas protein to a target sequence(s) on one or more target genes as those disclosed herein, where the Cas protein cleaves the target gene at the target site. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

In some embodiments, the indel frequency (editing frequency) of a particular CRISPR/Cas nuclease system, comprising one or more specific gRNAs, may be determined using a TIDE analysis, which can be used to identify highly efficient gRNA molecules for editing a target gene. In some embodiments, a highly efficient gRNA yields a gene editing frequency of higher than 80%. For example, a gRNA is considered to be highly efficient if it yields a gene editing frequency of at least 80%, at least 85%, at least 90%, at least 95%, or 100%.

Delivery of Guide RNAs and Nucleases to T Cells

The CRISPR/Cas nuclease system disclosed herein, comprising one or more gRNAs and at least one RNA-guided nuclease, optionally a donor template as disclosed below, can be delivered to a target cell (e.g., a T cell) for genetic editing of a target gene, via a conventional method. In some embodiments, components of a CRISPR/Cas nuclease system as disclosed herein may be delivered to a target cell separately, either simultaneously or sequentially. In other embodiments, the components of the CRISPR/Cas nuclease system may be delivered into a target together, for example, as a complex. In some instances, gRNA and a RNA-guided nuclease can be pre-complexed together to form a ribonucleoprotein (RNP), which can be delivered into a target cell.

RNPs are useful for gene editing, at least because they minimize the risk of promiscuous interactions in a nucleic acid-rich cellular environment and protect the RNA from degradation. Methods for forming RNPs are known in the art. In some embodiments, an RNP containing an RNA-guided nuclease (e.g., a Cas nuclease, such as a Cas9 nuclease) and one or more gRNAs targeting one or more genes of interest can be delivered a cell (e.g., a T cell). In some embodiments, an RNP can be delivered to a T cell by electroporation.

In some embodiments, an RNA-guided nuclease can be delivered to a cell in a DNA vector that expresses the RNA-guided nuclease in the cell. In other examples, an RNA-guided nuclease can be delivered to a cell in an RNA that encodes the RNA-guided nuclease and expresses the nuclease in the cell. Alternatively or in addition, a gRNA targeting a gene can be delivered to a cell as a RNA, or a DNA vector that expresses the gRNA in the cell.

Delivery of an RNA-guided nuclease, gRNA, and/or an RNP may be through direct injection or cell transfection using known methods, for example, electroporation or chemical transfection. Other cell transfection methods may be used.

Other Gene Editing Methods

Besides the CRISPR method disclosed herein, additional gene editing methods as known in the art can also be used in making the genetically engineered T cells disclosed herein. Some examples include gene editing approaching involve zinc finger nuclease (ZFN), transcription activator-like effector nucleases (TALEN), restriction endonucleases, meganucleases homing endonucleases, and the like.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination.

Any of the nucleases disclosed herein may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids. Some specific examples are provided below.

II. Genetically Engineered T Cells Expression a Chimeric Antigen Receptor (CAR)

The genetically engineered T cells having a disrupted Reg1 gene, a disrupted TGFBRII gene, or a combination of disrupted Reg1 gene and disrupted TGFBRII gene. Optionally, such genetically engineered T cells may comprise one or more of additional disrupted genes, e.g., β2M, TRAC, CD70, or a combination thereof as disclosed herein, may further express a chimeric antigen receptor (CAR) targeting an antigen of interest or cells expressing such an antigen.

(a) Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., *Blood.* 2015; 125(26):4017-4023; Kakarla and Gottschalk, *Cancer J.* 2014; 20(2):151-155). Any of the various generations of CAR constructs is within the scope of the present disclosure.

Generally, a CAR is a fusion polypeptide comprising an extracellular domain that recognizes a target antigen (e.g., a single chain fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8):498-505). A CAR construct may further comprise a hinge and transmembrane domain between the extracellular domain and the intracellular domain, as well as a signal peptide at the N-terminus for surface expression. Examples of signal peptides include SEQ ID NO: 95 and SEQ ID NO: 96 as provided in Table 27 below. Other signal peptides may be used.

(i) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

In some embodiments, the antigen-binding extracellular domain can be a single-chain variable fragment (scFv) that binds a tumor antigen as disclosed herein. The scFv may comprise an antibody heavy chain variable region ($V_H$) and an antibody light chain variable region ($V_L$), which optionally may be connected via a flexible peptide linker. In some instances, the scFv may have the $V_H$ to $V_L$ orientation (from N-terminus to C-terminus). Alternatively the scFv may have the $V_L$ to $V_H$ orientation (from N-terminus to C-terminus).

Exemplary tumor antigens include, but are not limited to, CD19, BCMA, CD70, CD33, and PTK7. Any known antibodies specific to such tumor antigens, for example, those approved for marketing and those in clinical trials, can be used for making the CAR constructs disclosed herein. Non-limiting examples of CAR constructs are provided in WO2019097305 and WO2019215500, WO2020/095107, and International Patent Application No. PCT/IB2021/053849, the relevant disclosures of which are herein incorporated by reference for the purposes and subject matter referenced herein.

In some examples, the antigen-binding extracellular domain can be a single-chain variable fragment (scFv) that binds human CD19. In some instances, the anti-CD19 scFv may comprises (i) a heavy chain variable region ($V_H$) that comprises the same heavy chain complementary determining regions (CDRs) as those in SEQ ID NO: 124; and (ii) a light chain variable region ($V_L$) that comprises the same light chain CDRs as those in SEQ ID NO: 125. In some specific examples, the anti-CD19 antibody discloses herein may comprise the heavy chain CDR1, heavy chain CDR2, and heavy chain CDR3 set forth as SEQ ID NOs: 108-110, respectively as determined by the Kabat method. Alternatively or in addition, the anti-CD19 antibody discloses herein may comprise the light chain CDR1, light chain CDR2, and light chain CDR3 set forth as SEQ ID NOs: 105-107 as determined by the Kabat method. Alternatively, the anti-CD19 antibody discloses herein may comprise the heavy chain CDR1, heavy chain CDR2, and heavy chain CDR3 set forth as SEQ ID NOs: 114-116, respectively as determined by the Chothia method. Alternatively or in addition, the anti-CD19 antibody discloses herein may comprise the light chain CDR1, light chain CDR2, and light chain CDR3 set forth as SEQ ID NOs:111-113 as determined by the Chothia method. In one specific example, the anti-CD19 scFv may comprise a $V_H$ comprising the amino acid sequence of SEQ ID NO: 124 and a $V_L$ comprises the amino acid sequence of SEQ ID NO: 125. See Sequence Table 27 below.

In some examples, the antigen-binding extracellular domain can be a single-chain variable fragment (scFv) that binds human CD70. In some instances, the anti-CD70 scFv may comprises (i) a heavy chain variable region ($V_H$) that comprises the same heavy chain complementary determining regions (CDRs) as those in SEQ ID NO: 143; and (ii) a light chain variable region ($V_L$) that comprises the same light chain CDRs as those in SEQ ID NO: 144. In some specific examples, the anti-CD70 antibody discloses herein may comprise the heavy chain CDR1, heavy chain CDR2, and heavy chain CDR3 set forth as SEQ ID NOs: 132, 134, and 136, respectively as determined by the Kabat method. Alternatively or in addition, the anti-CD70 antibody discloses herein may comprise the light chain CDR1, light chain CDR2, and light chain CDR3 set forth as SEQ ID NOs:127, 129, and 130, respectively as determined by the Kabat method. Alternatively, the anti-CD70 antibody discloses herein may comprise the heavy chain CDR1, heavy chain CDR2, and heavy chain CDR3 set forth as SEQ ID NOs: 133, 135, and 137, respectively as determined by the Chothia method. Alternatively or in addition, the anti-CD70 antibody discloses herein may comprise the light chain CDR1, light chain CDR2, and light chain CDR3 set forth as SEQ ID NO:128, LAS, and SEQ ID NO:131, respectively as determined by the Chothia method. In one specific example, the anti-CD70 scFv may comprise a $V_H$ comprising the amino acid sequence of SEQ ID NO: 143 and a $V_L$ comprises the amino acid sequence of SEQ ID NO: 144. See Sequence Table 27 below.

In some examples, the antigen-binding extracellular domain can be a single-chain variable fragment (scFv) that binds human BCMA. In some instances, the anti-BCMA scFv may comprises (i) a heavy chain variable region ($V_H$) that comprises the same heavy chain complementary determining regions (CDRs) as those in SEQ ID NO: 149; and (ii) a light chain variable region ($V_L$) that comprises the same light chain CDRs as those in SEQ ID NO: 150. In some specific examples, the anti-BCMA antibody discloses herein may comprise the heavy chain CDR1, heavy chain CDR2, and heavy chain CDR3 set forth as SEQ ID NOs: 155, 157, and 159, respectively as determined by the Kabat method. Alternatively or in addition, the anti-BCMA antibody discloses herein may comprise the light chain CDR1, light chain CDR2, and light chain CDR3 set forth as SEQ ID NOs:151, 152, and 153, respectively as determined by the Kabat method. Alternatively, the anti-BCMA antibody discloses herein may comprise the heavy chain CDR1, heavy chain CDR2, and heavy chain CDR3 set forth as SEQ ID NOs: 156, 158, and 160, respectively as determined by the Chothia method. Alternatively or in addition, the anti-BCMA antibody discloses herein may comprise the light chain CDR1, light chain CDR2, and light chain CDR3 set forth as SEQ ID NOs:151, 152, and 154, respectively as determined by the Chothia method. In one specific example, the anti-BCMA scFv may comprise a $V_H$ comprising the amino acid sequence of SEQ ID NO: 149 and a $V_L$ comprises the amino acid sequence of SEQ ID NO: 150. See Sequence Table 27 below.

In some examples, the antigen-binding extracellular domain can be a single-chain variable fragment (scFv) that binds human CD33. Exemplary anti-CD33 scFv and anti-CD33 CAR constructs can be found, for example, in Sequence Table 27 below and in WO2020/095107, the relevant disclosures of which are incorporated by reference for the subject matter and purpose noted herein.

In some examples, the antigen-binding extracellular domain can be a single-chain variable fragment (scFv) that binds human CD33. In some instances, the anti-CD33 scFv may comprises (i) a heavy chain variable region ($V_H$) that comprises the same heavy chain complementary determining regions (CDRs) as those in SEQ ID NO: 334; and (ii) a light chain variable region ($V_L$) that comprises the same light chain CDRs as those in SEQ ID NO: 335. In some specific examples, the anti-CD33 antibody discloses herein may comprise the heavy chain CDR1, heavy chain CDR2, and heavy chain CDR3 set forth as SEQ ID NOs: 328-330, respectively as determined by the Kabat method. Alternatively or in addition, the anti-CD33 antibody discloses herein may comprise the light chain CDR1, light chain CDR2, and light chain CDR3 set forth as SEQ ID NOs: 331-333, respectively as determined by the Kabat method. In one specific example, the anti-BCMA scFv may comprise a V$_H$ comprising the amino acid sequence of SEQ ID NO: 149 and a V$_L$ comprises the amino acid sequence of SEQ ID NO: 150. See Sequence Table 27 below.

In some examples, the antigen-binding extracellular domain can be a single-chain variable fragment (scFv) that binds human PTK7. In some instances, the anti-PTK7 scFv may comprises (i) a heavy chain variable region (V$_H$) that comprises the same heavy chain complementary determining regions (CDRs) as those in SEQ ID NO: 346; and (ii) a light chain variable region (V$_L$) that comprises the same light chain CDRs as those in SEQ ID NO: 347. In some specific examples, the anti-PTK7 antibody discloses herein may comprise the heavy chain CDR1, heavy chain CDR2, and heavy chain CDR3 set forth as SEQ ID NOs: 340-342, respectively as determined by the Kabat method. Alternatively or in addition, the anti-PTK7 antibody discloses herein may comprise the light chain CDR1, light chain CDR2, and light chain CDR3 set forth as SEQ ID NOs: 343-345, respectively as determined by the Kabat method. In one specific example, the anti-BCMA scFv may comprise a V$_H$ comprising the amino acid sequence of SEQ ID NO: 346 and a V$_L$ comprises the amino acid sequence of SEQ ID NO: 347. See Sequence Table 27 below.

Two antibodies having the same V$_H$ and/or V$_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/ abs/ or abysis.org/abysis/sequence_input).

(ii) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain containing the sequence of SEQ ID NO: 97 as provided below in Table 27. Other transmembrane domains may be used.

(iii) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(iv) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3ζ. In some examples, the CAR disclosed herein comprises a CD28 co-stimulatory molecule. In other examples, the CAR disclosed herein comprises a 4-1BB co-stimulatory molecule. In some embodiments, a CAR includes a CD3ζ signaling domain and a CD28 co-stimulatory domain. In other embodiments, a CAR includes a CD3ζ signaling domain and 4-1BB co-stimulatory domain. In still other embodiments, a CAR includes a CD3ζ signaling domain, a CD28 co-stimulatory domain, and a 4-1BB co-stimulatory domain.

Table 27 provides examples of signaling domains derived from 4-1BB, CD28 and CD3-zeta that may be used herein.

In specific examples, the anti-CD19 CAR disclosed herein may comprise the amino acid sequence of SEQ ID NO: 118, which may be encoded by the nucleotide sequence of SEQ ID NO: 117. Alternatively, the anti-CD19 CAR may be a mature form without the N-terminal signal peptide, e.g., comprising the amino acid sequence of SEQ ID NO:353.

In other examples, the anti-BCMA CAR disclosed herein may comprise the amino acid sequence of SEQ ID NO: 146, which may be encoded by the nucleotide sequence of SEQ ID NO: 145. Alternatively, the anti-CDBCMA CAR may be a mature form without the N-terminal signal peptide, e.g., comprising the amino acid sequence of SEQ ID NO:355.

In other examples, the anti-CD70 CAR disclosed herein may comprise the amino acid sequence of SEQ ID NO: 138, which may be encoded by the nucleotide sequence of SEQ ID NO: 141. Alternatively, the anti-CD70 CAR may be a mature form without the N-terminal signal peptide, e.g., comprising the amino acid sequence of SEQ ID NO:354.

In some examples, the anti-CD33 CAR disclosed herein may comprise the amino acid sequence of SEQ ID NO: 338 or 339. Alternatively, the anti-CD33 CAR may be a mature form without the N-terminal signal peptide, e.g., comprising the amino acid sequence of SEQ ID NO:356 or 357.

In some examples, the anti-PTK7 CAR disclosed herein may comprise the amino acid sequence of SEQ ID NO: 349 or 350. Alternatively, the anti-PTK7 CAR may be a mature form without the N-terminal signal peptide, e.g., comprising the amino acid sequence of SEQ ID NO:358 or 359.

See sequence Table 27 provided below.

(b) Delivery of CAR Construct to T Cells

In some embodiments, a nucleic acid encoding a CAR can be introduced into any of the genetically engineered T cells disclosed herein by methods known to those of skill in the art. For example, a coding sequence of the CAR may be cloned into a vector, which may be introduced into the genetically engineered T cells for expression of the CAR. A variety of different methods known in the art can be used to introduce any of the nucleic acids or expression vectors disclosed herein into an immune effector cell. Non-limiting examples of methods for introducing nucleic acid into a cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

In specific examples, a nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions disclosed herein can be used for this purpose.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some embodiments, a disruption in the TRAC gene can be created with an endonuclease as those disclosed herein and one or more gRNAs targeting one or more TRAC genomic regions, and inserting a CAR coding segment into the TRAC gene.

In some embodiments, a nucleic acid encoding a CAR (e.g., via a donor template, which can be carried by a viral vector such as an adeno-associated viral (AAV) vector) can be designed such that it can insert into a location within a β2M gene to disrupt the β2M gene in the genetically engineered T cells and express the CAR polypeptide. Disruption of β2M leads to loss of function of the endogenous MHC Class I complexes. For example, a disruption in the β2M gene can be created with an endonuclease such as those described herein and one or more gRNAs targeting one or more β2M genomic regions. Any of the gRNAs specific to a β2M gene and the target regions disclosed herein can be used for this purpose.

In some examples, a genomic deletion in the β2M gene and replacement by a CAR coding segment can be created by homology directed repair or HDR (e.g., using a donor template, which may be part of a viral vector such as an adeno-associated viral (AAV) vector). In some embodiments, a disruption in the β2M gene can be created with an endonuclease as those disclosed herein and one or more gRNAs targeting one or more β2M genomic regions, and inserting a CAR coding segment into the β2M gene.

In some embodiments, a nucleic acid encoding a CAR (e.g., via a donor template, which can be carried by a viral vector such as an adeno-associated viral (AAV) vector) can be designed such that it can insert into a location within a CD 70 gene to disrupt the CD 70 gene in the genetically engineered T cells and express the CAR polypeptide. Disruption of CD 70 leads to loss of function of the endogenous CD70 protein. For example, a disruption in the CD 70 gene can be created with an endonuclease such as those described herein and one or more gRNAs targeting one or more CD 70 genomic regions. Any of the gRNAs specific to a CD 70 gene and the target regions disclosed herein can be used for this purpose.

In some examples, a genomic deletion in the CD 70 gene and replacement by a CAR coding segment can be created by homology directed repair or HDR (e.g., using a donor template, which may be part of a viral vector such as an adeno-associated viral (AAV) vector). In some embodiments, a disruption in the CD 70 gene can be created with an endonuclease as those disclosed herein and one or more gRNAs targeting one or more CD 70 genomic regions, and inserting a CAR coding segment into the CD 70 gene.

In some embodiments, a nucleic acid encoding a CAR (e.g., via a donor template, which can be carried by a viral vector such as an adeno-associated viral (AAV) vector) can be designed such that it can insert into a location within a Reg1 gene to disrupt the Reg1 gene in the genetically engineered T cells and express the CAR polypeptide. Disruption of Reg1 leads to loss of function of the endogenous Reg1 protein. For example, a disruption in the Reg1 gene can be created with an endonuclease such as those described herein and one or more gRNAs targeting one or more Reg1 genomic regions. Any of the gRNAs specific to a Reg1 gene and the target regions disclosed herein can be used for this purpose.

In some examples, a genomic deletion in the Reg1 gene and replacement by a CAR coding segment can be created by homology directed repair or HDR (e.g., using a donor template, which may be part of a viral vector such as an adeno-associated viral (AAV) vector). In some embodiments, a disruption in the Reg1 gene can be created with an endonuclease as those disclosed herein and one or more gRNAs targeting one or more Reg1 genomic regions, and inserting a CAR coding segment into the Reg1 gene.

In some embodiments, a nucleic acid encoding a CAR (e.g., via a donor template, which can be carried by a viral vector such as an adeno-associated viral (AAV) vector) can be designed such that it can insert into a location within a TGFBRII gene to disrupt the TGFBRII gene in the genetically engineered T cells and express the CAR polypeptide. Disruption of Reg1 leads to loss of function of the endogenous TGFBRII receptor. For example, a disruption in the TGFBRII gene can be created with an endonuclease such as those described herein and one or more gRNAs targeting one or more TGFBRII genomic regions. Any of the gRNAs specific to a TGFBRII gene and the target regions disclosed herein can be used for this purpose.

In some examples, a genomic deletion in the TGFBRII gene and replacement by a CAR coding segment can be created by homology directed repair or HDR (e.g., using a donor template, which may be part of a viral vector such as an adeno-associated viral (AAV) vector). In some embodiments, a disruption in the TGFBRII gene can be created with an endonuclease as those disclosed herein and one or more gRNAs targeting one or more TGFBRII genomic regions, and inserting a CAR coding segment into the TGFBRII gene.

A donor template as disclosed herein can contain a coding sequence for a CAR. In some examples, the CAR-coding sequence may be flanked by two regions of homology to allow for efficient HDR at a genomic location of interest, for example, at a TRAC gene using a gene editing method known in the art. In some examples, a CRISPR-based method can be used. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

A donor template, in some embodiments, can be inserted at a site nearby an endogenous prompter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter, see, e.g., SEQ ID NO: 167 provided in Table 28 below. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

When needed, additional gene editing (e.g., gene knock-in or knock-out) can be introduced into therapeutic T cells as disclosed herein to improve T cell function and therapeutic efficacy. For example, if β2M disruption can be performed to reduce the risk of or prevent a host-versus-graft response. Other examples include knock-in or knock-out genes to improve target cell lysis, knock-in or knock-out genes to enhance performance of therapeutic T cells such as CAR-T cells.

In some embodiments, a donor template for delivering an anti-CD19 CAR may be an AAV vector inserted with a nucleic acid fragment comprising the coding sequence of the anti-CD19 CAR, and optionally regulatory sequences for expression of the anti-CD19 CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-CD19 CAR may comprise a nucleotide sequence of SEQ ID NO: 117, which can be inserted into a disrupted TRAC gene, for example, replacing the fragment of SEQ ID NO: 69.

In some embodiments, a donor template for delivering an anti-BCMA CAR may be an AAV vector inserted with a nucleic acid fragment comprising the coding sequence of the anti-BCMA CAR, and optionally regulatory sequences for expression of the anti-BCMA CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-BCMA CAR may comprise a nucleotide sequence of SEQ ID NO: 145, which can be inserted into a disrupted TRAC gene, for example, replacing the fragment of SEQ ID NO: 69.

In some embodiments, a donor template for delivering an anti-CD70 CAR may be an AAV vector inserted with a nucleic acid fragment comprising the coding sequence of the anti-CD70 CAR, and optionally regulatory sequences for expression of the anti-CD70 CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-CD70 CAR may comprise a nucleotide sequence of SEQ ID NO: 139, which can be inserted into a disrupted TRAC gene, for example, replacing the fragment of SEQ ID NO: 69.

The genetically engineered T cells having a disrupted Reg1 gene, additional disrupted genes, e.g., β2M, TRAC, CD70, and further expressing a chimeric antigen receptor (CAR) can be produced by sequential targeting of the genes of interest. For example, in some embodiments, the Reg1 gene may be disrupted first, followed by disruption of TRAC and β2M genes and CAR insertion. In other embodiments, TRAC and β2M genes may be disrupted first, followed by CAR insertion and disruption of the Reg1 gene. Accordingly, in some embodiments, the genetically engineered T cells disclosed herein may be produced by multiple, sequential electroporation events with multiple RNPs targeting the genes of interest, e.g., Reg1, β2M, TRAC, CD70, etc.

In other embodiments, the genetically engineered CAR T cells disclosed herein may be produced by a single electroporation event with an RNP complex comprising an RNA-guided nuclease and multiple gRNAs targeting the genes of interest, e.g., Reg1, β2M, TRAC, CD70, etc.

(c) Exemplary Genetically Engineered T Cells Expression a Chimeric Antigen Receptor It should be understood that gene disruption encompasses gene modification through gene editing (e.g., using CRISPR/Cas gene editing to insert or delete one or more nucleotides). A disrupted gene may contain one or more mutations (e.g., insertion, deletion, or nucleotide substitution, etc.) relative to the wild-type counterpart so as to substantially reduce or completely eliminate the activity of the encoded gene product. The one or more mutations may be located in a non-coding region, for example, a promoter region, a regulatory region that regulates transcription or translation; or an intron region. Alternatively, the one or more mutations may be located in a coding region (e.g., in an exon). In some instances, the disrupted gene does not express or expresses a substantially reduced level of the encoded protein. In other instances, the disrupted gene expresses the encoded protein in a mutated form, which is either not functional or has substantially reduced activity. In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a β2M gene edit may be considered a β2M knockout cell if β2M protein cannot be detected at the cell surface using an antibody that specifically binds β2M protein.

In some embodiments, a population of genetically engineered T cells disclosed herein express a CAR (e.g., anti-CD19, anti-BCMA, or anti-CD70 CAR), a disrupted Reg1 gene, a disrupted TGFBRII gene, a disrupted TRAC gene, and optionally a disrupted β2M gene, and optionally a disrupted CD70 gene. The nucleotide sequence encoding the CAR may be inserted in the disrupted TRAC gene (e.g., replacing the site targeted by a sgRNA such as TA-1). In some examples, such a population of genetically engineered T cells may comprise about 70-99% Reg1⁻ cells, for example about 90-97% Reg1⁻ cells, about 70-99% TGFBRII⁻ cells, e.g., for example about 80-89% TGFBRII⁻ cells, about 70-99% TCR⁻ cells, for example about 90-99% TCR⁻ cells, and/or optionally about 60-99% β2M⁻ cells, for example about 60-82% β2M⁻ cells, and/or optionally about 70-99% CD70⁻ cells, for example about 90-99% CD70⁻ cells. The cell population may also contain at least about 30%-50% (e.g., at least 60%) cells expressing the CAR.

i. Anti-CD19 CAR T Cells Having Reg1 and/or TGFBRII Gene Disruption

Also provided herein is population of genetically engineered immune cells (e.g., T cells such as human T cells) comprising a disrupted Reg1 gene, a disrupted TGFBRII gene, or a combination thereof, and expressing an anti-CD19 CAR, e.g., those disclosed herein. In some instances, the population of genetically engineered immune cells (e.g., T cells such as human T cells) comprising both a disrupted Reg1 gene and a disrupted TGFBRII gene, and expressing an anti-CD19 CAR, e.g., those disclosed herein. In some examples, the anti-CD19 CAR-T cells disclosed herein, which express any of the anti-CD19 CAR disclosed herein (e.g., the anti-CD19 CAR comprising the amino acid sequence of SEQ ID NO: 106), may also comprise a disrupted TRAC gene and/or a disrupted β2M gene as also disclosed herein.

In some examples, the population of genetically engineered T cells are anti-CD19 CAR cells that further comprise a disrupted Regnanse-1 gene. In some examples, anti-CD19 CAR cells are CD19-directed T cells having disrupted TRAC gene and β2M gene. The nucleic acid encoding the anti-CD19 CAR can be inserted in the disrupted TRAC gene at the site of SEQ ID NO: 69, which is replaced by the nucleic acid encoding the anti-CD19 CAR, thereby disrupting expression of the TRAC gene. The disrupted TRAC gene in the anti-CD19 CAR cells may comprise the nucleotide sequence of SEQ ID NO: 119.

Anti-CD19 CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, optionally TRAC and/or β2M genes), and adeno-associated virus (AAV) transduction to deliver the anti-CD19 CAR construct. CRISPR-Cas9-mediated gene editing involves at least a sgRNA targeting Reg1 (e.g., REG1-Z03 (SEQ ID NO: 22), REG1-Z05 (SEQ ID NO: 30), REG1-Z06 (SEQ ID NO: 34) or REG1-Z10 (SEQ ID NO: 50)), and optionally TA-1 sgRNA (SEQ ID NO: 59), which targets the TRAC locus, and β2M-1 sgRNA (SEQ ID NO: 63), which targets the β2M locus. For any of the gRNA sequences provided herein, those that do not explicitly indicate modifications are meant to encompass both unmodified sequences and sequences having any suitable modifications.

Anti-CD19 CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, optionally TRAC and/or β2M genes), and adeno-associated virus (AAV) transduction to deliver the anti-CD19 CAR construct. CRISPR-Cas9-mediated gene editing involves at least a sgRNA targeting TGFBRII (e.g., those listed in Table 39, for example, TGFBRII_EX1_T2, TGFBRII_EX4_T1, TGFBRII_EX4_T2, TGFBRII_EX5_T1), and optionally TA-1 sgRNA (SEQ ID NO: 59), which targets the TRAC locus, and β2M-1 sgRNA (SEQ ID NO: 63), which targets the β2M locus.

Anti-CD19 CAR T cells that comprise both a disrupted TGFBRII gene and a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, optionally TRAC and/or β2M genes), and adeno-associated virus (AAV) transduction to deliver the anti-CD19 CAR construct. CRISPR-Cas9-mediated gene editing involves at least a sgRNA targeting TGFBRII (e.g., those listed in Table 39) and a sgRNA targeting Reg1 (e.g., those listed in Table 22), optionally TA-1 sgRNA (SEQ ID NO: 59), which targets the TRAC locus, and β2M-1 sgRNA (SEQ ID NO: 63), which targets the β2M locus.

The anti-CD19 CAR T cells are composed of an anti-CD19 single-chain antibody fragment (scFv, which may comprise the amino acid sequence of SEQ ID NO: 120), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3 signaling domain (e.g., SEQ ID NO: 103). In specific examples, the anti-CD19 CAR T cells comprises the amino acid sequence of SEQ ID NO: 118.

In some embodiments, at least 30% of a population of anti-CD19 CAR T cells express a detectable level of the anti-CD19 CAR. For example, at least 40%, at least 50%, at least 60%, at least 70%, at least 75%, at least 80%, at least 85%, at least 90%, or at least 95% of the anti-CD19 CAR T cells express a detectable level of the anti-CD19 CAR.

In some embodiments, at least 50% of a population of anti-CD19 CAR T cells may not express a detectable level of β2M surface protein. For example, at least 55%, at least 60%, at least 70%, at least 75%, at least 80%, at least 85%, at least 90%, or at least 95% of the anti-CD19 CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-CD19 CAR T cells may not express a detectable level of TRAC surface protein. For example, at least 55%, at least 60%, at least 70%, at least 75%, at least 80%, at least 85%, at least 90%, or at least 95% of the anti-CD19 CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-CD19 CAR T cells do not express a detectable TRAC surface protein.

In some embodiments, a substantial percentage of the population of anti-CD19 CAR T cells may comprise more than one gene edit, which results in a certain percentage of cells not expressing more than one gene and/or protein.

For example, at least 50% of a population of anti-CD19 CAR T cells may not express a detectable level of two surface proteins, e.g., does not express a detectable level of β2M and TRAC proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the anti-CD19 CAR T cells do not express a detectable level of TRAC and β2M surface proteins. In another example, at least 50% of a population of the anti-CD19 CAR T cells do not express a detectable level of TRAC and β2M surface proteins.

In some embodiments, the population of anti-CD19 CAR T cells may comprise more than one gene edit (e.g., in more than one gene), which may be an edit described herein. For example, the population of anti-CD19 CAR T cells may comprise a disrupted TRAC gene via the CRISPR/Cas technology using the TA-1 TRAC gRNA. In some examples, the anti-CD19 CAR T cells may comprise a deletion in the TRAC gene relative to unmodified T cells. For example, the anti-CD19 CAR T cells may comprise a deletion of the fragment AGAGCAACAGTGCTGTGGCC (SEQ ID NO: 69) in the TRAC gene. This fragment can be replaced by the nucleic acid encoding the anti-CD19 CAR (e.g., SEQ ID NO: 117). Alternatively or in addition, the population of anti-CD19 CAR T cells may comprise a disrupted β2M gene via CRISPR/Cas9 technology using the gRNA of β2M-1. Such anti-CD19 CAR T cells may comprise Indels in the β2M gene, which comprise one or more of the nucleotide sequences of SEQ ID NOs: 83-88. In specific examples, anti-CD19 CAR T cells comprise ≥30% CAR⁺ T cells, ≤50% β2M⁺ cells, and ≤30% TCRαβ⁺ cells. In additional specific examples, anti-CD19 CAR T cells comprise ≥30% CAR⁺ T cells, ≤30% β2M⁺ cells, and ≤0.5% TCRαβ⁺ cells.

See also WO 2019/097305A2, and WO2019215500, the relevant disclosures of each of which are incorporated by reference for the subject matter and purpose referenced herein.

In specific examples, the genetically engineered T cell population may be the anti-CD19 CAR T cells disclosed herein that further comprise a disrupted Reg1 gene. The disrupted Reg1 gene may comprise any of the sequences provided in Tables 29-38 below. In some examples, the anti-CD19 CAR T cells may comprise at least 80% Reg1⁻ cells, for example, at least 85%, at least 90%, at least 95%, at least 98% or above Reg1⁻ cells.

In specific examples, the genetically engineered T cell population may be the anti-CD19 CAR T cells disclosed herein that further comprise a disrupted TGFBRII gene. In some examples, the disrupted TGFBRII gene may comprise a nucleotide sequence selected from those listed in Tables 40-48 below. In some examples, the anti-CD19 CAR T cells may comprise at least 80% TGFBRII⁻ cells, for example, at least 85%, at least 90%, at least 95%, at least 98% or above TGFBRII⁻ cells.

In specific examples, the genetically engineered T cell population may be the anti-CD19 CAR T cells disclosed herein that further comprise a disrupted TGFBRII gene and a disrupted Reg1 gene. The disrupted Reg1 gene may comprise any of the sequences provided in Tables 29-38 below. Alternatively or in addition, the disrupted TGFBRII gene may comprise a nucleotide sequence selected from those listed in Tables 40-48 below. In some examples, the anti-CD19 CAR T cells may comprise at least 80% TGFBRII⁻ cells, for example, at least 85%, at least 90%, at least 95%, at least 98% or above TGFBRII⁻ cells. Alternatively or in addition, the anti-CD19 CAR T cells may comprise at least 80% Reg1⁻ cells, for example, at least 85%, at least 90%, at least 95%, at least 98% or above Reg⁻ cells. In some examples, the anti-CD19 CAR T cells may comprise at least 60% Reg1⁻/TGPBRII⁻ cells, for example, at least 65%, at least 70%, at least 75%, at least 80%, at least 85%, at least 90%, at least 95%, at least 98% or above Reg1⁻/TGFBRII⁻ cells.

In some examples, such a population of genetically engineered T cells may comprise about 90-97% Reg1⁻ cells, about 80-89% TGFBRII⁻ cells, about 90-99% TCR⁻ cells, and/or about 60-82% β2M⁻ cells. The cell population may also contain at least 50% (e.g., at least 60%) cells expressing the anti-CD19 CAR.

ii Anti-BCMA CAR-T Cells Having Reg1 and/or TGFBRII Gene Disruption

Also provided herein is population of genetically engineered immune cells (e.g., T cells such as human T cells) comprising a disrupted Reg1 gene and expressing an anti-BCMA CAR, e.g., those disclosed herein. In some examples, the anti-BCMA CAR T cells disclosed herein, which express any of the anti-BCMA CAR disclosed herein (e.g., the anti-BCMA CAR comprising the amino acid sequence of SEQ ID NO: 146), may also comprise a disrupted TRAC gene and/or a disrupted β2M gene as also disclosed herein.

In some examples, the population of genetically engineered T cells are anti-BCMA CAR T cells that further comprise a disrupted Reg1 gene, a disrupted TGFBRII gene, or a combination thereof. In some instances, the population of genetically engineered immune cells (e.g., T cells such as human T cells) comprising both a disrupted Reg1 gene and a disrupted TGFBRII gene, and expressing an anti-BCMA CAR, e.g., those disclosed herein. In some examples anti-BCMA CAR T cells are anti-BCMA CAR T cells having disrupted TRAC gene and β2M gene. The nucleic acid encoding the anti-BCMA CAR can be inserted in the disrupted TRAC gene at the site of SEQ ID NO: 69, which is replaced by the nucleic acid encoding the anti-BCMA CAR, thereby disrupting expression of the TRAC gene. The disrupted TRAC gene in the anti-BCMA CAR T cells may comprise the nucleotide sequence of SEQ ID NO: 145.

Anti-BCMA CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-CD19 CAR T cells.

Anti-BCMA CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-BCMA CAR T cells.

Anti-BCMA CAR T cells that comprise a disrupted Reg1 gene and a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-BCMA CAR T cells.

The anti-BCMA CAR T cells are composed of an anti-BCMA single-chain antibody fragment (scFv, which may comprise the amino acid sequence of SEQ ID NO: 148), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3 signaling domain (e.g., SEQ ID NO: 103). In specific examples, the anti-BCMA CAR T cells comprises the amino acid sequence of SEQ ID NO: 146.

In some embodiments, at least 30% of a population of anti-BCMA CAR T cells express a detectable level of the anti-BCMA CAR. For example, at least 40%, at least 50%, at least 60%, at least 70%, at least 75%, at least 80%, at least 85%, at least 90%, or at least 95% of the anti-BCMA CAR T cells express a detectable level of the anti-BCMA CAR.

In some embodiments, at least 50% of a population of anti-BCMA CAR T cells may not express a detectable level of β2M surface protein. For example, at least 55%, at least 60%, at least 70%, at least 75%, at least 80%, at least 85%, at least 90%, or at least 95% of the anti-BCMA CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-BCMA CAR T cells may not express a detectable level of TRAC surface protein. For example, at least 55%, at least 60%, at least 70%, at least 75%, at least 80%, at least 85%, at least 90%, or at least 95% of the anti-BCMA CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-BCMA CAR T cells do not express a detectable TRAC surface protein.

In some embodiments, a substantial percentage of the population of anti-BCMA CAR T cells may comprise more than one gene edit, which results in a certain percentage of cells not expressing more than one gene and/or protein.

For example, at least 50% of a population of anti-BCMA CAR T cells may not express a detectable level of two surface proteins, e.g., does not express a detectable level of β2M and TRAC proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the anti-BCMA CAR T cells do not express a detectable level of TRAC and β2M surface proteins. In another example, at least 50% of a population of anti-BCMA CAR T cells do not express a detectable level of TRAC and β2M surface proteins.

In some embodiments, the population of anti-BCMA CAR T cells may comprise more than one gene edit (e.g., in more than one gene), which may be an edit described herein. For example, the population of anti-BCMA CAR T cells may comprise a disrupted TRAC gene via the CRISPR/Cas technology using the TA-1 TRAC gRNA. In some examples, the anti-BCMA CAR T cells may comprise a deletion in the TRAC gene relative to unmodified T cells. For example, the anti-CD19 CAR T cells may comprise a deletion of the fragment AGAGCAACAGTGCTGTGGCC (SEQ ID NO: 69) in the TRAC gene. This fragment can be replaced by the nucleic acid encoding the anti-BCMA CAR (e.g., SEQ ID NO: 145). Alternatively or in addition, the population of anti-BCMA CAR T cells may comprise a disrupted β2M gene via CRISPR/Cas9 technology using the gRNA of β2M-1. Such anti-BCMA CAR T cells may comprise Indels in the β2M gene, which comprise one or more of the nucleotide sequences of SEQ ID NOs: 83-88. In specific examples, anti-BCMA CAR T cells comprise ≥30% CAR$^+$ T cells, ≤50% β2M$^+$ cells, and <30% TCRαβ$^+$ cells. In additional specific examples, anti-BCMA CAR T cells comprise ≥30% CAR$^+$ T cells, ≤30%β2M$^+$ cells, and ≤0.5% TCRαβ$^+$ cells.

See also WO 2019/097305A2, and WO2019215500, the relevant disclosures of each of which are incorporated by reference for the subject matter and purpose referenced herein.

In specific examples, the genetically engineered T cell population may be the anti-BCMA CAR T cells disclosed herein that further comprise a disrupted Reg1 gene. The disrupted Regnase 1 (Reg1) gene may comprise any of the sequences provided in Tables 29-38 below. In some examples, the anti-BCMA CAR T cells may comprise at least 80% Reg1$^-$ cells, for example, at least 85%, at least 90%, at least 95%, at least 98% or above Reg1$^-$ cells.

In specific examples, the genetically engineered T cell population may be the anti-BCMA CAR T cells disclosed herein that further comprise a disrupted TGFBRII gene. In some examples, the disrupted TGFBRII gene may comprise a nucleotide sequence selected from those listed in Tables 40-48 below. In some examples, the anti-BCMA CAR T cells may comprise at least 80% TGFBRII$^-$ cells, for example, at least 85%, at least 90%, at least 95%, at least 98% or above TGFBRII$^-$ cells.

In specific examples, the genetically engineered T cell population may be the anti-BCMA CAR T cells disclosed herein that further comprise a disrupted TGFBRII gene and a disrupted Reg1 gene. The disrupted Reg1 gene may comprise any of the sequences provided in Tables 29-38 below. Alternatively or in addition, the disrupted TGFBRII gene may comprise a nucleotide sequence selected from those listed in Tables 40-48 below. In some examples, the anti-BCMA CAR T cells may comprise at least 80% TGFBRII$^-$ cells, for example, at least 85%, at least 90%, at least 95%, at least 98% or above TGFBRII$^-$ cells. Alternatively or in addition, the anti-BCMA CAR T cells may comprise at least 80% Reg1$^-$ cells, for example, at least 85%, at least 90%, at least 95%, at least 98% or above Reg$^-$ cells. In some examples, the anti-BCMA CAR T cells may comprise at least 60% Reg1$^-$/TGFBRII$^-$ cells, for example, at least 65%, at least 70%, at least 75%, at least 80%, at least 85%, at least 90%, at least 95%, at least 98% or above Reg1$^-$/TGFBRII$^-$ cells.

iii. Anti-CD70 CAR-T Cells Having Reg1 and/or TGFBRII Gene Disruption

Also provided herein is population of genetically engineered immune cells (e.g., T cells such as human T cells) comprising a disrupted Reg1 gene, a disrupted TRFBRII gene, or a combination thereof, and expressing anti-CD70 CAR, e.g., those disclosed herein. In some instances, the population of genetically engineered immune cells (e.g., T cells such as human T cells) comprising both a disrupted Reg1 gene and a disrupted TGFBRII gene, and expressing an anti-CD70 CAR, e.g., those disclosed herein. In some examples, the anti-CD70 CART cells disclosed herein, which express any of the anti-CD70 CAR disclosed herein (e.g., the anti-CD70 CAR comprising the amino acid sequence of SEQ ID NO: 138), may also comprise a disrupted TRAC gene, a disrupted β2M gene, and/or a disrupted CD70 gene as also disclosed herein.

In some examples anti-CD70 CAR T cells are anti-CD70 CAR T cells having disrupted TRAC gene, a disrupted β2M gene, and a disrupted CD70 gene. The nucleic acid encoding the anti-CD70 CAR can be inserted in the disrupted TRAC gene at the site of SEQ ID NO: 69, which is replaced by the nucleic acid encoding the anti-CD70 CAR, thereby disrupting expression of the TRAC gene. The disrupted TRAC gene in the anti-CD70 CAR T cells may comprise the nucleotide sequence of SEQ ID NO: 139.

Anti-CD70 CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, and optionally TRAC, β2M and/or CD70 genes), and adeno-associated virus (AAV) transduction to deliver the anti-CD70 CAR construct. CRISPR-Cas9-mediated gene editing involves at least an sgRNA targeting the Reg1 gene as those disclosed herein (see, e.g., Table 22), and optionally an sgRNA (SEQ ID NO: 55) which targets the CD70 locus, TA-1 sgRNA (SEQ ID NO: 59) which targets the TRAC locus, and β2M-1 sgRNA (SEQ ID NO: 63) which targets the β2M locus.

Anti-CD70 CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, and optionally, TRAC, β2M, and/or CD70 genes), and adeno-associated virus (AAV) transduction to deliver the anti-CD70 CAR construct. CRISPR-Cas9-mediated gene editing involves at least an sgRNA targeting the TGFBRII gene as those disclosed herein (see, e.g., Table 39), and optionally an sgRNA (SEQ ID NO: 43) which targets the CD70 locus, TA-1 sgRNA (SEQ ID NO: 59) which targets the TRAC locus, and β2M-1 sgRNA (SEQ ID NO: 63) which targets the β2M locus.

Anti-CD70 CAR T cells that comprise a disrupted TGFBRII gene and a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, and optionally, TRAC, β2M, and/or CD70 genes), and adeno-associated virus (AAV) transduction to deliver the anti-CD70 CAR construct. CRISPR-Cas9-mediated gene editing involves at least an sgRNA targeting the TGFBRII gene as those disclosed herein (see, e.g., Table 39), and an sgRNA targeting the Reg1 gene as those disclosed herein (see, e.g., Table 22), and optionally an sgRNA (SEQ ID NO: 55) which targets the CD70 locus, TA-1 sgRNA (SEQ ID NO: 59) which targets the TRAC locus, and β2M-1 sgRNA (SEQ ID NO: 63) which targets the β2M locus.

The anti-CD70 CAR T cells are composed of an anti-CD70 CAR single-chain antibody fragment (scFv, which may comprise the amino acid sequence of SEQ ID NO: 138), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3 signaling domain (e.g., SEQ ID NO: 103). In specific examples, the anti-CD70 CAR T cells comprise the amino acid sequence of SEQ ID NO: 138.

In some embodiments, at least 30% of a population of anti-CD70 CAR T cells express a detectable level of the anti-CD70 CAR. For example, at least 40%, at least 50%, at least 60%, at least 70%, at least 75%, at least 80%, at least 85%, at least 90%, or at least 95% of the anti-CD70 CAR T cells express a detectable level of the anti-CD70 CAR.

In some embodiments, at least 50% of a population of anti-CD70 CAR T cells may not express a detectable level of β2M surface protein. For example, at least 55%, at least 60%, at least 70%, at least 75%, at least 80%, at least 85%, at least 90%, or at least 95% of the anti-CD70 CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-CD70 CAR T cells may not express a detectable level of TRAC surface protein. For example, at least 55%, at least 60%, at least 70%, at least 75%, at least 80%, at least 85%, at least 90%, or at least 95% of the anti-CD70 CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-CD70 CAR T cells do not express a detectable TRAC surface protein.

In some embodiments, at least 50% of a population of the anti-CD70 CAR T cells may not express a detectable level of CD70 surface protein. For example, at least 55%, at least 60%, at least 70%, at least 75%, at least 80%, at least 85%, at least 90%, at least 95%, or at least 98% of the engineered T cells of a population may not express a detectable level of CD70 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, or 95%-100% of the engineered T cells of a population does not express a detectable level of CD70 surface protein.

In some embodiments, a substantial percentage of the population of anti-CD70 CAR T cells may comprise more than one gene edit, which results in a certain percentage of cells not expressing more than one gene and/or protein.

For example, at least 50% of a population of anti-CD70 CAR T cells may not express a detectable level of two surface proteins, e.g., does not express a detectable level of β2M and TRAC proteins, β2M and CD70 proteins, or TRAC and CD70 proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of two surface proteins. In another example, at least 50% of a population of the CTX130 cells may not express a detectable level of all of the three target surface proteins β2M, TRAC, and CD70 proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M, TRAC, and CD70 surface proteins.

In some embodiments, the population of anti-CD70 CAR T cells may comprise more than one gene edit (e.g., in more than one gene), which may be an edit described herein. For example, the population of anti-CD70 CAR T cells may comprise a disrupted TRAC gene via the CRISPR/Cas technology using the TA-1 TRAC gRNA. In some examples, the anti-CD70 CAR T cells may comprise a deletion in the TRAC gene relative to unmodified T cells. For example, the anti-CD70 CAR T cells may comprise a deletion of the fragment AGAGCAACAGTGCTGTGGCC (SEQ ID NO: 69) in the TRAC gene. This fragment can be replaced by the nucleic acid encoding the anti-CD70 CAR (e.g., SEQ ID NO: 139). Alternatively or in addition, the population of anti-CD70 CAR T cells may comprise a disrupted β2M gene via CRISPR/Cas9 technology using the gRNA of β2M-1. Such anti-CD70 CAR T cells may comprise indels in the β2M gene, which comprise one or more of the nucleotide sequences of SEQ ID NOs: 83-88. In specific examples, anti-CD70 CAR T cells comprise ≥30% CAR$^+$ T cells, ≤50% β2M$^+$ cells, and ≤30% TCRαβ$^+$ cells. In additional specific examples, anti-CD70 CAR T cells comprise ≥30% CAR$^+$ T cells, ≤30% β2M$^+$ cells, and ≤0.5% TCRαβ$^+$ cells.

See also WO 2019/097305A2, and WO2019215500, the relevant disclosures of each of which are incorporated by reference for the subject matter and purpose referenced herein.

In specific examples, the genetically engineered T cell population may be the anti-CD70 CAR T cells disclosed herein that further comprise a disrupted Reg1 gene. The disrupted Regnase 1 gene may comprise any of the sequences provided in Tables 22-31 below. Such a genetically engineered T cells may have ≥30% CAR+ T cells, ≤0.4% TCR$^+$ T cells, ≤30% β2M$^+$ T cells, and ≤2% CD70$^+$ T cells. In some examples, the anti-CD70 CAR T cells may comprise at least 80% Reg1$^-$ cells, for example, at least 85%, at least 90%, at least 95%, at least 98% or above Reg1$^-$ cells.

In specific examples, the genetically engineered T cell population may be the anti-CD70 CAR T cells disclosed herein that further comprise a disrupted TGFBRII gene. Such a genetically engineered T cells may have ≥30% CAR+ T cells, ≤0.4% TCR$^+$ T cells, ≤30% β2M$^+$ T cells, and ≤2% CD70$^+$ T cells. In some examples, the anti-CD70 CAR T cells may comprise at least 80% TGFBRII$^-$ cells, for example, at least 85%, at least 90%, at least 95%, at least 98% or above TGFBRII$^-$ cells.

In specific examples, the genetically engineered T cell population may be the anti-CD70 CAR T cells disclosed herein that further comprise a disrupted TGFBRII gene and a disrupted Reg1 gene. The disrupted Regnase 1 gene may comprise any of the sequences provided in Tables 29-38 below. Alternatively or in addition, the disrupted TGFBRII gene may comprise a nucleotide sequence selected from those listed in Tables 40-48 below. Such a genetically engineered T cells may have ≥30% CAR+ T cells, ≤0.4% TCR$^+$ T cells, ≤30% β2M$^+$ T cells, and ≤2% CD70$^+$ T cells. In some examples, the anti-CD70 CAR T cells may comprise at least 80% TGFBRII$^-$ cells, for example, at least 85%, at least 90%, at least 95%, at least 98% or above TGFBRII$^-$ cells. In some examples, the anti-CD70 CAR T cells may comprise at least 60% Reg1$^-$/TGFBRII$^-$ cells, for example, at least 65%, at least 70%, at least 75%, at least 80%, at least 85%, at least 90%, at least 95%, at least 98% or above Reg1$^-$/TGFBRII$^-$ cells.

III. Therapeutic Applications

The therapeutic T cells generated using the genetically engineered T cells disclosed herein would be expected to maintain T cell health enabled by the disruption of the Reg1 gene, the disruption of the TGFBRII gene, the disruption of the CD70 gene, or a combination thereof. For example, maintaining T cell health may extend expansion during manufacturing, thereby increasing yield and consistency. In another example, maintaining T cell health may rescue exhausted/unhealthy T cells, thereby enabling potentially lower doses in patients and more robust responses. Further, the disruption of the Reg1 gene and the TGFBRII gene showed synergistic effects in enhancing CAR-T cell potency and in vivo expansion.

The therapeutic T cells disclosed herein can be administered to a subject for therapeutic purposes, for example, treatment of a solid tumor targeted by the CAR construct expressed by the therapeutic T cells.

The step of administering may include the placement (e.g., transplantation) of the therapeutic T cells into a subject by a method or route that results in at least partial localization of the therapeutic T cells at a desired site, such as a tumor site, such that a desired effect(s) can be produced. Therapeutic T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of the therapeutic T cells can be administered via a systemic route of administration, such as an intraperitoneal or intravenous route.

In some embodiments, the therapeutic T cells are administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

A subject may be any subject for whom diagnosis, treatment, or therapy is desired. In some embodiments, the subject is a mammal. In some embodiments, the subject is a human.

In some instances, the therapeutic T cells may be autologous ("self") to the subject, i.e., the cells are from the same subject. Alternatively, the therapeutic T cells can be non-autologous ("non-self," e.g., allogeneic, syngeneic or xenogeneic) to the subject. "Allogeneic" means that the therapeutic T cells are not derived from the subject who receives the treatment but from different individuals (donors) of the same species as the subject. A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient (e.g., subject). For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

Because of the enhanced persistence and efficacy of the therapeutic T cells disclosed herein, the dose of the therapeutic T cells provided herein would be lower than the standard dose of CAR-T cells prepared by conventional approaches (e.g., using T cells that do not have one or more of the genetic editing events disclosed herein, including a disrupted Reg1 gene and/or a disrupted CD70 gene). In some examples, the effective amount of the therapeutic T cells disclosed herein may be at least 2-fold lower, at least 5-fold lower, at least 10-fold lower, at least 20-fold lower, at least 50-fold lower, or at least 100-fold lower than a standard dose of a CAR-T therapy. In some examples, an effective amount of the therapeutic T cells disclosed herein may be less than $10^6$ cells, e.g., $10^5$ cells, $5 \times 10^4$ cells, $10^4$ cells, $5 \times 10^3$ cells, or $10^3$ cells. In some examples described herein, the cells are expanded in culture prior to administration to a subject in need thereof.

The efficacy of a treatment using the therapeutic T cells disclosed herein can be determined by the skilled clinician. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Combination therapies are also encompassed by the present disclosure. For example, the therapeutic T cells disclosed herein may be co-used with other therapeutic agents, for treating the same indication, or for enhancing efficacy of the therapeutic T cells and/or reducing side effects of the therapeutic T cells.

IV. Kits

The present disclosure also provides kits for use in producing the genetically engineered T cells, the therapeutic T cells, and for therapeutic uses, In some embodiments, a kit provided herein may comprise components for performing genetic edit of one or more of Reg1 gene, TGFBRII gene, and CD70 gene, and optionally a population of immune cells to which the genetic editing will be performed (e.g., a leukopak). A leukopak sample may be an enriched leukapheresis product collected from peripheral blood. It typically contains a variety of blood cells including monocytes, lymphocytes, platelets, plasma, and red cells. The components for genetically editing one or more of the target genes may comprise a suitable endonuclease such as an RNA-guided endonuclease and one or more nucleic acid guides, which direct cleavage of one or more suitable genomic sites by the endonuclease. For example, the kit may comprise a Cas enzyme such as Cas 9 and one or more gRNAs targeting a Reg1 gene, a TGFBRII gene, and/or a CD70 gene. Any of the gRNAs specific to these target genes can be included in the kit. Such a kit may further comprise components for further gene editing, for example, gRNAs and optionally additional endonucleases for editing other target genes such as β2M and/or TRAC.

In some embodiments, a kit provided herein may comprise a population of genetically engineered T cells as disclosed herein, and one or more components for producing the therapeutic T cells as also disclosed herein. Such components may comprise an endonuclease suitable for gene editing and a nucleic acid coding for a CAR construct of interest. The CAR-coding nucleic acid may be part of a donor template as disclosed herein, which may contain homologous arms flanking the CAR-coding sequence. In some instances, the donor template may be carried by a viral vector such as an AAV vector.

The kit may further comprise gRNAs specific to a TRAC gene for inserting the CAR-coding sequence into the TRAC gene. In other examples, the kit may further comprise gRNAs specific to a β2M gene for inserting the CAR-coding sequence into the β2M gene. In other examples, the kit may further comprise gRNAs specific to a CD70 gene for inserting the CAR-coding sequence into the CD70 gene. In yet other examples, the kit may further comprise gRNAs specific to a Reg1 gene for inserting the CAR-coding sequence into the Reg1 gene. In still other examples, the kit may further comprise gRNAs specific to a TGFBRII gene for inserting the CAR-coding sequence into the TGFBRII gene.

In yet other embodiments, the kit disclosed herein may comprise a population of therapeutic T cells as disclosed for the intended therapeutic purposes.

Any of the kit disclosed herein may further comprise instructions for making the therapeutic T cells, or therapeutic applications of the therapeutic T cells. In some examples, the included instructions may comprise a description of using the gene editing components to genetically engineer one or more of the target genes (e.g., Reg1, TGFBRII, CD70, or a combination thereof). In other examples, the included instructions may comprise a description of how to introduce a nucleic acid encoding a CAR construction into the T cells for making therapeutic T cells.

Alternatively, the kit may further comprise instructions for administration of the therapeutic T cells as disclosed herein to achieve the intended activity, e.g., eliminating disease cells targeted by the CAR expressed on the therapeutic T cells. The kit may further comprise a description of selecting a subject suitable for treatment based on identifying whether the subject is in need of the treatment. The instructions relating to the use of the therapeutic T cells described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the therapeutic T cells are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an infusion device for administration of the therapeutic T cells. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobi-* lized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Screening of Reg1 Targeting Site by CRISPR/Cas-Mediated Gene Editing (A) Efficient Disruption of Reg1 by Cas9:sgRNA RNPs in T Cells The Reg1 gene was efficiently edited in primary human T cells ex vivo using CRISPR/Cas9 gene editing. Genomic segments of the Reg1 gene containing the six (6) protein coding exon5 were used as input in gRNA design software. Desired gRNAs were those that would lead to insertions or deletions in the coding sequence, disrupting the amino acid sequence of Reg1, leading to out of frame/loss of function allele(s) (referred to as "Reg1 knockout (KO)" alleles or "Reg1 disrupted alleles"). All ten (10) in silico-identified gRNA spacer sequences targeting the Reg1 gene were synthesized, and the gRNAs were specifically modified, as indicated in Table 1. While the gRNAs used in this example were modified with 2'-O-methyl phosphorothioate modifications, unmodified gRNAs, or gRNAs with other modifications, may be used. The target sequences and gRNA sequences of the Reg1 guides Z01-Z10 are provided in Table 22 below.

TABLE 1

Indel Rate of Reg1 Gene by Ten gRNAs

| Guide Name | Indel Efficiency (TIDE) |
|---|---|
| REG1-Z01 | 98.3% |
| REG1-Z02 | 97.2% |
| REG1-Z03 | 96.8% |
| REG1-Z04 | 92.7% |
| REG1-Z05 | 98.5% |
| REG1-Z06 | 95% |
| REG1-Z07 | 94.8% |
| REG1-Z08 | 71% |
| REG1-Z09 | 88.2% |
| REG1-Z10 | 94.9% |

Primary human T cells were transfected (electroporated) with a ribonucleoprotein particle (RNP) containing Cas9 nuclease and a synthetic modified sgRNA targeting the Reg1 gene (sequences in Table 22) or controls (no Cas9, no gRNA). Four (4) days post transfection, cells were subjected to a TIDE analysis to assess indel frequency.

Ten (10) gRNAs yielded measurable data by TIDE analysis, as indicated in Table 1. Eight (8) gRNA sequences yielded indel percentages (editing frequencies) above 90%, indicating highly efficient gene editing.

Four gRNAs which target either exon 2 or 4 were selected for subsequent studies (REG1-Z03, REG1-Z05, REG1-Z06 and REG1-Z10, which showed 96.8%, 98.5%, 95% and 94.9% editing rate of Reg1, respectively as shown in (Table 1).

(B) On-Target and Off-Target Editing of REG1 Guide RNAs

On-target and off-target editing efficiencies of various REG1-targeting gRNAs noted above were examined following the method disclosed in the above section. Briefly, activated T cells were transfected (electroporated) with a ribonucleoprotein particle (RNP) containing Cas9 nuclease and a synthetic modified sgRNA targeting the Reg1 gene (sequences in Table 22 below) or controls (no Cas9, no gRNA).

For genomic on- and off-target assessment, these electroporation methods were used to generate two cell populations of edited cells from two different donor T cells (termed 1 and 2). Cells were gene edited with each of the ten guides noted above, and then collected ten (10) days post transfection. These samples were analyzed with hybrid capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions (indels) indicating repair following CRISPR editing.

(i) Analysis of On-Target Indel Profiles in T Cells

The data used to quantify off-target editing were also used to quantify and summarize the most frequent on-target indels for all Reg1 guides listed in Table 22. This data was generated from hybrid capture of the Reg1 locus combined with next-generation sequencing in two donors (termed Donor 1 and Donor 2).

Following gene editing, hybrid capture analysis of the Reg1 locus in a population of T cells following CRISPR/Cas9 gene editing to produce Reg1 KO T cells results in specific indel frequencies and edited gene sequences at the Reg1 locus (Tables 29-38; deletions as dashes and insertions in bold).

For the purposes of individual sequence quantification from hybrid capture data, sequence reads aligning across the Regnase 1 on-target site, 20 bp upstream and downstream of the cut site, were selected and considered for indel sequence quantification. From the selected reads, the sequence within 10 bp upstream and downstream of each putative cut site (~3 bp upstream of the PAM (Jinek, et al., Science 2012) was quantified as a representative region of on-target non-homologous end joining (NHEJ) editing.

Table 2 below shows the on and off target editing results (from two donors) of exemplary Reg1 gRNAs obtained by the hybrid capture assay disclosed herein.

TABLE 2

On and Off Target Results by Hybrid Capture

| Guide | Number of predicted off target sites tested | On-target mean editing hyb cap | Detected off-targets |
|---|---|---|---|
| REG1-Z01 | 35 | 97.0% | 1 0.75% off-target; 1 0.25% off-target |
| REG1-Z02 | 27 | 97.7% | No off-target editing detected |

TABLE 2-continued

On and Off Target Results by Hybrid Capture

| Guide | Number of predicted off target sites tested | On-target mean editing hyb cap | Detected off-targets |
|---|---|---|---|
| REG1-Z03 | 52 | 99.0% | 1 5.0% off-target; 1 0.6% off-target; 1 0.4% off-target; 1 0.3% off-target; 1 0.2% off-target |
| REG1-Z04 | 6 | 97.0% | No off-target editing detected |
| REG1-Z05 | 14 | 98.6% | No off-target editing detected |
| REG1-Z06 | 1 | 94.2% | No off-target editing detected |
| REG1-Z07 | 16 | 94.2% | 1 0.2% off-target |
| REG1-Z08 | 6 | 53.8% | No off-target editing detected |
| REG1-Z)9 | 6 | 86.2% | No off-target editing detected |
| REG1-Z10 | 14 | 98.2% | No off-target editing detected |

On-target gene edited sequences by the exemplary Reg1 gRNAs are presented in Tables 29-38 below, with the frequencies of these sequences representing the percent of all sequences spanning the on-target site within 20 bp upstream and downstream of each cut site. The indels for each guide are shown relative to an on-target reference sequence in Tables 29-38. The reference sequence is centered on the cleavage site with 10 bp in either direction, ending 4 bp 3' of the PAM.

Example 2: Regnase/Disruption Improves CAR-T Cell Expansion

Using T cells expressing an anti-CD70 CAR disclosed herein as an example, this study demonstrated that knocking out Reg1 in the CAR-T cells resulted in enhanced in vitro CAR-T cell culture expansion.

Allogeneic human T cells that lack expression of the TRAC gene, β2M gene, CD70 gene, and Regnase-1 gene, and express a chimeric antigen receptor (CAR) targeting CD70 were produced. Briefly, activated human T cells were first isolated and then Cas9:sgRNA RNPs (1 µM Cas9, 5 µM gRNA) were delivered to the activated human T cells by electroporation, followed by incubation with recombinant adeno-associated adenoviral vectors (AAVs), serotype 6 (AAV6) (MOI 50,000). The nucleofection mix contained the Nucleofector™ Solution, 5×10$^6$ cells, 1 µM Cas9, and 5 µM gRNA (as described in Hendel et al., *Nat Biotechnol*. 2015; 33(9):985-989, PMID: 26121415). The RNP complex comprised Cas9 and sgRNA targeting the TRAC, B2M, and CD70 (shown in Table 23) and optionally Regnase-1 genes (using the REG1-Z01 to REG1-Z10 sgRNAs shown in Table 22). The rAAV vector included the nucleotide sequence encoding an anti-CD70 CAR (the donor template in SEQ ID NO: 169, encoding an anti-CD70 CAR amino acid sequence of SEQ ID NO: 138).

To assess the ability of anti-CD70 CAR T cells to expand in cytokine containing media (IL-2+IL-7), anti-CD70 CAR T cells were utilized. Specifically, 2.5 to 3.8×10$^6$ total anti-CD70 CAR T cells comprising a quadruple disruption (TRAC-/β2M-/CD70-/Reg1-) were generated and compared to anti-CD70 CAR T cells with unedited Reg1 (TRAC-/β2M-/CD70-).

Cells were plated and allowed to grow in flasks with cytokine containing media. Every 3-4 days the total number of cells were enumerated and re-plated as needed. This process was repeated each week for a total of 21 days. Allogeneic anti-CD70 CAR-T cells containing a disruption in the Reg1 gene show an increase in cell expansion after 21 days (FIG. 1A). Reg1 guides REG1-Z01, REG1-Z03, REG1-Z07, REG1-Z09, and REG1-Z10 appear to have a greater effect on cell expansion than cells made using Reg1 guides REG1-Z02 or REG1-Z08.

Figure 1B:
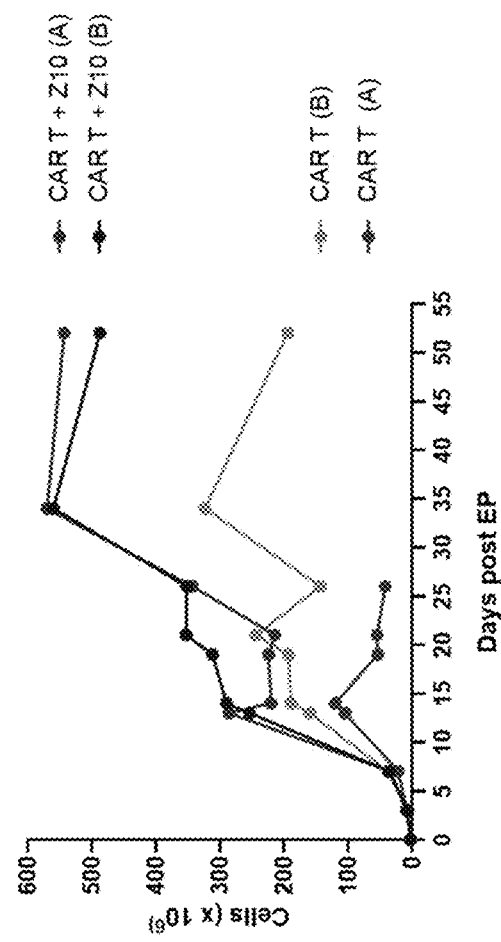

In a second experiment, Reg1 guide REG1-Z10 was used in CAR T cells made from a different T cell donor in replicates by two operators (labelled A and B). The effect of increased cell culture expansion was demonstrated again. The increase in cell expansion can be seen as early as day 13 and continues throughout the experiment to day 52 (FIG. 1B). Furthermore, anti-CD70 CAR-T cells containing a Reg1 disruption are maintained over a longer time in culture (at least up to day 52) as compared to anti-CD70 CAR-T cells with an unedited Regnase 1 gene, one of which was no longer viable on day 26. Collectively, these data show that disruption of the Reg1 gene results in greater cell culture yields and longer cell maintenance in culture as compared to CAR T cells with an unedited Reg1 gene.

Example 3: Cell Killing Function of Anti-CD70 CAR T Cells with Reg1 Disruption

Allogeneic human T cells that lack expression of the TRAC gene, β2M gene and CD70 gene, and express a chimeric antigen receptor (CAR) targeting CD70 were produced. The edited CAR T cells further comprised knock out of Reg1 gene. As in the examples above, activated human T cells we electroporated with Cas9:sgRNA RNPs (1 µM Cas9, 5 µM gRNA), followed by incubation with a recombinant adeno-associated adenoviral vectors, serotype 6 (AAV6) (MOI 50, 000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54), and optionally Reg1 (e.g., REG1-Z03, Z05, Z06, and Z10; see Table 22 and FIGS. 2A to 2E).

At time points of one week and one month post-electroporation, T cells were checked for CAR expression by flow cytometry. Both anti-CD70 CAR T cells and anti-CD70 CAR T cells that lack Reg1 (using four gRNAs REG1-Z03, Z05, Z06, Z10) expressed nearly equivalent amount of CAR on their surface at day 7 (85.6% and 81.8%, 80%, 84.4%, 85.6%) and day 32 (97.6% and 90.7%, 91.5%, 92.6%, 93.2%) post HDR.

Cell Killing Function of Anti-CD70 CAR T Cells with Regnase-1 (Reg1) Disruption

A cell killing assay was used to assess the ability of the TRAC-/β2M-/CD70-/Reg1-/anti-CD70 CAR+ cells to kill CD70+ adherent renal cell carcinoma (RCC)-derived cell lines (ACHN, Caki-1, and/or 769P cell lines). Adherent cells were seeded in 96-well plates at 50,000 cells per well and incubated overnight at 37° C. The next day edited anti-CD70 CAR T cells (cultured until day 12 post HDR or day 27 post HDR) were added to the wells containing target cells at 1:1, 2:1 or 1.5:1 CAR T:Target cell ratios. After 24 hours co-culture, CART cells were removed from the culture by aspiration and 100 µL Cell titer-Glo (Promega) was added to each well of the plate to assess the number of remaining viable target cells. The amount of light emitted per well was then quantified using a plate reader.

Figure 2A:
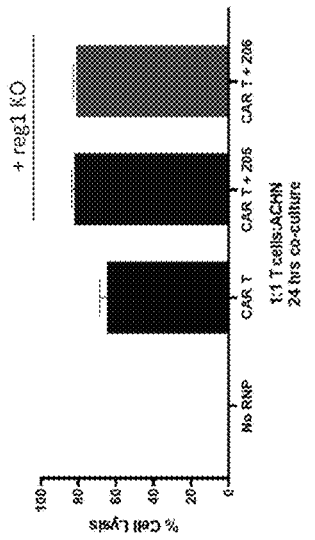
FIGS. 2A-2E include diagrams showing that exemplary CAR T cells (anti-CD70 CAR T cells) with Reg1 KO (+reg1 KO) exhibit superior in vitro potency against tumor cell lines relative to CAR T cells with an unedited Reg1 gene (CAR T).
Figure 2B:
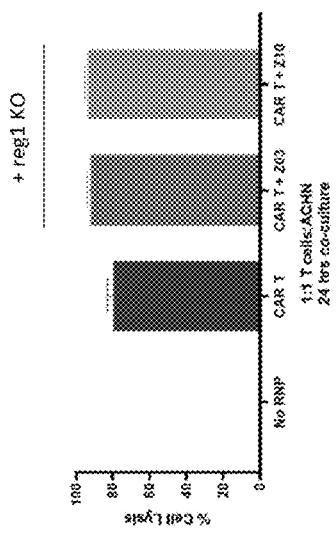
Figure 2E:
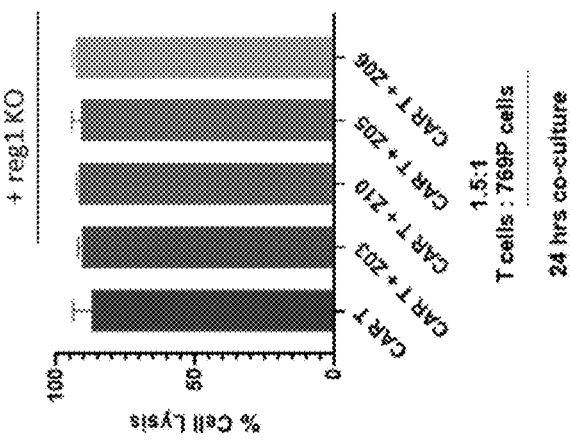
Figure 2D:
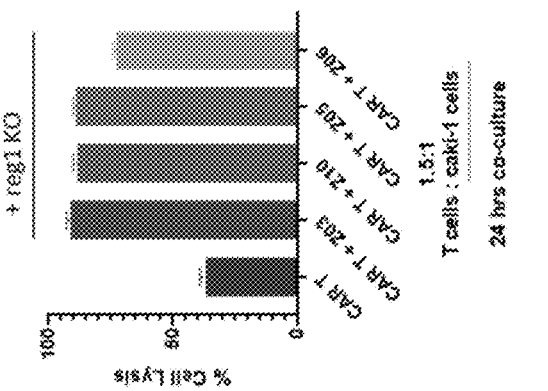
Figure 2C:
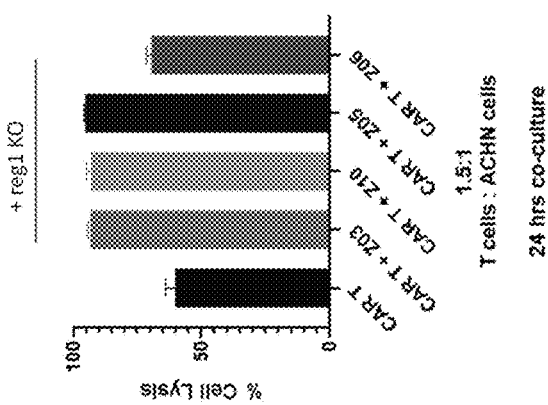

Cells with Reg1 disruption exhibited a more potent cell killing of RCC-derived cells following 24-hour co-incubation. The anti-CD70 CAR T cells at day 12 post HDR (FIGS. 2A and 2B) demonstrated slightly higher potency when Reg1 was knocked out, and much higher potency at day 27 post HDR (FIGS. 2C, 2D, and 2E). This suggests that knocking-out the Reg1 gene gives a maintained/persistent higher cell kill potency to anti-CD70 CAR+ T cells over time post HDR. This finding was consistent across the three tumor lines from Renal cell carcinoma tumor lines. CD70 CAR+ T cells with Reg1 disruption using gRNAs REG1-Z03, REG1-Z05, REG1-Z10 gave a higher persistent potency than when using gRNA REG1-Z06. CAR-T cells with Reg1 disruption demonstrated a visible increased in potency after 24 h co-culture with caki-1 (FIGS. 2A, 2B, and 2C) and ACHN (FIG. 2D), and after 6 hours co-culture with 769P (difference not visible anymore after 24 h) (FIG. 2E).

Figure 6A:
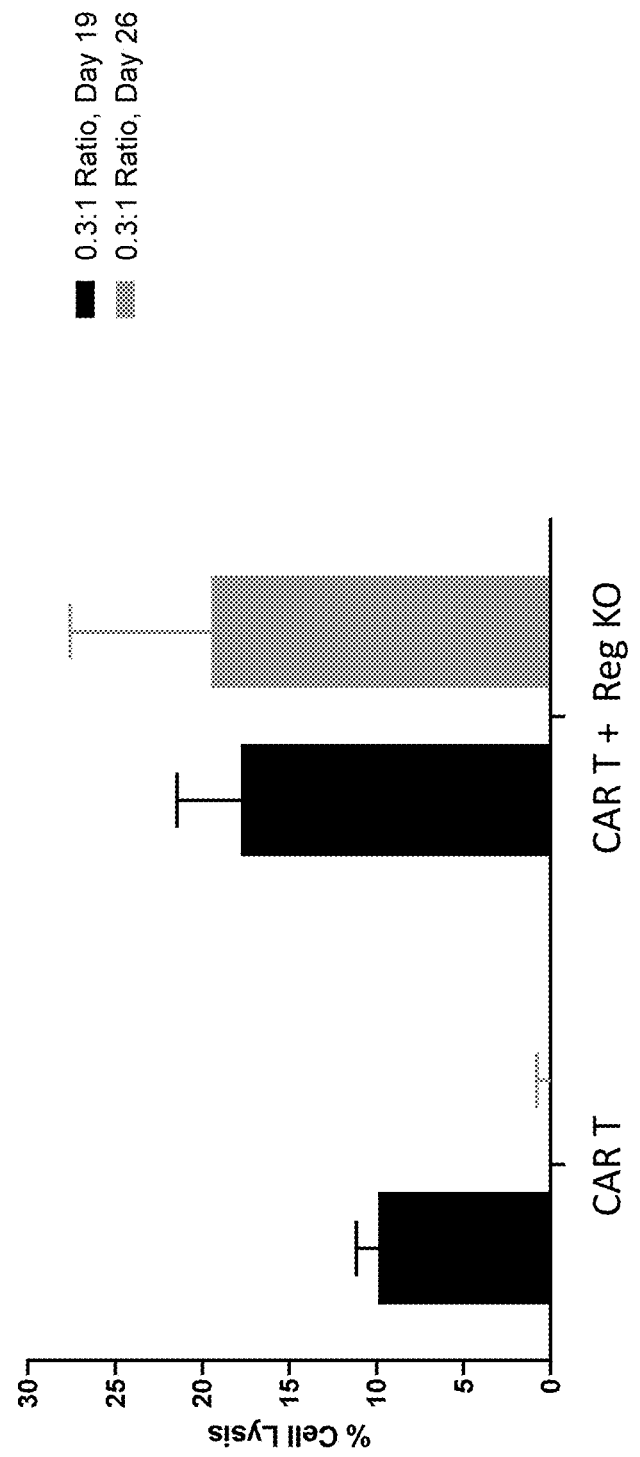
FIGS. 6A-6B include diagrams showing that exemplary CAR T cells (anti-CD70 CAR T cells) with Reg1 KO (CAR T+Reg KO) exhibit superior in vitro potency against tumor cell lines relative to Reg1 wild-type counterparts (CAR T).
Figure 6B:
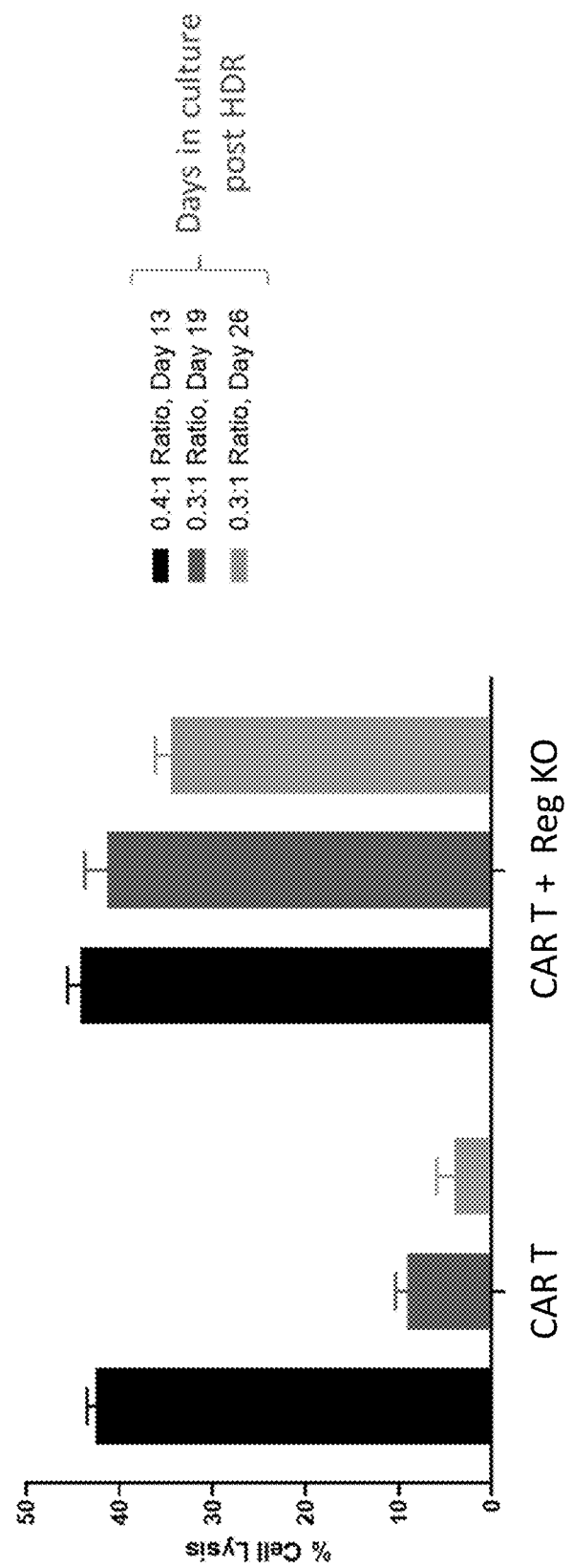

While CAR-T cells with or without the Regnase KO show similar efficacy at Day 13 post HDR, efficacy appears to be diminished in older cells (Day 19 and Day 26) without the Regnase KO. Surprisingly, TRAC−/β2M−/CD70−/Reg1−/anti-CD70 CAR+ cells still retain the ability to kill with similar activity ACHN and Caki-1 cells in culture (FIGS. 6A and 6B).

This suggests that disrupting the Reg1 gene gives a persistent activity and higher cell kill potency to CAR+ T cells over a longer period of time post HDR editing.

Example 4. Effect of Regnase-1 (Reg1) Disruption on Exhaustion Marker Expression The levels of the T cell exhaustion markers were assessed on TRAC−/β2M−/CD70−/anti-CD70 CAR+ and TRAC−/β2M−/CD70−/Reg1−/anti-CD70 CAR+ cells. CD4+ and CD8+ T cells were assessed for PD-1 expression (FIGS. 3A and 3B) and TIM3 expression (FIGS. 3C and 3D) by flow cytometry at Day 13 (FIGS. 3A and 3C) and Day 26 (FIGS. 3B and 3D) post HDR.

The data demonstrate that Reg1 KO (using Z10 guide as an example) reduces exhaustion marker expression in CAR T cells at all time points measured. The data demonstrate that knocking out Reg1 could reduce the potential exhaustion of CD8+ and CD4+ gene edited populations of CAR+ T cells leading to better therapeutics.

Example 5. Regnase-1 (Reg1) Disruption Increases the Proportion of Central Memory Cells in CAR T Cells Population Upon activation of antigen peptides presented by antigen-presenting cells, native T cells differentiate to various types of T cells in the order of T stem cell memory ($T_{SCM}$), T central memory cell ($T_{CM}$), T effector memory cell ($T_{EM}$), and T effector cell ($T_{EFF}$). Exemplary surface markers of T cells at different differentiation stages are provided below. $T_{CM}$ cells have been associated with T cell long term persistence in vivo: CD8+ clones isolated from $T_{CM}$ cells were shown to persist long term in vivo during adoptive T cell transfer in non-human primates while clones isolated from effector cells did not. (Berger et al., J. Clin. Investig. (2008) 118:294-305). Representative cell surface markers of the various types of T cells are provided in Table 3 below.

TABLE 3

Representative Cell Surface Markers of Various Types of T Cells

|  | Naïve | Stem Central Memory | Central Memory | Effector Memory |
|---|---|---|---|---|
| CD27 | + | + | + | − |
| CD45RO | − | − | + | + |
| CD45RA | + | + | − | − |
| CD62L | + | + | + | − |
| CD95 | − | + | + | + |

The levels of CD27 and CD45 RO T central memory T cell markers were assessed on TRAC−/β2M−/CD70−/anti-CD70 CAR+ and TRAC−/β2M−/CD70−/Reg1−/anti-CD70 CAR+ cells. Cells were stained using commercial antibodies for CD27 (Biolegend, clone M-T271) and CD45 RO (Biolegend, clone UCHL1) and analyzed by flow cytometry.

CAR-T cells with Reg1 knock out were more likely to exhibit central memory T cell identity (double positive for CD27 and CD45 RO) and less likely to exhibit effector memory cell identity (identified as CD27− and CD45 RO+), as shown in Table 4.

TABLE 4

Central memory and effector memory T cell markers in cells with and without Reg1 KO

| Experiment | Cells | CD27+/CD45 RO+ Central memory cells | CD27−/CD45 RO+ Effector memory cells |
|---|---|---|---|
| 1 | TRAC−/β2M−/anti-CD70 CAR+ | 62.3% | 30% |
|  | TRAC−/β2M−/CD70−/Reg1−/anti-CD70 CAR+ | 82.3% | 15.1% |
| 2 | TRAC−/β2M−/anti-CD70 CAR+ | 61.8% | 27.5% |
|  | TRAC−/β2M−/CD70−/Reg1−/anti-CD70 CAR+ | 74.3% | 22.2% |

The results obtained from this study indicate that Reg1 disruption led to an enhanced level of $T_{CM}$ cells in the total T cell population compared to the Reg1 WT counterparts, indicating that Reg1 disruption could increase T cell long term persistence in vivo, which would benefit CAR-T therapy.

Example 6. Reg1 Disruption does not Affect Cytokine Dependency of CAR T Cells To determine whether the gene editing resulted in unwanted off-target editing that could generate cells with adverse properties, such as uncontrolled cell growth, the ability of TRAC−/β2M−/anti-CD19 CAR+ and TRAC−/β2M−/Reg1−/anti-CD19 CAR+ cells to grow in the absence of cytokines and/or serum was assessed. $5 \times 10^6$ cells were plated approximately 2 weeks post cell production (Day 0) in 10 mL of full media containing IL2, IL7 and human serum, or in serum-containing media lacking cytokines (IL-2 and IL-7). Fresh full media or media lacking cytokines were added to the respective cultures once per week. The volume of media added allowed for the cultures to maintain a density of approximately 1-2 million cells/mL. If the cell density was below 1 million cells/mL, media was not added to the cultures. The number of viable cells were enumerated twice weekly until 40 days post plating. TRAC−/β2M−/anti-CD19 CAR+ or TRAC−/β2M−/Reg1−/anti-CD19 CAR+ were no longer detectable at 40 days in the cultures that lacked cytokines, indicating that any potential off-target effects due to genome editing did not induce growth factor independent growth/proliferation to the cells (FIG. 4). The cells only proliferated in the presence of cytokines (full media that contains cytokines) and did not proliferate in the presence of serum alone. Thus, genome editing did not induce any adverse events that allow the cells to grow in the absence of cytokine, growth factor or antigen stimulation.

Example 7: In Vivo Effect of Reg1 KO on Allogeneic CAR T Cells in the Intravenous Disseminated Nalm-6 Human Acute Lymphoblastic Leukemia Tumor Xenograft Model A disseminated mouse model was utilized to further assess the in vivo efficacy of allogeneic CAR T cells lacking β2M and TRAC, as well as Reg1. The intravenous disseminated model (disseminated model) utilized CD19+B-ALL derived Nalm-6 Human Acute Lymphoblastic Leukemia tumor cell line in NOG mice to demonstrate the efficacy of TRAC−/β2M−/anti-CD19 CAR+ T cells (anti-CD19 CAR T cells) with or without editing of the Reg1 locus. The Reg1 gene was edited via CRISPR/Cas-mediated gene editing using REG1-Z10 guide RNA (see Table 22). The anti-CD19 CAR T cells express an anti-CD19 CAR comprising the amino acid sequence of SEQ ID NO: 118. See also the sequence Tables 27 and 28 below, and WO2019/097305, the relevant disclosures of which are incorporated by reference for the subject matter and purpose referenced herein.

Efficacy of the anti-CD19 CAR T cells was evaluated in the disseminated model using methods employed by Translations Drug Development, LLC (Scottsdale, Ariz.) and described herein. In brief, 25, 5-8 week old female CIEA NOG (NOD.Cg-Prkdcscid Il2rgtm1Sug/JicTac) mice were individually housed in ventilated microisolator cages, maintained under pathogen-free conditions, 5-7 days prior to the start of the study. At the start of the study, the mice were divided into 5 treatment groups as shown in Table 5. The mice were inoculated with Nalm6-Fluc-GFP (Nalm6-Fluc-Neo/eGFP-Puro) cells intravenously to model disseminated disease. On Day 1, all mice received an intravenous injection of $0.5 \times 10^6$ Nalm6 cells/mouse. On Day 4, Groups 2-5 received an intravenous injection of CAR T cells ($4 \times 10^6$ CAR+ cells/mouse) as indicated in Table 5.

TABLE 5

Treatment groups for intravenous disseminated disease study

| Group | Nalm6 tumor cells $0.5 \times 10^6$ cells/mouse | CAR T cells (i.v.) $4 \times 10^6$ cells/mouse | N |
| --- | --- | --- | --- |
| 1 | X | NA | 5 |
| 2 | X | anti-CD19 CAR/TRAC−/β2M− (4e6 CAR+) | 5 |
| 3 | X | anti-CD19 CAR/TRAC−/β2M− (8e6 CAR+) | 5 |
| 4 | X | anti-CD19 CAR/TRAC−/β2M−/Reg1− (4e6 CAR+) | 5 |
| 5 | X | anti-CD19 CAR/TRAC−/β2M−/Reg1− (8e6 CAR+) | 5 |

During the course of the study, the mice were monitored daily and body weight was measured two times weekly. Bioluminescence (BLI; total ROI, photon/s) was measured twice weekly beginning on Day 4 of the study. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;

Tumors that inhibit normal physiological function such as eating, drinking, mobility and ability to urinate and or defecate;

Prolonged, excessive diarrhea leading to excessive weight loss (>20%); or

Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

In Vivo Survival Rate

Mice in groups receiving TRAC−/β2M−/anti-CD19 CAR+ T cells with or without an additional Reg1 disruption exhibited an increase in survival relative to mice in the untreated group (Group 1). Mice receiving either dose of TRAC−/β2M−/Reg1−/anti-CD19 CAR+ T cells exhibited increased survival in comparison to TRAC−/β2M−/anti-CD19 CAR+ T cells at each respective dose (FIGS. 5A and 5B). In addition, mice receiving either dose of TRAC−/β2M−/Reg1−/anti-CD19 CAR+ T cells had reduced leukemia burdens as indicated by diminished bioluminescence signal in comparison to TRAC−/β2M−/anti-CD19 CAR+ T cells at each respective dose (FIGS. 5C and 5D).

These data demonstrate that the Reg1 disruption in CAR T cells increases efficacy of CAR T cells in vivo, decreasing tumor burden and increasing survival.

Example 8: Efficient Disruption of TGFBRII by Cas9:sgRNA RNPs in T Cells

This example describes efficient editing of the TGFBRII gene in primary human T cells ex vivo using CRISPR/Cas9 gene editing. Genomic segments of the TGFBRII gene containing the first five (5) protein coding exon5 were used as input in gRNA design software. The genomic segments also included flanking splice site acceptor/donor sequences. Desired gRNAs were those that would lead to insertions or deletions in the coding sequence, disrupting the amino acid sequence of TFBRII, leading to out of frame/loss of function allele(s) (referred to as "TGFBRII knockout alleles" or "TGFBRII disrupted alleles"). Eight (8) in silico-identified gRNA spacer sequences targeting the CD70 gene were synthesized, and the gRNAs were specifically modified, as indicated in Table 39 and FIGS. 7A and 7B. While the modified gRNAs in Table 39 were modified with 2'-O-methyl phosphorothioate modifications, unmodified gRNAs, or gRNAs with other modifications, can be used.

Primary human T cells were transfected (electroporated) with a ribonucleoprotein particle (RNP) containing Cas9 nuclease and a synthetic modified sgRNA targeting the TGFBRII gene (sequences in Table 39) or controls (no Cas9, no gRNA). Four to six (4-6) days post transfection, cells were: (1) subjected to a TIDE analysis to assess indel frequency, and (2) processed by western blot (primary antibody: anti-human TGFBRII antibody, clone #16H2L4) to assess TGFBRII expression levels at the cell surface (FIG. 7B).

Figure 7A:
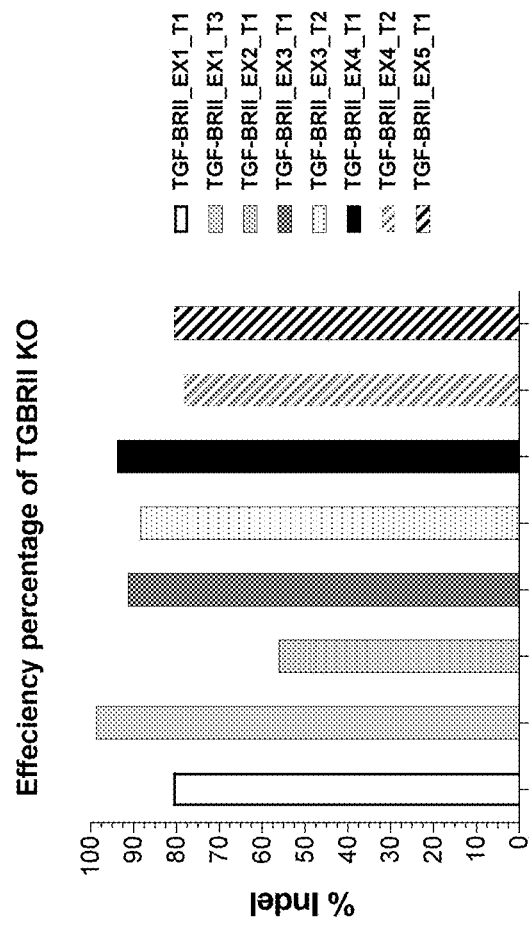
FIGS. 7A and 7B include diagrams showing knock out of TGFBRII using various guide RNAs as indicated.
Figure 7B:
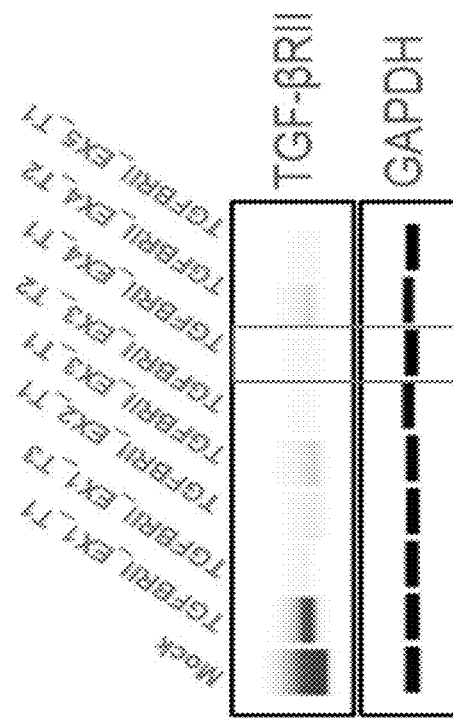

Eight (8) gRNAs yielded measurable data by TIDE analysis, as indicated in FIG. 7A. Seven (7) gRNA sequences yielded indel percentages (editing frequencies) above 80% indicating highly efficient gene editing (FIG. 7A). The level of TGFBRII protein expression was assessed by western blot to confirm the TIDE analysis data and GAPDH was used as a loading control. Seven (7) of the gRNAs showed nearly complete knock out of TGFBRII on the T cells (FIG. 7B).

On-Target and Off-Target Editing of TGFBRII Guide RNAs

On-target and off-target editing efficiencies of various TGFBRII-targeting gRNAs noted above were examined following the method disclosed in the above section. Briefly, activated T cells were transfected (electroporated) with a ribonucleoprotein particle (RNP) containing Cas9 nuclease and a synthetic modified sgRNA targeting the TGFBRII gene (sequences in Table 39 below) or controls (no Cas9, no gRNA).

For genomic on- and off-target assessment, these electroporation methods were used to generate two cell populations of edited cells from two different donor T cells. Cells were gene edited with each of the nine guides noted in Table 39 and then collected ten (10) days post transfection. These samples were analyzed with hybrid capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions (indels) indicating repair following CRISPR editing.

Five (5) gRNAs showed no off-target effect with an on-target editing rate greater than 85%, which includes TGFBRII_Ex1_T1, TGFBRII-Ex1-T2, TGFBRII_Ex1_T3, TGFBRII_Ex2_T1 and TGFBRII_Ex5_T1 as shown in Table 6 below.

TABLE 6

On-Targeting Editing Efficiency and Off-Target Effects of Anti-TGFBRII gRNAs

| Guide | gRNA target sequence + (PAM) | Number of predicted off-target sites tested | On-target mean editing hyb cap | Detected off-targets |
|---|---|---|---|---|
| TGFBRII-Ex1-T1 | CCGACTTCTGAACGTGCGGT (GGG)(SEQ ID NO: 2) | 7 | 86.80% | None |
| TGFBRII-Ex1-T2 | TGCTGGCGATACGCGTCCAC (AGG)(SEQ ID NO: 3) | 8 | 98.30% | None |
| TGFBRII-Ex1-T3 | TCGGTCTATGACGAGCAGCG (GGG)(SEQ ID NO: 4) | 7 | 99.60% | None |
| TGFBRII-Ex2-T1 | ATGGGCAGTCCTATTACAGC (TGG)(SEQ ID NO: 5) | 82 | 96.00% | None |
| TGFBRII-Ex3-T1 | ATTGTTCACTTGTTAGCCCC (AGG)(SEQ ID NO: 6) | 83 | 98.50% | One <1% off-target |
| TGFBRII-Ex3-T2 | GCTGAAGAACTGCCTCTATA (TGG)(SEQ ID NO: 7) | 133 | 98.10% | One 1-10% off-target |
| TGFBRII-Ex4-T1 | GCAGGATTTCTGGTTGTCAC (AGG)(SEQ ID NO: 8) | 222 | 98.80% | One <1% off-target |
| TGFBRII-Ex4-T2 | CTCCATCTGTGAGAAGCCAC (AGG)(SEQ ID NO: 9) | 255 | 99.40% | Four <1% off-targets |
| TGFBRII-Ex5-T1 | CCCCTACCATGACTTTATTC (TGG)(SEQ ID NO: 10) | 85 | 94.20% | None |

Tables 29-38 list potential indel sequences that may be generated by the gRNAs disclosed herein (deletions as dashes and insertions in bold).

Example 9: Generation of Genetically Modified T Cells that Lack TGFBRII Expression and are Resistant to TGF-β

This example describes the production of CAR T cells that lack expression of TGFBRII and the assessment of the effect of TGF-β on CAR T cell expansion with TGFBRII KO cells grown in complete media (X-Vivo 15 supplemented with IL-2 and IL-7).

Briefly, human T cells were first isolated and Cas9:sgRNA RNPs (1 μM Cas9, 5 μM gRNA) were delivered to activated human T cells by electroporation, followed by incubation with the recombinant adeno-associated adenoviral vectors (AAVs), serotype 6 (AAV6) (MOI 50,000). The nucleofection mix contained the Nucleofector™ Solution, $5\times10^6$ cells, 1 μM Cas9, and 5 μM gRNA (as described in Hendel et al., *Nat Biotechnol.* 2015; 33(9):985-989, PMID: 26121415). The RNP complex comprised Cas9 and sgRNA targeting the TRAC, B2M, CD70, and optionally TGFBRII genes (sgRNA sequences are shown in Table 23 and Tables 39, SEQ ID NOs: 58, 62, 54, and 301, respectively). The rAAV vector included the nucleotide sequence encoding an anti-CD70 CAR (the donor template in SEQ ID NO: 169 and the anti-CD70 CAR amino acid sequence of SEQ ID NO: 138.

Figure 8C:
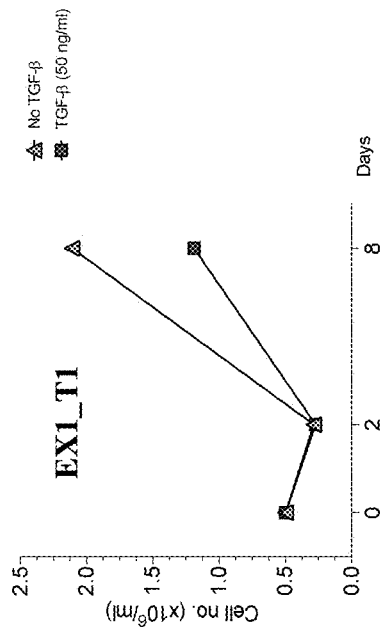
Figure 8E:
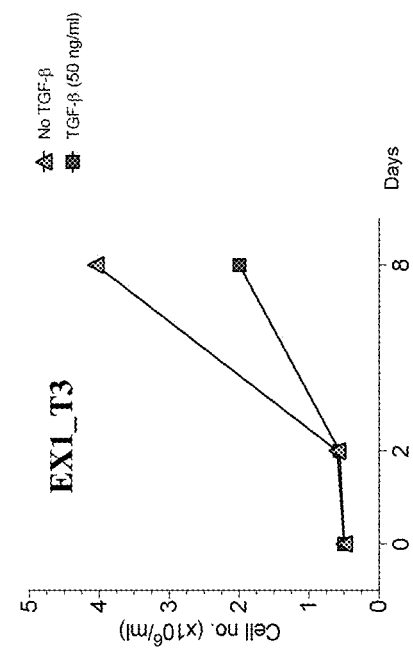

About one week post-electroporation, CAR T cells with an intact (i.e.: wild-type or non-engineered counterpart) TGFBRII gene were exposed to varying amounts recombinant human TGF-β (10, 20, 50 and 100 ng/ml) and cell expansion was recorded over time. TGF-β significantly inhibited CAR T expansion, a concentration as low as 10 ng/ml was sufficient to reduce CAR T expansion in cells with an intact TGFBRII gene (FIG. 8A).

Figure 8B:
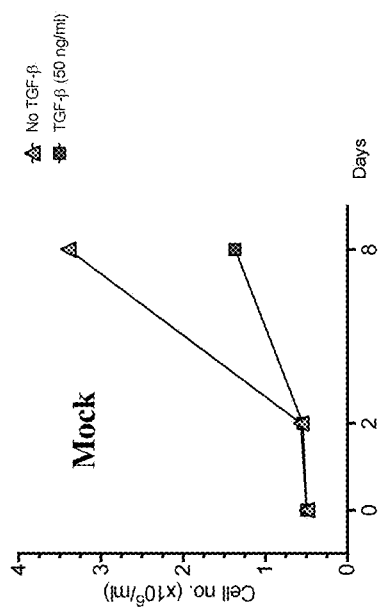
Figure 8D:
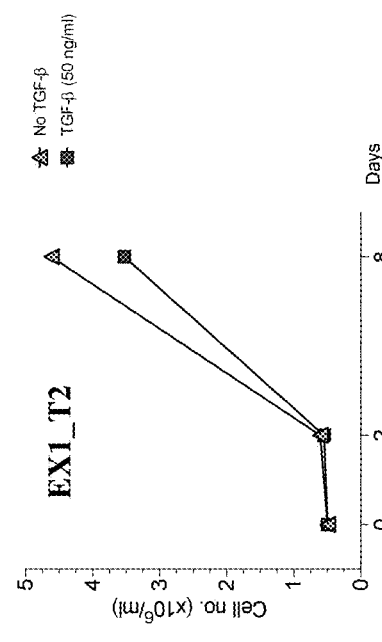
Figure 8F:
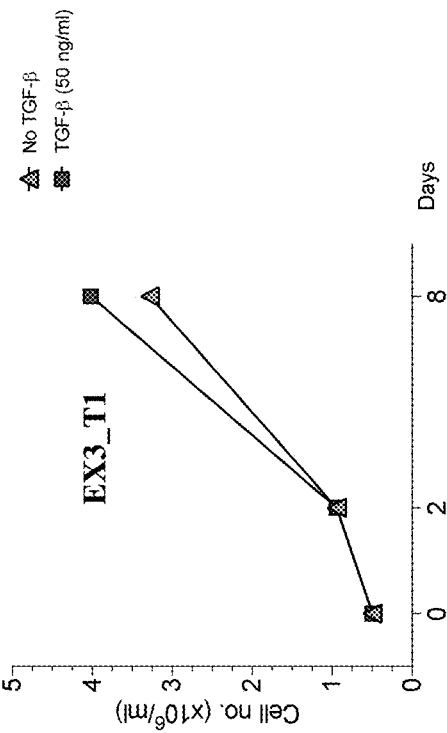
Figure 8G:
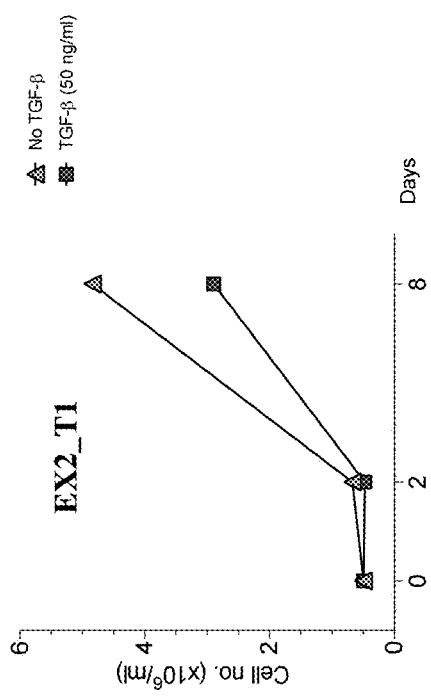
Figure 8H:
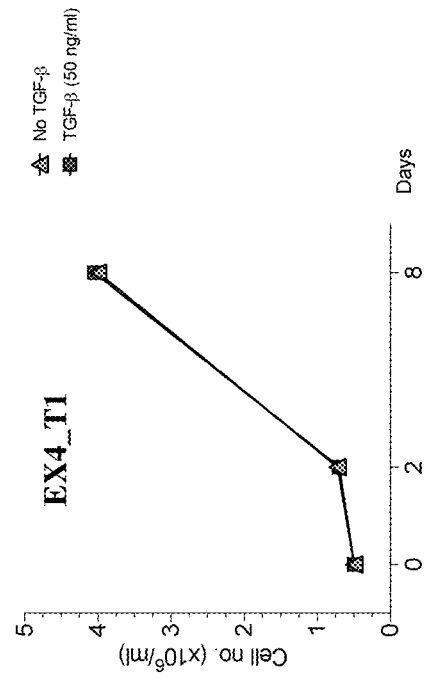
Figure 8I:
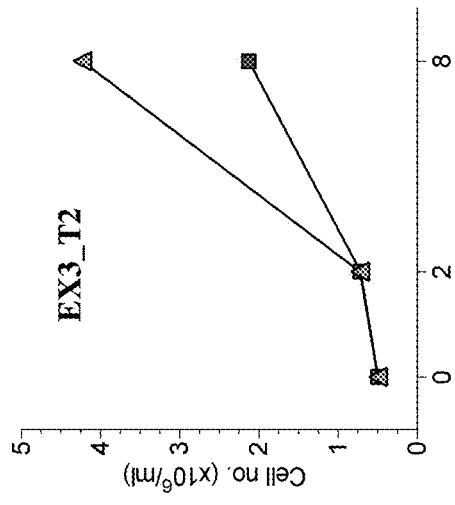
Figure 8K:
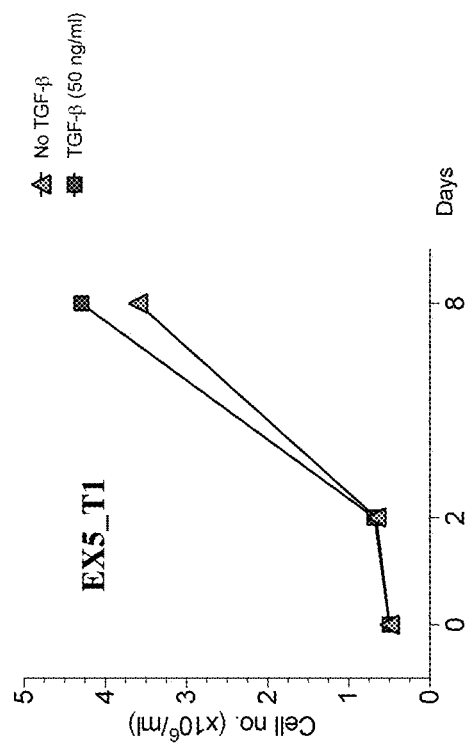
Figure 8J:
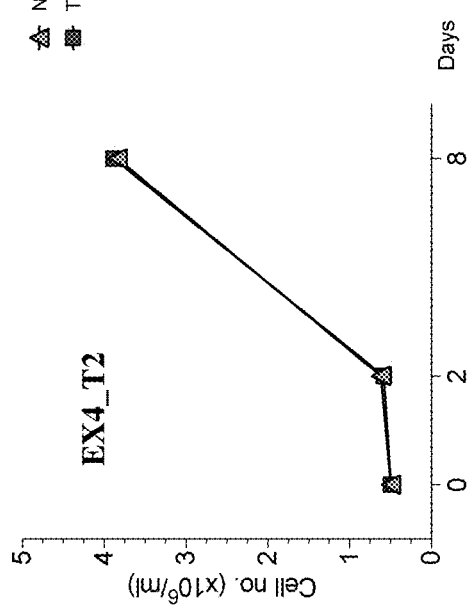

In another study, anti-CD70 CAR T cells with TGFBRII disruption were incubated with or without 50 ng/ml of recombinant human TGF-0, and the T cell expansion was monitored at day 2 and day 8 post-incubation with TGF-β and compared to mock cells. Mock cells (FIG. 8B) were anti-CD70 CAR T cells that did not have a disrupted TGFBRII gene. As shown in FIGS. 8C-8K, T cells with TGFBRII knocked-out were protected against the inhibitory effect of TGF-β on T cell expansion. The extent of protection varied with the sgRNA used to disrupt the TGFBRII gene. T cells that were transfected with gRNA targeting exon 1, 4 and 5 (TGFBRII_EX1_T2, TGFBRII_EX4_T1, TGFBRII_EX4_T2, TGFBRII_EX5_T1) showed the most resistance against a TGF-β inhibitory effect. Sequences of these gRNAs are provided in Table 39 below.

Example 10: Cell Killing Function of Anti-CD70 CAR T Cells with TGFBRII Disruption This example describes the production of allogeneic human T cells that lack expression of the TRAC gene, β2M gene and CD70 gene, and express a chimeric antigen receptor (CAR) targeting CD70. The edited CAR T cells further comprised knock out of the TGFBRII gene. As in the examples above, activated human T cells were electroporated with Cas9:sgRNA RNPs (1 μM Cas9, 5 μM gRNA), followed by incubation with a recombinant adeno-associated adenoviral vectors, serotype 6 (AAV6) (MOI 50, 000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54) and TGFBRII (SEQ ID NO: 301).

About one week post-electroporation, T cells were checked for CAR expression by flow cytometry. Both anti-CD70 CAR T cells and anti-CD70 CAR T cells lacking TGFBRII expressed nearly equivalent amount of CAR on their surface (71.5% CAR⁺ cells versus 73.7% CARP cells).

Figure 9:
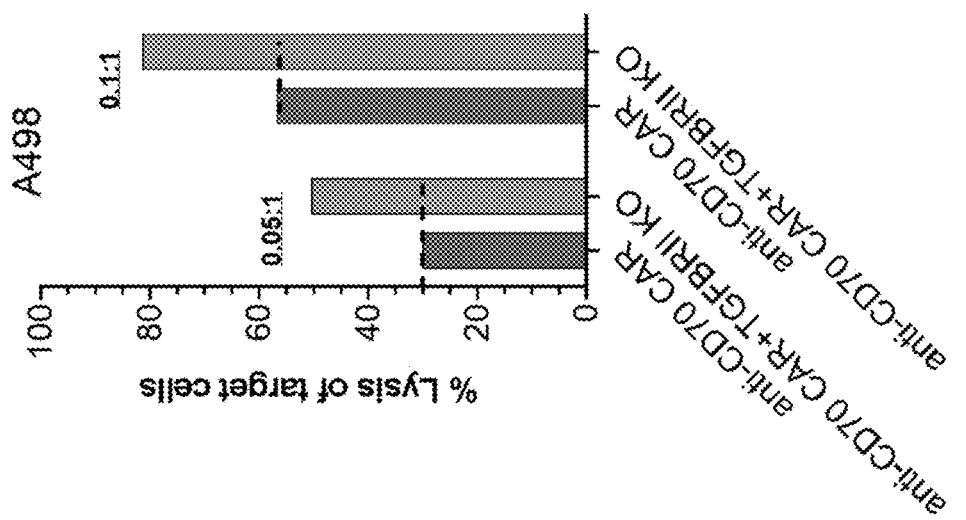
FIG. 9 is a diagram showing the effect of TGFBRII KO on CAR T cell killing ability against A498 cells at various E:T ratios as indicated. TGFBRII KO improves cytotoxicity of CAR-T cells.
Figures 10D, 10E:
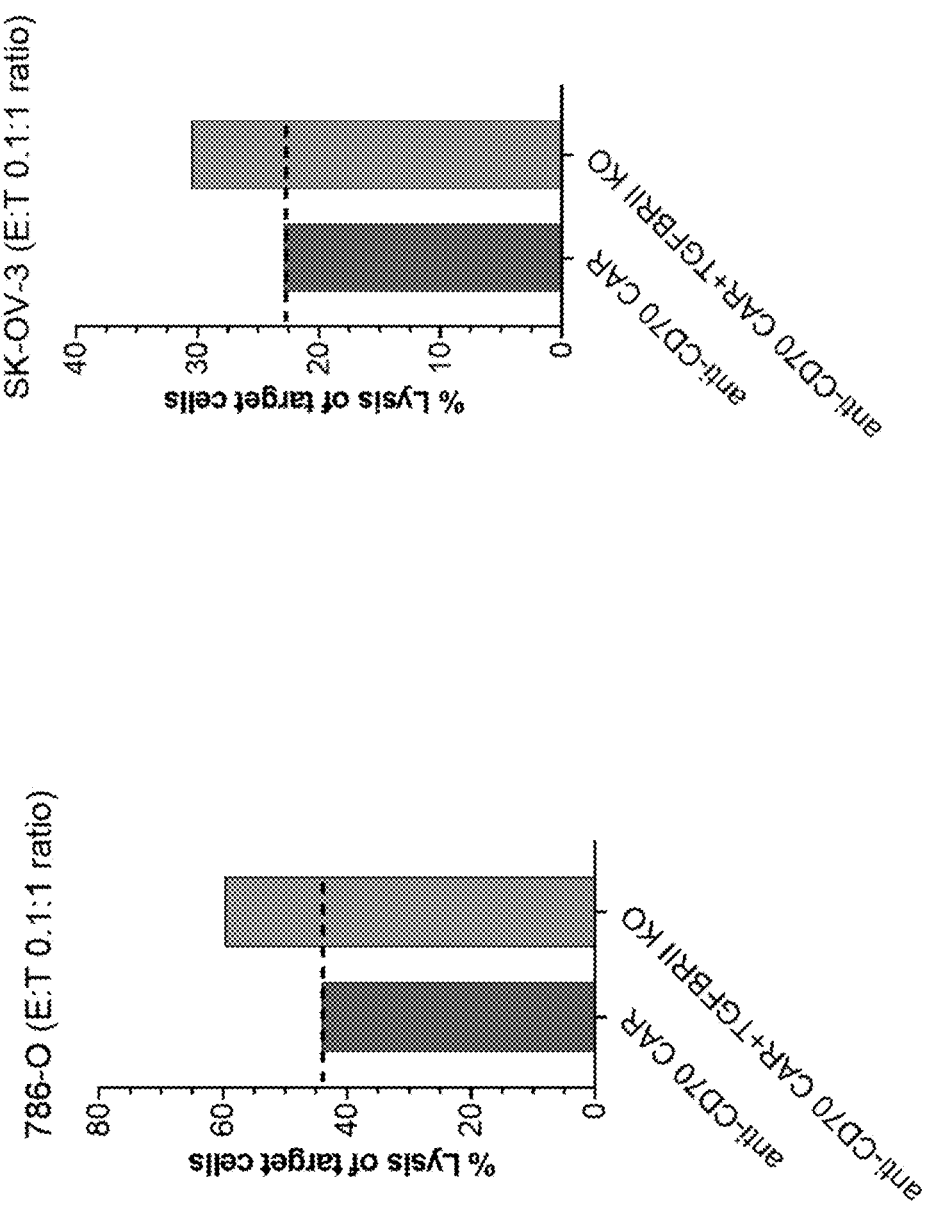

A cell killing assay was used to assess the ability of the TRAC–/β2M–/CD70–/TGFBRII–/anti-CD70 CAR+ cells to kill a CD70+ adherent renal cell carcinoma (RCC)-derived cell line (A498 cells). Adherent cells were seeded in 96-well plates at 50,000 cells per well and left overnight at 37° C. The next day edited anti-CD70 CAR T cells were added to the wells containing target cells at 0.05:1 or 0.1:1 CAR T:T cell (E:T) ratios. After the indicated incubation period, CAR T cells were removed from the culture by aspiration and 100 μL Cell titer-Glo (Promega) was added to each well of the plate to assess the number of remaining viable cells. The amount of light emitted per well was then quantified using a plate reader. Cells with TGFBRII knock out exhibited a more potent cell killing of RCC-derived cells following 24-hour co-incubation. The anti-CD70 CAR T cells demonstrated higher potency when TGFBRII was knocked out, which is clearly visible at two T cell: A498 ratios (0.05:1 and 0.1:1) (FIG. 9). This suggests that knocking-out the TGFBRII gene gives a higher cell kill potency to anti-CD70 CAR+ T cells. This finding was consistent across a wide panel of tumor lines from different tissues as shown in FIGS. 10A-10E. Knocking-out the TGFBRII gene enhances the cell killing capacity of anti-CD70 CAR T cells against 786-0 and CAM-1 (Renal cell carcinoma tumor lines), H1975 (Non-small cell lung cancer), Hs-766T (Pancreatic carcinoma) and SK-OV3 (Ovarian cancer) (FIGS. 10A-10E).

In another study, anti-CD70 CAR T was incubated with 50 ng/ml of recombinant human TGF-β for 24 hours and the expression of CD25 (IL-2R) on cell surface was assessed by flow cytometry. As shown in FIG. 11, anti-CD70 CAR T cells are susceptible to the inhibitory effect of TGF-β that causes downregulation of CD25. CD25 is an activation marker and involved in T cell proliferation. When the TGFBRII gene was knocked out, these cells become resistant to TGF-β and the CAR T cells retain activity and CD25 expression.

Also, when the cell kill of target cells (A498) was repeated in presence of 1, 10 and 50 ng/ml of recombinant human TGF-β. Anti-CD70 CAR T cells were adversely affected by presence of TGF-β as demonstrated by reduction in the cell kill capacity by CAR T cells with an intact TGFBRII gene (FIG. 12). However, anti-CD70 CAR T cells with a TGFBRII KO (anti-CD70 CAR+TGFBRII_EX4_T1) did not exhibit reduced cell killing ability in the presence of TGF-β (FIG. 12). In addition, T cell proliferation upon exposure to target antigen and effector cytokines production (IFN-γ and IL-2) were reduced in the presence of TGF-β (FIGS. 13A-13C). However, when the cells lacked the expression of TGFBRII, they we were completely protected against TGF-β inhibitory effects, also shown in FIGS. 13A-13C. This suggests that knocking out TGFBRII on the surface of CAR T cells protects the CAR T cells from the adverse effect of TGF-β in the tumor microenvironment.

Example 11: Generation of Anti-CD70 CAR T Cells that Lack TGFBRII Expression and are Resistant to the Inhibitory Effect of Fibroblasts This example describes the production of allogeneic human T cells that lack expression of the TRAC gene, β2M gene and CD70 gene, and express a chimeric antigen receptor (CAR) targeting CD70 and how they are susceptible to the inhibitory effect of fibroblasts, which are a major component of solid tumor microenvironment (TME). The edited CAR T cells further comprised knock out of the TGFBRII gene. As in the examples above, activated human T cells we electroporated with a recombinant adeno-associated adenoviral vectors, serotype 6 (AAV6) (MOI 50, 000), and Cas9:sgRNA RNPs (1 µM Cas9, 5 µM gRNA).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54) and TGFBRII (SEQ ID NO: 301).

A cell killing assay was used to assess the inhibitory effect of fibroblast on anti-CD70 CAR T cells to kill CD70+ adherent tumor cell lines: H1975 (Non-small cell lung cancer), Hs-766T (Pancreatic carcinoma), or SK-OV3 (Ovarian cancer). The cell kill assay was performed as described in example 3. Briefly, Adherent cells were seeded in 96-well plates at 50,000 cells per well and left overnight at 37° C. and the fibroblast cells (LL 86 (LeSa) ATCC® CCL-190™) were added to the top chamber of a transwell plate without direct contact with target cells. The next day edited anti-CD70 CAR T cells were added to the wells containing target cells. After the indicated incubation period, CAR T cells were removed from the culture by aspiration and 100 µL Cell titer-Glo (Promega) was added to each well of the plate to assess the number of remaining viable cells. The amount of light emitted per well was then quantified using a plate reader. As shown in FIG. 14, the presence of the fibroblast cells on the top chamber led to a decrease of the cell kill capacity of anti-CD70 CAR T cells against the target cells which might suggest that these fibroblast secreted a factor that decrease anti-CD70 CAR T killing effect.

Figure 15A:
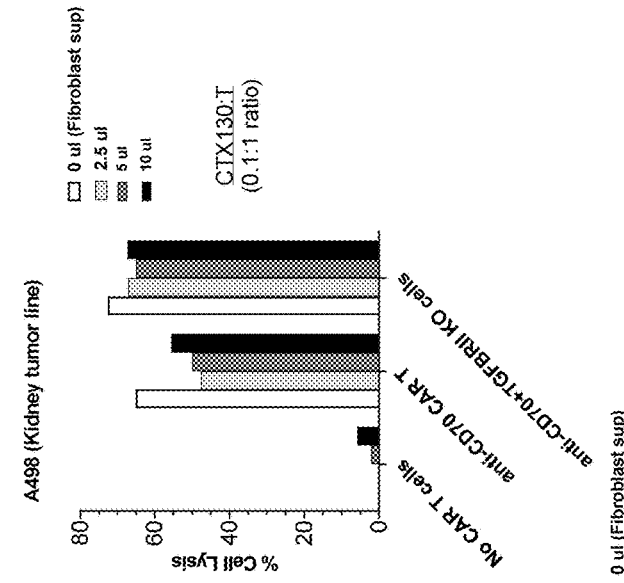
FIGS. 15A-15C include graphs showing that TGFBRII KO protects CAR-T cells against the inhibitory effect of fibroblasts. Anti-CD70 CAR T was co-cultured with target cells (A498) at 0.1:1 (E:T) in presence of different volumes of conditioned media from CCL-190 (2.5, 5, 10 µL) and the cell kill capacity was evaluated and compared to cells with TGFBRII KO. The ability of anti-CD70 CAR T cells (with or without TGFBRII KO) to kill target cells is shown in Hs-766T pancreatic tumor cells (FIG. 15A), A498 kidney tumor cells (FIG. 15B), and H1975 lung tumor cells (FIG. 15C).
Figure 15B:
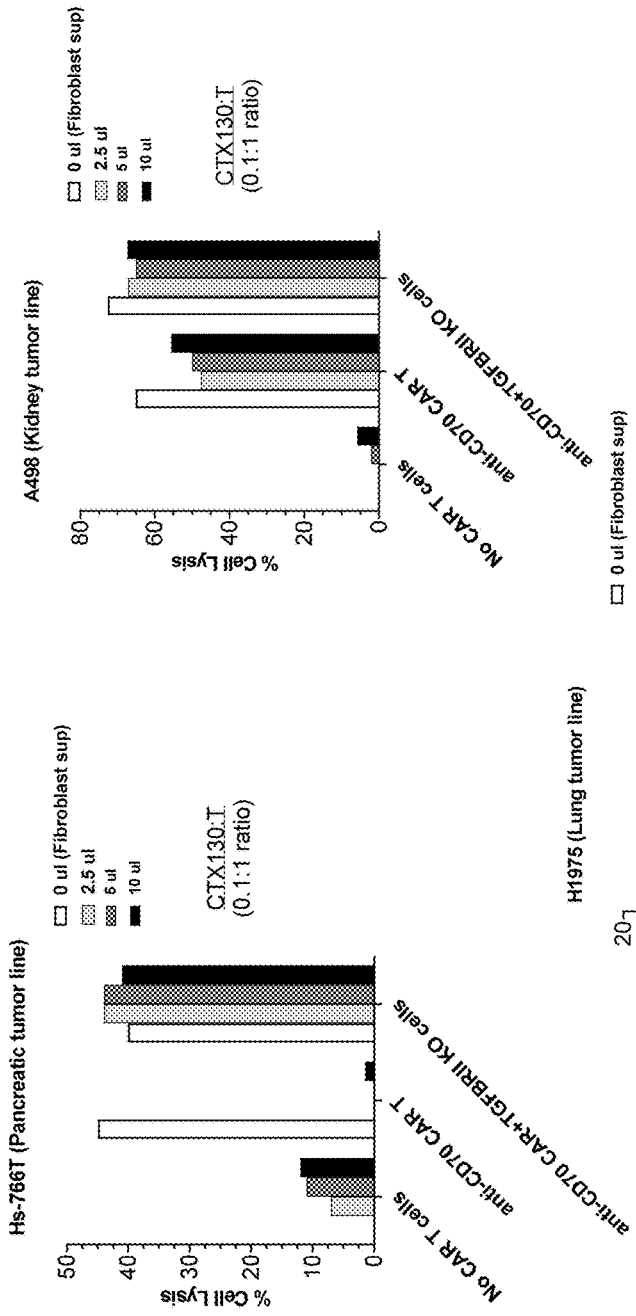
Figure 15C:
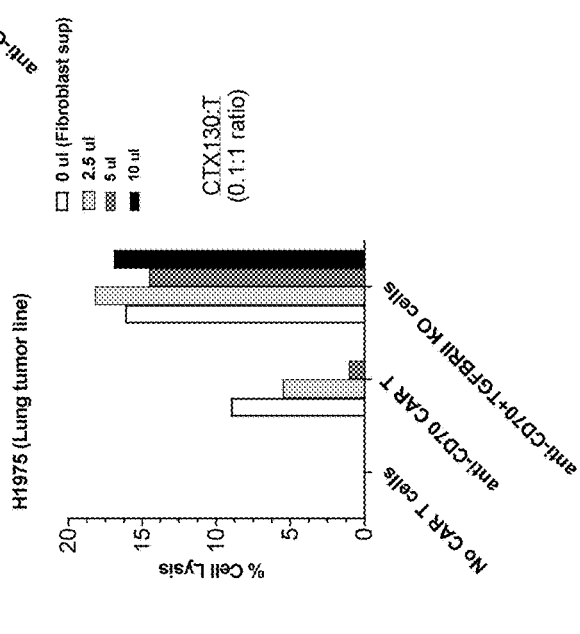

This finding was confirmed when this experiment was repeated with the presence of conditioned media from the fibroblast instead on the cells and similar inhibition was observed. Briefly, 1×10⁶ CCL-190 fibroblast cells we seeded/0.5 ml in a 24 well plate and incubated overnight and supernatants were collected. A cell kill assay as previously described was carried out with anti-CD70 CAR T cells and tumors cells at a ratio of 0.1:1 effector to target cell ratio, in the presence or absence of fibroblast supernatant and incubated overnight. Cell kill was measured using the CellTiter-Glo® Luminescent Cell Viability Assay. This experiment confirms that fibroblasts secrete a factor that causes a reduction in the killing capacity of anti-CD70 CAR T cells. Disruption of the TGFBRII gene on the surface of anti-CD70 CAR T protected these cells against this inhibitory effect. The TGFBRII KO improved the cell killing ability of anti-CD70 CAR T cells against pancreatic tumor cells, Hs-766T (FIG. 15A), kidney tumor cells, A498 (FIG. 15B), and lung tumor cells, H1975 (FIG. 15C) in the presence of fibroblasts. These data suggest that fibroblasts are contributing to the TGF-β production in TME and reduce the cell kill capacity of anti-CD70 CAR T cells and this could be avoided by disrupting TGFBRII on the surface of the CAR T cell.

Example 12: Generation of CAR T Cells with Disrupted TGFBRII and Regnase-1 Genes Allogeneic human T cells that lack expression of the TRAC gene, β2M gene, CD70 gene, TGFBRII gene and Regnase-1 gene, and express a chimeric antigen receptor (CAR) targeting CD70 were produced. Activated human T cells were electroporated with Cas9:sgRNA RNPs (1 µM Cas9, 5 µM gRNA), followed by incubation with a recombinant adeno-associated adenoviral vectors, serotype 6 (AAV6) (MOI 50, 000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO:54), TGFBRII (SEQ ID NO: 313) and REG-1 (SEQ ID NO: 51). The sgRNAs, which form RNPs with the Cas9 enzyme, can be introduced into the T cells in a single electroporation event to produce the resulting modified cell populations shown in Table 7 below. Alternatively, they can be introduced into the T cells in two sequential electroporation events to produce the resulting cell populations. After the electroporation, the cells were transduced with the recombinant AAVs to introduce the donor template encoding for the anti-CD70 CAR.

TABLE 7

Genetically Engineered CAR-T Cell Populations

| Population | Edits |
| --- | --- |
| Anti-CD70 CAR T cells | anti-CD70 CAR+/TRAC−/B2M−/CD70− |
| Anti-CD70 CAR T + Reg KO cells | anti-CD70 CAR+/TRAC−/B2M−/CD70−/Reg− |
| Anti-CD70 CAR T + TGBBRII KO cells | anti-CD70 CAR+/TRAC−/B2M−/CD70−/TGFBRII− |
| Anti-CD70 CAR T + Reg KO + TGFBRII KO cells | anti-CD70 CAR+/TRAC−/B2M−/CD70−/Reg−/TGFBRII− |

At 7 days post-electroporation, T cells were checked for CAR expression by flow cytometry. Both anti-CD70 CAR T cells and anti-CD70 CAR T cells that lack Regnase expressed nearly equivalent amount of CAR on their surface at day 7 post HDR. The results are provided in Table 7A below.

TABLE 7A

CAR Expression Levels in Genetically Engineered Anti-CD70 CAR T Cells

| Population | Edits | CAR % |
| --- | --- | --- |
| Anti-CD70 CAR T cells | anti-CD70 CAR+/TRAC−/B2M−/CD70− | 82.2 |
| Anti-CD70 CAR T + Reg KO cell | anti-CD70 CAR+/TRAC−/B2M−/CD70−/Reg− | 83.1 |
| Anti-CD70 CAR T + TGIFBRII KO cells | anti-CD70 CAR+/TRAC−/B2M−/CD70−/TGFBRII− | 79.7 |
| Anti-CD70 CAR T + Reg KO + TGFBRII KO cells | anti-CD70 CAR+/TRAC−/B2M−/CD70−/Reg−/TGFBRII− | 81.8 |

Example 13: Disruption of Regnase-1 and TGFBRII Increases CAR T Cell Killing Upon Serial Rechallenge In Vitro The anti-CD70 CARP T cells generated above were serially rechallenged with CD70+ kidney cancer cell line, ACHN, and evaluated for their ability to kill the CD70+ kidney cancer cell line ACHN.

The anti-CD70 CAR⁺ T cells used in this experiment contained the following edits:

Anti-CD70 CAR T cells: anti-CD70 CAR+/TRAC−/B2M−/CD70−

Anti-CD70 CAR T+Reg KO cells: anti-CD70 CAR+/TRAC−/B2M−/CD70−/Reg−

Anti-CD70 CAR T+TGFBRII KO cells: anti-CD70 CAR+/TRAC−/B2M−/CD70−/TGFBRII−

Anti-CD70 CAR T+Reg KO+TGFBRII KO cells: anti-CD70 CAR+/TRAC−/B2M−/CD70−/Reg−/TGFBRII−

In a 96-well plate format, CAR T cells were first co-cultured with ACHN cells (4,000 CAR T cells, 16,000 tumor cells) on D0 and re-challenged with tumor cells as follows: 16,000 tumor cells on D2 and D4; 40,000 cells on D7; 50,000 cells on D9; 50,000 cells on D11).

Analysis of tumor cell and CAR T cell number was performed at D1, D3, D6, D8, D10 and D12 using flow cytometry (method adapted from Wang et al., JoVE 2019). The following antibodies in Table 8 were used at 1:100 dilution.

TABLE 8

Antibody Information

| Antibody | Flour | cat # | Dilution | Vendor |
|---|---|---|---|---|
| CD4 | BV510 | 344718 | 1:100 | Biolegend |
| CD8 | PacBlue | 300546 | 1:100 | Biolegend |
| CD70 | FITC | 355106 | 1:100 | Biolegend |
| CD62L | BV605 | 304833 | 1:100 | Biolegend |
| human CD45 | BV785 | 304048 | 1:100 | Biolegend |
| PD1 | APC/Cy7 | 329922 | 1:100 | Biolegend |
| CD45RO | PE/Cy7 | 304230 | 1:100 | Biolegend |
| Streptavidin | APC | 405207 | 1:100 | Biolegend |

TABLE 8-continued

Antibody Information

| Antibody | Flour | cat # | Dilution | Vendor |
|---|---|---|---|---|
| Tim3 | PE | 345006 | 1:100 | Biolegend |
| Live/Dead | 7AAD | BDB559925 | 1:500 | BD |

Figure 16A:
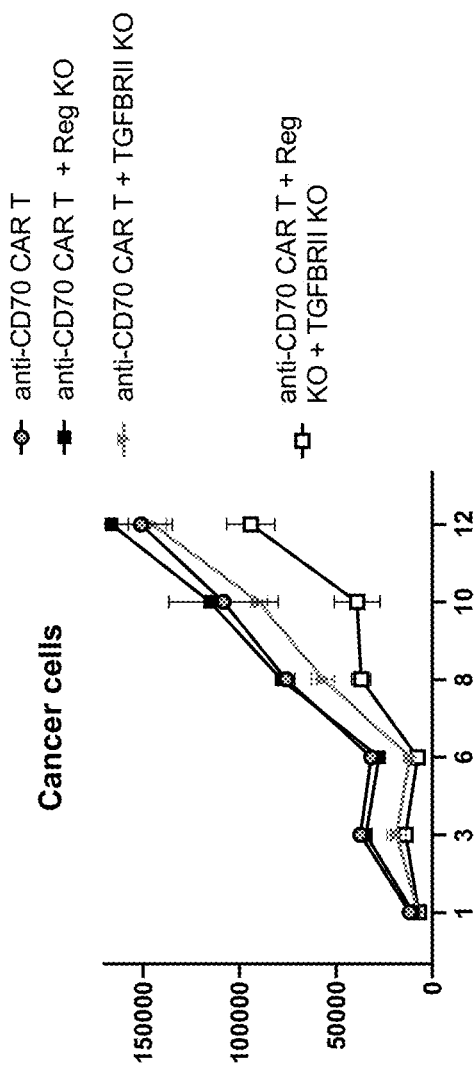
FIG. 16A-16B include diagrams showing synergistic effects of TGFBRII and Regnase double disruptions with in vitro rechallenge of CAR T Cells with ACHN.
Figure 16B:
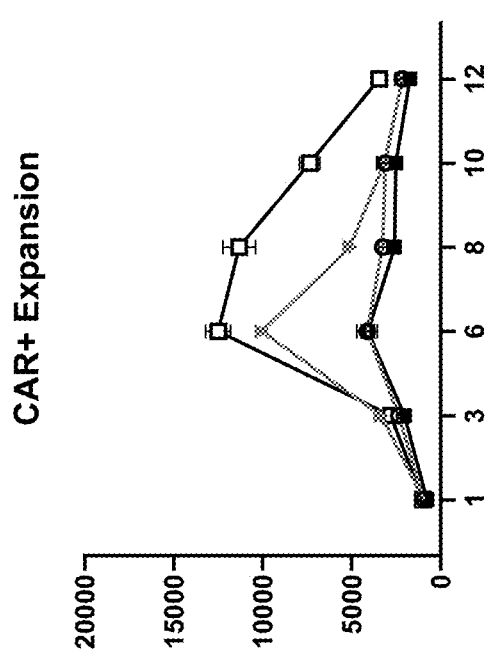

The results demonstrate that disrupting both the TGFBRII gene and the Regnase gene improved potency (FIG. 16A) and CAR+ T cell expansion (FIG. 16B) when CAR T cells are repeatedly challenged with CD70+ positive target cells. Potency and expansion is improved compared to CAR T cells that have neither, or only one (i.e.: TGFBRII or Regnase), of the genes disrupted.

Example 14: Treatment Efficacy of Anti-CD70 CART Cells with Multiple Gene Disruptions in the Subcutaneous Renal Cell Carcinoma Tumor Xenograft Model Treatment in the Renal Cell Carcinoma Tumor Model The ability of T cells expressing a CD70 CAR with TGFBRII and/or Regnase gene edits to eliminate renal cell carcinoma cells that express medium levels of CD70 was evaluated in vivo using a subcutaneous renal cell carcinoma (CAKI-1) tumor xenograft mouse model. Anti-CD70 CAR+ T cells were produced as described above. See, e.g., Example 13.

The ability of these anti-CD70 CAR+ T cells to ameliorate disease caused by a CD70+ renal carcinoma cell line was evaluated in NSG mice using methods employed by Translational Drug Development, LLC (Scottsdale, Ariz.). In brief, 20, 5-8 week old female, NSG mice were individually housed in ventilated microisolator cages, maintained under pathogen-free conditions, 5-7 days prior to the start of the study. Mice received a subcutaneous inoculation of $5 \times 10^6$ Caki-1 renal cell carcinoma cells/mouse in the right hind flank. When mean tumor size reached target of ~70 mm$^3$, the mice were further divided into 5 treatment groups as shown in Table 9. On Day 1, treatment four groups received a single 200 μl intravenous dose of $1 \times 10^7$ anti-CD70 CAR+ T cells according to Table 9.

TABLE 9

Treatment groups

| Group | CAR-T | Caki-1 cells | CAR-T cell treatment (i.v.) | N |
|---|---|---|---|---|
| 1 | None | $5 \times 10^6$ cells/mouse | None | 4 |
| 2 | Anti-CD70 CAR T cells: anti-CD70 CAR+/TRAC−/B2M−/CD70− | $5 \times 10^6$ cells/mouse | $1 \times 10^7$ cells/mouse | 4 |
| 3 | Anti-CD70 CAR T + Reg KO cells: anti-CD70 CAR+/TRAC−/B2M−/CD70−/Reg− | $5 \times 10^6$ cells/mouse | $1 \times 10^7$ cells/mouse | 4 |
| 4 | Anti-CD70 CAR T + TGFBRII KO cells: anti-CD70 CAR+/TRAC−/B2M−/CD70−/TGFBRII− | $5 \times 10^6$ cells/mouse | $1 \times 10^7$ cells/mouse | 4 |
| 5 | Anti-CD70 CAR T + Reg KO + TGFBRII KO cells: anti-CD70 CAR+/TRAC−/B2M−/CD70−/Reg−/TGFBRII− | $5 \times 10^6$ cells/mouse | $1 \times 10^7$ cells/mouse | 4 |

Figure 17A:
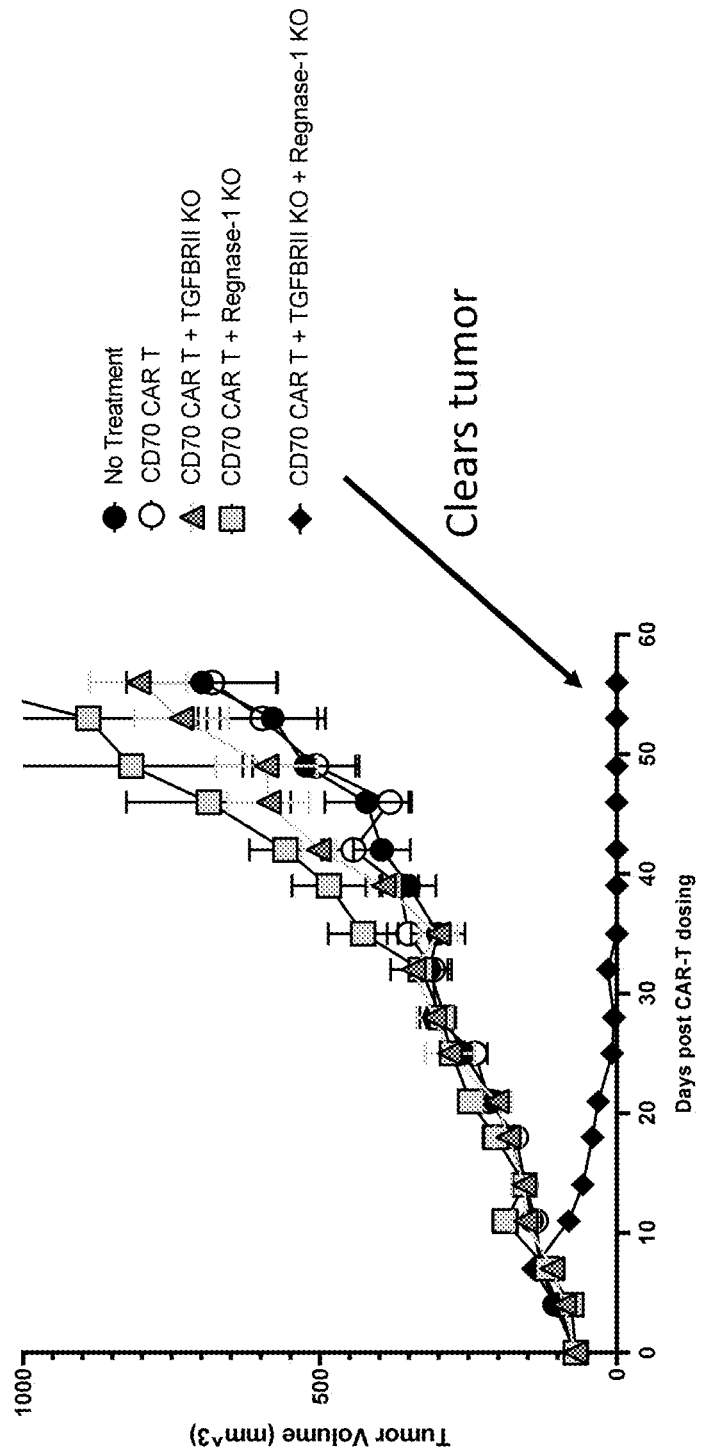
FIG. 17A-17B include diagrams showing synergistic effects of disrupting both TGFBRII and Regnase genes in cancer xenograph models.

Tumor volume was measured 2 times weekly (~every 3-4 days) from day of treatment initiation. By day 11 post-injection, anti-CD70 CAR T cells with both TGFBRII and Regnase genes KO began to show a significant effect on reducing tumor volume compared to other treatment groups. Approximately one month later the anti-CD70 CAR T+Reg KO+TGFBRII KO cells had completely eliminated tumor growth in the subcutaneous CAM-1 model (FIG. 17A).

These results demonstrated that disrupting both the TGFBRII and Regnase genes in CAR T cells increased the potency of the CAR T Cells and effectively cleared tumors in the subcutaneous CAM-1 renal cell carcinoma tumor xenograft model.

Treatment in the Non-Small Cell Lung Carcinoma (NSCLC) Tumor Model

The ability of T cells expressing a CD70 CAR with TGFBRII and/or Regnase gene edits to eliminate lung adenocarcinoma cells that express moderate levels of CD70 was evaluated in vivo using a subcutaneous lung carcinoma (NCI-H1975) tumor xenograft mouse model. Anti-CD70 CAR+ T cells were produced as described herein. See, e.g., Example 13.

The ability of these anti-CD70 CAR+ T cells to ameliorate disease caused by a CD70+ lung carcinoma cell line was evaluated in NSG mice using methods employed by Translational Drug Development, LLC (Scottsdale, Ariz.). In brief, 20, 5-8 week old female, NSG mice were individually housed in ventilated microisolator cages, maintained under pathogen-free conditions, 5-7 days prior to the start of the study. Mice received a subcutaneous inoculation of $5 \times 10^6$ NCI-H1975 lung carcinoma cells/mouse in the right hind flank. When mean tumor size reached target of ~85 mm$^3$, the mice were further divided into 5 treatment groups as shown in Table 10. On Day 1, treatment four groups received a single 200 µl intravenous dose of $1 \times 10^7$ anti-CD70 CAR+ T cells according to Table 10.

TABLE 10

Treatment groups

| Group | CAR-T | NCI-H1975 cells | CAR+ T cell treatment (i.v.) | N |
|---|---|---|---|---|
| 1 | None | $5 \times 10^6$ cells/mouse | None | 4 |
| 2 | Anti-CD70 CAR T cells: anti-CD70 CAR+/TRAC−/B2M−/CD70− | $5 \times 10^6$ cells/mouse | $1 \times 10^7$ cells/mouse | 4 |
| 3 | Anti-CD70 CAR T + Reg KO cells: anti-CD70 CAR+/TRAC−/B2M−/CD70−/Reg− | $5 \times 10^6$ cells/mouse | $1 \times 10^7$ cells/mouse | 4 |
| 4 | Anti-CD70 CAR T + TGFBRII KO cells: anti-CD70 CAR+/TRAC−/B2M−/CD70−/TGFBRII− | $5 \times 10^6$ cells/mouse | $1 \times 10^7$ cells/mouse | 4 |
| 5 | Anti-CD70 CAR T + Reg KO + TGFBRII KO cells: anti-CD70 CAR+/TRAC−/B2M−/CD70−/Reg−/TGFBRII− | $5 \times 10^6$ cells/mouse | $1 \times 10^7$ cells/mouse | 4 |

Figure 17B:
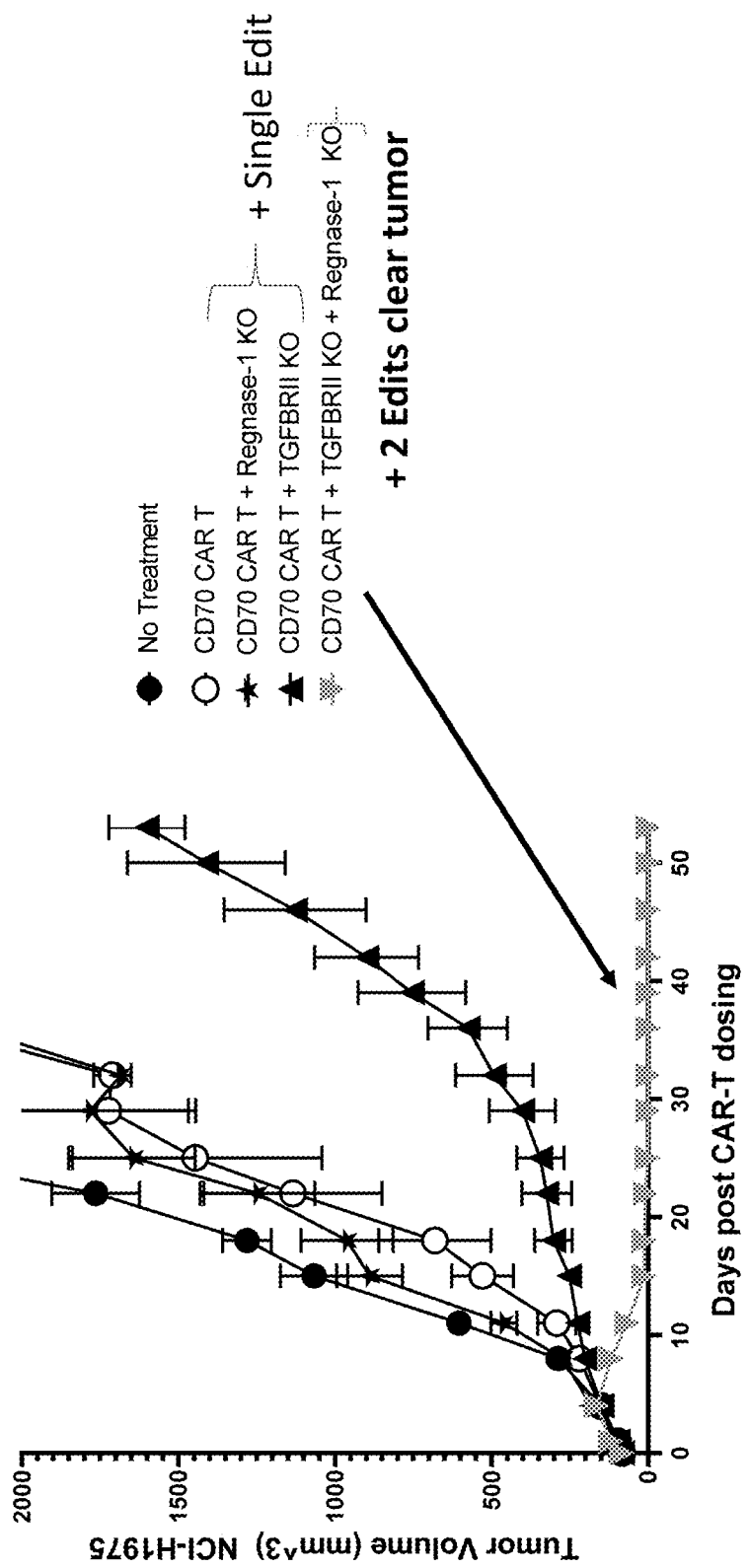

Tumor volume was measured 2 times weekly from day of treatment initiation. By day 12 post-injection, animal treated with anti-CD70 CAR T cells having the TGFBRII edit exhibited attenuated tumor growth. Tumors treated with anti-CAR T cells with both TGFBRII and Regnase genes disrupted began to show a decrease in tumor volume by day 8 post-injection and cleared tumors by day 29 in 4 mice out of 4. This complete regression of tumors in treated animals continued through day 53 post injection. Treatment with anti-CD70 CAR+/TRAC−/B2M−/CD70−/Reg−/TGFBRII− T cells resulted in potent activity against established H1975 lung cancer xenografts through 53 days post injection (FIG. 17B). These data demonstrate that disrupting TGFBRII alone or TGFBRII and Regnase-1 in CAR T cells have potent activity against human CD70+ lung cancer tumors in vivo.

Example 15: Tumor Re-Challenge Model Renal Cell Carcinoma Large Tumor Xenograft Model The efficacy of anti-CD70 CAR T cells having TGFBRII and/or Regnase-1 genes disrupted (see, e.g., Example 10) were tested in a subcutaneous A498 xenograft model with an ACHN re-challenge. In brief, five million A498 cells were injected subcutaneously in the right flank of NSG mice. Tumors were allowed to grow to an average size of approximately 425 mm$^3$ after which the tumor-bearing mice were randomized in five groups (N=5/group). Group 1 was left untreated (no treatment) while Groups 2-5 received one of the anti-CD70 CAR T cell treatments shown Table 11.

TABLE 11

Treatment Conditions

| Group | CAR-T | A498 cells | CAR+ T cell treatment (i.v.) | N |
|---|---|---|---|---|
| 2 | Anti-CD70 CAR T cells: anti-CD70 CAR+/TRAC−/B2M−/CD70− | $5 \times 10^6$ cells/mouse | $8 \times 10^6$ cells/mouse | 5 |
| 3 | Anti-CD70 CAR T + Reg KO cells: anti-CD70 CAR+/TRAC−/B2M−/CD70−/Reg− | $5 \times 10^6$ cells/mouse | $8 \times 10^6$ cells/mouse | 5 |
| 4 | Anti-CD70 CAR T + TGFBRII KO cells: anti-CD70 CAR+/TRAC−/B2M−/CD70−/TGFBRII− | $5 \times 10^6$ cells/mouse | $8 \times 10^6$ cells/mouse | 5 |
| 5 | Anti-CD70 CAR T + Reg KO + TGFBRII KO cells: anti-CD70 CAR+/TRAC−/B2M−/CD70−/Reg−/TGFBRII− | $5 \times 10^6$ cells/mouse | $8 \times 10^6$ cells/mouse | 5 |

On Day 56, a tumor re-challenge was initiated whereby $1 \times 10^7$ ACHN cells were injected into the left flank of treated mice and into a new control group (no treatment).

Figure 18A:
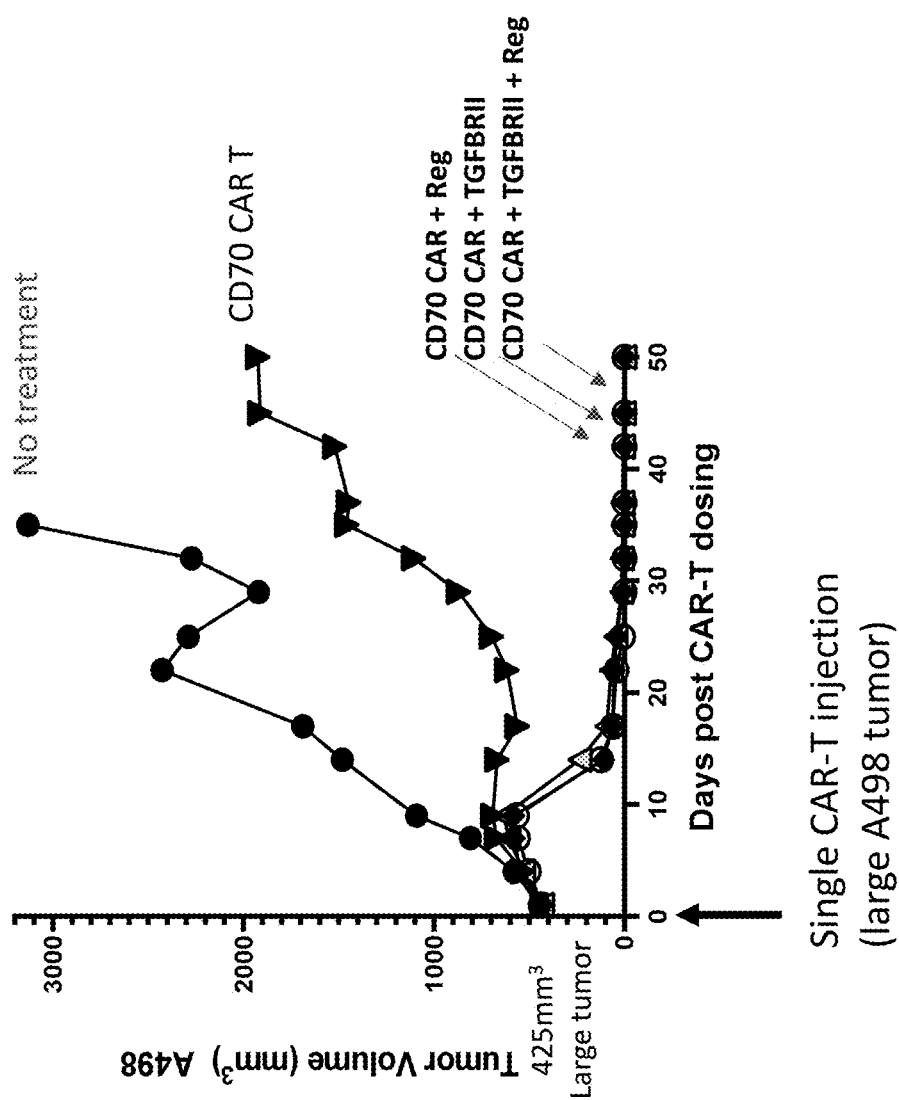
FIG. 18A-18B include diagrams showing synergistic effects of disrupting both TGFBRII and Regnase genes in an RCC rechallenge xenograph model.
Figure 18B:
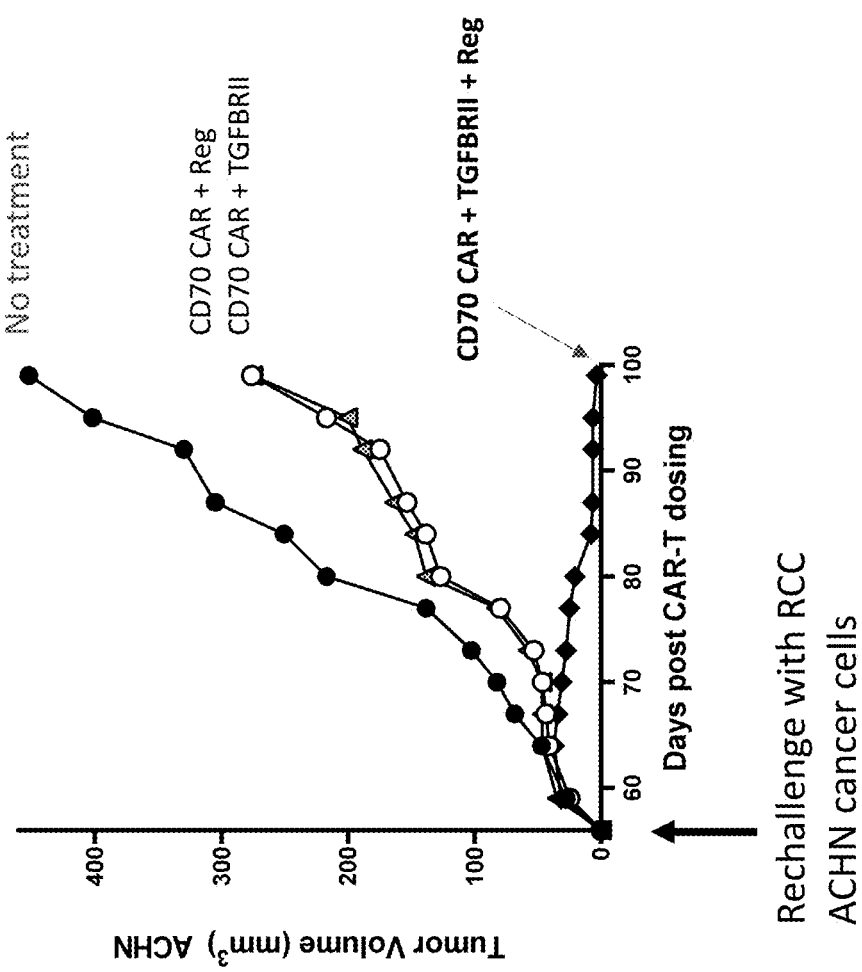

As shown in FIG. 18A, all mice treated with all CAR T cell populations having a disrupted TGFBRII and/or Regnase gene showed complete clearance of the A498 tumor by day 50. However, when mice were rechallenged with a new RCC tumor cell (ACHN) only CAR T Cells with both Regnase and TGFBRII edits were able to clear the tumor compared to cells with either Regnase-1 or TGFBRII disruptions alone (FIG. 18B).

Example 16: Analysis of T Cell Fraction in Renal Cell Carcinoma (CAKI-1) Tumor Xenograft Model Blood samples were taken from mice with CAKI-1 RCC tumors, 44 days after CAR T administration. Briefly, 100 ul of mouse whole blood was collected via submandibular vein. Red blood cell lysis buffer was used to achieve optimal lysis of erythrocytes with minimal effect on lymphocytes. Human CD45 and mouse CD45 were used as a biomarker to separate human and mouse cells by FACS. The blood samples were evaluated by flow cytometry looking for absolute CAR T counts as well as memory T cell subsets. An anti-CD70 CAR anti-idiotype antibody was used to detect CAR T cells and CD45RO+CD27+ to define central memory T cells. See U.S. Patent Application No. 63/069,889, the relevant disclosures of which are incorporated by reference for the subject matter and purpose referenced herein.

Figure 19A:
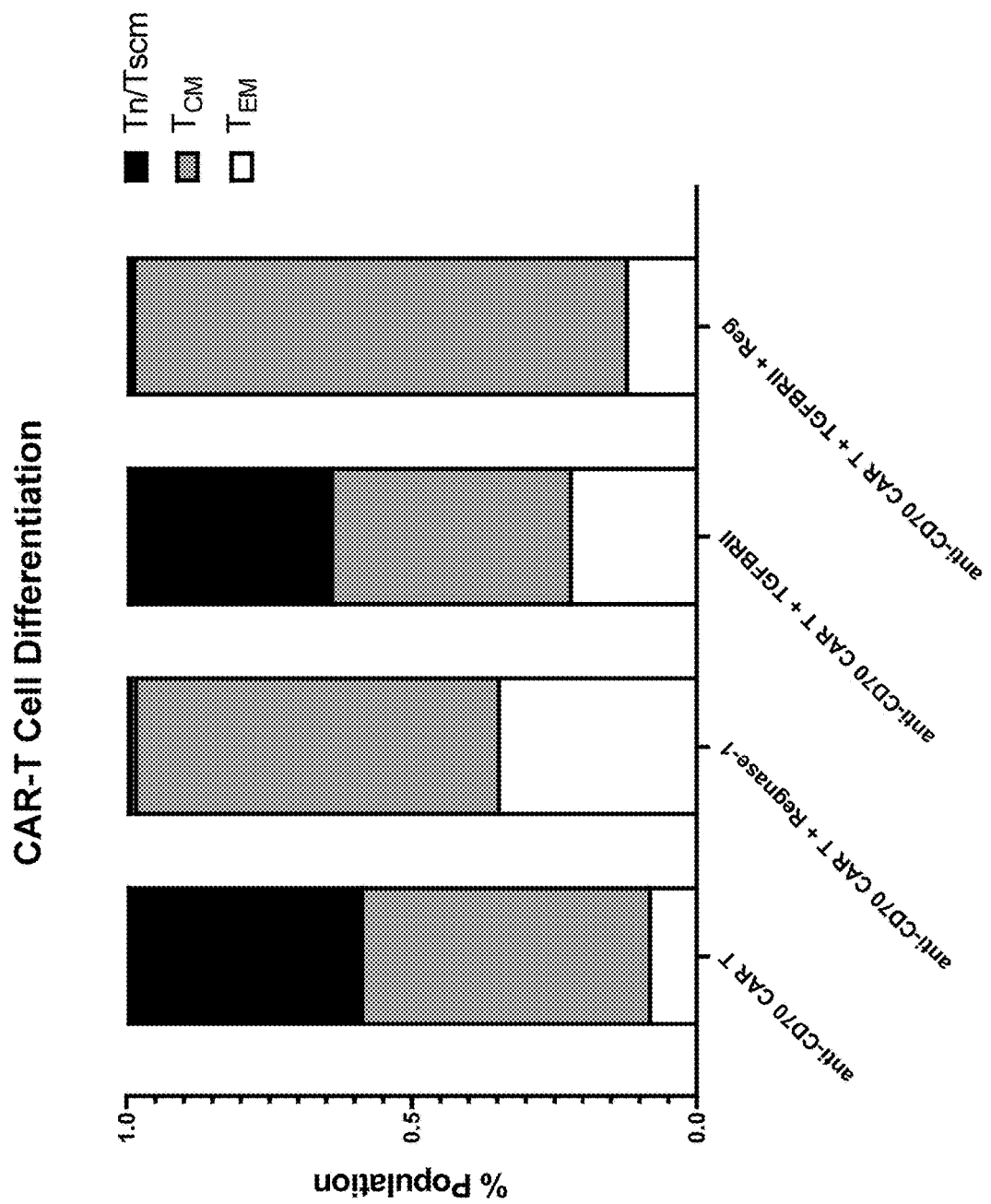
FIG. 19A-19B include diagrams showing impact of Reg1 and/or TGFBRII disruption on CAR-T cell differentiation and expansion in vivo.
Figure 19B:
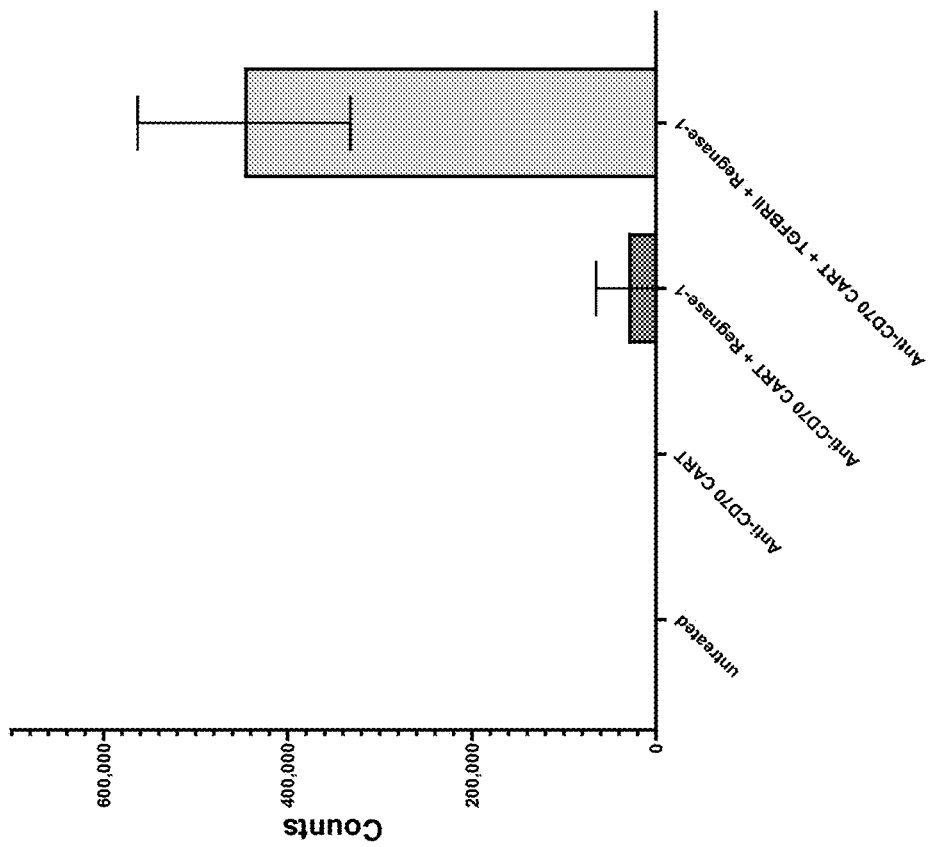

The results demonstrate that the addition of the TGFBRII and Regnase-1 gene edit significantly enhanced the population of central memory T cells compared to the edit of either TFGBRII or Regnase-1 alone, which correlates with massive expansion of CAR T cells (FIG. 19A) seen in these animals. And the TGFBRII edit further promoted the potential of CAR T cell proliferation in vivo, suggesting a robust synergistic effect along with the Regnase edit (FIG. 19B).

Example 17: Assessment of Anti-CD19 CAR-T Cells Having TGFBRII and/or Regnase-1 Gene Disruptions in an Intravenous Disseminated Models in NOG Mice Intravenous Disseminated Nalm-6 Human Acute Lymphoblastic Leukemia Tumor Xenograft Model
The Intravenous Disseminated Model (Disseminated Model) using the Nalm-6 Human Acute Lymphoblastic Leukemia tumor cell line in NOG mice was used to further demonstrate the efficacy of anti-CD19 CAR T cells with TGFBRII and/or Regnase-1 gene edits. Efficacy of various anti-CD19 CAR T populations were evaluated in the Disseminated Model using methods employed by Translations Drug Development, LLC (Scottsdale, Ariz.) and described herein. In brief, 24, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 12. On Day 1 mice in Groups 2-4 received an intravenous injection of 0.5×10$^6$ Nalm6 cells/mouse. The mice were inoculated intravenously to model disseminated disease. On Day 4 (3 days post injection with the Nalm6 cells), treatment Groups 2-4 received a single 200 μl intravenous dose of CAR+ T cells per Table 12.

TABLE 12

Treatment groups.

| Group | CAR T | Nalm6 Cells (i.v.) | anti-CD19 CAR T Treatment (i.v.) | N |
|---|---|---|---|---|
| 1 | Untreated | 0.5 × 10$^6$ cells/mouse | None | 5 |
| 2 | Anti-CD19 CAR T cells: anti-CD19 CAR+/TRAC−/B2M− | 0.5 × 10$^6$ cells/mouse | 4 × 10$^6$ CAR-T positive cells/mouse | 5 |
| 3 | Anti-CD19 CAR T + Reg KO cells: anti-CD19 CAR+/TRAC−/B2M−/Reg− | 0.5 × 10$^6$ cells/mouse | 4 × 10$^6$ CAR-T positive cells/mouse | 5 |
| 4 | Anti-CD19 CAR T + TGFBRII KO cells: anti-CD19 CAR+/TRAC−/B2M−/TGFBRII− | 0.5 × 10$^6$ cells/mouse | 4 × 10$^6$ CAR-T positive cells/mouse | 5 |
| 5 | Anti-CD19 CAR T + Reg KO + TGFBRII KO cells: anti-CD19 CAR+/TRAC−/B2M−/Reg− | 0.5 × 10$^6$ cells/mouse | 4 × 10$^6$ CAR-T positive cells/mouse | 5 |

During the course of the study mice were monitored daily and body weight was measured two times weekly as described above.

Figure 20A:
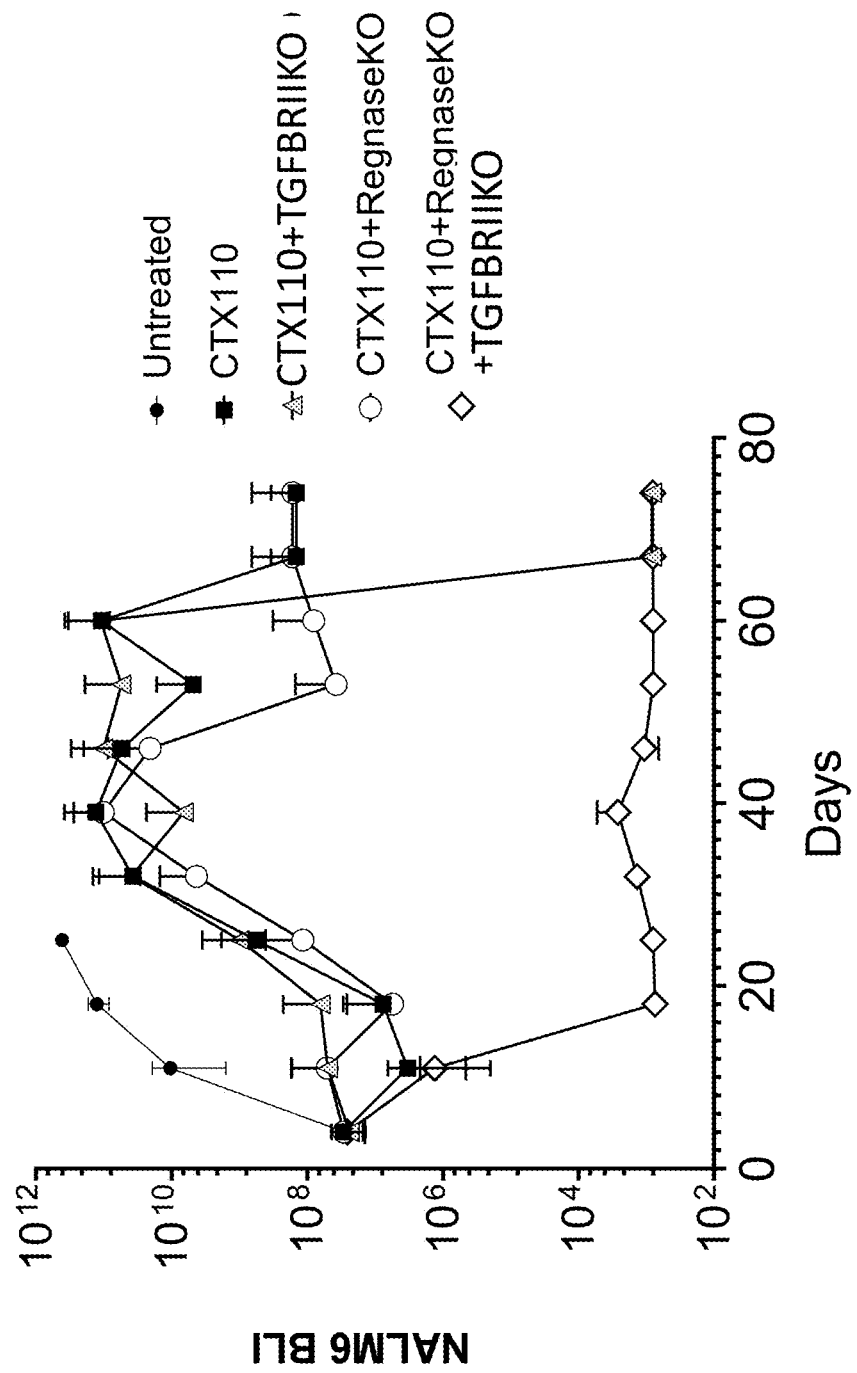
FIG. 20A-20B include diagrams showing synergistic effects of TGFBRII and Regnase double knock-out in a Nalm6-leukemia (B-ALL) mouse model.

TGFBRII gene editing combined with Regnase editing induced a maintained NALM6 tumor regression at an early time point (day 18) post tumor inoculation, compared to either edit alone. This reduction in tumor size was maintain (FIG. 20A). The sharp decline in tumor size in the TGFBRII KO group at day 74 post tumor inoculation represents only 5 of 15 mince. Ten of the 15 mice in TGFBRIIKO group had already reached the tumor BLI endpoint.

Figure 20B:
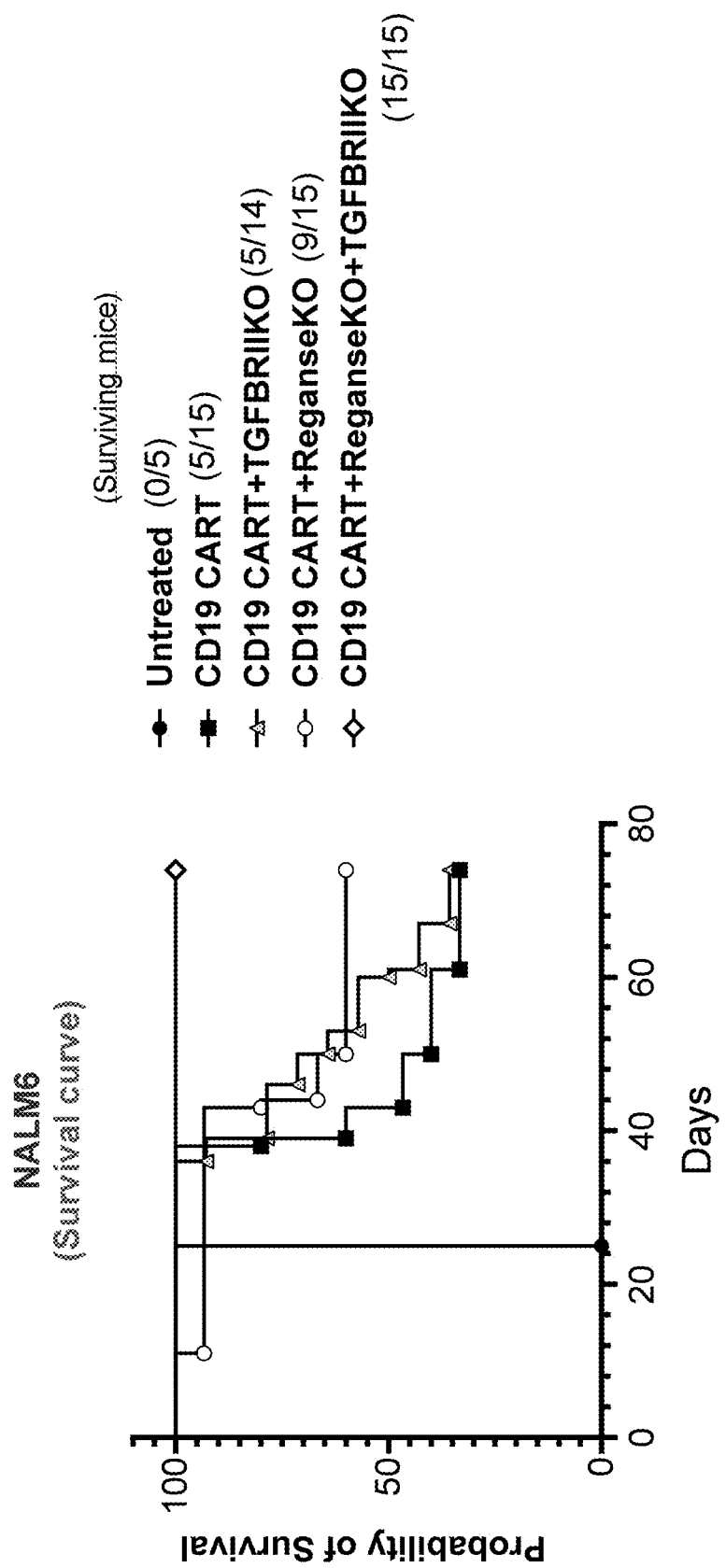

While disruption of either TGFBRII or Regnase showed some survival advantage in the Nalm6 Model mice treated with anti-CD19 CAR+ cells, having both TGFBRII and Regnase gene disruptions exhibited the greatest survival advantage (FIG. 20B).

Intravenous Disseminated JeKo-1 Tumor Xenograft Model

The Intravenous Disseminated Model (Disseminated Model) using the JeKo-1 Human Mantle cell lymphoma (MCL) tumor cell line in NOG mice was used to further demonstrate the efficacy of anti-CD19 CAR T cells with TGFBRII and/or Regnase-1 gene edits. Efficacy of various anti-CD19 CAR T populations were evaluated in the Disseminated Model using methods employed by Translations Drug Development, LLC (Scottsdale, Ariz.) and described herein. In brief, 24, 5-8 week old female CIEA NOG (NOD.Cg-Prkdc$^{scid}$Il2rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 13. On Day 1 mice in Groups 2-4 received an intravenous injection of 0.5×10$^6$ JeKo-1 cells/mouse. The mice were inoculated intravenously to model disseminated disease. On Day 4 (3 days post injection with the JeKo-1 cells), treatment Groups 2-4 received a single 200 μl intravenous dose of CAR T cells per Table 13.

TABLE 13

Treatment groups.

| Group | CAR T | JeKo-1 Cells (i.v.) | anti-CD19 CAR+ T cell Treatment (i.v.) | N |
|---|---|---|---|---|
| 1 | Untreated | 5 × 10$^6$ cells/mouse | None | 5 |
| 2 | Anti-CD19 CAR T cells: anti-CD19 CAR+/TRAC−/B2M− | 5 × 10$^6$ cells/mouse | 4 × 10$^6$ cells/mouse* | 5 |
| 3 | Anti-CD19 CAR T + Reg KO cells: anti-CD19 CAR+/TRAC−/B2M−/Reg− | 5 × 10$^6$ cells/mouse | 4 × 10$^6$ cells/mouse* | 5 |
| 4 | Anti-CD19 CAR T + TGFBRII KO cells: anti-CD19 CAR+/TRAC−/B2M−/TGFBRII− | 5 × 10$^6$ cells/mouse | 4 × 10$^6$ cells/mouse* | 5 |
| 5 | Anti-CD19 CAR T + Reg KO + TGFBRII KO cells: anti-CD19 CAR+/TRAC−/B2M−/Reg−/TGFBRII− | 5 × 10$^6$ cells/mouse | 4 × 10$^6$ cells/mouse* | 5 |

During the course of the study mice were monitored daily and body weight was measured two times weekly as described above.

Figure 21:
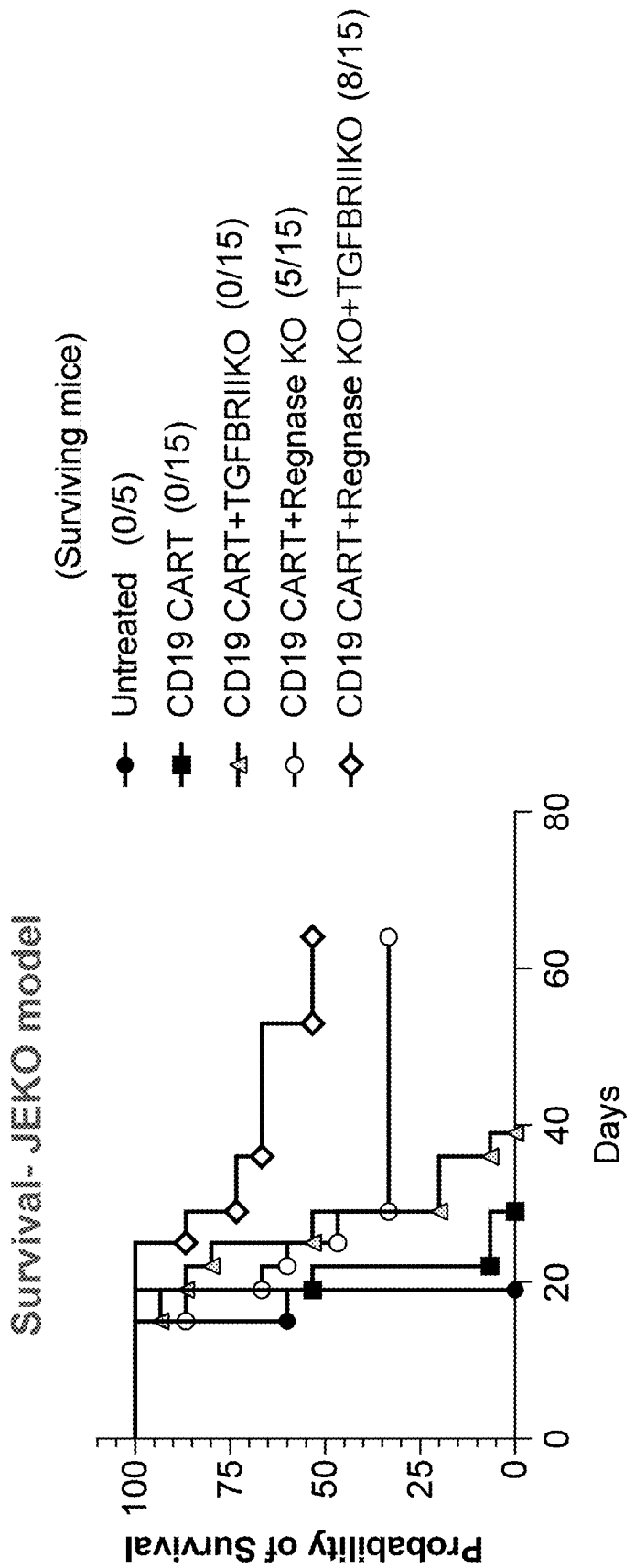
FIG. 21 is a diagram showing survival advantage arising from TGFBRII and Regnase double disruptions in a NOG Mantle cell lymphoma (MCL) tumor xenograft mouse model.

While either TGFBRII or Regnase showed some survival advantage in the JeKo-1 Model, mice treated with anti-CD19 CAR+ cells having both TGFBRII and Regnase gene edits exhibited the greatest survival advantage FIG. 21.

CAR T Cell Expansion In Vivo

CAR T cell expansion was assessed by measuring the CAR copy number by ddPCR of DNA isolated from blood samples collected throughout the Jeko-1 and Nalm-6 studies as described above.

DNA was isolated from mouse tissue using the Qiagen Dneasy blood and tissue kit (Qiagen, Venlo, Netherlands). Total mass of nucleic acid from RBC-lysed samples was quantitated using either Nanodrop (Thermo Fisher Scientific) or DropSense96 (trinean, Gentbrugge, Belgium) machines. Primers and 6-carboxyfluorescein (FAM)-labeled probe sets (provided in Table 14 below) were designed to quantitate the levels of the integrated CAR construct into the human TRAC locus by droplet digital PCR (ddPCR). ddPCR was performed using the Bio-Rad Automated Droplet Generator, Bio-Rad T100 Thermal Cycler, and Bio-Rad QX200 Droplet Reader machine(s) (Bio-rad Laboratories, Hercules, Calif.). QuantaSoft Version 1.7.4.0917 (Bio-rad Laboratories) software was used to calculate the absolute number of integrated CAR copies per sample. Finally, the number of detected CAR alleles was divided by the input total DNA amount to compute the absolute number of CAR copies per mass of input sample. The ddPCR assay detects the number of copies of integrated CAR transgene per mass of genomic DNA (gDNA) by amplifying an 866 bp amplicon spanning endogenous TRAC sequence and the CAR expression cassette promoter (EF-1α). In brief, qualification of the assay yielded linear data ($R^2$>0.95) within the range tested (2 to 300,000 copies per ug of gDNA) as well as generated a % relative error (% RE) and % coefficient of variation (% CV) within normal ranges (% RE≤100% and % CV≤20%) for conditions≥LLOQ. The LLOD and LLOQ were calculated based on the available data and the LLOD was set to 5 copies per 0.2 μg of gDNA and the LLOQ was set to 40 copies per 0.2 μg.

TABLE 14

Primers and probes used for ddPCR CAR primers and probe

| | |
|---|---|
| CTX110-20-30_dd_1 Forward | GGCACCATATTCATTTTGCAGGTGAA (SEQ ID NO: 11) |
| CTX110-20-30_dd_1 Reverse | ATGTGCGCTCTGCCCACTGACGGGC (SEQ ID NO: 12) |
| CTX110-20-30_dd_1 Probe (FAM) | AGACATGAGGTCTATGGACTTCAGGCTCC (SEQ ID NO: 13) |

Figure 22A:
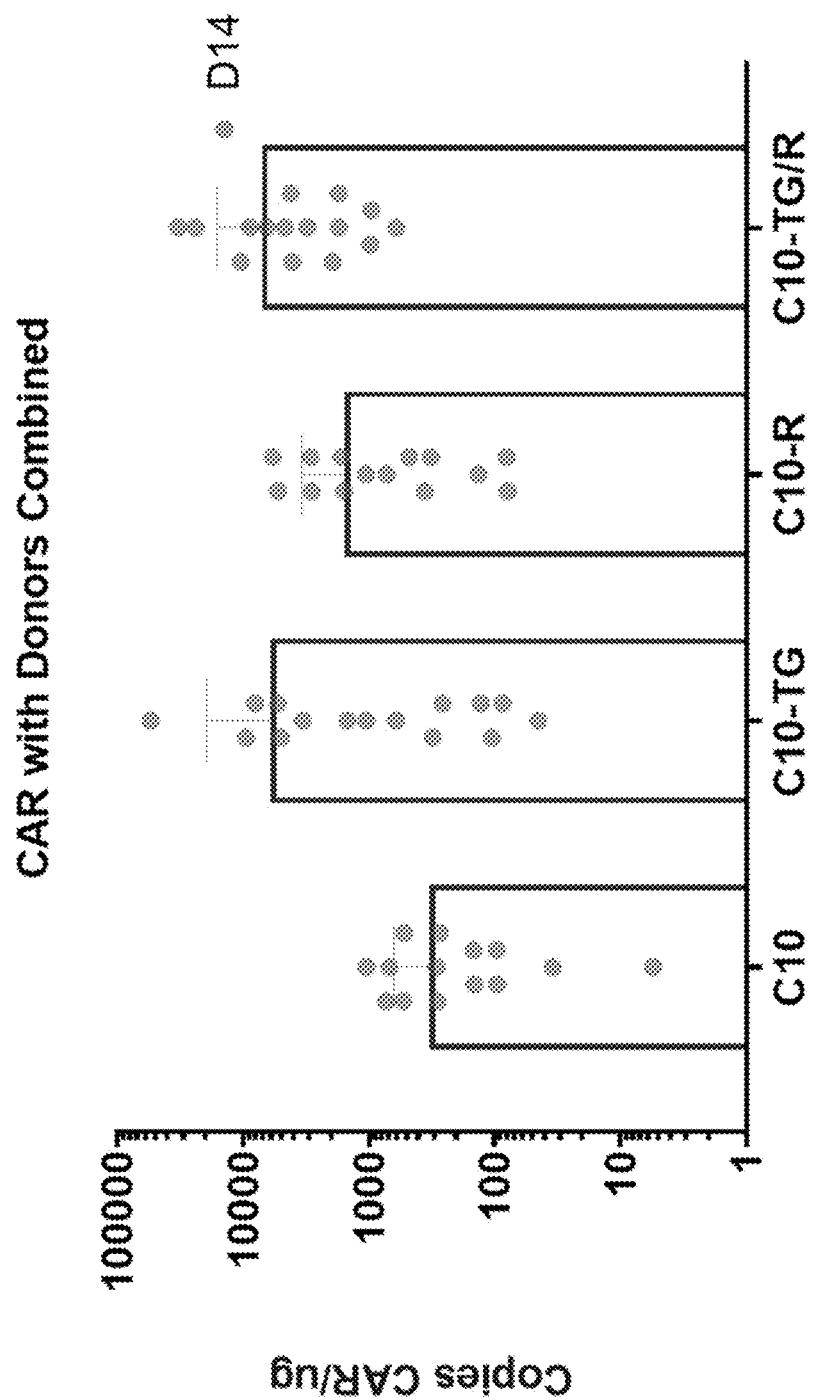
FIGS. 22A-22B include diagrams showing increased in vivo expansion of CAR-T cells having TGFBRII and/or Regnase knock-out.
Figure 22B:
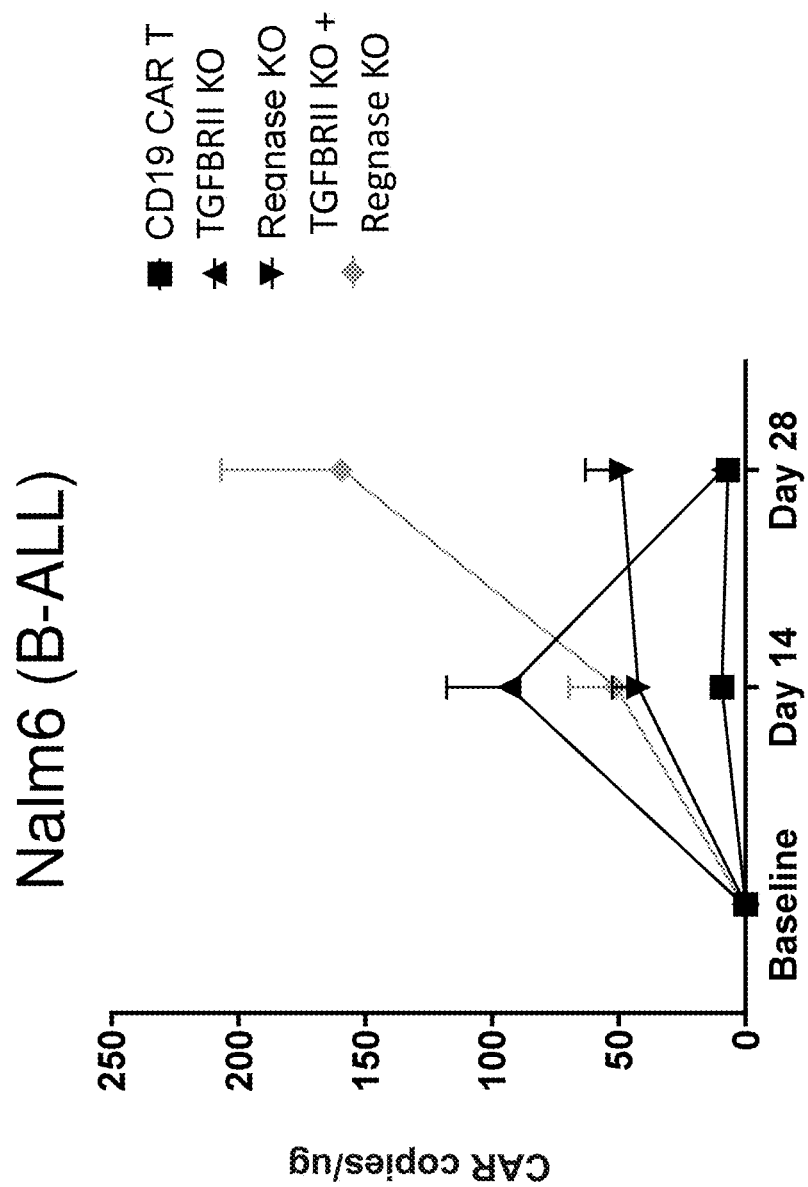

These analysis demonstrate that the addition of either TGFBRII or Regnase-1 KO to allogeneic CAR T cells (TRAC⁻/B2M⁻; Group C-10) allowed the T cells to expand to larger levels in the blood of treated mice (e.g., Groups C10-TG, C10-R, C10-TG/R) compared to groups treated with the allogeneic CART cells without those KOs (e.g., Group C10) (FIG. 22A). This expansion was apparent at day 14 of the Jeko-1 study. Loss of both TGFBRII and Regnase-1 (FIG. 22A, C10-TG/R) led to a more uniform expansion relative to TGFBRII (FIG. 22A, C10-TG) or Regnase-1 (FIG. 22A, C10-R) single KOs. In the Nalm-6 study, disruption of both TGFBRII and Regnase-1 had a synergistic effect on CAR T cell expansion at day 28 as shown in FIG. 22B In sum, all groups with loss of either TGFBRII or Regnase-1 had expanded CAR-T cells in the peripheral blood.

Example 18: Generation of CAR T Cells with Multiple Gene Editing and Verification of Gene Edits Activated primary human T cells were electroporated with Cas9/sgRNA RNP complexes (200 pmol Cas9, 1000 pmol gRNA) to generate cells edited for TRAC-/β2M-, TRAC-/β2M-/Regnase-1-, TRAC-/β2M-/TGFBRII- and TRAC-/β2M-/Regnase-1-/TGFBRII-. Sequence encoding anti-BCMA CAR was inserted into the TRAC locus using recombinant AAV6 carrying the DNA sequence for anti-BCMA CAR (SEQ ID NO: 170). The following sgRNAs were used: TRAC (SEQ ID NO: 58), β2M (SEQ ID NO: 62), Reg-1 (SEQ ID NO: 51; REG1-Z10) and TGFBRII (SEQ ID NO: 313).

Flowcytometry was used to verify the editing for TRAC, β2M and the insertion and expression of anti-BCMA CAR. Briefly, about one week post electroporation, cells were stained with anti-human TCR, anti-human β2M and recombinant biotinylated human BCMA/streptavidin-APC to assess the levels of editing for TRAC and β2M, and insertion of the nucleotide sequence encoding anti-BCMA CAR.

Figure 23A:
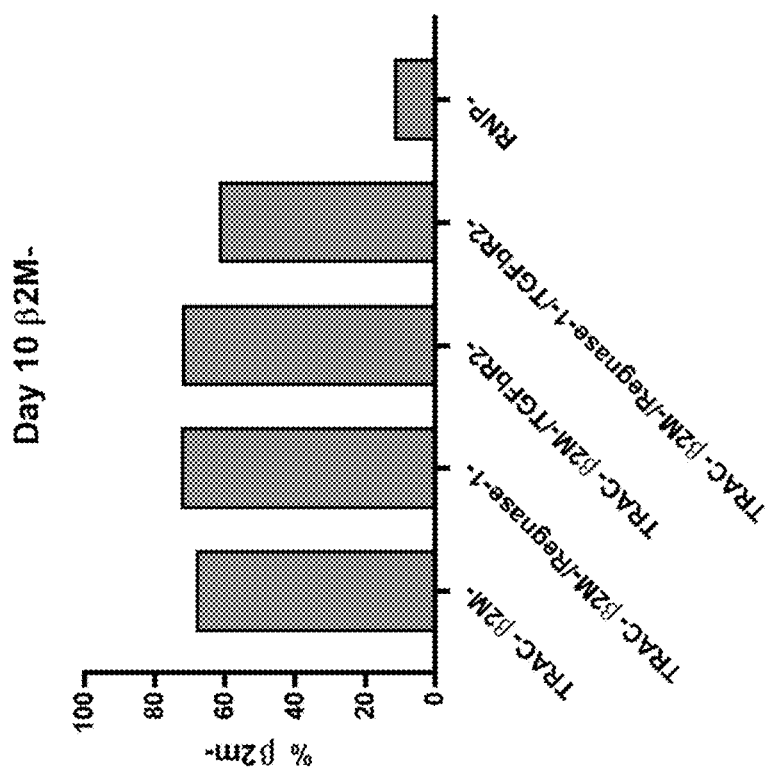
Figure 23B:
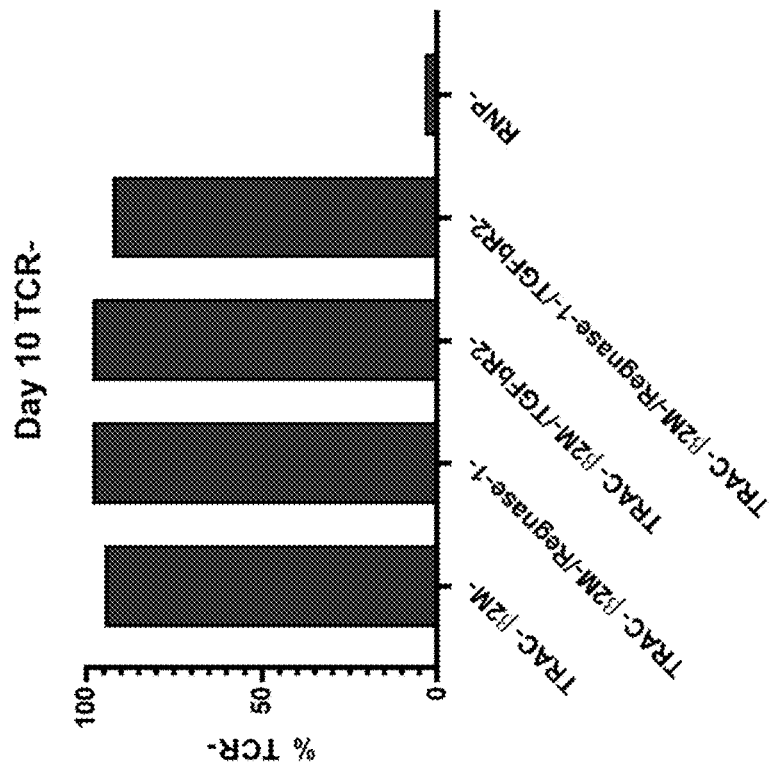
Figure 23C:
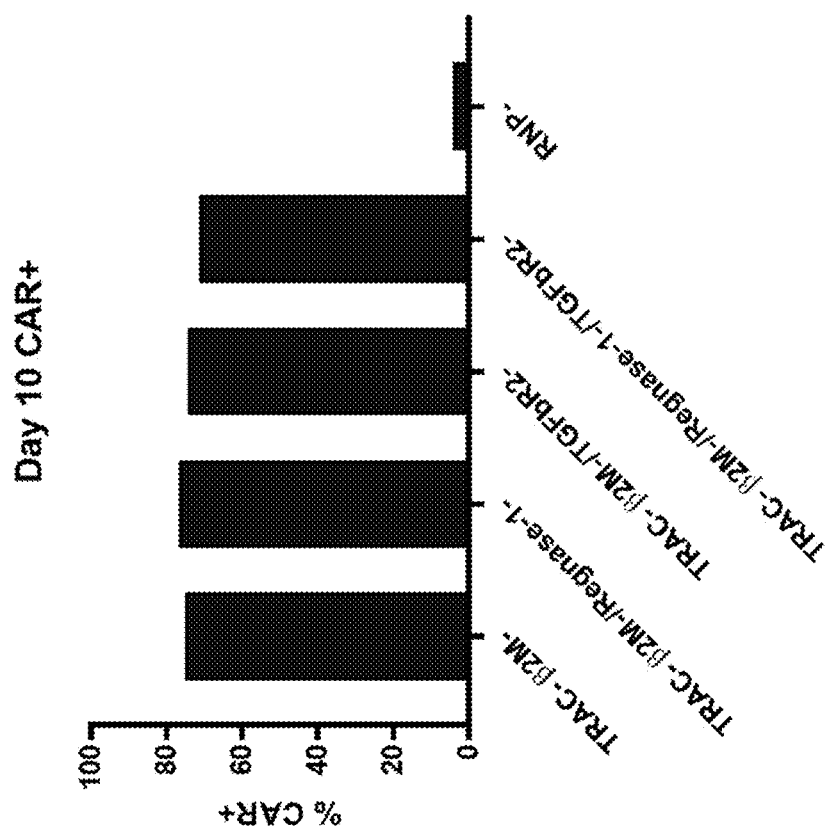

TRAC-/β2M-, TRAC-/β2M-/Reg-1-, TRAC-/β2M-/TGFBRII- and TRAC-/P2M-/Reg-1-/TGFBRII- anti-BCMA CAR+ T-cells show consistent rates of TCR and β2M disruptions at >90% and >60% rates, respectively as determined by flow cytometry (FIGS. 23A and 23B). Anti-BCMA CAR expression was measured flow cytometrically by determining the percentage of cells that bound recombinant biotinylated BCMA/streptavidin-APC conjugate. All the conditions including TRAC-/β2M-, TRAC-/β2M-/Reg-1-, TRAC-/β2M-/TGFBRII- and TRAC-/β2M-/Reg-1-/TGFBRII- anti-BCMA CAR+ T-cells show consistent rates of CAR insertion (>70%), while the unedited RNP-T-cells have no detectable staining for anti-BCMA CAR (FIG. 23C). The ratio of CD4/CD8 T cells as assessed by flow cytometry in the TRAC-/β2M-, TRAC-/β2M-/Reg-1-, TRAC-/β2M-/TGFBRII- and TRAC-/β2M-/Reg-1-/TGFBRII- anti-BCMA CAR+ T-cells were found to be consistent in the range of 55-60%/40-45% across all the samples (FIG. 23D).

TIDE analysis was performed for the verification of editing rates for Reg-1 and TGFBRII genes. Briefly, about one week post electroporation, two million cells from TRAC-/β2M-, TRAC-/β2M-/Reg-1-, TRAC-/β2M-/TGFBRII- and TRAC-/β2M-/Reg-1-/TGFBRII- anti-BCMA CAR+ T-cells and two million unedited T-cells from the same donor were removed from culture and transferred to 1.5 mL microcentrifuge tubes. Cells were spun down in a tabletop microcentrifuge at 300 g for 10 minutes and the resulting supernatant was discarded. The cells were washed twice with 1000 uL 1×PBS and the cell pellets were frozen at −80° C. The frozen cell pellets were then used for the extraction of genomic DNA using QIAamp DNA Blood Mini Kit (Qiagen, catalog #51106). Gene-specific primers were used to amplify the region flanking the cut sites of Reg-1 and TGFBRII (Invitrogen™ Platinum™ SuperFi™ II Green PCR Master Mix; catalog #12369050) and the PCR amplicons derived were subsequently sequenced and analyzed by TIDE to determine the indel patterns/frequencies (editing frequencies).

Figure 24A:
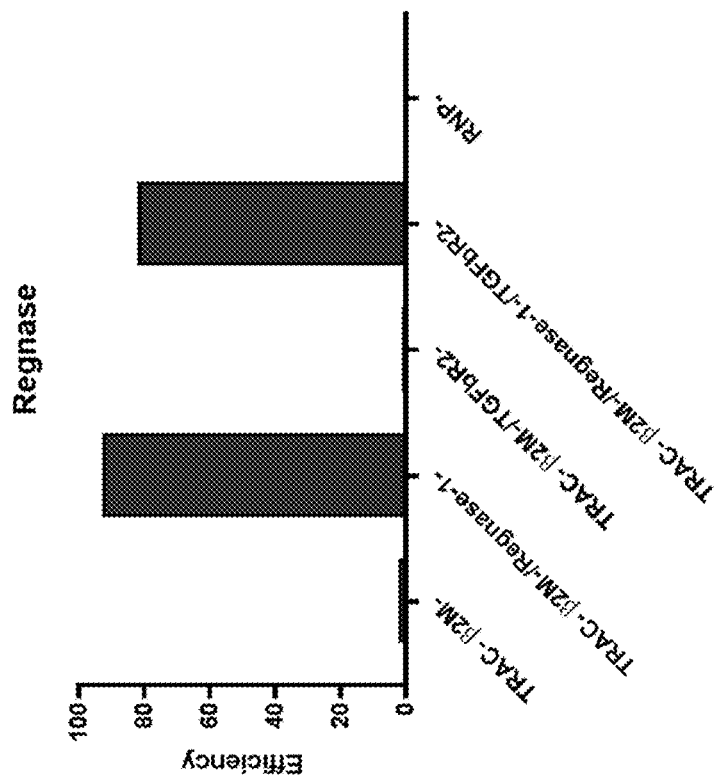
FIGS. 24A-24B include diagrams showing consistent edit editing rates in anti-BCMA CAR-T cells with Reg-1 and/or TGFBRII disruptions.
Figure 24B:
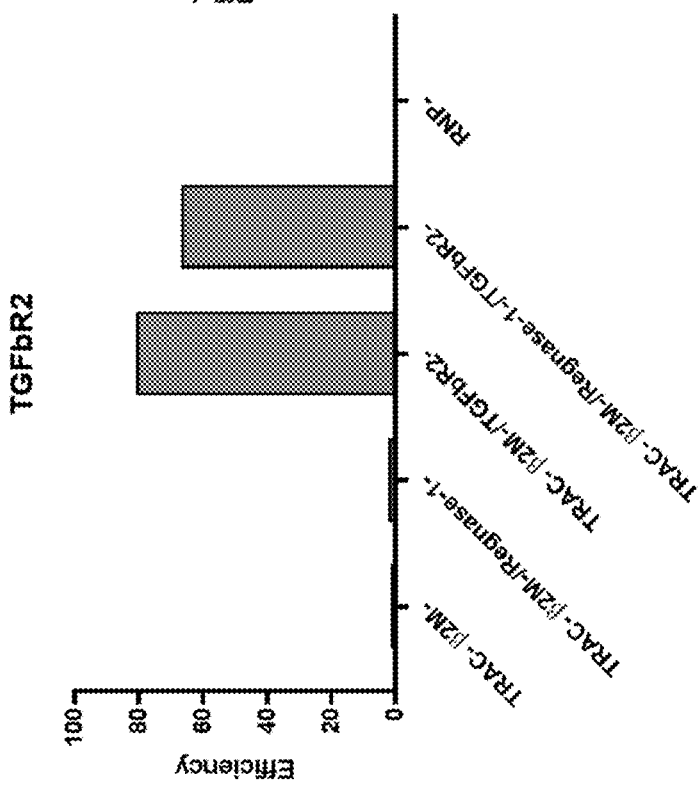

The analyzed indel frequencies were found to be within the expected range of 65-80% for TGF sgRNA and >80% for the Regnase-1 sgRNA, respectively (FIGS. 24A and 24B).

Example 19: Cytotoxicity of Anti-BCMA CAR T Cells with Multiple Gene Edits

A cytotoxicity (cell kill) assay was used to assess the ability of the TRAC-/β2M-, TRAC-/β2M-/Reg-1-, TRAC-/β2M-/TGFBRII- and TRAC-/β2M-/Reg-1-/TGFBRII- anti-BCMA CAR+ T-cells (produced by the methods disclosed herein, see, e.g., Example 18) to cause cell lysis in two target cell lines, MM.1S (multiple myeloma cell line) and JeKo-1 (mantle cell lymphoma cell line). Unedited RNP- cells without CAR were used as a negative control to determine the specific lysis by CAR+ T cells. Briefly, the target cell lines were stained with eBioscience™ Cell Proliferation Dye eFluor™ 670 (Thermofisher Scientific; catalog #65-0840-85) per manufacturer's instructions and seeded into 96-well plates at 50,000 cells per well. Next, CAR T-cells or RNP-T cells were added to the wells containing target cells at ratios of 0, 0.5:1, 1:1, 2:1, or 4:1 (T cell:target cell) and incubated further for approximately 4 hours for MM.1S and 24 hours for JeKo-1. After the respective incubation period, the 96-well plates were spun down at 300 g for 10 minutes and 100 μL of supernatant was removed for cytokine quantification. Cells were then washed once with 1×PBS and stained with 150 ul of 1×PBS supplemented with 0.5% BSA and 5 μg/mL DAPI (Invitrogen; catalog #D3571) and incubated for 15 minutes in dark. Post-incubation, cells were washed-off DAPI, resuspended in 150 μl of 1×PBS supplemented with 0.5% BSA, and acquired and analyzed using a flow cytometer. Target cells were identified via eFluor-based fluorescence and then divided into live and dead cells based on their DAPI fluorescence.

Figure 25A:
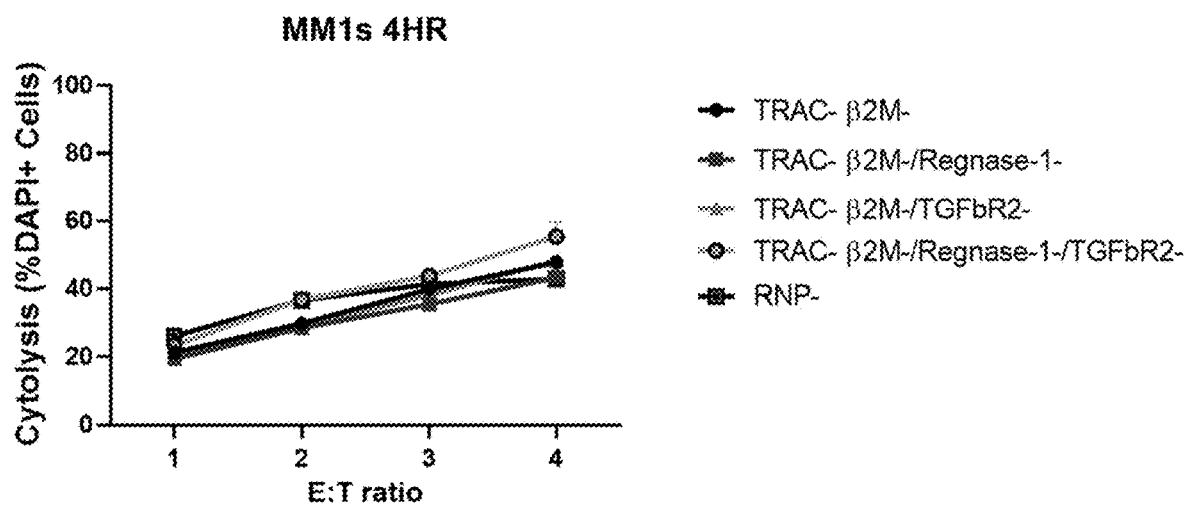
FIGS. 25A-25D include diagrams showing superior cell cytotoxicity of TRAC–/β2M–/Reg-1– TGFBRII– anti-BCMA CAR+ T-cells.
Figure 25B:
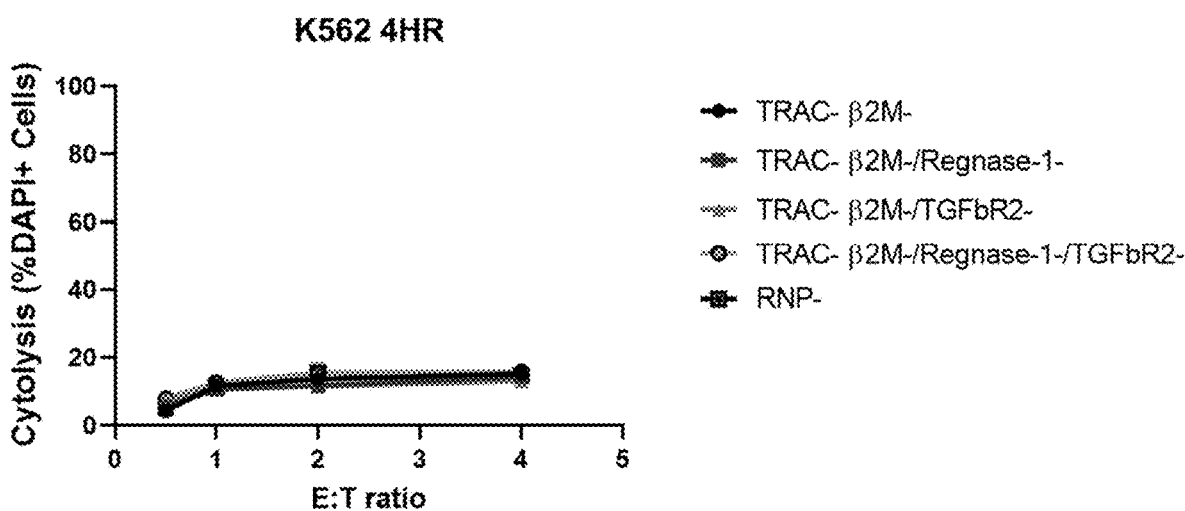
Figure 25C:
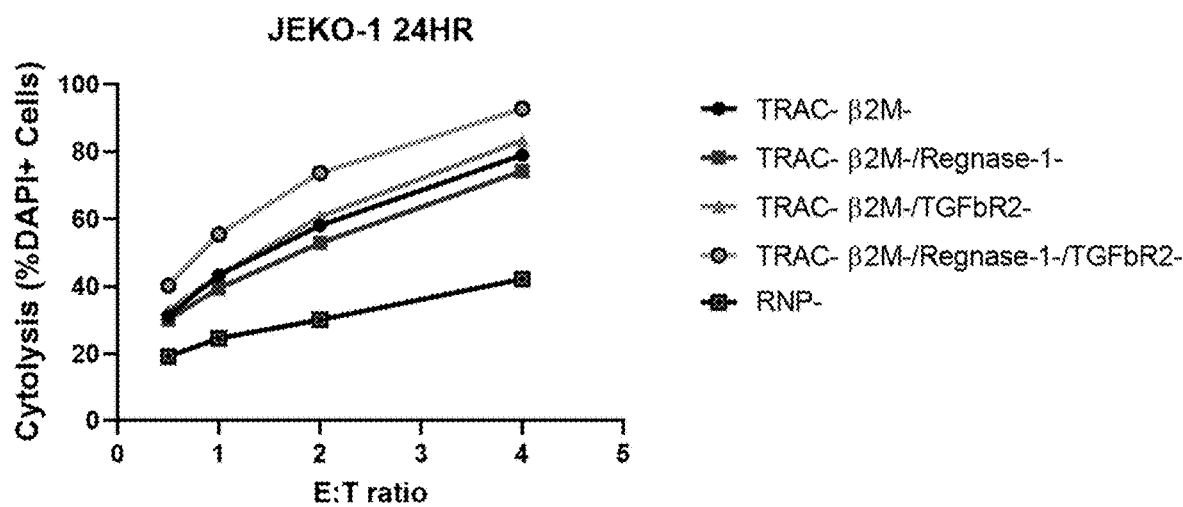
Figure 25D:
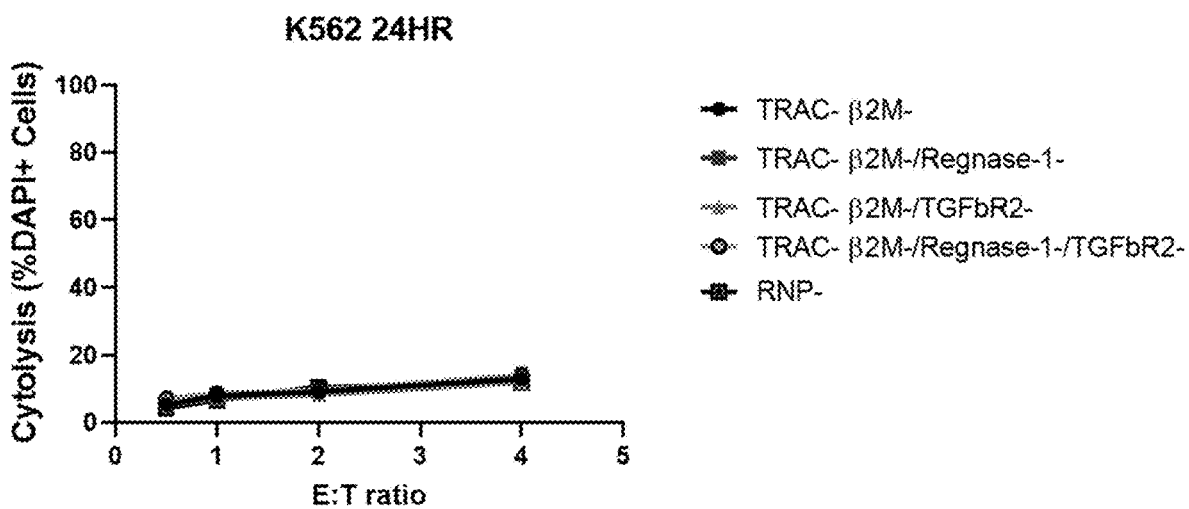

The TRAC−/β2M−/Reg-1−/TGFBRII− anti-BCMA CAR+ T-cells exhibited greater cytotoxicity towards the MM.1S (FIG. 25A) and JeKo-1 cell lines (FIG. 25C) compared to TRAC−/β2M−, TRAC−/β2M−/Regnase-1− or TRAC−/β2M−/TGFBRII− anti-BCMA CAR+ T-cells. Comparative data from K562 cells (as controls) are provided in FIG. 25B and FIG. 25D.

Example 20: In Vivo Effects of TGFBRII+Regnase-1 Disruption on Allogeneic CAR T Cells in the Subcutaneous RPMI-8226 Xenograft Tumor Model A subcutaneous tumor mouse model was utilized to assess the in vivo efficacy of allogeneic anti-BCMA CARs with the following gene disruptions: 1) β2M and TRAC, 2) β2M, TRAC, and TGFBRII, 3) β2M, TRAC, and Reg-1, and 4) β2M, TRAC, TGFBRII, and Reg-1. The subcutaneous tumor mouse model utilized the BCMA+ multiple myeloma derived RPMI-8226 tumor cell line in NSG mice. The TGFBRII gene was edited via CRISPR/Cas-mediated gene editing using the TGFBRII Ex5_T1 guide (SEQ ID NO. 313). The Reg-1 gene was edited via CRISPR/Cas-mediated gene editing using the Z10 guide (SEQ ID NO. 51). The anti-BCMA CAR T cells express an anti-BCMA CAR comprising the amino acid sequence of SEQ ID NO: 146). See also the sequence Tables 22, 23, 27, and 39 below.

Efficacy of the anti-BCMA CAR T cells was evaluated in the subcutaneous xenograft model using methods employed by Translations Drug Development, LLC (Scottsdale, Ariz.) and described herein. In brief, 25 5-8 week old female NSG mice were individually housed in ventilated microisolator cages, maintained under pathogen-free conditions, 5-7 days prior to the start of the study. On day 1, mice received a subcutaneous inoculation of 1×10$^7$ RPMI-8226 cells/mouse in the right hind flank. Nine days later (Day 10), the tumor inoculation sites were inspected to determine if the tumors were palpable. After confirming palpability, the mice were further divided into 5 treatment groups as shown in Table 1. All treatment groups received a single 200 ul intravenous dose of 1e6 anti-BCMA CAR+ T cells.

TABLE 15

Treatment Groups for the RMPI-8226 Xenograft Study

| Group | CAR T cells (i.v.) | N |
|---|---|---|
| 1 | NA | 5 |
| 2 | anti-BCMA CAR/TRAC−/β2M− | 5 |
| 3 | anti-BCMA CAR/TRAC−/β2M−/TGFBRII− | 5 |
| 4 | anti-BCMA CAR/TRAC−/β2M−/TGFBRII−/Regnase− | 5 |
| 5 | anti-BCMA CAR/TRAC−/β2M−/TGFBRII−/Regnase− | 5 |

Throughout the course of the study, the mice were subjected to gross observations daily, while tumor volume and body weight were measured twice weekly (~every 3-4 days) starting on Day 10. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;
Tumors that inhibit normal physiological function such as eating, drinking, mobility and ability to urinate and or defecate;
Prolonged, excessive diarrhea leading to excessive weight loss (>20%); or
Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Figure 26B:
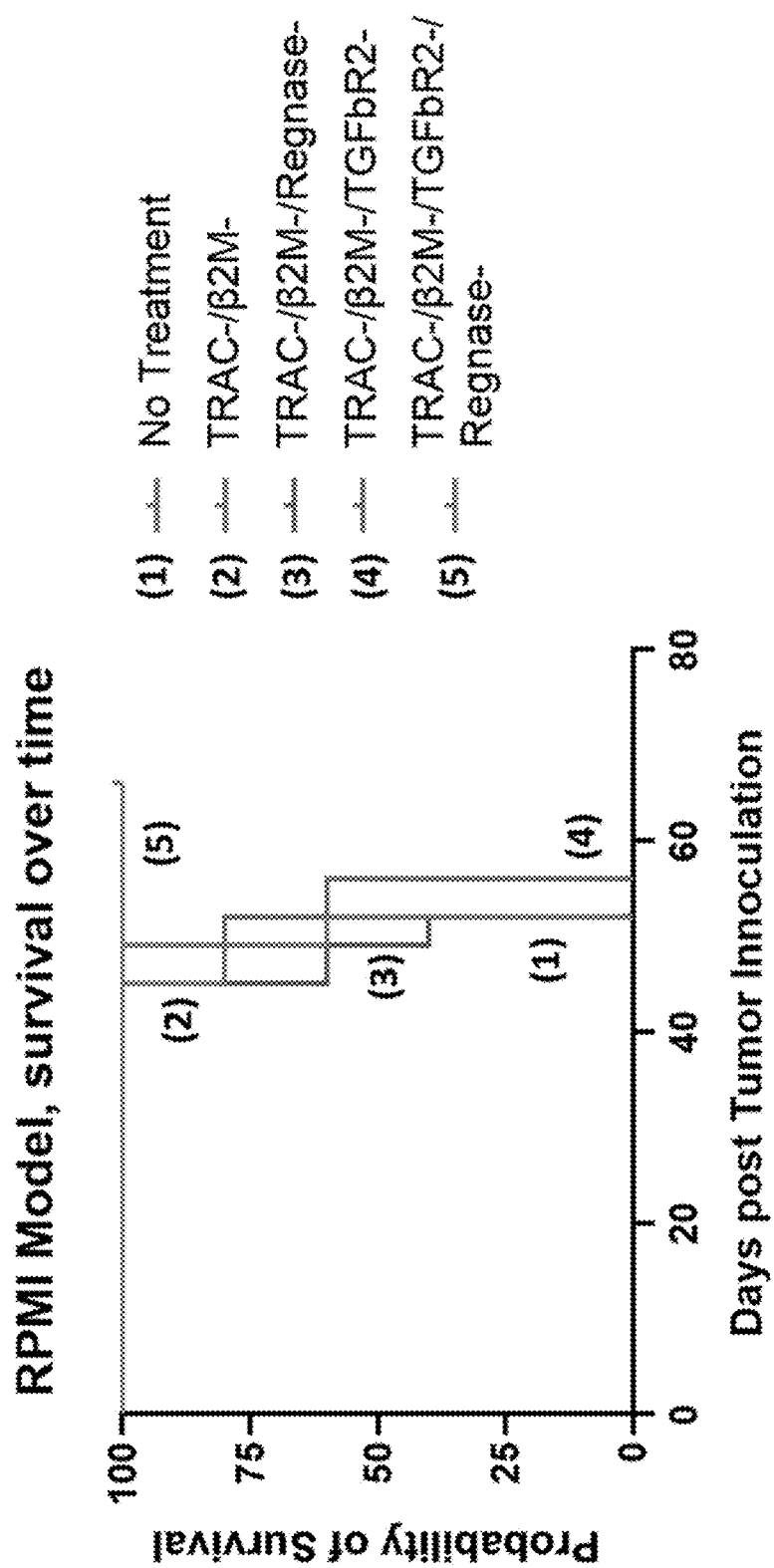

Mice in groups receiving TRAC−/β2M−/TGFBRII−/Reg-1− anti-BCMA CAR+ T-cells saw an increase in survival relative to untreated mice; mice treated TRAC−/β2M− anti-BCMA CAR+ T-cells, TRAC−/β2M−/TGFBRII anti-BCMA CAR+ T-cells, or TRAC−/β2M−/Reg-1− anti-BCMA CAR+ T-cells (FIG. 26B). Mice receiving TRAC−/B2M−/TGFBRII−/Regnase− anti-BCMA CAR+ T cells showed significant tumor regression, while none of the other conditions tested showed significant inhibition of tumor growth (FIG. 26A). These data demonstrate that disruption of TGFBRII and Reg-1 in CAR T cells increases efficacy of CAR T cells in a mouse xenograft tumor model.

Next, small amounts of blood were taken from each mouse for FACS analysis to characterize circulating CAR-T cells and determine drug pharmacokinetics. Approximately 75 uL of blood was drawn 2 weeks post CAR-T dosing via submandibular bleeds. The blood was then transferred into K2 EDTA tubes and shipped overnight to CRISPR Therapeutics on 4C cold packs. The following day, blood samples were processed with RBC (Red Blood Cell) Lysis Buffer (BioLegend®, catalog #420301) per manufacturer's instructions. The samples then underwent anti-mouse CD16/32 blocking via anti-mouse Trustain FcX™ (BioLegend®, catalog #101320) per manufacturer's instructions. The samples were then processed via flow cytometry to determine prevalence of human CD45 expressing cells, which would represent the circulating CAR-T cells. Blood from mice that had received TRAC−/β2M−/TGFBRII−/Regnase− anti-BCMA CAR+ T-cells showed a high amount of circulating human CD45+ cells, which was not seen in any other treatment groups (FIG. 26C). This indicates that the TGFBRII and Reg-1 knockouts confer superior expansion of CAR-T cells in a multiple myeloma mouse xenograft model.

Example 21: In Vivo Synergistic Effects of TGFBRII+Regnase-1 Disruptions on Allogeneic CAR T Cells in the Subcutaneous JeKo-1 Xenograft Tumor Model A subcutaneous tumor mouse model was utilized to further assess the in vivo efficacy of TRAC−/β2M− anti-BCMA CAR+ T-cells and TRAC−/β2M−/TGFBRII−/Reg-1/anti-BCMA CAR+ T-cells. The subcutaneous tumor mouse model utilized the low BCMA expressing mantle cell lymphoma derived JeKo-1 tumor cell line in NSG mice. The TGFBRII gene was edited via CRISPR/Cas-mediated gene editing using TGFBRII Ex5_T1 guide (SEQ ID NO: 313). The Reg-1 gene was edited via CRISPR/Cas-mediated gene editing using the Z10 guide (SEQ ID NO: 51). The anti-BCMA CAR T cells express an anti-BCMA CAR comprising the amino acid sequence of SEQ ID NO: 146. See also the sequence Tables 22, 23, 27, and 39 below.

Efficacy of the anti-BCMA CAR T cells was evaluated in the subcutaneous xenograft model using methods employed by Translations Drug Development, LLC (Scottsdale, Ariz.) and described herein. In brief, 15 5-8 week old female NSG mice were individually housed in ventilated microisolator cages, maintained under pathogen-free conditions, 5-7 days prior to the start of the study. On day 1, mice received a subcutaneous inoculation of 5×10⁶ JeKo-1 cells/mouse in the right hind flank. Tumors were then periodically sized in via calipers. Once average tumor size reached an average of 150 mm³ (with an acceptable range of 125-175 mm³), the mice were further divided into 3 treatment groups as shown in Table 1. All treatment groups received a single 200 ul intravenous dose of 10e6 anti-BCMA CAR+ T cells. The day of T-cell injection was marked as Day 1.

TABLE 16

Treatment Groups for the RMPI-8226 Xenograft Study

| Group | CAR T cells (i.v.) | N |
|---|---|---|
| 1 | NA | 5 |
| 2 | anti-BCMA CAR/TRAC−/β2M− | 5 |
| 5 | anti-BCMA CAR/TRAC−/β2M−/TGFBRII−/Regnase− | 5 |

Throughout the course of the study, the mice were subjected to gross observations daily, while tumor volume and body weight were measured twice weekly (~every 3-4 days) starting on Day 1. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;
Tumors that inhibit normal physiological function such as eating, drinking, mobility and ability to urinate and or defecate;
Prolonged, excessive diarrhea leading to excessive weight loss (>20%); or
Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Figure 27A:
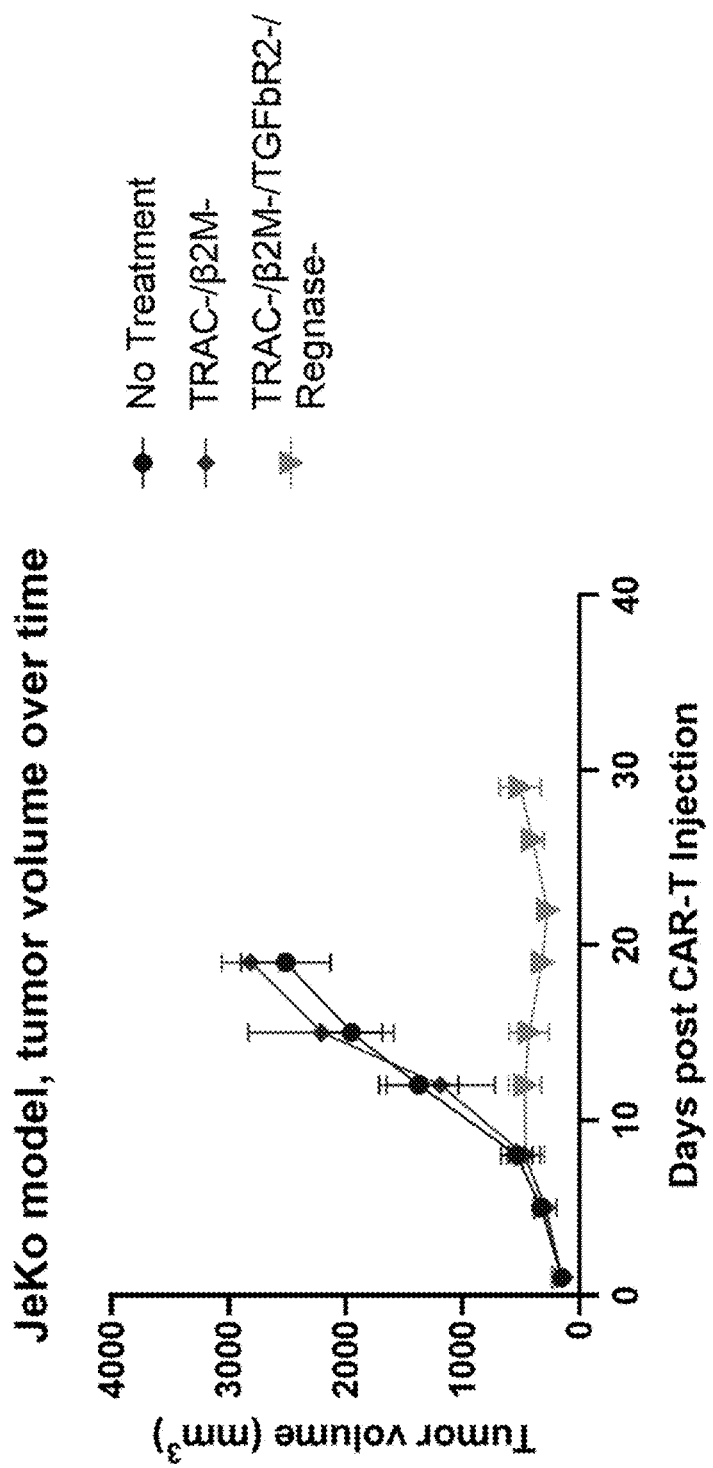
Figure 27B:
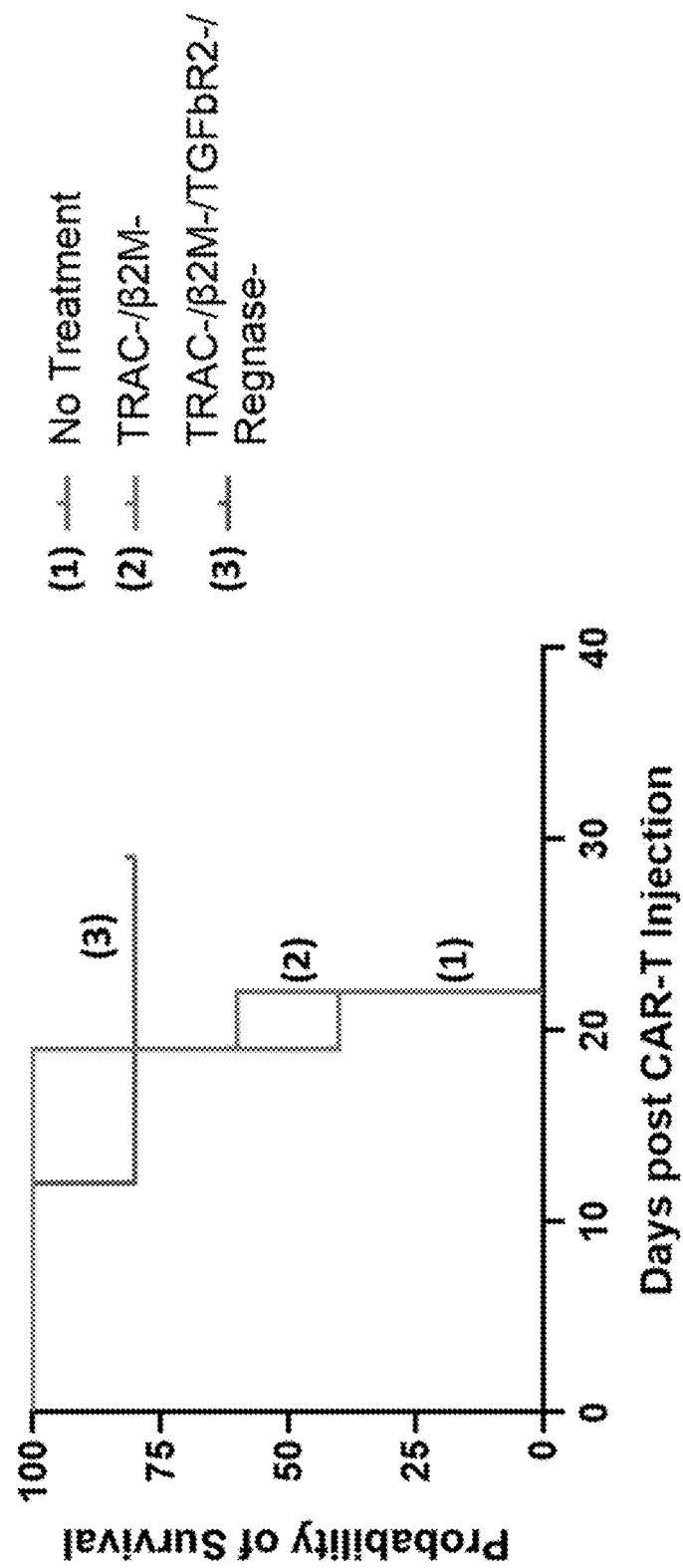

Mice in groups receiving TRAC−/β2M−/TGFBRII−/Reg-1− anti-BCMA CAR+ T-cells saw a significant increase in survival relative to both untreated mice and mice treated TRAC−/β2M− anti-BCMA CAR+ T-cells (FIG. 27B). Mice receiving TRAC−/B2M−/TGFBRII−/Reg-1− anti-BCMA CAR+ T cells arrested tumor growth, while TRAC−/β2M− anti-BCMA CAR+ T-cells did not significant inhibit tumor growth (FIG. 27A). These data demonstrate that disruption of TGFBRII and Reg-1 genes in CAR T cells increases efficacy of CAR-T cells in a mouse xenograft tumor model.

Figure 27C:
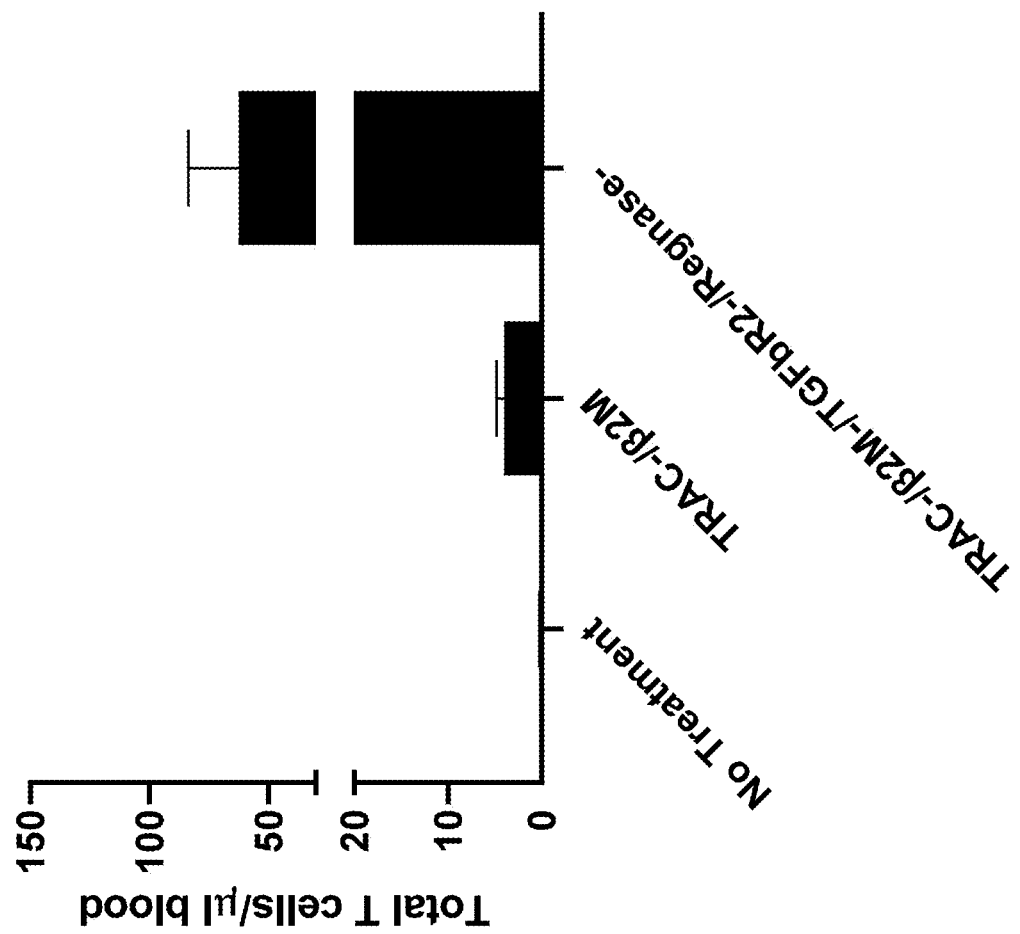

Next, small amounts of blood were taken from each mouse for FACS analysis to characterize circulating CAR-T cells and determine drug pharmacokinetics. Approximately 75 uL of blood was drawn 2 and 3 weeks post CAR-T dosing via submandibular bleeds. The blood was then transferred into K2 EDTA tubes and shipped overnight to CRISPR Therapeutics on 4C cold packs. The following day, blood samples were processed with RBC (Red Blood Cell) Lysis Buffer (BioLegend®, catalog #420301) per manufacturer's instructions. The samples then underwent anti-mouse CD16/32 blocking via anti-mouse Trustain FcX™ (BioLegend®, catalog #101320) per manufacturer's instructions. To quantify the number of circulating T-cells, the sum of cells positive for human CD4 and CD8 was determined. At the two week timepoint, blood from mice that had received TRAC−/β2M−/TGFBRII−/Reg-1− anti-BCMA CAR+ T-cells showed significantly higher concentrations of human CD4 and human CD8+ expressing cells relative to blood from mice that received TRAC−/β2M-anti-BCMA CAR+ T-cells (FIG. 27C).

Figure 27D:
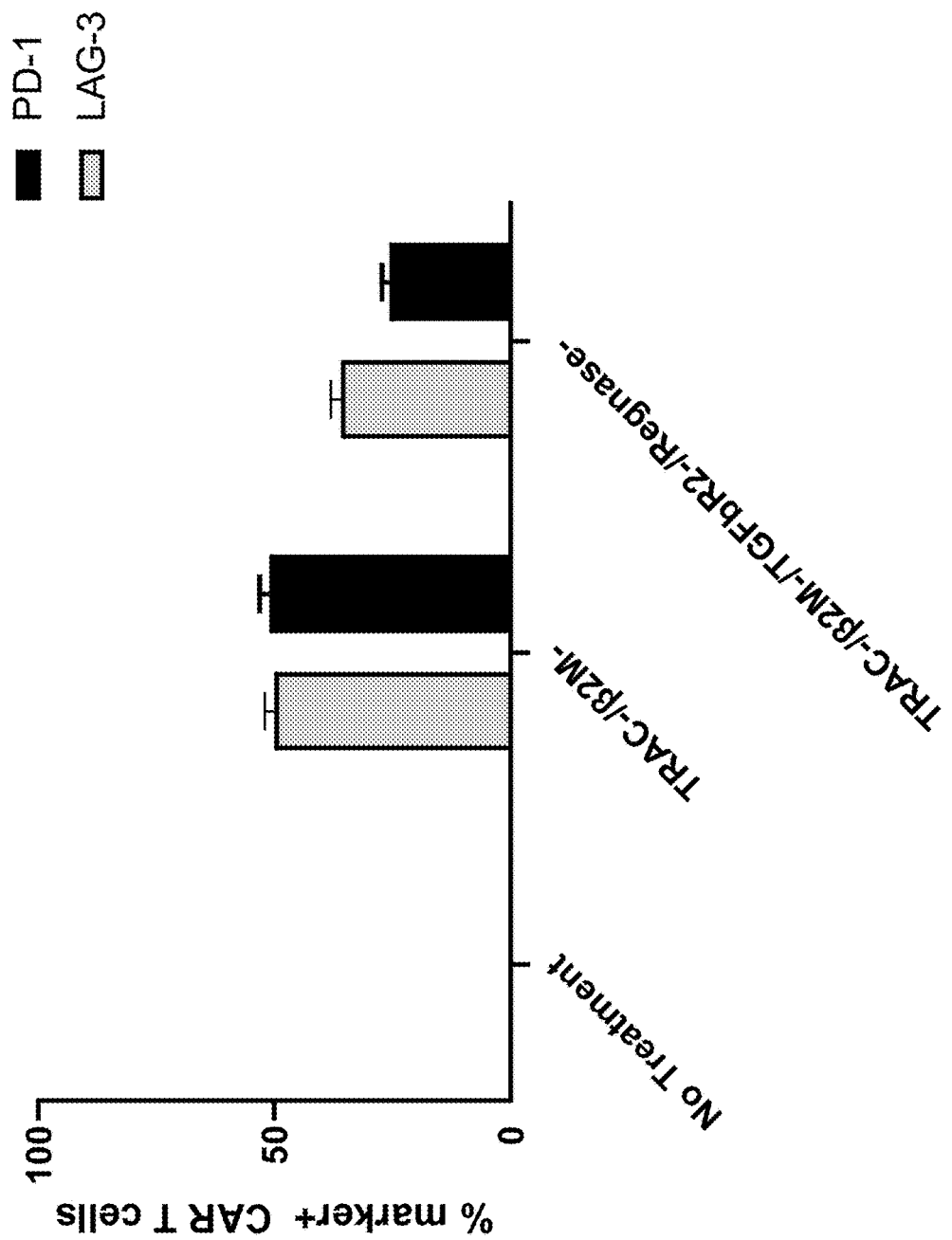
Figure 27E:
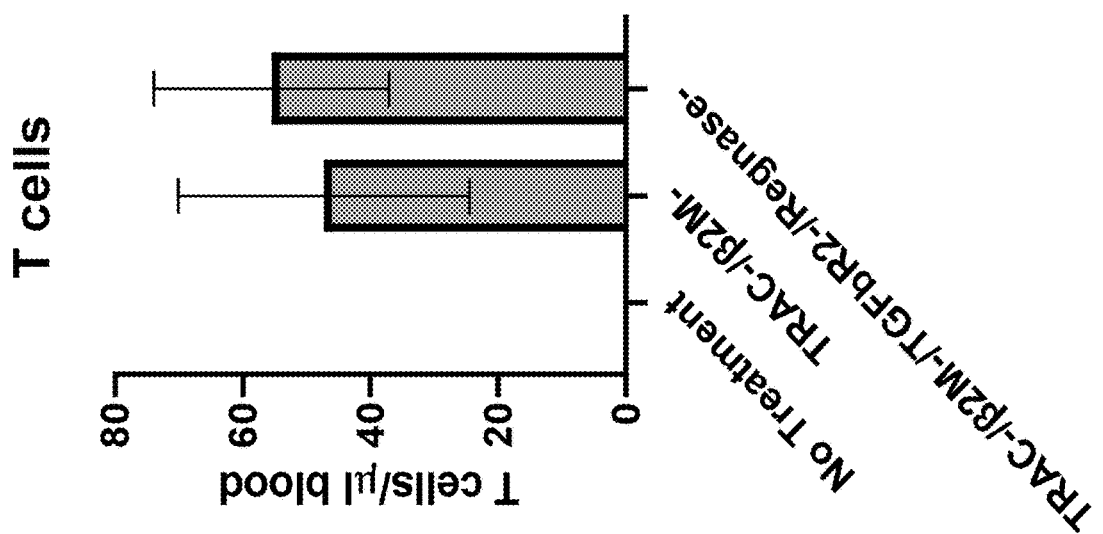

Furthermore, the TRAC−/β2M-TGFBRII−/Reg-1− anti-BCMA CAR+ T-cells showed lower expression of the T-cell exhaustion markers Lag3 and PD1 relative to the TRAC−/β2M-anti-BCMA CAR+ T-cells (FIG. 27D). At the three week timepoint, the overall level of hCD45+ cells in circulation had equalized between groups (FIG. 27E), but the expression of Lag3 and PD1 remained lower in mice treated with TRAC−/β2M-TGFBRII−/Reg-1− anti-BCMA CAR+ T-cells (FIG. 27F). This indicates that CAR-T cells containing the TGFBRII and Regnase knockouts have a superior ability to expand when compared to CAR-T cells lacking those edits while also reducing the expression of T-cell exhaustion markers PD-1 and Lag3.

Example 22: Generation of Anti-PTK7 CAR T Cells with Disrupted TGFBRII and Regnase-1 Genes Allogeneic human T cells that lack expression of the TRAC gene, β2M gene, TGFBRII gene and Reg-1 gene, and express a chimeric antigen receptor (CAR) targeting PTK7 were produced. Activated human T cells were electroporated with Cas9:sgRNA RNPs (1 μM Cas9, 5 μM gRNA), followed by incubation with a recombinant adeno-associated adenoviral vectors, serotype 6 (AAV6) (MOI 50, 000).

Recombinant AAV comprised a nucleotide sequence encoding an anti-PTK7 CAR comprising the amino acid sequence of SEQ ID NO: 349. The following sgRNAs were used: TRAC (SEQ ID NO: 58), β2M (SEQ ID NO: 62), TGFBRII (SEQ ID NO: 313) and REGNASE-1 (SEQ ID NO: 51). The sgRNAs, which form RNPs with the Cas9 enzyme, can be introduced into the T cells in a single electroporation event to produce the resulting modified cell populations shown in Table 17 below. After the electroporation, the cells were transduced with the recombinant AAV to introduce the donor template encoding for the anti-PTK7 CAR.

TABLE 17

Genetically Engineered CAR-T Cell Populations

| Population | Edits |
|---|---|
| Anti-PTK7 CAR T cells | anti-PTK7 CAR+/TRAC−/B2M− |
| Anti-PTK7 CAR T + TGFBRII KO cells | anti-PTK7 CAR+/TRAC−/B2M−/TGFBRII− |
| Anti-PTK7 CAR T + TGFBRII KO + Reg KO cells | anti-PTK7 CAR+/TRAC−/B2M−/TGFBRII−/Reg− |

At 7 days post-electroporation, T cells were checked for CAR expression by flow cytometry. Both anti-PTK7 CAR T cells and anti-PTK7 CAR T cells that lack TGFBRII and anti-PTK7 CAR T cells that lack TGFBRII and Regnase expressed nearly equivalent amount of CAR on their surface at day 7 post HDR. The results are provided in Table 18 below.

TABLE 18

Percentage of CAR, TCR, and b2M Expression on Day 7 Post HDR

| Treatment | CAR+ % | TCR+ % | β2M+ % |
|---|---|---|---|
| No RNP | 3.33 | 92 | 93.7 |
| No AAV | 5.16 | 2.63 | 3.87 |
| Anti-Ptk7 CAR | 82.2 | 1.24 | 2.49 |
| Anti-Ptk7 CAR & TGFBRII KO | 83.2 | 0.82 | 2.1 |
| Anti-Ptk7 CAR & TGFBRII/Reg-1 KO | 81.7 | 0.77 | 2 |

Figure 28:
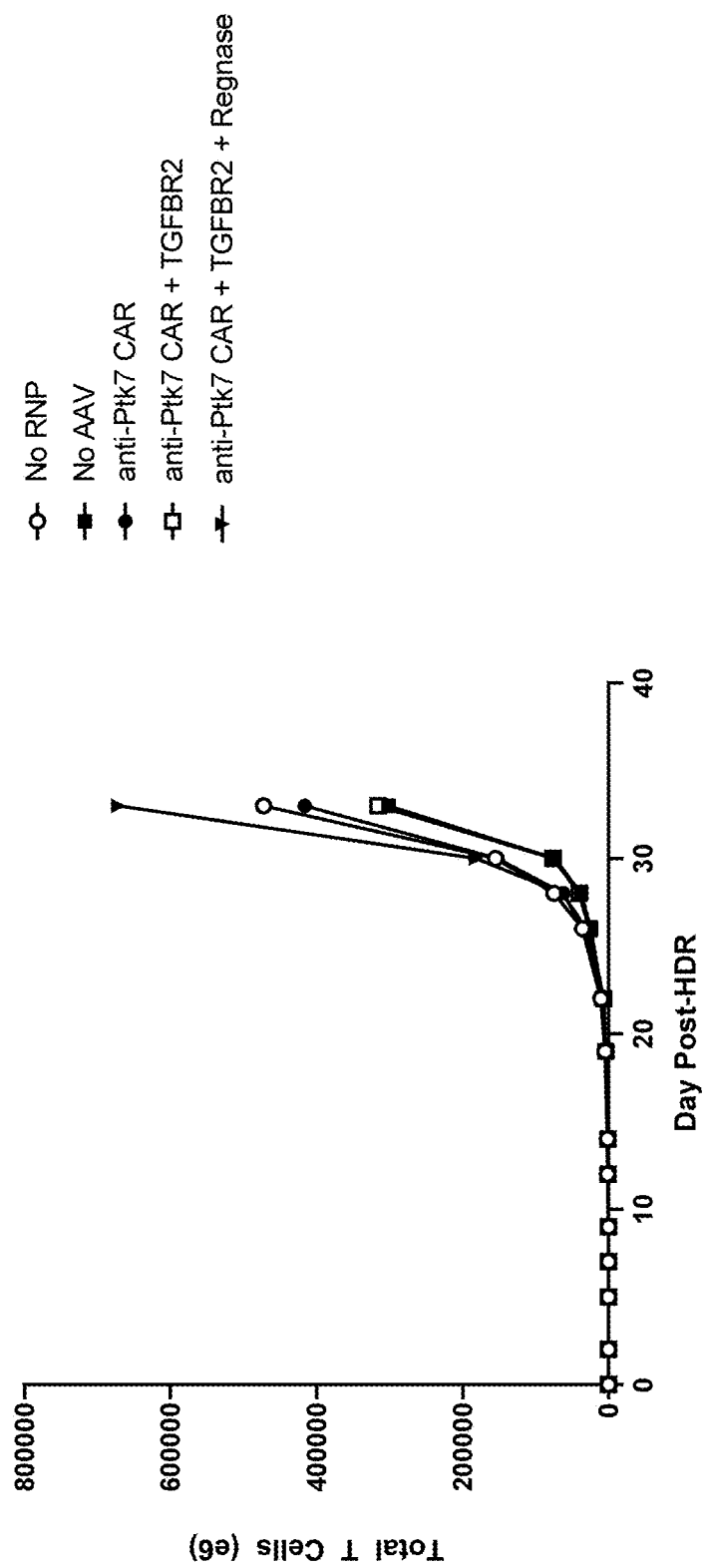
FIG. 28 is a diagram showing disruption of TGFBRII and Reg-1 genes increases proliferation of anti-PTK7 CAR T cells.

Efficient editing of TGFBRII and/or Regnase was achieved in the engineered anti-Ptk7 CAR T cell (Table 19 below) and show an increase in cell proliferation with TGFBRII and Reg-1 disruption (FIG. 28), while cell viability and CD4+/CD8+ T cells ratios remain unchanged.

TABLE 19

Indel Percentage in TGFBRII and Regnase-1 on Day 7 Post HDR

| Treatment | TGFBRII Indel % | Reg-1 Indel % |
|---|---|---|
| No RNP | 1.8 | 1.6 |
| No AAV | 97.75 | 88.8 |
| Anti-Ptk7 CAR | 1.45 | 2.2 |
| Anti-Ptk7 CAR & TGFBRII KO | 97.15 | 3 |
| Anti-Ptk7 CAR & TGFBRII/Reg-1 KO | 97.7 | 92.2 |

In summary, the data presented in this example demonstrated that TGFBRII and/or Reg-1 disruption in anti-Ptk7 CAR T cells (e.g., anti-PTK7 CAR+/TRAC−/B2M−/TGFBRII− or anti-PTK7 CAR+/TRAC−/B2M−/TGFBRII−/Reg-1−), can increase cell proliferation, while not affecting cell viability or CD4/CD8 cell ratios.

Example 23: Disruption of TGFBRII Alone Increases CAR T Cell Killing Upon Serial Rechallenge In Vitro The anti-PTK7 CAR+ T cells generated above were serially rechallenged with PTK7+ osteosarcoma cancer cell line, Saos2, and evaluated for their ability to kill the PTK7+ osteosarcoma cancer cell line Saos2.

The anti-PTK7 CAR+ T cells used in this experiment contained the following edits:

Anti-PTK7 CAR T cells: anti-PTK7 CAR+/TRAC−/B2M−

Anti-PTK7 CAR T+TGFBRII KO cells: anti-PTK7 CAR+/TRAC−/B2M−/TGFBRII−

Anti-PTK7 CAR T+TGFBRII KO+Reg KO cells: anti-PTK7 CAR+/TRAC−/B2M−/TGFBRII−/Reg−

In a 96-well plate format, CAR T cells were first co-cultured with Saos2 cells (6,250 CAR T cells, 50,000 tumor cells) on D0 and re-challenged with 50,000 tumor cells on D2, D4, D6, D8, D10, D12 and D14.

Analysis of tumor cell and CAR T cell number was performed at D1, D3, D5, D7, D9, D11 and D13 using flow cytometry (method adapted from Wang et al., JoVE 2019). The following antibodies in Table 20 were used at 1:100 dilution.

TABLE 20

Antibody Information

| Antibody | Flour | cat # | Dilution | Vendor |
|---|---|---|---|---|
| CD4 | BV510 | 300546 | 1:100 | Biolegend |
| CD8 | FITC | 344704 | 1:100 | Biolegend |
| PTK7 | PE | 130-091-364 | 1:50 | Miltenyi |
| CD62L | BV605 | 304833 | 1:100 | Biolegend |
| human CD45 | BV785 | 304048 | 1:100 | Biolegend |
| PD1 | APC/Cy7 | 329922 | 1:100 | Biolegend |
| CD45RO | PE/Cy7 | 304230 | 1:100 | Biolegend |
| Streptavidin | APC | 405207 | 1:100 | Biolegend |
| Tim3 | BV421 | 345008 | 1:100 | Biolegend |
| Live/Dead | 7AAD | BDB559925 | 1:500 | BD |

Figure 29A:
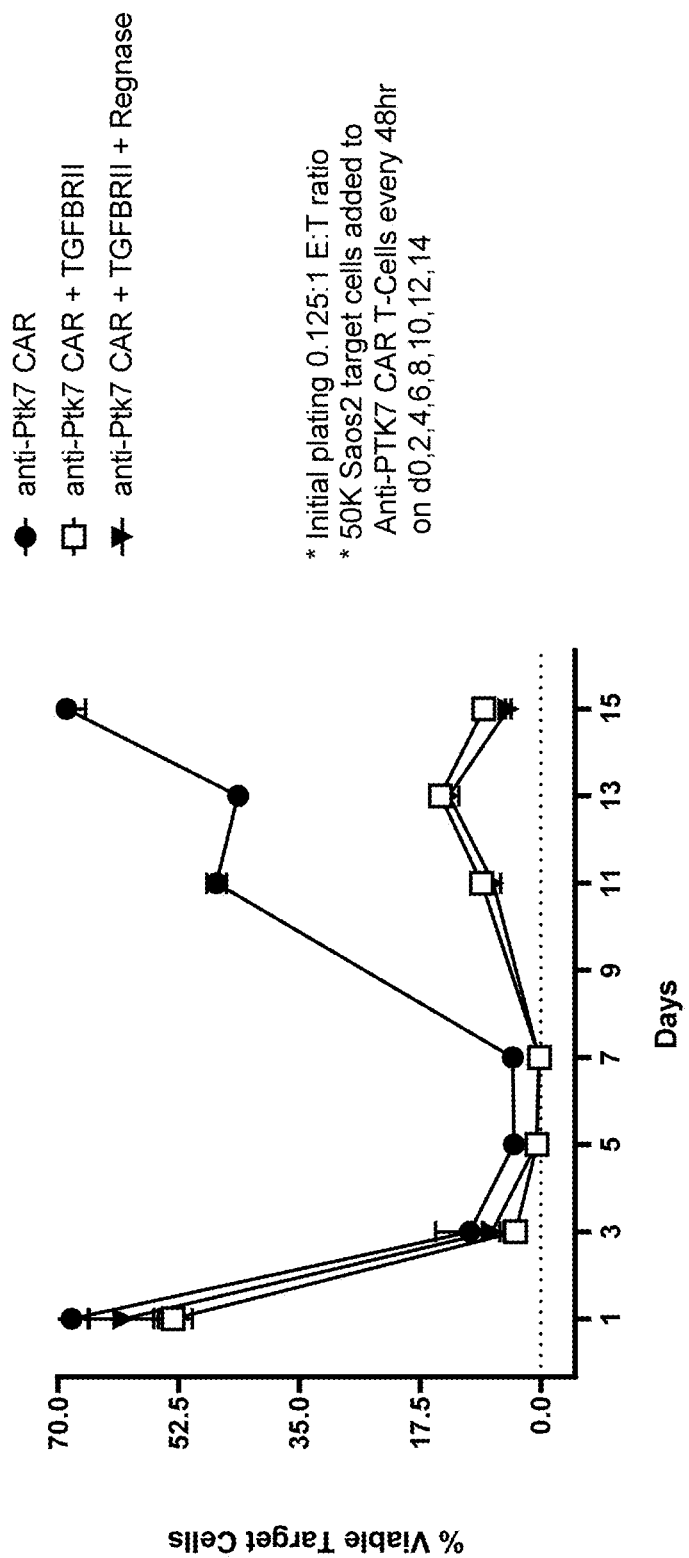
FIGS. 29A-29D include diagrams showing impact of TGFBRII disruption, optionally in combination with Reg-1 disruption, in long-term in vitro rechallenge assays.
Figure 29B:
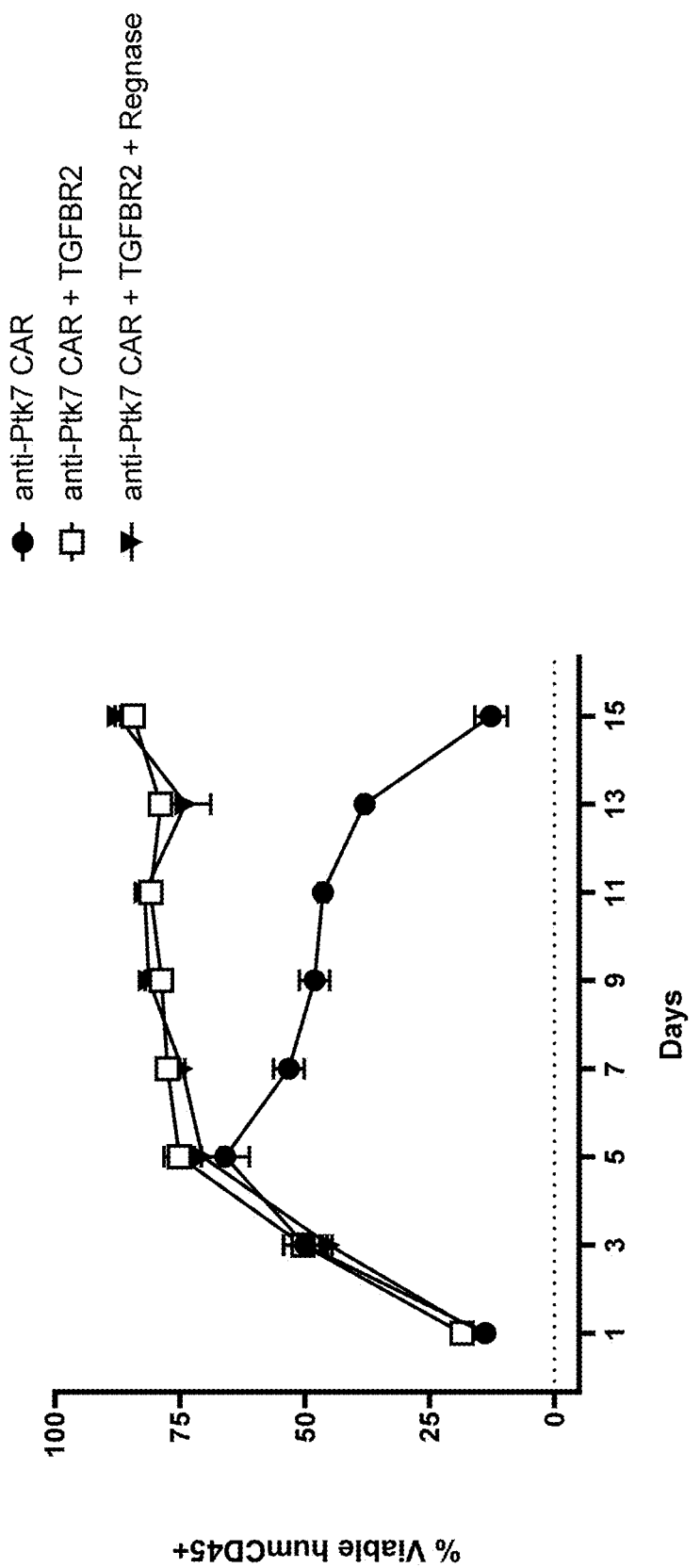
Figure 29D:
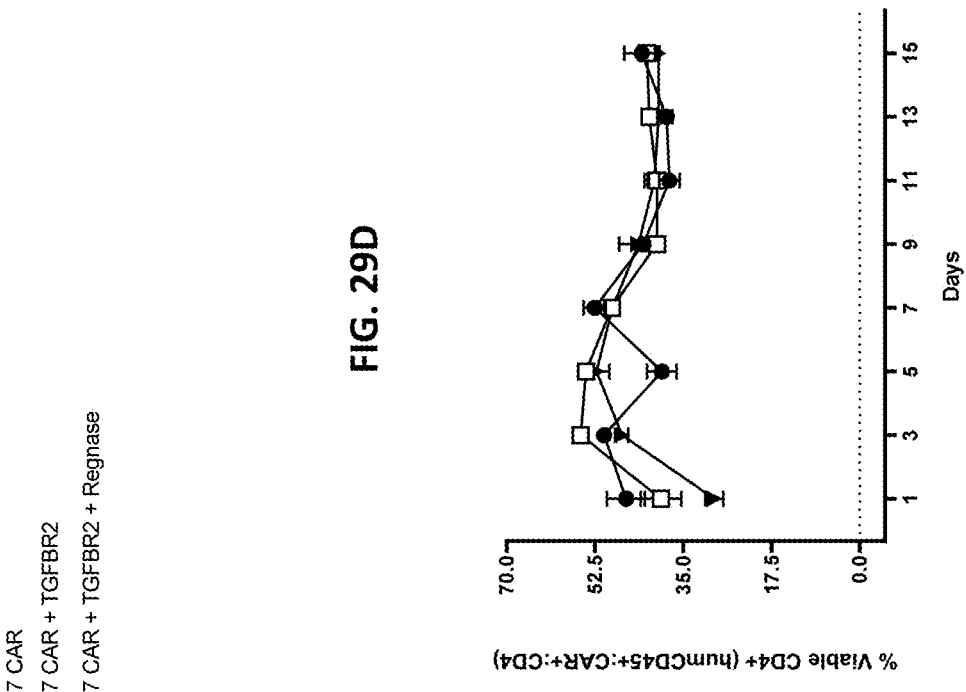
Figure 29C:
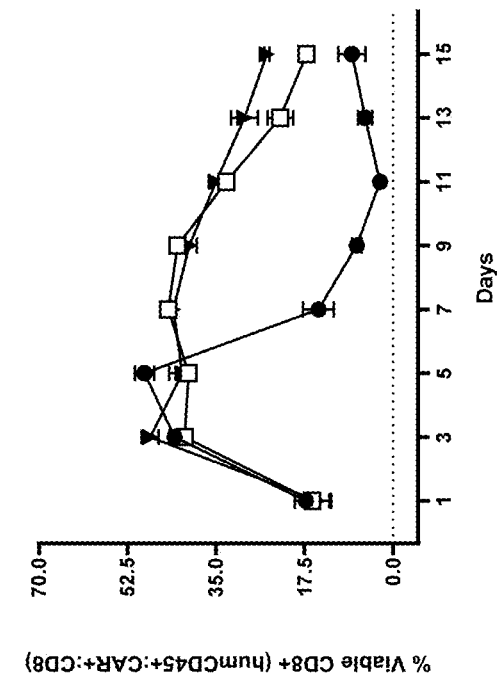

The results demonstrate that disrupting the TGFBRII gene improved potency (FIG. 29A) and CAR T cell expansion (FIG. 29B) as measured by hum CD45 staining, when CAR T cells are repeatedly challenged with PTK7+ positive target cells. The addition of Regnase gene disruption does not provide an added advantage in potency over TGFBRII deletion alone. Potency and expansion is improved compared to CAR T cells that have neither, or both (i.e.: TGFBRII and Regnase), of the genes disrupted. In addition, the results demonstrate that cytotoxic CD8+ CAR T cells persist longer during serial rechallenge (FIG. 29C) with tumor cells if the TGFBRII gene is disrupted compared to anti-PTK7 CAR T cells that have neither or both (i.e.: TGFBRII and Regnase) of the genes disrupted. CD4+ CAR T cells remain consistent regardless of whether TGFBRII and/or Regnase genes are disrupted (FIG. 29D).

Example 24: Treatment Efficacy of Anti-PTK7 CART Cells with Multiple Gene Disruptions in the Subcutaneous Pancreatic Cell Carcinoma Tumor Xenograft Model Treatment in the Pancreatic Cell Carcinoma Tumor Model The ability of T cells expressing a PTK7 CAR with TGFBRII and/or Reg-1 gene edits to eliminate pancreatic cell carcinoma cells that express medium levels of PTK7 was evaluated in vivo using a subcutaneous renal cell carcinoma (Hs766T) tumor xenograft mouse model. Anti-PTK7 CAR+ T cells were produced as described above. See, e.g., Example 22.

The ability of these anti-PTK7 CAR+ T cells to ameliorate disease caused by a PTK7+ pancreatic carcinoma cell line was evaluated in NSG mice using methods employed by Translational Drug Development, LLC (Scottsdale, Ariz.). In brief, 20, 5-8 week old female, NSG mice were individually housed in ventilated microisolator cages, maintained under pathogen-free conditions, 5-7 days prior to the start of the study. Mice received a subcutaneous inoculation of $5 \times 10^6$ Hs766T pancreatic cell carcinoma cells/mouse in the right hind flank. When mean tumor size reached target of ~50 mm$^3$, the mice were further divided into 3 treatment groups as shown in Table 21. On Day 1, treatment four groups received a single 200 µl intravenous dose of $0.5 \times 10^7$ anti-PTK7 CAR+ T cells according to Table 21.

TABLE 21

Treatment groups

| Group | CAR-T | Hs766T cells | CAR-T cell treatment (i.v.) | N |
|---|---|---|---|---|
| 1 | None | $5 \times 10^6$ cells/mouse | None | 5 |

TABLE 21-continued

Treatment groups

| Group | CAR-T | Hs766T cells | CAR-T cell treatment (i.v.) | N |
|---|---|---|---|---|
| 2 | Anti-PTK7 CAR T cells: anti-PTK7 CAR+/TRAC−/B2M− | 5 × 10⁶ cells/mouse | 0.5 × 10⁷ cells/mouse | 5 |
| 3 | Anti-PTK7 CAR T + TGFBRII KO cells: anti-PTK7 CAR+/TRAC−/B2M−/TGFBRII− | 5 × 10⁶ cells/mouse | 0.5 × 10⁷ cells/mouse | 5 |

Figure 30A:
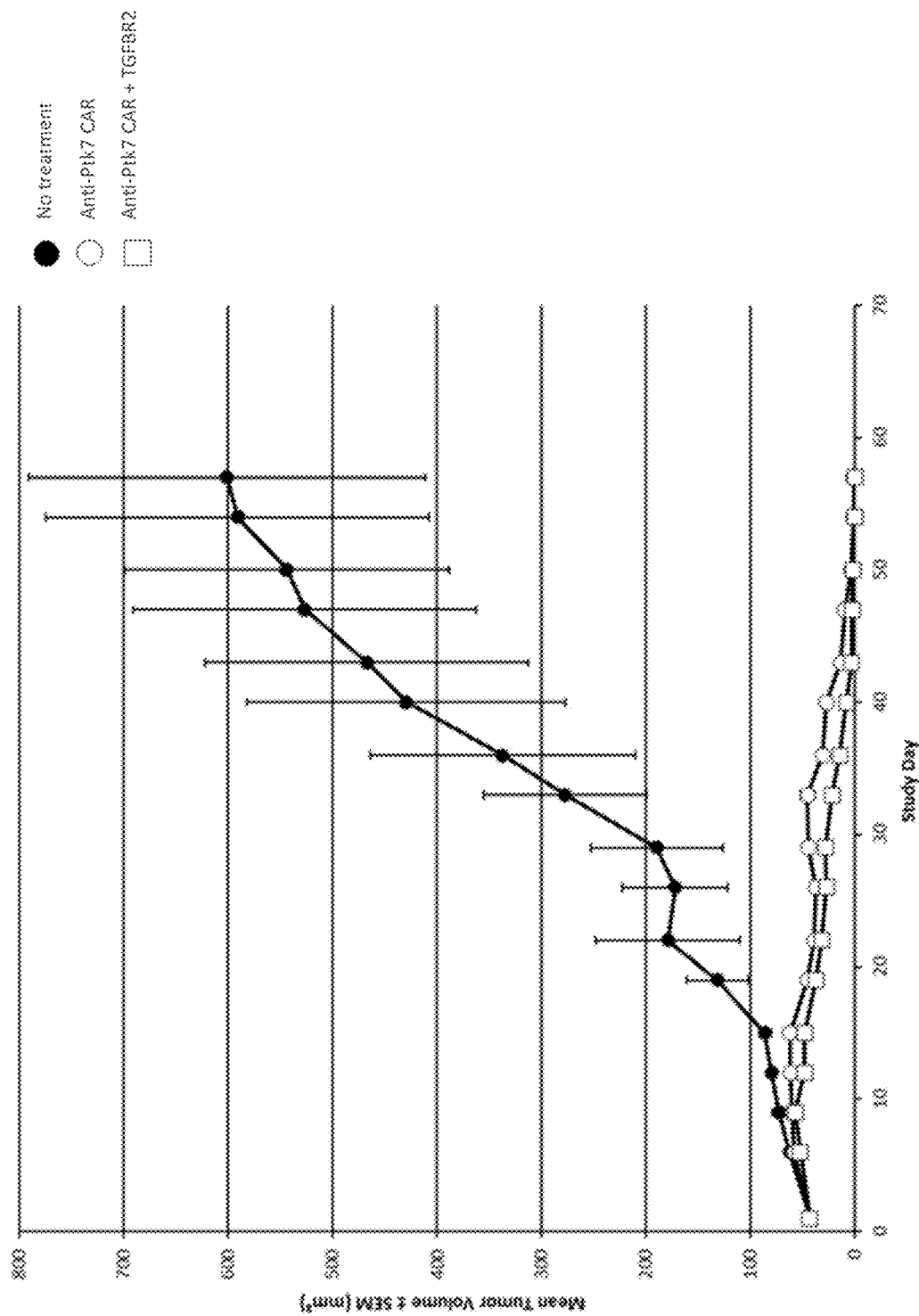
FIGS. 30A-30B include diagrams showing anti-tumor activity of anti-PTK7 CAR T-cells with or without TGFBRII disruption.

Tumor volume was measured 2 times weekly (~every 3-4 days) from day of treatment initiation. By day 11 post-injection, anti-PTK7 CAR T cells with and without TGFBRII gene KO began to show a significant effect on reducing tumor volume compared to no treatment group 1. Approximately one month later the anti-PTK7CAR T with and without TGFBRII KO cells had completely eliminated tumor growth in the subcutaneous Hs766T model (FIG. 30A).

Figure 30B:
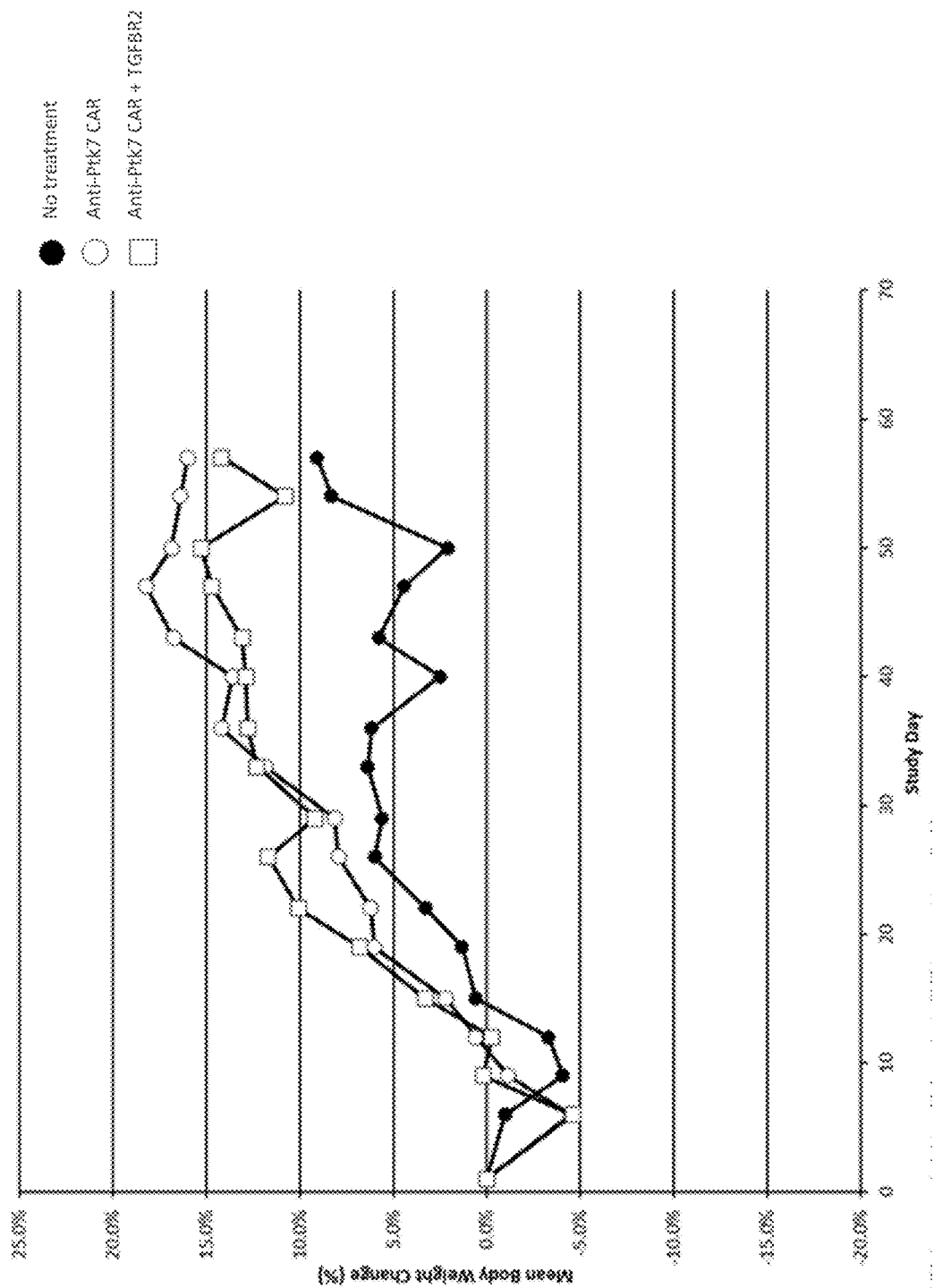

These results demonstrated that disrupting the TGFBRII gene in CAR T cells effectively cleared tumors in the subcutaneous Hs766T renal cell carcinoma tumor xenograft model. No clinical signs of GvHD were observed in anti-PTK7 CAR T cells with and without TGFBRII KO cells (FIG. 30B).

Example 25: Analysis of T Cell Fraction in Pancreatic Cell Carcinoma (Hs766T) Tumor Xenograft Model Blood samples were taken from mice with Hs766T tumors, 47 days after CAR T administration. Briefly, 100 ul of mouse whole blood was collected via submandibular vein. Red blood cell lysis buffer was used to achieve optimal lysis of erythrocytes with minimal effect on lymphocytes. Human CD45 and mouse CD45 were used as a biomarker to separate human and mouse cells by FACS. The blood samples were evaluated by flow cytometry looking for absolute human CD45+ counts as well as memory T cell subsets. Staining for CD45RO+CD27+ was used to define central memory T cells.

The results demonstrate that the addition of the TGFBRII gene edit significantly enhanced the population of central memory T cells (FIG. 31B) compared to anti-PTK7 CAR T cells without TGFBRII KO which correlates with massive expansion of CAR T cells (FIG. 31A) seen in these animals. And the TGFBRII edit further promoted the potential of CAR T cell proliferation in vivo (FIG. 31B).

Sequence Tables

The following tables provide details for the various nucleotide and amino acid sequences disclosed herein.

TABLE 22 sgRNA Sequences and Target Gene Sequences for Reg1

| Name | Unmodified Sequence | Modified Sequence | Target Sequences (PAM) |
|---|---|---|---|
| REG1-Z01 sgRNA (EX2_T1) | GGUCAUCGAUGGGAGCAACGguuuuagagcuagaaauagcaaguuaaaauaaggcuaguccguuaucaacuugaaaaaguggcaccgagucggugcUUUU (SEQ ID NO: 14) | G*G*U*CAUCGAUGGGAGCAACGguuuuagagcuagaaauagcaaguuaaaauaaggcuaguccguuaucaacuugaaaaaguggcaccgagucggugcU*U*U (SEQ ID NO: 15) | GGTCATCGATGGGAGCAACG (TGG) (SEQ ID NO: 171) GGTCATCGATGGGAGCAACG (SEQ ID NO: 318) |
| REG1-Z01 sgRNA (EX2_T1) spacer | GGUCAUCGAUGGGAGCAACG (SEQ ID NO: 16) | G*G*U*CAUCGAUGGGAGCAACG (SEQ ID NO: 17) | |
| REG1-Z02 sgRNA (EX2_T2) | CACCACCCCGCGGGACUAGAguuuuagagcuagaaauagcaaguuaaaauaaggcuaguccguuaucaacuugaaaaaguggcaccgagucggugcUUUU (SEQ ID NO: 18) | C*A*C*CACCCCGCGGGACUAGAguuuuagagcuagaaauagcaaguuaaaauaaggcuaguccguuaucaacuugaaaaaguggcaccgagucggugcU*U*U (SEQ ID NO: 19) | CACCACCCCGCGGGACTAGA (GGG) (SEQ ID NO: 172) CACCACCCCGCGGGACTAGA (SEQ ID NO: 319) |
| REG1-Z02 sgRNA (EX2_T2) spacer | CACCACCCCGCGGGACUAGA (SEQ ID NO: 20) | mC*mA*mC*CACCCCGCGGGACUAGA (SEQ ID NO: 21) | |
| REG1-Z03 sgRNA (EX2_T3) | GGUCUGGCGCUCCCGCUCGGguuuuagagcuagaaauagcaaguuaaaauaaggcuaguccguuaucaacuugaaaaaguggcaccgagucggugcUUUU (SEQ ID NO: 22) | G*G*U*CUGGCGCUCCCGCUCGGguuuuagagcuagaaauagcaaguuaaaauaaggcuaguccguuaucaacuugaaaaaguggcaccgagucggugcU*U*U (SEQ ID NO: 23) | GGTCTGGCGCTCCCGCTCGG (TGG) (SEQ ID NO: 173) GGTCTGGCGCTCCCGCTCGG (SEQ ID NO: 320) |
| REG1-Z03 sgRNA (EX2_T3) spacer | GGUCUGGCGCUCCCGCUCGG (SEQ ID NO: 24) | mG*mG*mU*CUGGCGCUCCCGCUCGG (SEQ ID NO: 25) | |

TABLE 22-continued sgRNA Sequences and Target Gene Sequences for Reg1

| Name | Unmodified Sequence | Modified Sequence | Target Sequences (PAM) |
|---|---|---|---|
| REG1-Z04 sgRNA (EX4_T1) | UUCACACCAUCACGACGC GUguuuuagagcuagaaa uagcaaguuaaaauaagg cuaguccguuaucaacuu gaaaaaguggcaccgagu cggugcUUUU (SEQ ID NO: 26) | U*U*C*ACACCAUCACGACGCG Uguuuuagagcuagaaauagca aguuaaaauaaggcuaguccgu uaucaacuugaaaaaguggcac cgagucggugcU*U*U*U (SEQ ID NO: 27) | TTCACACCATCACGACGCGT (GGG) (SEQ ID NO: 174) TTCACACCATCACGACGCGT (SEQ ID NO: 321) |
| REG1-Z04 sgRNA (EX4_T1) spacer | UUCACACCAUCACGACGC GU (SEQ ID NO: 28) | U*U*C*ACACCAUCACGACGCG U (SEQ ID NO: 29) | |
| REG1-Z05 sgRNA (EX4_T2) | ACACCAUCACGACGCGUG GGguuuuagagcuagaaa uagcaaguuaaaauaagg cuaguccguuaucaacuu gaaaaaguggcaccgagu cggugcUUUU (SEQ ID NO: 30) | A*C*A*CCAUCACGACGCGUGG Gguuuuagagcuagaaauagca aguuaaaauaaggcuaguccgu uaucaacuugaaaaaguggcac cgagucggugcU*U*U*U (SEQ ID NO: 31) | ACACCATCACGACGCGTGGG (TGG) (SEQ ID NO: 175) ACACCATCACGACGCGTGGG (SEQ ID NO: 322) |
| REG1-Z05 sgRNA (EX4_T2) spacer | ACACCAUCACGACGCGUG GG (SEQ ID NO: 32) | A*C*A*CCAUCACGACGCGUGG G (SEQ ID NO: 33) | |
| REG1-Z06 sgRNA (EX4_T3) | CUACGAGUCUGACGGGAU CGguuuuagagcuagaaa uagcaaguuaaaauaagg cuaguccguuaucaacuu gaaaaaguggcaccgagu cggugcUUUU (SEQ ID NO: 34) | C*U*A*CGAGUCUGACGGGAUC Gguuuuagagcuagaaauagca aguuaaaauaaggcuaguccgu uaucaacuugaaaaaguggcac cgagucggugcU*U*U*U (SEQ ID NO: 35) | CTACGAGTCTGACGGGATCG (TGG) (SEQ ID NO: 176) CTACGAGTCTGACGGGATCG (SEQ ID NO: 323) |
| REG1-Z06 sgRNA (EX4_T3) spacer | CUACGAGUCUGACGGGAU CG (SEQ ID NO: 36) | C*U*A*CGAGUCUGACGGGAUC G (SEQ ID NO: 37) | |
| REG1-Z07 sgRNA (EX4_T4) | UUGCCACCCACGCGUCGU GAguuuuagagcuagaaa uagcaaguuaaaauaagg cuaguccguuaucaacuu gaaaaaguggcaccgagu cggugcUUUU (SEQ ID NO: 38) | U*U*G*CCACCCACGCGUCGUG Aguuuuagagcuagaaauagca aguuaaaauaaggcuaguccgu uaucaacuugaaaaaguggcac cgagucggugcU*U*U*U (SEQ ID NO: 39) | TTGCCACCCACGCGTCGTGA (TGG) TTGCCACCCACGCGTCGTGA (SEQ ID NO: 324) |
| REG1-Z07 sgRNA (EX4_T4) spacer | UUGCCACCCACGCGUCGU GA (SEQ ID NO: 40) | U*U*G*CCACCCACGCGUCGUG A (SEQ ID NO: 41) | |
| REG1-Z08 sgRNA (EX4_T5) | GUUCACACCAUCACGACG CGguuuuagagcuagaaa uagcaaguuaaaauaagg cuaguccguuaucaacuu gaaaaaguggcaccgagu cggugcUUUU (SEQ ID NO: 42) | G*U*U*CACACCAUCACGACGC Gguuuuagagcuagaaauagca aguuaaaauaaggcuaguccgu uaucaacuugaaaaaguggcac cgagucggugcU*U*U*U (SEQ ID NO: 43) | GTTCACACCATCACGACGCG (TGG) (SEQ ID NO: 178) GTTCACACCATCACGACGCG (SEQ ID NO: 325) |
| REG1-Z08 sgRNA (EX4_T5) spacer | GUUCACACCAUCACGACG CG (SEQ ID NO: 44) | G*U*U*CACACCAUCACGACGC G (SEQ ID NO: 45) | |
| REG1-Z09 sgRNA (EX4_T6) | CACGAUCCCGUCAGACUC GUguuuuagagcuagaaa uagcaaguuaaaauaagg cuaguccguuaucaacuu gaaaaaguggcaccgagu cggugcUUUU (SEQ ID NO: 46) | C*A*C*GAUCCCGUCAGACUCG Uguuuuagagcuagaaauagca aguuaaaauaaggcuaguccgu uaucaacuugaaaaaguggcac cgagucggugcU*U*U*U (SEQ ID NO: 47) | CACGATCCCGTCAGACTCGT (AGG) (SEQ ID NO: 179) CACGATCCCGTCAGACTCGT (SEQ ID NO: 326) |

TABLE 22-continued sgRNA Sequences and Target Gene Sequences for Reg1

| Name | Unmodified Sequence | Modified Sequence | Target Sequences (PAM) |
|---|---|---|---|
| REG1-Z09 sgRNA (EX4_T6) spacer | CACGAUCCCGUCAGACUCGU (SEQ ID NO: 48) | C*A*C*GAUCCCGUCAGACUCGU (SEQ ID NO: 49) | |
| REG1-Z10 sgRNA (EX4_T7) | ACGACGCGUGGGUGGCAAGCguuuuagagcuagaaauagcaaguuaaaauaaggcuaguccguuaucaacuugaaaaaguggcaccgagucggugcUUUU (SEQ ID NO: 50) | A*C*G*ACGCGUGGGUGGCAAGCguuuuagagcuagaaauagcaaguuaaaauaaggcuaguccguuaucaacuugaaaaaguggcaccgagucggugcU*U*U*U (SEQ ID NO: 51) | ACGACGCGTGGGTGGCAAGC (GGG) (SEQ ID NO: 180) ACGACGCGTGGGTGGCAAGC (SEQ ID NO: 327) |
| REG1-Z10 sgRNA (EX4_T7) spacer | ACGACGCGUGGGUGGCAAGC (SEQ ID NO: 52) | A*C*G*ACGCGUGGGUGGCAAGC (SEQ ID NO: 53) | |

*indicates a nucleotide with a 2'-O-methyl phosphorothioate modification.

TABLE 23 sgRNA Sequences and Target Gene Sequences for TRAC, β2M, and CD70

| | | sgRNA Sequences | SEQ ID NO: |
|---|---|---|---|
| CD70 sgRNA (CD70-7) | Modified | G*C*U*UUGGUCCCAUUGGUCGCguuuuagagcuagaaauagcaaguuaaaauaaggcuaguccguuaucaacuugaaaaaguggcaccgagucggugcU*U*U*U | 54 |
| | Unmodified | GCUUUGGUCCCAUUGGUCGCguuuuagagcuagaaauagcaaguuaaaauaaggcuaguccguuaucaacuugaaaaaguggcaccgagucggugcUUUU | 55 |
| CD70 sgRNA spacer | Modified | G*C*U*UUGGUCCCAUUGGUCGC | 56 |
| | Unmodified | GCUUUGGUCCCAUUGGUCGC | 57 |
| TRAC sgRNA (TA-1) | Modified | A*G*A*GCAACAGUGCUGUGGCCguuuuagagcuagaaauagcaaguuaaaauaaggcuaguccguuaucaacuugaaaaaguggcaccgagucggugcU*U*U*U | 58 |
| | Unmodified | AGAGCAACAGUGCUGUGGCCguuuuagagcuagaaauagcaaguuaaaauaaggcuaguccguuaucaacuugaaaaaguggcaccgagucggugcUUUU | 59 |
| TRAC sgRNA spacer | Modified | A*G*A*GCAACAGUGCUGUGGCC | 60 |
| | Unmodified | AGAGCAACAGUGCUGUGGCC | 61 |
| β2M sgRNA (β2M-1) | Modified | G*C*U*ACUCUCUCUUUCUGGCCguuuuagagcuagaaauagcaaguuaaaauaaggcuaguccguuaucaacuugaaaaaguggcaccgagucggugcU*U*U*U | 62 |
| | Unmodified | GCUACUCUCUCUUUCUGGCCguuuuagagcuagaaauagcaaguuaaaauaaggcuaguccguuaucaacuugaaaaaguggcaccgagucggugcUUUU | 63 |
| β2M sgRNA spacer | Modified | G*C*U*ACUCUCUCUUUCUGGCC | 64 |
| | Unmodified | GCUACUCUCUCUUUCUGGCC | 65 |
| Target Sequences (PAM) | | | |
| CD70 target sequence with (PAM) | | GCTTTGGTCCCATTGGTCGC (GGG) | 66 |
| CD70 target sequence | | GCTTTGGTCCCATTGGTCGC | 67 |
| TRAC target sequence with (PAM) | | AGAGCAACAGTGCTGTGGCC (TGG) | 68 |
| TRAC target sequence | | AGAGCAACAGTGCTGTGGCC | 69 |
| β2M target sequence with (PAM) | | GCTACTCTCTCTTTCTGGCC (TGG) | 70 |

TABLE 23-continued sgRNA Sequences and Target Gene Sequences for TRAC, β2M, and CD70

| | sgRNA Sequences | SEQ ID NO: |
|---|---|---|
| β2M target sequence | GCTACTCTCTCTTTCTGGCC | 71 |

Exemplary sgRNA Formulas

| | | |
|---|---|---|
| sgRNA sequence | nnnnnnnnnnnnnnnnnnnnguuuuagagcuagaaauagcaaguuaaaauaaggcuaguccguuaucaacuugaaaaaguggcaccgagucggugcuuuu | 72 |
| sgRNA sequence | nnnnnnnnnnnnnnnnnnnnguuuuagagcuagaaauagcaaguuaaaauaaggcuaguccguuaucaacuugaaaaaguggcaccgagucggugc | 73 |
| sgRNA sequence | n(17-30)guuuuagagcuagaaauagcaaguuaaaauaaggcuaguccguuaucaacuugaaaaaguggcaccgagucggugcu(1-8) | 74 |

*indicates a nucleotide with a 2'-O-methyl phosphorothioate modification.
"n" refers to the spacer sequence at the 5' end.

SEQUENCE TABLE 24

Edited TRAC Gene Sequence.

| Description | Sequence (Deletions indicated by dashes (-); insertions indicated by bold) | SEQ ID NO: |
|---|---|---|
| TRAC gene edit | AA--------------------GAGCAACAAATCTGACT | 75 |
| TRAC gene edit | AAGAGCAACAGTGCTGT-GCCTGGAGCAACAAATCTGACT | 76 |
| TRAC gene edit | AAGAGCAACAGTG-------CTGGAGCAACAAATCTGACT | 77 |
| TRAC gene edit | AAGAGCAACAGT------GCCTGGAGCAACAAATCTGACT | 78 |
| TRAC gene edit | AAGAGCAACAGTG--------------------CTGACT | 79 |
| TRAC gene edit | AAGAGCAACAGTGCTGTGGGCCTGGAGCAACAAATCTGACT | 80 |
| TRAC gene edit | AAGAGCAACAGTGC--TGGCCTGGAGCAACAAATCTGACT | 81 |
| TRAC gene edit | AAGAGCAACAGTGCTGTGTGCCTGGAGCAACAAATCTGACT | 82 |

SEQUENCE TABLE 25

Edited β2M Gene Sequence.

| Description | Sequence (Deletions indicated by dashes (-); insertions indicated by bold) | SEQ ID NO: |
|---|---|---|
| β2M gene-edit | CGTGGCCTTAGCTGTGCTCGCGCTACTCTCTCTTTCT-GCCTGGAGGCTATCCAGCGTGAGTCTCTCCTACCCTCCCGCT | 83 |
| β2M gene-edit | CGTGGCCTTAGCTGTGCTCGCGCTACTCTCTCTTTC--GCCTGGAGGCTATCCAGCGTGAGTCTCTCCTACCCTCCCGCT | 84 |
| β2M gene-edit | CGTGGCCTTAGCTGTGCTCGCGCTACTCTCTCTTT-----CTGGAGGCTATCCAGCGTGAGTCTCTCCTACCCTCCCGCT | 85 |
| β2M gene-edit | CGTGGCCTTAGCTGTGCTCGCGCTACTCTCTCTTTCTGGATAGCCTGGAGGCTATCCAGCGTGAGTCTCTCCTACCCTCCCGCT | 86 |
| β2M gene-edit | CGTGGCCTTAGCTGTGCTCGC------------------------GCTATCCAGCGTGAGTCTCTCCTACCCTCCCGCT | 87 |
| β2M gene-edit | CGTGGCCTTAGCTGTGCTCGCGCTACTCTCTCTTTCTGTGGCCTGGAGGCTATCCAGCGTGAGTCTCTCCTACCCTCCCGCT | 88 |

SEQUENCE TABLE 26

Edited CD70 Gene Sequence.

| Description | Sequence (Deletions indicated by dashes (-); insertions indicated by bold) | SEQ ID NO: |
|---|---|---|
| CD70 gene-edit | CACACCACGAGGCAGATCACCAAGCCCGCG--CAATGGGACCAAAGCAGCCCGCAGGACG | 89 |
| CD70 gene-edit | CACACCACGAGGCAGATCACCAAGCCCGCGAACCAATGGGACCAAAGCAGCCCGCAGGACG | 90 |
| CD70 gene-edit | CACACCACGAGGCAGATC-----------ACCAATGGGACCAAAGCAGCCCGCAGGACG | 91 |
| CD70 gene-edit | CACAccAcGAGGcAGATCACCAAGCCCGCG-CCAATGGGACCAAAGCAGCCCGCAGGACG | 92 |
| CD70 gene-edit | CACACCACGAGGCAGATCACCAAGCCCGC-ACCAATGGGACCAAAGCAGCCCGCAGGACG | 93 |
| CD70 gene-edit | CACACCACGAGGCAGATCACCA------------------------AGCCCGCAGGACG | 94 |

SEQUENCE TABLE 27

Chimeric Antigen Receptor Sequences

| SEQ ID NO | Description | Sequence |
|---|---|---|
| 95 | signal peptide | MLLLVTSLLLCELPHPAFLLIP |
| 96 | signal peptide | MALPVTALLLPLALLLHAARP |
| 97 | CD8a transmembrane domain | IYIWAPLAGTCGVLLLSLVITLY |
| 98 | 4-1BB nucleotide sequence | AAACGGGGCAGAAAGAAACTCCTGTATATATTCAAACAACCATTTATGAGACCAGTACAAACTACTCAAGAGGAAGATGGCTGTAGCTGCCGATTTCCAGAAGAAGAAGAAGGAGGATGTGAACTG |
| 99 | 4-1BB amino acid sequence | KRGRKKLLYIFKQPFMRPVQTTQEEDGCSCRFPEEEEGGCEL |
| 100 | CD28 nucleotide sequence | TCAAAGCGGAGTAGGTTGTTGCATTCCGATTACATGAATATGACTCCTCGCCGGCCTGGGCCGACAAGAAAACATTACCAACCCTATGCCCCCCCACGAGACTTCGCTGCGTACAGGTCC |
| 101 | CD28 amino acid sequence | SKRSRLLHSDYMNMTPRRPGPTRKHYQPYAPPRDFAAYRS |
| 102 | CD3-zeta nucleotide sequence | CGAGTGAAGTTTTCCCGAAGCGCAGACGCTCCGGCATATCAGCAAGGACAGAATCAGCTGTATAACGAACTGAATTTGGGACGCCGCGAGGAGTATGACGTGCTTGATAAACGCCGGGGGAGAGACCCGGAAATGGGGGGTAAACCCCGAAGAAAGAATCCCCAAGAAGGACTCTACAATGAACTCCAGAAGGATAAGATGGCGGAGGCCTACTCAGAAATAGGTATGAAGGGCGAACGACGACGGGGAAAAGGTCACGATGGCCTCTACCAAGGGTTGAGTACGGCAACCAAAGATACGTACGATGCACTGCATATGCAGGCCCTGCCTCCCAGA |
| 103 | CD3-zeta amino acid sequence | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 105 | anti-CD19 VL CDR1 (Kabat) | RASQDISKYLN |
| 106 | anti-CD19 VL CDR2 (Kabat) | HTSRLHS |
| 107 | anti-CD19 VL CDR3 (Kabat) | QQGNTLPYT |
| 108 | anti-CD19 VH CDR1 (Kabat) | DYGVS |

SEQUENCE TABLE 27-continued

Chimeric Antigen Receptor Sequences

| SEQ ID NO | Description | Sequence |
|---|---|---|
| 109 | anti-CD19 VH CDR2 (Kabat) | VIWGSETTYYNSALKS |
| 110 | anti-CD19 VH CDR3 (Kabat) | HYYYGGSYAMDY |
| 111 | anti-CD19 VL CDR1 (Chothia) | RASQDISKYLN |
| 112 | anti-CD19 VL CDR2 (Chothia) | HTSRLHS |
| 113 | anti-CD19 VL CDR3 (Chothia) | QQGNTLPYT |
| 114 | anti-CD19 VH CDR1 (Chothia) | GVSLPDY |
| 115 | anti-CD19 VH CDR2 (Chothia) | WGSET |
| 116 | anti-CD19 VH CDR3 (Chothia) | HYYYGGSYAMDY |
| 117 | Anti-CD19 CAR FMC63-28Z (FMC63-CD8[tm]-CD28[co-stimulatory domain]-CD3z) | ATGCTTCTTTTGGTTACGTCTCTGTTGCTTTGCGAACTTCCTCATCCAG CGTTCTTGCTGATCCCCGATATTCAGATGACTCAGACCACCAGTAGCTT GTCTGCCTCACTGGGAGACCGAGTAACAATCTCCTGCAGGGCAAGTCAA GACATTAGCAAATACCTCAATTGGTACCAGCAGAAGCCCGACGGAACGG TAAAACTCCTCATCTATCATACGTCAAGGTTGCATTCCGGAGTACCGTC ACGATTTTCAGGTTCTGGGAGCGGAACTGACTATTCCTTGACTATTTCA AACCTCGAGCAGGAGGACATTGCGACATATTTTTGTCAACAAGGTAATA CCCTCCCTTACACTTTCGGAGGAGGAACCAAACTCGAAATTACCGGGTC CACCAGTGGCTCTGGGAAGCCTGGCAGTGGAGAAGGTTCCACTAAAGGC GAGGTGAAGCTCCAGGAGAGCGGCCCCGGTCTCGTTGCCCCCAGTCAAA GCCTCTCTGTAACGTGCACAGTGAGTGGTGTATCATTGCCTGATTATGG CGTCTCCTGGATAAGGCAGCCCCCGCGAAAGGGTCTTGAATGGCTTGGG GTAATATGGGGCTCAGAGACAACGTATTATAACTCCGCTCTCAAAAGTC GCTTGACGATAATAAAAGATAACTCCAAGAGTCAAGTTTTCCTTAAAAT GAACAGTTTGCAGACTGACGATACCGCTATATATTATTGTGCTAAACAT TATTACTACGGCGGTAGTTACGCGATGGATTATTGGGGGCAGGGGACTT CTGTCACAGTCAGTAGTGCTGCTGCCTTTGTCCCGGTATTTCTCCCAGC CAAACCGACCACGACTCCCGCCCCGCGCCCTCCGACACCCGCTCCCACC ATCGCCTCTCAACCTCTTAGTCTTCGCCCCGAGGCATGCCGACCCGCCG CCGGGGGTGCTGTTCATACGAGGGGCTTGGACTTCGCTTGTGATATTTA CATTTGGGCTCCGTTGGCGGGTACGTGCGGCGTCCTTTTGTTGTCACTC GTTATTACTTTGTATTGTAATCACAGGAATCGCTCAAAGCGGAGTAGGT TGTTGCATTCCGATTACATGAATATGACTCCTCGCCGGCCTGGGCCGAC AAGAAAACATTACCAACCCTATGCCCCCCACGAGACTTCGCTGCGTAC AGGTCCCGAGTGAAGTTTTCCCGAAGCGCAGACGCTCCGGCATATCAGC AAGGACAGAATCAGCTGTATAACGAACTGAATTTGGGACGCCGCGAGGA GTATGACGTGCTTGATAAACGCCGGGGGAGAGACCCGGAAATGGGGGGT AAACCCCGAAGAAAGAATCCCCAAGAAGGACTCTACAATGAACTCCAGA AGGATAAGATGGCGGAGGCCTACTCAGAAATAGGTATGAAGGGCGAACG ACGACGGGGAAAAGGTCACGATGGCCTCTACCAAGGGTTGAGTACGGCA ACCAAAGATACGTACGATGCACTGCATATGCAGGCCCTGCCTCCCAGA |
| 118 | Anti-CD19 CAR FMC63-28Z (FMC63-CD8[tm]-CD28[co-stimulatory domain]-CD3z) Amino Acid with signal peptide | *MLLLVTSLLLCELPHPAFLLIP*DIQMTQTTSSLSASLGDRVTISCRASQ DISKYLNWYQQKPDGTVKLLIYHTSRLHSGVPSRFSGSGSGTDYSLTIS NLEQEDIATYFCQQGNTLPYTFGGGTKLEITGSTSGSGKPGSGEGSTKG EVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKH YYYGGSYAMDYWGQGTSVTVSSAAAFVPVFLPAKPTTTPAPRPPTPAPT IASQPLSLRPEACRPAAGGAVHTRGLDFACDIYIWAPLAGTCGVLLLSL VITLYCNHRNRSKRSRLLHSDYMNMTPRRPGPTRKHYQPYAPPRDFAAY RSRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTA TKDTYDALHMQALPPR |

SEQUENCE TABLE 27-continued

Chimeric Antigen Receptor Sequences

| SEQ ID NO | Description | Sequence |
|---|---|---|
| 353 | Anti-CD19 CAR FMC63-28Z (FMC63-CD8[tm]-CD28[co-stimulatory domain]-CD3z) Amino Acid without signal peptide | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEITGSTSGSGKPGSGEGSTKGEVKLQESGPGLVAPSQSLSVTC TVSGVSLPDYGVSWIRQPPRKGLEWLGVIWGSETTYYNSALKSRLTIIK DNSKSQVFLKMNSLQTDDTAIYYCAKHYYYGGSYAMDYWGQGTSVTVSS AAAFVPVFLPAKPTTTPAPRPPTPAPTIASQPLSLRPEACRPAAGGAVH TRGLDFACDIYIWAPLAGTCGVLLLSLVITLYCNHRNRSKRSRLLHSDY MNMTPRRPGPTRKHYQPYAPPRDFAAYRSRVKFSRSADAPAYQQGQNQL YNELNLGRREEYDVLDKRRGRDPEMGGKPRRKNPQEGLYNELQKDKMAE AYSEIGMKGERRRGKGHDGLYQGLSTATKDTYDALHMQALPPR |
| 119 | Anti-CD19 scFv coding sequence | GATATTCAGATGACTCAGACCACCAGTAGCTTGTCTGCCTCACTGGGAG ACCGAGTAACAATCTCCTGCAGGGCAAGTCAAGACATTAGCAAATACCT CAATTGGTACCAGCAGAAGCCCGACGGAACGGTAAAACTCCTCATCTAT CATACGTCAAGGTTGCATTCCGGAGTACCGTCACGATTTTCAGGTTCTG GGAGCGGAACTGACTATTCCTTGACTATTTCAAACCTCGAGCAGGAGGA CATTGCGACATATTTTTGTCAACAAGGTAATACCCTCCCTTACACTTTC GGAGGAGGAACCAAACTCGAAATTACCGGGTCCACCAGTGGCTCTGGGA AGCCTGGCAGTGGAGAAGGTTCCACTAAAGGCGAGGTGAAGCTCCAGGA GAGCGGCCCCGGTCTCGTTGCCCCCAGTCAAAGCCTCTCTGTAACGTGC ACAGTGAGTGGTGTATCATTGCCTGATTATGGCGTCTCCTGGATAAGGC AGCCCCCGCGAAAGGGTCTTGAATGGCTTGGGGTAATATGGGGCTCAGA GACAACGTATTATAACTCCGCTCTCAAAAGTCGCTTGACGATAATAAAA GATAACTCCAAGAGTCAAGTTTTCCTTAAAATGAACAGTTTGCAGACTG ACGATACCGCTATATATTATTGTGCTAAACATTATTACTACGGCGGTAG TTACGCGATGGATTATTGGGGCAGGGGACTTCTGTCACAGTCAGTAGT |
| 120 | Anti-CD19 scFv amino acid sequence Linker underlined | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEIT<u>GSTSGSGKPGSGEGSTKG</u>EVKLQESGPGLVAPSQSLSVTC TVSGVSLPDYGVSWIRQPPRKGLEWLGVIWGSETTYYNSALKSRLTIIK DNSKSQVFLKMNSLQTDDTAIYYCAKHYYYGGSYAMDYWGQGTSVTVSS |
| 121 | CD8a extracellular + CD8a transmembrane + 5' Linker (underlined) | <u>GCTGCTGCC</u>TTTGTCCCGGTATTTCTCCCAGCCAAACCGACCACGACTC CCGCCCCGCGCCCTCCGACACCCGCTCCCACCATCGCCTCTCAACCTCT TAGTCTTCGCCCCGAGGCATGCCGACCCGCCGCCGGGGGTGCTGTTCAT ACGAGGGGCTTGGACTTCGCTTGTGATATTTACATTTGGGCTCCGTTGG CGGGTACGTGCGGCGTCCTTTTGTTGTCACTCGTTATTACTTTGTATTG TAATCACAGGAATCGC |
| 122 | CD8a extracellular + CD8a transmembrane (without linker) | TTTGTCCCGGTATTTCTCCCAGCCAAACCGACCACGACTCCCGCCCCGC GCCCTCCGACACCCGCTCCCACCATCGCCTCTCAACCTCTTAGTCTTCG CCCCGAGGCATGCCGACCCGCCGCCGGGGGTGCTGTTCATACGAGGGGC TTGGACTTCGCTTGTGATATTTACATTTGGGCTCCGTTGGCGGGTACGT GCGGCGTCCTTTTGTTGTCACTCGTTATTACTTTGTATTGTAATCACAG GAATCGC |
| 123 | CD8a extracellular + CD8a transmembrane | FVPVFLPAKPTTTPAPRPPTPAPTIASQPLSLRPEACRPAAGGAVHTRG LDFACDIYIWAPLAGTCGVLLLSLVITLYCNHRNR |
| 124 | Anti-CD19 VH | EVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKH YYYGGSYAMDYWGQGTSVTVSS |
| 125 | Anti-CD19 VL | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEIT |
| 126 | CD19 linker | GSTSGSGKPGSGEGSTKG |
| 127 | CD70 VL CDR1 (Kabat) | RASKSVSTSGYSFMH |
| 128 | CD70 VL CDR1 (Chothia) | SKSVSTSGYSF |
| 129 | CD70 VL CDR2 (Kabat) | LASNLES |
| N/A | CD70 VL CDR2 (Chothia) | LAS |

SEQUENCE TABLE 27-continued

Chimeric Antigen Receptor Sequences

| SEQ ID NO | Description | Sequence |
|---|---|---|
| 130 | CD70 VL CDR3 (Kabat) | QHSREVPWT |
| 131 | CD70 VL CDR3 (Chothia) | SREVPW |
| 132 | CD70 VH CDR1 (Kabat) | NYGMN |
| 133 | CD70 VH CDR1 (Chothia) | GYTFTNYGMN |
| 134 | CD70 VH CDR2 (Kabat) | WINTYTGEPTYADAFKG |
| 135 | CD70 VH CDR2 (Chothia) | NTYTGE |
| 136 | CD70 VH CDR3 (Kabat) | DYGDYGMDY |
| 137 | CD70 VH CDR3 (Chothia) | CARDYGDYGMDYWG |
| 138 | CD70 CAR amino acid sequence (CD70B scFv with 41BB) With signal peptide | *MALPVTALLLPLALLLHAARP*QVQLVQSGAEVKKPGASVKVSCKASGYT FTNYGMNWVRQAPGQGLKWMGWINTYTGEPTYADAFKGRVTMTRDTSIS TAYMELSRLRSDDTAVYYCARDYGDYGMDYWGQGTTVTVSSGGGGSGGG GSGGGGSGDIVMTQSPDSLAVSLGERATINCRASKSVSTSGYSFMHWYQ QKPGQPPKLLIYLASNLESGVPDRFSGSGSGTDFTLTISSLQAEDVAVY YCQHSREVPWTFGQGTKVEIKSAAAFVPVFLPAKPTTTPAPRPPTPAPT IASQPLSLRPEACRPAAGGAVHTRGLDFACDIYIWAPLAGTCGVLLLSL VITLYCNHRNRKRGRKKLLYIFKQPFMRPVQTTQEEDGCSCRFPEEEEG GCELRVKFSRSADAPAYQQGQNQLYNELNLGRREEYDVLDKRRGRDPEM GGKPRRKNPQEGLYNELQKDKMAEAYSEIGMKGERRRGKGHDGLYQGLS TATKDTYDALHMQALPPR |
| 354 | CD70 CAR amino acid sequence (CD70B scFv with 41BB) Without signal peptide | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSSGGGGSGGGGSGGGGSGDIVMTQSPDSLAV SLGERATINCRASKSVSTSGYSFMHWYQQKPGQPPKLLIYLASNLESGV PDRFSGSGSGTDFTLTISSLQAEDVAVYYCQHSREVPWTFGQGTKVEIK SAAAFVPVFLPAKPTTTPAPRPPTPAPTIASQPLSLRPEACRPAAGGAV HTRGLDFACDIYIWAPLAGTCGVLLLSLVITLYCNHRNRKRGRKKLLYI FKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| 139 | Anti-CD70A scFv nucleotide sequence | GATATAGTTATGACCCAATCACCCGATAGTCTTGCGGTAAGCCTGGGGG AGCGAGCAACAATAAACTGTCGGGCATCAAAATCCGTCAGTACAAGCGG GTATTCATTCATGCACTGGTATCAACAGAAACCCGGTCAGCCACCCAAG CTCCTGATTTATCTTGCGTCTAATCTTGAGTCCGGCGTCCCAGACCGGT TTTCCGGCTCCGGGAGCGGCACGGATTTTACTCTTACTATTTCTAGCCT TCAGGCCGAAGATGTGGCGGTATACTACTGCCAGCATTCAAGGGAAGTT CCTTGGACGTTCGGTCAGGGCACGAAAGTGGAAATTAAAGGCGGGGGGG GATCCGGCGGGGAGGGTCTGGAGGAGGTGGCAGTGGTCAGGTCCAACT GGTGCAGTCCGGGGCAGAGGTAAAAAAACCCGGCGCGTCTGTTAAGGTT TCATGCAAGGCCAGTGGATATACTTTCACCAATTACGGAATGAACTGGG TGAGGCAGGCCCCTGGTCAAGGCCTGAAATGGATGGGATGGATAAACAC GTACACCGGTGAACCTACCTATGCCGATGCCTTTAAGGGTCGGGTTACG ATGACGAGAGACACCTCCATATCAACAGCCTACATGGAGCTCAGCAGAT TGAGGAGTGACGATACGGCAGTCTATTACTGTGCAAGAGACTACGGCGA TTATGGCATGGATTACTGGGGCCAGGGCACTACAGTAACCGTTTCCAGC |
| 140 | Anti-CD70A scFv amino acid sequence (linker underlined) | DIVMTQSPDSLAVSLGERATINCRASKSVSTSGYSFMHWYQQKPGQPPK LLIYLASNLESGVPDRFSGSGSGTDFTLTISSLQAEDVAVYYCQHSREV PWTFGQGTKVEIK<u>GGGGSGGGGSGGGGS</u>QVQLVQSGAEVKKPGASVKV SCKASGYTFTNYGMNWVRQAPGQGLKWMGWINTYTGEPTYADAFKGRVT MTRDTSISTAYMELSRLRSDDTAVYYCARDYGDYGMDYWGQGTTVTVSS |
| 141 | Anti-CD70B scFv nucleotide sequence | CAGGTCCAGTTGGTGCAAAGCGGGGCGGAGGTGAAAAAACCCGGCGCTT CCGTGAAGGTGTCCTGTAAGGCGTCCGGTTATACGTTCACGAACTACGG GATGAATTGGGTTCGCCAAGCGCCGGGGCAGGGACTGAAATGGATGGGG TGGATAAATACCTACACCGGCGAACCTACATACGCCGACGCTTTTAAAG GGCGAGTCACTATGACGCGCGATACCAGCATATCCACCGCATACATGGA |

SEQUENCE TABLE 27-continued

Chimeric Antigen Receptor Sequences

| SEQ ID NO | Description | Sequence |
|---|---|---|
| | | GCTGTCCCGACTCCGGTCAGACGACACGGCTGTCTACTATTGTGCTCGG GACTATGGCGATTATGGCATGGACTACTGGGGTCAGGGTACGACTGTAA CAGTTAGTAGTGGTGGAGGCGGCAGTGGCGGGGGGGGAAGCGGAGGAGG GGGTTCTGGTGACATAGTTATGACCCAATCCCCAGATAGTTTGGCGGTT TCTCTGGGCGAGAGGGCAACGATTAATTGTCGCGCATCAAAGAGCGTTT CAACGAGCGGATATTCTTTTATGCATTGGTACCAGCAAAAACCCGGACA ACCGCCGAAGCTGCTGATCTACTTGGCTTCAAATCTTGAGTCTGGGGTG CCCGGACCGATTTTCTGGTAGTGGAAGCGGAACTGACTTTACGCTCACGA TCAGTTCACTGCAGGCTGAGGATGTAGCGGTCTATTATTGCCAGCACAG TAGAGAAGTCCCCTGGACCTTCGGTCAAGGCACGAAAGTAGAAATTAAA |
| 142 | Anti-CD70B scFv amino acid sequence (linker underlined) | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSS<u>GGGGSGGGGSGGGGSG</u>DIVMTQSPDSLAV SLGERATINCRASKSVSTSGYSFMHWYQQKPGQPPKLLIYLASNLESGV PDRFSGSGSGTDFTLTISSLQAEDVAVYYCQHSREVPWTFGQGTKVEIK |
| 143 | Anti-CD70 VH | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSS |
| 144 | Anti-CD70 VL | DIVMTQSPDSLAVSLGERATINCRASKSVSTSGYSFMHWYQQKPGQPPK LLIYLASNLESGVPDRFSGSGSGTDFTLTISSLQAEDVAVYYCQHSREV PWTFGQGTKVEIK |
| 145 | BCMA CAR nucleotide sequence | ATGGCGCTTCCGGTGACAGCACTGCTCCTCCCCTTGGCGCTGTTGCTCC ACGCAGCAAGGCCGCAGGTGCAGCTGGTGCAGAGCGGAGCCGAGCTCAA GAAGCCCGGAGCCTCCGTGAAGGTGAGCTGCAAGGCCAGCGGCAACACC CTGACCAACTACGTGATCCACTGGGTGAGACAAGCCCCCGGCCAAAGGC TGGAGTGGATGGGCTACATCCTGCCCTACAACGACCTGACCAAGTACAG CCAGAAGTTCCAGGGCAGGGTGACCATCACCAGGGATAAGAGCGCCTCC ACCGCCTATATGGAGCTGAGCAGCCTGAGGAGCGAGGACACCGCTGTGT ACTACTGTACAAGGTGGGACTGGGACGGCTTCTTTGACCCCTGGGGCCA GGGCACAACAGTGACCGTCAGCAGCGGCGGCGGAGGCAGCGGCGGCGGC GGCAGCGGCGGAGGCGGAAGCGAAATCGTGATGACCCAGAGCCCCGCCA CACTGAGCGTGAGCCCTGGCGAGAGGGCCAGCATCTCCTGCAGGGCTAG CCAAAGCCTGGTGCACAGCAACGGCAACACCCACCTGCACTGGTACCAG CAGAGACCCGGACAGGCTCCCAGGCTGCTGATCTACAGCGTGAGCAACA GGTTCTCCGAGGTGCCTGCCAGGTTTAGCGGCAGCGGAAGCGGCACCGA CTTTACCCTGACCATCAGCAGCGTGGAGTCCGAGGACTTCGCCGTGTAT TACTGCAGCCAGACCAGCCACATCCCTTACACCTTCGGCGGCGGCACCA AGCTGGAGATCAAAAGTGCTGCTGCCTTTGTCCCGGTATTTCTCCCAGC CAAACCGACCACGACTCCCGCCCCGCGCCCTCCGACACCCGCTCCCACC ATCGCCTCTCAACCTCTTAGTCTTCGCCCCGAGGCATGCCGACCCGCCG CCGGGGGTGCTGTTCATACGAGGGGCTTGGACTTCGCTTGTGATATTTA CATTTGGGCTCCGTTGGCGGGTACGTGCGGCGTCCTTTTGTTGTCACTC GTTATTACTTTGTATTGTAATCACAGGAATCGCAAACGGGGCAGAAAGA AACTTCCTGTATATATTCAAACAACCATTTATGAGACCAGTACAAACTAC TCAAGAGGAAGATGGCTGTAGCTGCCGATTTCCAGAAGAAGAAGAAGGA GGATGTGAACTGCGAGTGAAGTTTTCCCGAAGCGCAGACGCTCCGGCAT ATCAGCAAGGACAGAATCAGCTGTATAACGAACTGAATTTGGGACGCCG CGAGGAGTATGACGTGCTTGATAAACGCCGGGGAGAGACCCGGAAATG GGGGGGTAAACCCCGAAGAAAGAATCCCCAAGAAGGACTCTACAATGAAC TCCAGAAGGATAAGATGGCGGAGGCCTACTCAGAAATAGGTATGAAGGG CGAACGACGACGGGGAAAAGGTCACGATGGCCTCTACCAAGGGTTGAGT ACGGCAACCAAAGATACGTACGATGCACTGCATATGCAGGCCCTGCCTC CCAGA |
| 146 | BCMA CAR amino acid sequence With signal peptide | *MALPVTALLLPLALLLHAAR*PQVQLVQSGAELKKPGASVKVSCKASGNT LTNYVIHWVRQAPGQRLEWMGYILPYNDLTKYSQKFQGRVTITRDKSAS TAYMELSSLRSEDTAVYYCTRWDWDGFFDPWGQGTTVTVSSGGGGSGGG GSGGGGSEIVMTQSPATLSVSPGERASISCRASQSLVHSNGNTHLHWYQ QRPGQAPRLLIYSVSNRFSEVPARFSGSGSGTDFTLTISSVESEDFAVY YCSQTSHIPYTFGGGTKLEIKSAAAFVPVFLPAKPTTTPAPRPPTPAPT IASQPLSLRPEACRPAAGGAVHTRGLDFACDIYIWAPLAGTCGVLLLSL VITLYCNHRNRKRGRKKLLYIFKQPFMRPVQTTQEEDGCSCRFPEEEEG GCELRVKFSRSADAPAYQQGQNQLYNELNLGRREEYDVLDKRRGRDPEM GGKPRRKNPQEGLYNELQKDKMAEAYSEIGMKGERRRGKGHDGLYQGLS TATKDTYDALHMQALPPR |

SEQUENCE TABLE 27-continued

Chimeric Antigen Receptor Sequences

| SEQ ID NO | Description | Sequence |
|---|---|---|
| 355 | BCMA CAR amino acid sequence Without signal peptide | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSSGGGGSGGGGSGGGGSEIVMTQSPATLSVS PGERASISCRASQSLVHSNGNTHLHWYQQRPGQAPRLLIYSVSNRFSEV PARFSGSGSGTDFTLTISSVESEDFAVYYCSQTSHIPYTFGGGTKLEIK SAAAFVPVFLPAKPTTTPAPRPPTPAPTIASQPLSLRPEACRPAAGGAV HTRGLDFACDIYIWAPLAGTCGVLLLSLVITLYCNHRNRKRGRKKLLYI FKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| 147 | BCMA scFv nucleotide sequence | CAGGTGCAGCTGGTGCAGAGCGGAGCCGAGCTCAAGAAGCCCGGAGCCT CCGTGAAGGTGAGCTGCAAGGCCAGCGGCAACACCCTGACCAACTACGT GATCCACTGGGTGAGACAAGCCCCCGGCCAAAGGCTGGAGTGGATGGGC TACATCCTGCCCTACAACGACCTGACCAAGTACAGCCAGAAGTTCCAGG GCAGGGTGACCATCACCAGGGATAAGAGCGCCTCCACCGCCTATATGGA GCTGAGCAGCCTGAGGAGCGAGGACACCGCTGTGTACTACTGTACAAGG TGGGACTGGGACGGCTTCTTTGACCCCTGGGGCCAGGGCACAACAGTGA CCGTCAGCAGCGGCGGCGGAGGCAGCGGCGGCGGCGGCAGCGGCGGAGG CGGAAGCGAAATCGTGATGACCCAGAGCCCCGCCACACTGAGCGTGAGC CCTGGCGAGAGGGCCAGCATCTCCTGCAGGGCTAGCCAAAGCCTGGTGC ACAGCAACGGCAACACCCACCTGCACTGGTACCAGCAGAGACCCGGACA GGCTCCCAGGCTGCTGATCTACAGCGTGAGCAACAGGTTCTCCGAGGTG CCTGCCAGGTTTAGCGGCAGCGGAAGCGGCACCGACTTTACCCTGACCA TCAGCAGCGTGGAGTCCGAGGACTTCGCCGTGTATTACTGCAGCCAGAC CAGCCACATCCCTTACACCTTCGGCGGCGGCACCAAGCTGGAGATCAAA |
| 148 | BCMA scFv amino acid sequence (linker underlined) | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSS<u>GGGGSGGGGSGGGGS</u>EIVMTQSPATLSVS PGERASISCRASQSLVHSNGNTHLHWYQQRPGQAPRLLIYSVSNRFSEV PARFSGSGSGTDFTLTISSVESEDFAVYYCSQTSHIPYTFGGGTKLEIK |
| 149 | BCMA VH | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSS |
| 150 | BCMA VL | EIVMTQSPATLSVSPGERASISCRASQSLVHSNGNTHLHWYQQRPGQAP RLLIYSVSNRFSEVPARFSGSGSGTDFTLTISSVESEDFAVYYCSQTSH IPYTFGGGTKLEIK |
| 151 | BCMA VL CDR1 (Kabat & Chothia) | RASQSLVHSNGNTHLH |
| 152 | BCMA VL CDR2 (Kabat & Chothia) | SVSNRFS |
| 153 | BCMA VL CDR3 (Kabat) | SQTSHIPYT |
| 154 | BCMA VL CDR3 (Chothia) | SQTSHIPYT |
| 155 | BCMA VH CDR1 (Kabat) | NYVIH |
| 156 | BCMA VH CDR1 (Chothia) | GNTLTNY |
| 157 | BCMA VH CDR2 (Kabat) | YILPYNDLTKYSQKFQG |
| 158 | BCMA VH CDR2 (Chothia) | LPYNDL |
| 159 | BCMA VH CDR3 (Kabat) | WDWDGFFDP |
| 160 | BCMA VH CDR3 (Chothia) | WDWDGFFDP |
| 328 | anti-CD33 antibody VH CDR1 (Kabat) | <u>SYYIH</u> |

SEQUENCE TABLE 27-continued

Chimeric Antigen Receptor Sequences

| SEQ ID NO | Description | Sequence |
|---|---|---|
| 329 | anti-CD33 antibody VH CDR2 (Kabat) | VIYPGNDDISYNQKFQG |
| 330 | anti-CD33 antibody VH CDR3 (Kabat) | EVRLRYFDV |
| 331 | anti-CD33 antibody VL CDR1 (Kabat) | KSSQSVFFSSSQKNYLA |
| 332 | anti-CD33 antibody VL CDR2 (Kabat) | WASTRES |
| 333 | anti-CD33 antibody VL CDR3 (Kabat) | HQYLSSRT |
| 334 | anti-CD33 antibody VH | QVQLQQPGAEVVKPGASVKMSCKASGYTFTSYYIHWIKQTPGQGLEWVG VIYPGNDDISYNQKFQGKATLTADKSSTTAYMQLSSLTSEDSAVYYCAR EVRLRYFDVWGQGTTVTVSS |
| 335 | anti-CD33 antibody VL | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIK |
| 336 | Anti-CD33 and anti-CD33b scFv Linker underlined | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIK<u>GGGGGSGGGGSGGGGS</u>QVQLQQPGAEVVKPGASVK MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS S |
| 337 | Anti-CD33 and anti-CD33b scFv | GAAATCGTCCTCACACAATCCCCGGGGAGCCTCGCAGTCAGTCCTGGGG AACGAGTCACTATGAGCTGCAAATCCAGTCAGAGTGTTTTTTTCTCAAG TAGCCAGAAGAACTACCTCGCATGGTACCAACAAATACCGGGGCAATCT CCCCGCTTGCTTATATACTGGGCAAGTACCCGCGAATCCGGCGTACCGG ATCGATTCACGGGATCTGGGTCAGGTACTGATTTCACTTTGACTATCAG CTCTGTTCAGCCTGAAGATTTGGCAATTTACTACTGTCACCAATACTTG AGTAGCCGAACTTTCGGCCAGGGCACGAAGCTCGAAATCAAGGGCGGAG GGGGAGGTTCTGGTGGGGCGGTTCTGGCGGTGGAGGAAGCCAAGTACA GTTGCAACAGCCAGGGCGGAGGTCGTAAAACCTGGGGCGTCTGTCAAG ATGAGCTGTAAAGCAAGTGGATACACCTTCACCTCCTACTATATACATT GGATTAAGCAAACTCCGGGTCAGGGGCTGGAATGGGTTGGCGTTATATA CCCCGGGAACGATGATATATCATACAACAAAAATTTCAAGGCAAGGCG ACTCTGACTGCCGATAAGAGTAGCACAACAGCTTACATGCAGCTTTCTT CCCTGACCAGCGAAGATTCAGCAGTTTACTACTGCGCTCGGGAAGTGCG CCTGCGATACTTTGATGTCTGGGGTCAAGGAACTACAGTTACTGTATCA AGC |
| 338 | Anti-CD33 CAR CD28 costim. With signal peptide | *MALPVTALLLPLALLLHAARP*EIVLTQSPGSLAVSPGERVTMSCKSSQS VFFSSSQKNYLAWYQQIPGQSPRLLIYWASTRESGVPDRFTGSGSGTDF TLTISSVQPEDLAIYYCHQYLSSRTFGQGTKLEIKGGGGSGGGGSGGG GSQVQLQQPGAEVVKPGASVKMSCKASGYTFTSYYIHWIKQTPGQGLEW VGVIYPGNDDISYNQKFQGKATLTADKSSTTAYMQLSSLTSEDSAVYYC AREVRLRYFDVWGQGTTVTVSSSAAAFVPVFLPAKTTTPAPRPPTPAP TIASQPLSLRPEACRPAAGGAVHTRGLDFACDIYIWAPLAGTCGVLLLS LVITLYCNHRNRSKRSRLLHSDYMNMTPRRPGPTRKHYQPYAPPRDFAA YRSRVKFSRSADAPAYQQGQNQLYNELNLGRREEYDVLDKRRGRDPEMG GKPRRKNPQEGLYNELQKDKMAEAYSEIGMKGERRRGKGHDGLYQGLST ATKDTYDALHMQALPPR |
| 356 | Anti-CD33 CAR CD28 costim. Without signal peptide | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIKGGGGSGGGGSGGGGSQVQLQQPGAEVVKPGASVK MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS SSAAAFVPVFLPAKTTTPAPRPPTPAPTIASQPLSLRPEACRPAAGGA VHTRGLDFACDIYIWAPLAGTCGVLLLSLVITLYCNHRNRSKRSRLLHS DYMNMTPRRPGPTRKHYQPYAPPRDFAAYRSRVKFSRSADAPAYQQGQN QLYNELNLGRREEYDVLDKRRGRDPEMGGKPRRKNPQEGLYNELQKDKM AEAYSEIGMKGERRRGKGHDGLYQGLSTATKDTYDALHMQALPPR |

SEQUENCE TABLE 27-continued

Chimeric Antigen Receptor Sequences

| SEQ ID NO | Description | Sequence |
|---|---|---|
| 339 | Anti-CD33b CAR 41BB costim. With signal peptide | *MALPVTALLLPLALLLHAARP*EIVLTQSPGSLAVSPGERVTMSCKSSQS VFFSSSQKNYLAWYQQIPGQSPRLLIYWASTRESGVPDRFTGSGSGTDF TLTISSVQPEDLAIYYCHQYLSSRTFGQGTKLEIKGGGGSGGGGSGGG GSQVQLQQPGAEVVKPGASVKMSCKASGYTFTSYYIHWIKQTPGQGLEW VGVIYPGNDDISYNQKFQGKATLTADKSSTTAYMQLSSLTSEDSAVYYC AREVRLRYFDVWGQGTTVTVSSSAAAFVPVFLPAKPTTTPAPRPPTPAP TIASQPLSLRPEACRPAAGGAVHTRGLDFACDIYIWAPLAGTCGVLLLS LVITLYCNHRNRKRGRKKLLYIFKQPFMRPVQTTQEEDGCSCRFPEEEE GGCELRVKFSRSADAPAYQQGQNQLYNELNLGRREEYDVLDKRRGRDPE MGGKPRRKNPQEGLYNELQKDKMAEAYSEIGMKGERRRGKGHDGLYQGL STATKDTYDALHMQALPPR |
| 357 | Anti-CD33b CAR 41BB costim. Without signal peptide | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIKGGGGSGGGGSGGGGSQVQLQQPGAEVVKPGASVK MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS SSAAAFVPVFLPAKPTTTPAPRPPTPAPTIASQPLSLRPEACRPAAGGA VHTRGLDFACDIYIWAPLAGTCGVLLLSLVITLYCNHRNRKRGRKKLLY IFKQPFMRPVQTTQEEDGCSCRFPEEEEGGCELRVKFSRSADAPAYQQG QNQLYNELNLGRREEYDVLDKRRGRDPEMGGKPRRKNPQEGLYNELQKD KMAEAYSEIGMKGERRRGKGHDGLYQGLSTATKDTYDALHMQALPPR |
| 340 | Anti-PTK7 VH CDR1 | SYGMH |
| 341 | Anti-PTK7 VH CDR2 | VIWDDGSNKYYVDSVKG |
| 342 | Anti-PTK7 VH CDR3 | DDYYGSGSFNSYYGTDV |
| 343 | Anti-PTK7 VL CDR1 | RASQSVSIYLA |
| 344 | Anti-PTK7 VL CDR2 | DASNRAT |
| 345 | Anti-PTK7 VL CDR3 | QQRSNWPPFT |
| 346 | Anti-PTK7 $V_H$ | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSS |
| 347 | Anti-PTK7 $V_L$ | EIVLTQSPATLSLSPGERATLSCRASQSVSIYLAWYQQKPGQAPR LLIYDASNRATGIPARFSGSGSGTDFTLTISSLEPEDFAVYYCQQ RSNWPPFTFGPGTKVDIK |
| 348 | Anti-PTK7 scFv (linker underlined) | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSS<u>GGGGSGGGG SGGGGS</u>EIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIK |
| 349 | Anti-PTK7 CAR CD28 co-stim With signal peptide | *MALPVTALLLPLALLLHAARP*QVQLVESGGGVVQPGRSLRLSCAA SGFTFSSYGMHWVRQAPGKGLEWVAVIWDDGSNKYYVDSVKGRFT ISRDNSKNTLYLQMNSLRAEDTAVYYCARDDYYGSGSFNSYYGTD VWGQGTIVIVSSGGGGSGGGGSGGGGSEIVLTQSPATLSLSPGER ATLSCRASQSVSIYLAWYQQKPGQAPRLLIYDASNRATGIPARFS GSGSGTDFTLTISSLEPEDFAVYYCQQRSNWPPFTFGPGTKVDIK SAAAFVPVFLPAKPTTTPAPRPPTPAPTIASQPLSLRPEACRPAA GGAVHTRGLDFACDIYIWAPLAGTCGVLLLSLVITLYCNHRNSK RSRLLHSDYMNMTPRRPGPTRKHYQPYAPPRDFAAYRSRVKFSRS ADAPAYQQGQNQLYNELNLGRREEYDVLDKRRGRDPEMGGKPRRK NPQEGLYNELQKDKMAEAYSEIGMKGERRRGKGHDGLYQGLSTAT KDTYDALHMQALPPR |

SEQUENCE TABLE 27-continued

Chimeric Antigen Receptor Sequences

| SEQ ID NO | Description | Sequence |
|---|---|---|
| 358 | Anti-PTK7 CAR CD28 co-stim Without signal peptide | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSSGGGGSGGGG SGGGGSEIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIKSAAAFVPVFLPAKPTTTPAPR PPTPAPTIASQPLSLRPEACRPAAGGAVHTRGLDFACDIYIWAPL AGTCGVLLLSLVITLYCNHRNRSKRSRLLHSDYMNMTPRRPGPTR KHYQPYAPPRDFAAYRSRVKFSRSADAPAYQQGQNQLYNELNLGR REEYDVLDKRRGRDPEMGGKPRRKNPQEGLYNELQKDKMAEAYSE IGMKGERRRGKGHDGLYQGLSTATKDTYDALHMQALPPR |
| 350 | Anti-PTK7 CAR 41BB co-stim With signal peptide | *MALPVTALLLPLALLLHAARP*QVQLVESGGGVVQPGRSLRLSCAA SGFTFSSYGMHWVRQAPGKGLEWVAVIWDDGSNKYYVDSVKGRFT ISRDNSKNTLYLQMNSLRAEDTAVYYCARDDYYGSGSFNSYYGTD VWGQGTTVTVSSGGGGSGGGGSGGGGSEIVLTQSPATLSLSPGER ATLSCRASQSVSIYLAWYQQKPGQAPRLLIYDASNRATGIPARFS GSGSGTDFTLTISSLEPEDFAVYYCQQRSNWPPFTFGPGTKVDIK SAAAFVPVFLPAKPTTTPAPRPPTPAPTIASQPLSLRPEACRPAA GGAVHTRGLDFACDIYIWAPLAGTCGVLLLSLVITLYCNHRNRKR GRKKLLYIFKQPFMRPVQTTQEEDGCSCRFPEEEEGGCELRVKFS RSADAPAYQQGQNQLYNELNLGRREEYDVLDKRRGRDPEMGGKPR RKNPQEGLYNELQKDKMAEAYSEIGMKGERRRGKGHDGLYQGLST ATKDTYDALHMQALPPR |
| 359 | Anti-PTK7 CAR 41BB co-stim Without signal peptide | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSSGGGGSGGGG SGGGGSEIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIKSAAAFVPVFLPAKPTTTPAPR PPTPAPTIASQPLSLRPEACRPAAGGAVHTRGLDFACDIYIWAPL AGTCGVLLLSLVITLYCNHRNRKRGRKKLLYIFKQPFMRPVQTTQ EEDGCSCRFPEEEEGGCELRVKFSRSADAPAYQQGQNQLYNELNL GRREEYDVLDKRRGRDPEMGGKPRRKNPQEGLYNELQKDKMAEAY SEIGMKGERRRGKGHDGLYQGLSTATKDTYDALHMQALPPR |

TABLE 28

AAV Donor Template Sequences

| | | |
|---|---|---|
| 161 | Left ITR (5' ITR) | TTGGCCACTCCCTCTCTGCG CGCTCGCTCGCTCACTGAGG CCGGGCGACCAAAGGTCGCC CGACGCCCGGGCTTTGCCCG GGCGGCCTCAGTGAGCGAGC GAGCGCGCAGAGAGGGAGTG GCCAACTCCATCACTAGGGG TTCCT |
| 162 | Left ITR (5' ITR) (alternate) | CCTGCAGGCAGCTGCGCGCT CGCTCGCTCACTGAGGCCGC CCGGGCGTCGGGCGACCTTT GGTCGCCCGGCCTCAGTGAG CGAGCGAGCGCGCAGAGAGG GAGTGGCCAACTCCATCACT AGGGGTTCCT |
| 163 | Right ITR (3' ITR) | AGGAACCCCTAGTGATGGAG TTGGCCACTCCCTCTCTGCG CGCTCGCTCGCTCACTGAGG CCGCCCGGGCAAAGCCCGGG CGTCGGGCGACCTTTGGTCG CCCGGCCTCAGTGAGCGAGC GAGCGCGCAGAGAGGGAGTG GCCAA |
| 164 | Right ITR (3' ITR) (alternate) | AGGAACCCCTAGTGATGGAG TTGGCCACTCCCTCTCTGCG CGCTCGCTCGCTCACTGAGG CCGGGCGACCAAAGGTCGCC CGACGCCCGGGCTTTGCCCG GGCGGCCTCAGTGAGCGAGC GAGCGCGCAGCTGCCTGCAG G |
| 165 | TRAC-LHA (800 bp) | GAGATGTAAGGAGCTGCTGT GACTTGCTCAAGGCCTTATA TCGAGTAAACGGTAGTGCTG GGGCTTAGACGCAGGTGTTC TGATTTATAGTTCAAAACCT CTATCAATGAGAGAGCAATC TCCTGGTAATGTGATAGATT TCCCAACTTAATGCCAACAT ACCATAAACCTCCCATTCTG CTAATGCCCAGCCTAAGTTG GGGAGACCACTCCAGATTCC AAGATGTACAGTTTGCTTTG CTGGGCCTTTTTCCCATGCC TGCCTTTACTCTGCCAGAGT TATATTGCTGGGGTTTTGAA GAAGATCCTATTAAATAAAA GAATAAGCAGTATTATTAAG TAGCCCTGCATTTCAGGTTT CCTTGAGTGGCAGGCCAGGC CTGGCCGTGAACGTTCACTG AAATCATGGCCTCTTGGCCA AGATTGATAGCTTGTGCCTG TCCCTGAGTCCCAGTCCATC ACGAGCAGCTGGTTTCTAAG ATGCTATTTCCCGTATAAAG |

TABLE 28-continued

AAV Donor Template Sequences

| | | |
|---|---|---|
| | | CATGAGACCGTGACTTGCCA |
| | | GCCCCACAGAGCCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |
| | | ACAGACAAAACTGTGCTAGA |
| | | CATGAGGTCTATGGACTTCA |
| 166 | TRAC-RHA (800 bp) | TGGAGCAACAAATCTGACTT |
| | | TGCATGTGCAAACGCCTTCA |
| | | ACAACAGCATTATTCCAGAA |
| | | GACACCTTCTTCCCCAGCCC |
| | | AGGTAAGGGCAGCTTTGGTG |
| | | CCTTCGCAGGCTGTTTCCTT |
| | | GCTTCAGGAATGGCCAGGTT |
| | | CTGCCCAGAGCTCTGGTCAA |
| | | TGATGTCTAAAACTCCTCTG |
| | | ATTGGTGGTCTCGGCCTTAT |
| | | CCATTGCCACCAAAACCCTC |
| | | TTTTTACTAAGAAACAGTGA |
| | | GCCTTGTTCTGGCAGTCCAG |
| | | AGAATGACACGGGAAAAAAG |
| | | CAGATGAAGAGAAGGTGGCA |
| | | GGAGAGGGCACGTGGCCCAG |
| | | CCTCAGTCTCTCCAACTGAG |
| | | TTCCTGCCTGCCTGCCTTTG |
| | | CTCAGACTGTTTGCCCCTTA |
| | | CTGCTCTTCTAGGCCTCATT |
| | | CTAAGCCCCTTCTCCAAGTT |
| | | GCCTCTCCTTATTTCTCCCT |
| | | GTCTGCCAAAAAATCTTTCC |
| | | CAGCTCACTAAGTCAGTCTC |
| | | ACGCAGTCACTCATTAACCC |
| | | ACCAATCACTGATTGTGCCG |
| | | GCACATGAATGCACCAGGTG |
| | | TTGAAGTGGAGGAATTAAAA |
| | | AGTCAGATGAGGGGTGTGCC |
| | | CAGAGGAAGCACCATTCTAG |
| | | TTGGGGGAGCCCATCTGTCA |
| | | GCTGGGAAAAGTCCAAATAA |
| | | CTTCAGATTGGAATGTGTTT |
| | | TAACTCAGGGTTGAGAAAAC |
| | | AGCTACCTTCAGGACAAAAG |
| | | TCAGGGAAGGGCTCTCTGAA |
| | | GAAATGCTACTTGAAGATAC |
| | | CAGCCCTACCAAGGGCAGGG |
| | | AGAGGACCCTATAGAGGCCT |
| | | GGGACAGGAGCTCAATGAGA |
| | | AAGG |
| 167 | EF1a | GGCTCCGGTGCCCGTCAGTG |
| | | GGCAGAGCGCACATCGCCCA |
| | | CAGTCCCCGAGAAGTTGGGG |
| | | GGAGGGGTCGGCAATTGAAC |
| | | CGGTGCCTAGAGAAGGTGGC |
| | | GCGGGGTAAACTGGGAAAGT |
| | | GATGTCGTGTACTGGCTCCG |
| | | CCTTTTTCCCGAGGGTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCTGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTTCTGGC |
| | | AAGATAGTCTTGTAAATGCG |
| | | GGCCAAGATCTGCACACTGG |
| | | TATTTCGGTTTTTGGGGCCG |
| | | CGGGCGGCGACGGGGCCCGT |
| | | GCGTCCCAGCGCACATGTTC |
| | | GGCGAGGCGGGGCCTGCGAG |
| | | CGCGGCCACCGAGAATCGGA |
| | | CGGGGGTAGTCTCAAGCTGG |
| | | CCGGCCTGCTCTGGTGCCTG |
| | | GCCTCGCGCCGCCGTGTATC |
| | | GCCCCGCCCTGGGCGGCAAG |
| | | GCTGGCCCGGTCGGCACCAG |
| | | TTGCGTGAGCGGAAAGATGG |
| | | CCGCTTCCCGGCCCTGCTGC |
| | | AGGGAGCTCAAAATGGAGGA |
| | | CGCGGCGCTCGGGAGAGCGG |
| | | GCGGGTGAGTCACCCACACA |
| | | AAGGAAAAGGGCCTTTCCGT |
| | | CCTCAGCCGTCGCTTCATGT |
| | | GACTCCACGGAGTACCGGGC |
| | | GCCGTCCAGGCACCTCGATT |
| | | AGTTCTCGAGCTTTTGGAGT |
| | | ACGTCGTCTTTAGGTTGGGG |
| | | GGAGGGGTTTTATGCGATGG |
| | | AGTTTCCCCACACTGAGTGG |
| | | GTGGAGACTGAAGTTAGGCC |
| | | AGCTTGGCACTTGATGTAAT |
| | | TCTCCTTGGAATTTGCCCTT |
| | | TTTGAGTTTGGATCTTGGTT |
| | | CATTCTCAAGCCTCAGACAG |
| | | TGGTTCAAAGTTTTTTTCTT |
| | | CCATTTCAGGTGTCGTGA |
| 168 | CD19 LHA to RHA | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |
| | | TGATTTATAGTTCAAAACCT |
| | | CTATCAATGAGAGAGCAATC |
| | | TCCTGGTAATGTGATAGATT |
| | | TCCCAACTTAATGCCAACAT |
| | | ACCATAAACCTCCCATTCTG |
| | | CTAATGCCCAGCCTAAGTTG |
| | | GGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAAA |
| | | GAATAAGCAGTATTATTAAG |
| | | TAGCCCTGCATTTCAGGTTT |
| | | CCTTGAGTGGCAGGCCAGGC |
| | | CTGGCCGTGAACGTTCACTG |
| | | AAATCATGGCCTCTTGGCCA |
| | | AGATTGATAGCTTGTGCCTG |
| | | TCCCTGAGTCCCAGTCCATC |
| | | ACGAGCAGCTGGTTTCTAAG |
| | | ATGCTATTTCCCGTATAAAG |
| | | CATGAGACCGTGACTTGCCA |
| | | GCCCCACAGAGCCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |

TABLE 28-continued

AAV Donor Template Sequences

ACAGACAAAACTGTGCTAGA
CATGAGGTCTATGGACTTCA
GGCTCCGGTGCCCGTCAGTG
GGCAGAGCGCACATCGCCCA
CAGTCCCCGAGAAGTTGGGG
GGAGGGGTCGGCAATTGAAC
CGGTGCCTAGAGAAGGTGGC
GCGGGGTAAACTGGGAAAGT
GATGTCGTGTACTGGCTCCG
CCTTTTTCCCGAGGGTGGGG
GAGAACCGTATATAAGTGCA
GTAGTCGCCGTGAACGTTCT
TTTTCGCAACGGGTTTGCCG
CCAGAACACAGGTAAGTGCC
GTGTGTGGTTCCCGCGGGCC
TGGCCTCTTTACGGGTTATG
GCCCTTGCGTGCCTTGAATT
ACTTCCACTGGCTGCAGTAC
GTGATTCTTGATCCCGAGCT
TCGGGTTGGAAGTGGGTGGG
AGAGTTCGAGGCCTTGCGCT
TAAGGAGCCCCTTCGCCTCG
TGCTTGAGTTGAGGCCTGGC
CTGGGCGCTGGGGCCGCCGC
GTGCGAATCTGGTGGCACCT
TCGCGCCTGTCTCGCTGCTT
TCGATAAGTCTCTAGCCATT
TAAAATTTTTGATGACCTGC
TGCGACGCTTTTTTTCTGGC
AAGATAGTCTTGTAAATGCG
GGCCAAGATCTGCACACTGG
TATTTCGGTTTTTGGGGCCG
CGGGCGGCGACGGGGCCCGT
GCGTCCCAGCGCACATGTTC
GGCGAGGCGGGGCCTGCGAG
CGCGGCCACCGAGAATCGGA
CGGGGGTAGTCTCAAGCTGG
CCGGCCTGCTCTGGTGCCTG
GCCTCGCGCCGCCGTGTATC
GCCCCGCCCTGGGCGGCAAG
GCTGGCCCGGTCGGCACCAG
TTGCGTGAGCGGAAAGATGG
CCGCTTCCCGGCCCTGCTGC
AGGGAGCTCAAAATGGAGGA
CGCGGCGCTCGGGAGAGCGG
GCGGGTGAGTCACCCACACA
AAGGAAAAGGGCCTTTCCGT
CCTCAGCCGTCGCTTCATGT
GACTCCACGGAGTACCGGGC
GCCGTCCAGGCACCTCGATT
AGTTCTCGAGCTTTTGGAGT
ACGTCGTCTTTAGGTTGGGG
GGAGGGGTTTTATGCGATGG
AGTTTCCCCACACTGAGTGG
GTGGAGACTGAAGTTAGGCC
AGCTTGGCACTTGATGTAAT
TCTCCTTGGAATTTGCCCTT
TTTGAGTTTGGATCTTGGTT
CATTCTCAAGCCTCAGACAG
TGGTTCAAAGTTTTTTTCTT
CCATTTCAGGTGTCGTGACC
ACCATGCTTCTTTTGGTTAC
GTCTCTGTTGCTTTGCGAAC
TTCCTCATCCAGCGTTCTTG
CTGATCCCGATATTTCAGAT
GACTCAGACCACCAGTAGCT
TGTCTGCCTCACTGGGAGAC
CGAGTAACAATCTCCTGCAG
GGCAAGTCAAGACATTAGCA
AATACCTCAATTGGTACCAG
CAGAAGCCCGACGGAACGGT
AAAACTCCTCATCTATCATA
CGTCAAGGTTGCATTCCGGA
GTACCGTCACGATTTTCAGG
TTCTGGGAGCGGAACTGACT
ATTCCTTGACTATTTCAAAC
CTCAGCAGGAGGACATTGC
GACATATTTTGTCAACAAG

GTAATACCCTCCCTTACACT
TTCGGAGGAGGAACCAAACT
CGAAATTACCGGGTCCACCA
GTGGCTCTGGGAAGCCTGGC
AGTGGAGAAGGTTCCACTAA
AGGCGAGGTGAAGCTCCAGG
AGAGCGGCCCCGGTCTCGTT
GCCCCCAGTCAAAGCCTCTC
TGTAACGTGCACAGTGAGTG
GTGTATCATTGCCTGATTAT
GGCGTCTCCTGGATAAGGCA
GCCCCCGCGAAAGGGTCTTG
AATGGCTTGGGGTAATATGG
GGCTCAGAGACAACGTATTA
TAACTCCGCTCTCAAAAGTC
GCTTGACGATAATAAAAGAT
AACTCCAAGAGTCAAGTTTT
CCTTAAAATGAACAGTTTGC
AGACTGACGATACCGCTATA
TATTATTGTGCTAAACATTA
TTACTACGGCGGTAGTTACG
CGATGGATTATTGGGGGCAG
GGGACTTCTGTCACAGTCAG
TAGTGCTGCTGCCTTTGTCC
CGGTATTCTCCCAGCCAAA
CCGACCACGACTCCCGCCCC
GCGCCCTCCGACACCCGCTC
CCACCATCGCCTCTCAACCT
CTTAGTCTTCGCCCCGAGGC
ATGCCGACCCGCCGCCGGGG
GTGCTGTTCATACGAGGGGC
TTGGACTTCGCTTGTGATAT
TTACATTTGGGCTCCGTTGG
CGGGTACGTGCGGCGTCCTT
TTGTTGTCACTCGTTATTAC
TTTGTATTGTAATCACAGGA
ATCGCTCAAAGCGGAGTAGG
TTGTTGCATTCCGATTACAT
GAATATGACTCCTCGCCGGC
CTGGGCCGACAAGAAAACAT
TACCAACCCTATGCCCCCCC
ACGAGACTTCGCTGCGTACA
GGTCCCGAGTGAAGTTTTCC
CGAAGCGCAGACGCTCCGGC
ATATCAGCAAGGACAGAATC
AGCTGTATAACGAACTGAAT
TTGGGACGCCGCGAGGAGTA
TGACGTGCTTGATAAACGCC
GGGGGAGAGACCCGGAAATG
GGGGGTAAACCCCGAAGAAA
GAATCCCAAGAAGGACTCT
ACAATGAACTCCAGAAGGAT
AAGATGGCGGAGGCCTACTC
AGAAATAGGTATGAAGGGCG
AACGACGACGGGGAAAAGGT
CACGATGGCCTCTACCAAGG
GTTGAGTACGGCAACCAAAG
ATACGTACGATGCACTGCAT
ATGCAGGCCCTGCCTCCCAG
ATAATAATAAAATCGCTATC
CATCGAAGATGGATGTGTGT
TGGTTTTTTGTGTGTGGAGC
AACAAATCTGACTTTGCATG
TGCAAACGCCTTCAACAACA
GCATTATTCCAGAAGACACC
TTCTTCCCCAGCCCAGGTAA
GGGCAGCTTTGGTGCCTTCG
CAGGCTGTTTCCTTGCTTCA
GGAATGGCCAGGTTCTGCCC
AGAGCTCTGGTCAATGATGT
CTAAAACTCCTCTGATTGGT
GGTCTCGGCCTTATCCATTG
CCACCAAAACCCTCTTTTTA
CTAAGAAACAGTGAGCCTTG
TTCTGGCAGTCCAGAGAATG
ACACGGGAAAAAGCAGATG
AAGAGAAGGTGGCAGGAGAG
GGCACGTGGCCCAGCCTCAG

TABLE 28-continued

AAV Donor Template Sequences

| | | |
|---|---|---|
| | | TCTCTCCAACTGAGTTCCTG |
| | | CCTGCCTGCCTTTGCTCAGA |
| | | CTGTTTGCCCCTTACTGCTC |
| | | TTCTAGGCCTCATTCTAAGC |
| | | CCCTTCTCCAAGTTGCCTCT |
| | | CCTTATTTCTCCCTGTCTGC |
| | | CAAAAAATCTTTCCCAGCTC |
| | | ACTAAGTCAGTCTCACGCAG |
| | | TCACTCATTAACCCACCAAT |
| | | CACTGATTGTGCCGGCACAT |
| | | GAATGCACCAGGTGTTGAAG |
| | | TGGAGGAATTAAAAAGTCAG |
| | | ATGAGGGGTGTGCCCAGAGG |
| | | AAGCACCATTCTAGTTGGGG |
| | | GAGCCCATCTGTCAGCTGGG |
| | | AAAAGTCCAAATAACTTCAG |
| | | ATTGGAATGTGTTTTAACTC |
| | | AGGGTTGAGAAAACAGCTAC |
| | | CTTCAGGACAAAAGTCAGGG |
| | | AAGGGCTCTCTGAAGAAATG |
| | | CTACTTGAAGATACCAGCCC |
| | | TACCAAGGGCAGGGAGAGGA |
| | | CCCTATAGAGGCCTGGGACA |
| | | GGAGCTCAATGAGAAAGG |
| 169 | CD70 LHA to RHA (CD70B scFV with 41BB) | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |
| | | TGATTTATAGTTCAAAACCT |
| | | CTATCAATGAGAGAGCAATC |
| | | TCCTGGTAATGTGATAGATT |
| | | TCCCAACTTAATGCCAACAT |
| | | ACCATAAACCTCCCATTCTG |
| | | CTAATGCCCAGCCTAAGTTG |
| | | GGGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAAA |
| | | GAATAAGCAGTATTATTAAG |
| | | TAGCCCTGCATTTCAGGTTT |
| | | CCTTGAGTGGCAGGCCAGGC |
| | | CTGGCCGTGAACGTTCACTG |
| | | AAATCATGGCCTCTTGGCCA |
| | | AGATTGATAGCTTGTGCCTG |
| | | TCCCTGAGTCCCAGTCCATC |
| | | ACGAGCAGCTGGTTTCTAAG |
| | | ATGCTATTTCCCGTATAAAG |
| | | CATGAGACCGTGACTTGCCA |
| | | GCCCCACAGAGCCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |
| | | ACAGACAAAACTGTGCTAGA |
| | | CATGAGGTCTATGGACTTCA |
| | | GGCTCCGGTGCCCGTCAGTG |
| | | GGCAGAGCGCACATCGCCCA |
| | | CAGTCCCCGAGAAGTTGGGG |
| | | GGAGGGGTCGGCAATTGAAC |
| | | CGGTGCCTAGAGAAGGTGGC |
| | | GCGGGTAAACTGGGAAAGT |
| | | GATGTCGTGTACTGGCTCCG |
| | | CCTTTTTCCCAGGGTTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCTGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTCTGGC |
| | | AAGATAGTCTTGTAAATGCG |
| | | GGCCAAGATCTGCACACTGG |
| | | TATTTCGGTTTTTGGGGCCG |
| | | CGGGCGGCGACGGGGCCCGT |
| | | GCGTCCCAGCGCACATGTTC |
| | | GGCGAGGCGGGGCCTGCGAG |
| | | CGCGGCCACCGAGAATCGGA |
| | | CGGGGGTAGTCTCAAGCTGG |
| | | CCGGCCTGCTCTGGTGCCTG |
| | | GCCTCGCGCCGCCGTGTATC |
| | | GCCCCGCCCTGGGCGGCAAG |
| | | GCTGGCCCGGTCGGCACCAG |
| | | TTGCGTGAGCGGAAAGATGG |
| | | CCGCTTCCCGGCCCTGCTGC |
| | | AGGGAGCTCAAAATGGAGGA |
| | | CGCGGCGCTCGGAGAGCGG |
| | | GCGGGTGAGTCACCCACACA |
| | | AAGGAAAAGGGCCTTTCCGT |
| | | CCTCAGCCGTCGCTTCATGT |
| | | GACTCCACGGAGTACCGGGC |
| | | GCCGTCCAGGCACCTCGATT |
| | | AGTTCTCGAGCTTTTGGAGT |
| | | ACGTCGTCTTTAGGTTGGGG |
| | | GGAGGGGTTTTATGCGATGG |
| | | AGTTTCCCCACACTGAGTGG |
| | | GTGGAGACTGAAGTTAGGCC |
| | | AGCTTGGCACTTGATGTAAT |
| | | TCTCCTTGGAATTTGCCCTT |
| | | TTTGAGTTTGGATCTTGGTT |
| | | CATTCTCAAGCCTCAGACAG |
| | | TGGTTCAAAGTTTTTTTCTT |
| | | CCATTTCAGGTGTCGTGACC |
| | | ACCATGGCGCTTCCGGTGAC |
| | | AGCACTGCTCCTCCCCTTGG |
| | | CGCTGTTGCTCCACGCAGCA |
| | | AGGCCGCAGGTCCAGTTGGT |
| | | GCAAAGCGGGGCGGAGGTGA |
| | | AAAAACCCGGCGCTTCCGTG |
| | | AAGGTGTCCTGTAAGGCGTC |
| | | CGGTTATACGTTCACGAACT |
| | | ACGGGATGAATTGGGTTCGC |
| | | CAAGCGCCGGGCAGGGACT |
| | | GAAATGGATGGGGTGGATAA |
| | | ATACCTACACCGGCGAACCT |
| | | ACATACGCCGACGCTTTTAA |
| | | AGGGCGAGTCACTATGACGC |
| | | GCGATACCAGCATATCCACC |
| | | GCATACATGGAGCTGTCCCG |
| | | ACTCCGGTCAGACGACACGG |
| | | CTGTCTACTATTGTGCTCGG |
| | | GACTATGGCGATTATGGCAT |
| | | GGACTACTGGGGTCAGGGTA |
| | | CGACTGTAACAGTTAGTAGT |
| | | GGTGGAGGCGGCAGTGGCGG |
| | | GGGGGAAGCGGAGGAGGGG |
| | | GTTCTGGTGACATAGTTATG |
| | | ACCCAATCCCCAGATAGTTT |
| | | GGCGGTTTCTCTGGGCGAGA |
| | | GGGCAACGATTAATTGTCGC |
| | | GCATCAAAGAGCGTTTCAAC |
| | | GAGCGGATATTCTTTTATGC |
| | | ATTGGTACCAGCAAAAACCC |
| | | GGACAACCGCCGAAGCTGCT |
| | | GATCTACTTGGCTTCAAATC |

TABLE 28-continued

AAV Donor Template Sequences

| | | |
|---|---|---|
| | TTGAGTCTGGGGTGCCGGAC | |
| | CGATTTTCTGGTAGTGGAAG | |
| | CGGAACTGACTTTACGCTCA | |
| | CGATCAGTTCACTGCAGGCT | |
| | GAGGATGTAGCGGTCTATTA | |
| | TTGCCAGCACAGTAGAGAAG | |
| | TCCCCTGGACCTTCGGTCAA | |
| | GGCACGAAAGTAGAAATTAA | |
| | AAGTGCTGCTGCCTTTGTCC | |
| | CGGTATTTCTCCCAGCCAAA | |
| | CCGACCACGACTCCCGCCCC | |
| | GCGCCCTCCGACACCCGCTC | |
| | CCACCATCGCCTCTCAACCT | |
| | CTTAGTCTTCGCCCCGAGGC | |
| | ATGCCGACCCGCCGCCGGGG | |
| | GTGCTGTTCATACGAGGGGC | |
| | TTGGACTTCGCTTGTGATAT | |
| | TTACATTTGGGCTCCGTTGG | |
| | CGGGTACGTGCGGCGTCCTT | |
| | TTGTTGTCACTCGTTATTAC | |
| | TTTGTATTGTAATCACAGGA | |
| | ATCGCAAACGGGGCAGAAAG | |
| | AAACTCCTGTATATATTCAA | |
| | ACAACCATTTATGAGACCAG | |
| | TACAAACTACTCAAGAGGAA | |
| | GATGGCTGTAGCTGCCGATT | |
| | TCCAGAAGAAGAAGAAGGAG | |
| | GATGTGAACTGCGAGTGAAG | |
| | TTTTCCCGAAGCGCAGACGC | |
| | TCCGGCATATCAGCAAGGAC | |
| | AGAATCAGCTGTATAACGAA | |
| | CTGAATTTGGGACGCCGCGA | |
| | GGAGTATGACGTGCTTGATA | |
| | AACGCCGGGGAGAGACCCG | |
| | GAAATGGGGGTAAACCCCG | |
| | AAGAAAGAATCCCCAAGAAG | |
| | GACTCTACAATGAACTCCAG | |
| | AAGGATAAGATGGCGGAGGC | |
| | CTACTCAGAAATAGGTATGA | |
| | AGGGCGAACGACGACGGGGA | |
| | AAAGGTCACGATGGCCTCTA | |
| | CCAAGGGTTGAGTACGGCAA | |
| | CCAAAGATACGTACGATGCA | |
| | CTGCATATGCAGGCCCTGCC | |
| | TCCCAGATAATAATAAAATC | |
| | GCTATCCATCGAAGATGGAT | |
| | GTGTGTTGGTTTTTGTGTG | |
| | TGGAGCAACAAATCTGACTT | |
| | TGCATGTGCAAACGCCTTCA | |
| | ACAACAGCATTATTCCAGAA | |
| | GACACCTTCTTCCCCAGCCC | |
| | AGGTAAGGGCAGCTTTTGGTG | |
| | CCTTCGCAGGCTGTTTCCTT | |
| | GCTTCAGGAATGGCCAGGTT | |
| | CTGCCCAGAGCTCTGGTCAA | |
| | TGATGTCTAAAACTCCTCTG | |
| | ATTGGTGGTCTCGGCCTTAT | |
| | CCATTGCCACCAAAACCCTC | |
| | TTTTTACTAAGAAACAGTGA | |
| | GCCTTGTTCTGGCAGTCCAG | |
| | AGAATGACGGGAAAAAAG | |
| | CAGATGAAGAGAAGGTGGCA | |
| | GGAGAGGGCACGTGGCCCAG | |
| | CCTCAGTCTCTCCAACTGAG | |
| | TTCCTGCCTGCCTGCCTTTG | |
| | CTCAGACTGTTTGCCCCTTA | |
| | CTGCTCTTCTAGGCCTCATT | |
| | CTAAGCCCCTTCTCCAAGTT | |
| | GCCTCTCCTTATTTCTCCCT | |
| | GTCTGCCAAAAAATCTTTCC | |
| | CAGCTCACTAAGTCAGTCTC | |
| | ACGCAGTCACTCATTAACCC | |
| | ACCAATCACTGATTGTGCCG | |
| | GCACATGAATGCACCAGGTG | |
| | TTGAAGTGGAGGAATTAAAA | |
| | AGTCAGATGAGGGGTGTGCC | |
| | CAGAGGAAGCACCATTCTAG | |
| | TTGGGGGAGCCCATCTGTCA | |

TABLE 28-continued

AAV Donor Template Sequences

| | | |
|---|---|---|
| | GCTGGGAAAAGTCCAAATAA | |
| | CTTCAGATTGGAATGTGTTT | |
| | TAACTCAGGGTTGAGAAAAC | |
| | AGCTACCTTCAGGACAAAAG | |
| | TCAGGGAAGGGCTCTCTGAA | |
| | GAAATGCTACTTGAAGATAC | |
| | CAGCCCTACCAAGGGCAGGG | |
| | AGAGGACCCTATAGAGGCCT | |
| | GGGACAGGAGCTCAATGAGA | |
| | AAGG | |
| 170 | BCMA RHA to LHA | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |
| | | TGATTTATAGTTCAAAACCT |
| | | CTATCAATGAGAGAGCAATC |
| | | TCCTGGTAATGTGATAGATT |
| | | TCCCAACTTAATGCCAACAT |
| | | ACCATAAACCTCCCATTCTG |
| | | CTAATGCCCAGCCTAAGTTG |
| | | GGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAAA |
| | | GAATAAGCAGTATTATTAAG |
| | | TAGCCCTGCATTTCAGGTTT |
| | | CCTTGAGTGGCAGGCCAGGC |
| | | CTGGCCGTGAACGTTCACTG |
| | | AAATCATGGCCTCTTGGCCA |
| | | AGATTGATAGCTTGTGCCTG |
| | | TCCCTGAGTCCCAGTCCATC |
| | | ACGAGCAGCTGGTTTCTAAG |
| | | ATGCTATTTCCCGTATAAAG |
| | | CATGAGACCGTGACTTGCCA |
| | | GCCCCACAGAGCCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |
| | | ACAGACAAAACTGTGCTAGA |
| | | CATGAGGTCTATGGACTTCA |
| | | GGCTCCGGTGCCCGTCAGTG |
| | | GGCAGAGCGCACATCGCCCA |
| | | CAGTCCCGAGAAGTTGGGG |
| | | GGAGGGGTCGGCAATTGAAC |
| | | CGGTGCCTAGAGAAGGTGGC |
| | | GCGGGGTAAACTGGGAAAGT |
| | | GATGTCGTGTACTGGCTCCG |
| | | CCTTTTTCCCGAGGGTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCTGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTTCTGGC |

TABLE 28-continued

AAV Donor Template Sequences

AAGATAGTCTTGTAAATGCG
GGCCAAGATCTGCACACTGG
TATTTCGGTTTTTGGGGCCG
CGGGCGGCGACGGGGCCCGT
GCGTCCCAGCGCACATGTTC
GGCGAGGCGGGGCCTGCGAG
CGCGGCCACCGAGAATCGGA
CGGGGGTAGTCTCAAGCTGG
CCGGCCTGCTCTGGTGCCTG
GCCTCGCGCCGCCGTGTATC
GCCCCGCCCTGGGCGGCAAG
GCTGGCCCGGTCGGCACCAG
TTGCGTGAGCGGAAAGATGG
CCGCTTCCCGGCCCTGCTGC
AGGGAGCTCAAAATGGAGGA
CGCGGCGCTCGGGAGAGCGG
GCGGGTGAGTCACCCACACA
AAGGAAAAGGGCCTTTCCGT
CCTCAGCCGTCGCTTCATGT
GACTCCACGGAGTACCGGGC
GCCGTCCAGGCACCTCGATT
AGTTCTCGAGCTTTTGGAGT
ACGTCGTCTTTAGGTTGGGG
GGAGGGGTTTTATGCGATGG
AGTTTCCCCACACTGAGTGG
GTGGAGACTGAAGTTAGGCC
AGCTTGGCACTTGATGTAAT
TCTCCTTGGAATTTGCCCTT
TTTGAGTTTTGGATCTTGGTT
CATTCTCAAGCCTCAGACAG
TGGTTCAAAGTTTTTTTCTT
CCATTTCAGGTGTCGTGACC
ACCATGGCGCTTCCGGTGAC
AGCACTGCTCCTCCCCTTGG
CGCTGTTGCTCCACGCAGCA
AGGCCGCAGGTGCAGCTGGT
GCAGAGCGGAGCCGAGCTCA
AGAAGCCCGGAGCCTCCGTG
AAGGTGAGCTGCAAGGCCAG
CGGCAACACCCTGACCAACT
ACGTGATCCACTGGGTGAGA
CAAGCCCCCGGCCAAAGGCT
GGAGTGGATGGGCTACATCC
TGCCCTACAACGACCTGACC
AAGTACAGCCAGAAGTTCCA
GGGCAGGGTGACCATCACCA
GGGATAAGAGCGCCTCCACC
GCCTATATGGAGCTGAGCAG
CCTGAGGAGCGAGGACACCG
CTGTGTACTACTGTACAAGG
TGGGACTGGGACGGCTTCTT
TGACCCCTGGGGCCAGGGCA
CAACAGTGACCGTCAGCAGC
GGCGGCGAGGCAGCGGCGG
CGGCGGCAGCGGCGGAGGCG
GAAGCGAAATCGTGATGACC
CAGAGCCCCGCCACACTGAG
CGTGAGCCCTGGCGAGAGGG
CCAGCATCTCCTGCAGGGCT
AGCCAAAGCCTGGTGCACAG
CAACGGCAACACCCACCTGC
ACTGGTACCAGCAGAGACCC
GGACAGGCTCCCAGGCTGCT
GATCTACAGCGTGAGCAACA
GGTTCTCCGGGTGCCTGCC
AGGTTTAGCGGCAGCGGAAG
CGGCACCGACTTTACCCTGA
CCATCAGCAGCGTGGAGTCC
GAGGACTTCGCCGTGTATTA
CTGCAGCCAGACCAGCCACA
TCCCTTACACCTTCGGCGGC
GGCACCAAGCTGGAGATCAA
AAGTGCTGCTTTGTCC
CGGTATTTCTCCCAGCCAAA
CCGACCACGACTCCCGCCC
GCGCCCTCCGACACCCGCTC
CCACCATCGCCTCTCAACCT
CTTAGTCTTCGCCCCGAGGC

ATGCCGACCCGCCGCCGGGG
GTGCTGTTCATACGAGGGGC
TTGGACTTCGCTTGTGATAT
TTACATTTGGGCTCCGTTGG
CGGGTACGTGCGGCGTCCTT
TTGTTGTCACTCGTTATTAC
TTTGTATTGTAATCACAGGA
ATCGCAAACGGGGCAGAAAG
AAACTCCTGTATATATTCAA
ACAACCATTTATGAGACCAG
TACAAACTACTCAAGAGGAA
GATGGCTGTAGCTGCCGATT
TCCAGAAGAAGAAGAAGGAG
GATGTGAACTGCGAGTGAAG
TTTTCCCGAAGCGCAGACGC
TCCGGCATATCAGCAAGGAC
AGAATCAGCTGTATAACGAA
CTGAATTTGGGACGCCGCGA
GGAGTATGACGTGCTTGATA
AACGCCGGGGAGAGACCCG
GAAATGGGGGGTAAACCCCG
AAGAAAGAATCCCCAAGAAG
GACTCTACAATGAACTCCAG
AAGGATAAGATGGCGGAGGC
CTACTCAGAAATAGGTATGA
AGGGCGAACGACGACGGGGA
AAAGGTCACGATGGCCTCTA
CCAAGGGTTGAGTACGGCAA
CCAAAGATACGTACGATGCA
CTGCATATGCAGGCCCTGCC
TCCCAGATAATAATAAAATC
GCTATCCATCGAAGATGGAT
GTGTGTTGGTTTTTTGTGTG
TGGAGCAACAAATCTGACTT
TGCATGTGCAAACGCCTTCA
ACAACAGCATTATTCCAGAA
GACACCTTCTTCCCCAGCCC
AGGTAAGGGCAGCTTTGGTG
CCTTCGCAGGCTGTTTCCTT
GCTTCAGGAATGGCCAGGTT
CTGCCCAGAGCTCTGGTCAA
TGATGTCTAAAACTCCTCTG
ATTGGTGGTCTCGGCCTTAT
CCATTGCCACCAAAACCCTC
TTTTTACTAAGAAACAGTGA
GCCTTGTTCTGGCAGTCCAG
AGAATGACACGGGAAAAAAG
CAGATGAAGAGAAGGTGGCA
GGAGAGGGCACGTGGCCCAG
CCTCAGTCTCTCCAACTGAG
TTCCTGCCTGCCTGCCTTTG
CTCAGACTGTTTGCCCCTTA
CTGCTCTTCTAGGCCTCATT
CTAAGCCCCTTCTCCAAGTT
GCCTCTCCTTATTTCTCCCT
GTCTGCCAAAAAATCTTTCC
CAGCTCACTAAGTCAGTCTC
ACGCAGTCACTCATTAACCC
ACCAATCACTGATTGTGCCG
GCACATGAATGCACCAGGTG
TTGAAGTGGAGGAATTAAAA
AGTCAGATGAGGGGTGTGCC
CAGAGGAAGCACCATTCTAG
TTGGGGGAGCCCATCTGTCA
GCTGGGAAAAGTCCAAATAA
CTTCAGATTGGAATGTGTTT
TAACTCAGGGTTGAGAAAAC
AGCTACCTTCAGGACAAAAG
TCAGGGAAGGGCTCTCTGAA
GAAATGCTACTTGAAGATAC
CAGCCCTACCAAGGGCAGGG
AGAGGACCCTATAGAGGCCT
GGGACAGGAGCTCAATGAGA
AAGG

TABLE 28-continued

AAV Donor Template Sequences

| 351 | Anti-CD33 CAR Donor LHA to RHA CD28 costim. | GAGATGTAAGGAGCTGCTGT GACTTGCTCAAGGCCTTATA TCGAGTAAACGGTAGTGCTG GGGCTTAGACGCAGGTGTTC TGATTTATAGTTCAAAACCT CTATCAATGAGAGAGCAATC TCCTGGTAATGTGATAGATT TCCCAACTTAATGCCAACAT ACCATAAACCTCCCATTCTG CTAATGCCCAGCCTAAGTTG GGGAGACCACTCCAGATTCC AAGATGTACAGTTTGCTTTG CTGGGCCTTTTTCCCATGCC TGCCTTTACTCTGCCAGAGT TATATTGCTGGGGTTTTGAA GAAGATCCTATTAAATAAAA GAATAAGCAGTATTATTAAG TAGCCCTGCATTTCAGGTTT CCTTGAGTGGCAGGCCAGGC CTGGCCGTGAACGTTCACTG AAATCATGGCCTCTTGGCCA AGATTGATAGCTTGTGCCTG TCCCTGAGTCCCAGTCCATC ACGAGCAGCTGGTTTCTAAG ATGCTATTTCCCGTATAAAG CATGAGACCGTGACTTGCCA GCCCCACAGAGCCCCGCCCT TGTCCATCACTGGCATCTGG ACTCCAGCCTGGGTTGGGGC AAAGAGGGAAATGAGATCAT GTCCTAACCCTGATCCTCTT GTCCCACAGATATCCAGAAC CCTGACCCTGCCGTGTACCA GCTGAGAGACTCTAAATCCA GTGACAAGTCTGTCTGCCTA TTCACCGATTTTGATTCTCA AACAAATGTGTCACAAAGTA AGGATTCTGATGTGTATATC ACAGACAAAACTGTGCTAGA CATGAGGTCTATGGACTTCA ggctccggtgcccgtcagtg ggcagagcgcacatcgccca cagtccccgagaagtttgggg ggaggggtcggcaattgaac cggtgcctagagaaggtggc gcggggtaaactgggaaagt gatgtcgtgtactggctccg cctttttccccgagggtgggg gagaaccgtatataagtgca gtagtcgccgtgaacgttct ttttcgcaacgggtttgccg ccagaacacaggtaagtgcc gtgtgtggttcccgcgggcc tggcctctttacgggttatg gcccttgcgtgccttgaatt acttccactggctgcagtac gtgattcttgatcccgagct tcgggttggaagtgggtggg agagttcgaggccttgcgct taaggagcccccttcgcctcg tgcttgagttgaggcctggc ctgggcgctggggccgccgc gtgcgaatctggtggcacct tcgcgcctgtctcgctgctt tcgataagtctctagccatt taaaattttttgatgacctgc tgcgacgcttttttttctgg aagatagtcttgtaaatgcg ggccaagatctgcacactgg tatttcggtttttggggccg cgggcggcgacggggcccgt gcgtcccagcgcacatgttc ggcgaggcggggcctgcgag cgcggccaccgagaatcgga cgggggtagtctcaagctgg ccggcctgctctggtgcctg gcctcgcgccgccgtgtatc | 5<br><br>10<br><br>15<br><br>20<br><br>25<br><br>30<br><br>35<br><br>40<br><br>45<br><br>50<br><br>55<br><br>60<br><br>65 | gccccgccctgggcggcaag gctggcccggtcggcaccag ttgcgtgagcggaaagatgg ccgcttcccggccctgctgc agggagctcaaaatggagga cgcggcgctcgggagagcgg gcgggtgagtcacccacaca aaggaaaagggcctttccgt cctcagccgtcgcttcatgt gactccacggagtaccgggc gccgtccaggcacctcgatt agttctcgagcttttggagt acgtcgtctttaggttgggg ggaggggttttatgcgatgg agtttccccacactgagtgg gtggagactgaagttaggcc agcttggcacttgatgtaat tctccttggaatttgccctt tttgagtttggatcttggtt cattctcaagcctcagacag tggttcaaagttttttttctt ccatttcaggtgtcgtgaCC ACCATGGCGCTTCCGGTGAC AGCACTGCTCCTCCCCTTGG CGCTGTTGCTCCACGCAGCA AGGCCGGAAATCGTCCTCAC ACAATCCCCGGGGAGCCTCG CAGTCAGTCCTGGGGAACGA GTCACTATGAGCTGCAAATC CAGTCAGAGTGTTTTTTTCT CAAGTAGCCAGAAGAACTAC CTCGCATGGTACCAACAAAT ACCGGGGCAATCTCCCCGCT TGCTTATATACTGGGCAAGT ACCCGCGAATCCGGCGTACC GGATCGATTCACGGGATCTG GGTCAGGTACTGATTTCACT TTGACTATCAGCTCTGTTCA GCCTGAAGATTTGGCAATTT ACTACTGTCACCAATACTTG AGTAGCCGAACTTTCGGCCA GGGCACGAAGCTCGAAATCA AGGGCGGAGGGGGAGGTTCT GGTGGGGCGGTTCTGGCGG TGGAGGAAGCCAAGTACAGT TGCAACAGCCAGGGGCGGAG GTCGTAAAACCTGGGGCGTC TGTCAAGATGAGCTGTAAAG CAAGTGGATACACCTTCACC TCCTACTATATACATTGGAT TAAGCAAACTCCGGGTCAGG GGCTGGAATGGGTTGGCGTT ATATACCCCGGGAACGATGA TATATCATACAACCAAAAAT TTCAAGGCAAGGCGACTCTG ACTGCCGATAAGAGTAGCAC AACAGCTTACATGCAGCTTT CTTCCCTGACCAGCGAAGAT TCAGCAGTTTACTACTGCGC TCGGGAAGTGCGCCTGCGAT ACTTTGATGTCTGGGGTCAA GGAACTACAGTTACTGTATC AAGCAGTGCTGCTGCCTTTG TCCCGGTATTTCTCCCAGCC AAACCGACCACGACTCCCGC CCCGCGCCCTCCGACACCCG CTCCCACCATCGCCTCTCAA CCTCTTAGTCTTCGCCCCGA GGCATGCCGACCCGCCGCCG GGGGTGCTGTTCATACGAGG GGCTTGGACTTCGCTTGTGA TATTTACATTTGGGCTCCGT TGGCGGGTACGTGCGGCGTC CTTTTGTTGTCACTCGTTAT TACTTTGTATTGTAATCACA GGAATCGCTCAAAGCGGAGT AGGTTGTTGCATTCCGATTA CATGAATATGACTCCTCGCC |

TABLE 28-continued

AAV Donor Template Sequences

| | | |
|---|---|---|
| | GGCCTGGGCCGACAAGAAAA | |
| | CATTACCAACCCTATGCCCC | |
| | CCCACGAGACTTCGCTGCGT | |
| | ACAGGTCCCGAGTGAAGTTT | |
| | TCCCGAAGCGCAGACGCTCC | |
| | GGCATATCAGCAAGGACAGA | |
| | ATCAGCTGTATAACGAACTG | |
| | AATTTGGGACGCCGCGAGGA | |
| | GTATGACGTGCTTGATAAAC | |
| | GCCGGGGAGAGACCCGGAA | |
| | ATGGGGGGTAAACCCCGAAG | |
| | AAAGAATCCCCAAGAAGGAC | |
| | TCTACAATGAACTCCAGAAG | |
| | GATAAGATGGCGGAGGCCTA | |
| | CTCAGAAATAGGTATGAAGG | |
| | GCGAACGACGACGGGGAAAA | |
| | GGTCACGATGGCCTCTACCA | |
| | AGGGTTGAGTACGGCAACCA | |
| | AAGATACGTACGATGCACTG | |
| | CATATGCAGGCCCTGCCTCC | |
| | CAGATAATAATAAAATCGCT | |
| | ATCCATCGAAGATGGATGTG | |
| | TGTTGGTTTTTTGTGTGTGG | |
| | AGCAACAAATCTGACTTTGC | |
| | ATGTGCAAACGCCTTCAACA | |
| | ACAGCATTATTCCAGAAGAC | |
| | ACCTTCTTCCCCAGCCCAGG | |
| | TAAGGGCAGCTTTGGTGCCT | |
| | TCGCAGGCTGTTTCCTTGCT | |
| | TCAGGAATGGCCAGGTTCTG | |
| | CCCAGAGCTCTGGTCAATGA | |
| | TGTCTAAAACTCCTCTGATT | |
| | GGTGGTCTCGGCCTTATCCA | |
| | TTGCCACCAAACCCTCTTT | |
| | TTACTAAGAAACAGTGAGCC | |
| | TTGTTCTGGCAGTCCAGAGA | |
| | ATGACACGGGAAAAAGCAG | |
| | ATGAAGAGAAGGTGGCAGGA | |
| | GAGGGCACGTGGCCCAGCCT | |
| | CAGTCTCTCCAACTGAGTTC | |
| | CTGCCTGCCTGCCTTTGCTC | |
| | AGACTGTTTGCCCCTTACTG | |
| | CTCTTCTAGGCCTCATTCTA | |
| | AGCCCCTTCTCCAAGTTGCC | |
| | TCTCCTTATTTCTCCCTGTC | |
| | TGCCAAAAATCTTTCCCAG | |
| | CTCACTAAGTCAGTCTCACG | |
| | CAGTCACTCATTAACCCACC | |
| | AATCACTGATTGTGCCGGCA | |
| | CATGAATGCACCAGGTGTTG | |
| | AAGTGGAGGAATTAAAAAGT | |
| | CAGATGAGGGGTGTGCCCAG | |
| | AGGAAGCACCATTCTAGTTG | |
| | GGGGAGCCCATCTGTCAGCT | |
| | GGGAAAAGTCCAAATAACTT | |
| | CAGATTGGAATGTGTTTTAA | |
| | CTCAGGGTTGAGAAAACAGC | |
| | TACCTTCAGGACAAAAGTCA | |
| | GGGAAGGGCTCTCTGAAGAA | |
| | ATGCTACTTGAAGATACCAG | |
| | CCCTACCAAGGGCAGGGAGA | |
| | GGACCCTATAGAGGCCTGGG | |
| | ACAGGAGCTCAATGAGAAAG | |
| | G | |
| 352 | Anti-CD33b CAR Donor LHA to RHA 41BB costim. | GAGATGTAAGGAGCTGCTGT GACTTGCTCAAGGCCTTATA TCGAGTAAACGGTAGTGCTG GGGCTTAGACGCAGGTGTTC TGATTTATAGTTCAAAACCT CTATCAATGAGAGCAATC TCCTGGTAATGTGATAGATT TCCCAACTTAATGCCAACAT ACCATAAACCTCCCATTCTG CTAATGCCCAGCCTAAGTTG GGGAGACCACTCCAGATTCC AAGATGTACAGTTTGCTTTG CTGGGCCTTTTTCCCATGCC |

| | |
|---|---|
| | TGCCTTTACTCTGCCAGAGT |
| | TATATTGCTGGGGTTTTGAA |
| | GAAGATCCTATTAAATAAAA |
| | GAATAAGCAGTATTATTAAG |
| | TAGCCCTGCATTTCAGGTTT |
| | CCTTGAGTGGCAGGCCAGGC |
| | CTGGCCGTGAACGTTCACTG |
| | AAATCATGGCCTCTTGGCCA |
| | AGATTGATAGCTTGTGCCTG |
| | TCCCTGAGTCCCAGTCCATC |
| | ACGAGCAGCTGGTTTCTAAG |
| | ATGCTATTTCCCGTATAAAG |
| | CATGAGACCGTGACTTGCCA |
| | GCCCCACAGAGCCCCGCCCT |
| | TGTCCATCACTGGCATCTGG |
| | ACTCCAGCCTGGGTTGGGGC |
| | AAAGAGGGAAATGAGATCAT |
| | GTCCTAACCCTGATCCTCTT |
| | GTCCCACAGATATCCAGAAC |
| | CCTGACCCTGCCGTGTACCA |
| | GCTGAGAGACTCTAAATCCA |
| | GTGACAAGTCTGTCTGCCTA |
| | TTCACCGATTTTGATTCTCA |
| | AACAAATGTGTCACAAAGTA |
| | AGGATTCTGATGTGTATATC |
| | ACAGACAAAACTGTGCTAGA |
| | CATGAGGTCTATGGACTTCA |
| | ggctccggtgcccgtcagtg |
| | ggcagagcgcacatcgccca |
| | cagtccccgagaagttgggg |
| | ggaggggtcggcaattgaac |
| | cggtgcctagagaaggtggc |
| | gcggggtaaactgggaaagt |
| | gatgtcgtgtactggctccg |
| | ccttttttcccgagggtgggg |
| | gagaaccgtatataagtgca |
| | gtagtcgccgtgaacgttct |
| | ttttcgcaacgggtttgccg |
| | ccagaacacaggtaagtgcc |
| | gtgtgtggttcccgcgggcc |
| | tggcctcttacgggttatg |
| | gcccttgcgtgccttgaatt |
| | acttccactggctgcagtac |
| | gtgattcttgatcccgagct |
| | tcgggttggaagtgggtggg |
| | agagttcgaggccttgcgct |
| | taaggagcccttcgcctcg |
| | tgcttgagttgaggcctggc |
| | ctggggcgctggggccgccgc |
| | gtgcgaatctggtggcacct |
| | tcgcgcctgtctcgctgctt |
| | tcgataagtctctagccatt |
| | taaaattttttgatgacctgc |
| | tgcgacgcttttttttctggc |
| | aagatagtcttgtaaatgcg |
| | ggccaagatctgcacactgg |
| | tattcggttttttggggccg |
| | cggggcggcgacggggcccgt |
| | gcgtcccagcgcacatgttc |
| | ggcgaggcggggcctgcgag |
| | cgcggccaccgagaatcgga |
| | cgggggtagtctcaagctgg |
| | ccggcctgctctggtcctg |
| | gcctcgcgccgccgtgtatc |
| | gcccgccctgggcggcaag |
| | gctgccggtcggcaccag |
| | ttgcgtgagcggaaagatgg |
| | ccgcttcccggccctgctgc |
| | agggagctcaaaatgaggga |
| | cgcggcgctcgggagagcgg |
| | gcgggtgagtcacccacaca |
| | aaggaaaagggccttttccgt |
| | cctcagccgtcgcttcatgt |
| | gactccacggagtaccgggc |
| | gccgtccaggcacctcgatt |
| | agttctcgagcttttggagt |
| | acgtcgtctttaggttgggg |
| | ggaggggtttatgcgatgg |

TABLE 28-continued

AAV Donor Template Sequences

```
agtttccccacactgagtgg
gtggagactgaagttaggcc
agcttggcacttgatgtaat
tctccttggaatttgccctt
tttgagtttggatcttggtt
cattctcaagcctcagacag
tggttcaaagttttttttctt
ccatttcaggtgtcgtgaCC
ACCATGGCGCTTCCGGTGAC
AGCACTGCTCCTCCCCTTGG
CGCTGTTGCTCCACGCAGCA
AGGCCGGAAATCGTCCTCAC
ACAATCCCCGGGGAGCCTCG
CAGTCAGTCCTGGGGAACGA
GTCACTATGAGCTGCAAATC
CAGTCAGAGTGTTTTTTTCT
CAAGTAGCCAGAAGAACTAC
CTCGCATGGTACCAACAAAT
ACCGGGGCAATCTCCCCGCT
TGCTTATATACTGGGCAAGT
ACCCGCGAATCCGGCGTACC
GGATCGATTCACGGGATCTG
GGTCAGGTACTGATTTCACT
TTGACTATCAGCTCTGTTCA
GCCTGAAGATTTGGCAATTT
ACTACTGTCACCAATACTTG
AGTAGCCGAACTTTCGGCCA
GGGCACGAAGCTCGAAATCA
AGGGCGGAGGGGGAGGTTCT
GGTGGGGCGGTTCTGGCGG
TGGAGGAAGCCAAGTACAGT
TGCAACAGCCAGGGCGGAG
GTCGTAAAACCTGGGCGTC
TGTCAAGATGAGCTGTAAAG
CAAGTGGATACACCTTCACC
TCCTACTATATACATTGGAT
TAAGCAAACTCCGGGTCAGG
GGCTGGAATGGGTTGGCGTT
ATATACCCCGGGAACGATGA
TATATCATACAACCAAAAAT
TTCAAGGCAAGGCGACTCTG
ACTGCCGATAAGAGTAGCAC
AACAGCTTACATGCAGCTTT
CTTCCCTGACCAGCGAAGAT
TCAGCAGTTTACTACTGCGC
TCGGGAAGTGCGCCTGCGAT
ACTTTGATGTCTGGGGTCAA
GGAACTACAGTTACTGTATC
AAGCAGTGCTGCTGCCTTTG
TCCCGGTATTTCTCCCAGCC
AAACCGACCACGACTCCCGC
CCCGCGCCCTCCGACACCCG
CTCCCACCATCGCCTCTCAA
CCTCTTAGTCTTCGCCCCGA
GGCATGCCGACCCGCCGCCG
GGGGTGCTGTTCATACGAGG
GGCTTGGACTTCGCTTGTGA
TATTTACATTTGGGCTCCGT
TGGCGGGTACGTGCGGCGTC
CTTTTGTTGTCACTCGTTAT
TACTTTGTATTGTAATCACA
GGAATCGCAAACGGGGCAGA
AAGAAACTCCTGTATATATT
CAAACAACCATTTATGAGAC
CAGTACAAACTACTCAAGAG
GAAGATGGCTGTAGCTGCCG
ATTTCCAGAAGAAGAAGAAG
GAGGATGTGAACTGCGAGTG
AAGTTTCCCGAAGCGCAGA
CGCTCCGGCATATCAGCAAG
GACAGAATCAGCTGTATAAC
GAACTGAATTTGGGACGCCG
CGAGGAGTATGACGTGCTTG
ATAAACGCCGGGGAGAGAC
CCGGAAATGGGGGTAAACC
CCGAAGAAAGAATCCCCAAG
AAGGACTCTACAATGAACTC
CAGAAGGATAAGATGGCGGA
GGCCTACTCAGAAATAGGTA
TGAAGGGCAACGACGACGG
GGAAAAGGTCACGATGGCCT
CTACCAAGGGTTGAGTACGG
CAACCAAAGATACGTACGAT
GCACTGCATATGCAGGCCCT
GCCTCCCAGATAATAATAAA
ATCGCTATCCATCGAAGATG
GATGTGTGTTGGTTTTTTGT
GTGTGGAGCAACAAATCTGA
CTTTGCATGTGCAAACGCCT
TCAACAACAGCATTATTCCA
GAAGACACCTTCTTCCCCAG
CCCAGGTAAGGGCAGCTTTG
GTGCCTTCGCAGGCTGTTTC
CTTGCTTCAGGAATGGCCAG
GTTCTGCCCAGAGCTCTGGT
CAATGATGTCTAAAACTCCT
CTGATTGGTGGTCTCGGCCT
TATCCATTGCCACCAAAACC
CTCTTTTTACTAAGAAACAG
TGAGCCTTGTTCTGGCAGTC
CAGAGAATGACACGGGAAAA
AAGCAGATGAAGAGAAGGTG
GCAGGAGAGGGCACGTGGCC
CAGCCTCAGTCTCTCCAACT
GAGTTCCTGCCTGCCTGCCT
TTGCTCAGACTGTTTGCCCC
TTACTGCTCTTCTAGGCCTC
ATTCTAAGCCCCTTCTCCAA
GTTGCCTCTCCTTATTTCTC
CCTGTCTGCCAAAAAATCTT
TCCCAGCTCACTAAGTCAGT
CTCACGCAGTCACTCATTAA
CCCACCAATCACTGATTGTG
CCGGCACATGAATGCACCAG
GTGTTGAAGTGGAGGAATTA
AAAAGTCAGATGAGGGGTGT
GCCCAGAGGAAGCACCATTC
TAGTTGGGGGAGCCCATCTG
TCAGCTGGGAAAAGTCCAAA
TAACTTCAGATTGGAATGTG
TTTTAACTCAGGGTTGAGAA
AACAGCTACCTTCAGGACAA
AAGTCAGGGAAGGGCTCTCT
GAAGAAATGCTACTTGAAGA
TACCAGCCCTACCAAGGGCA
GGGAGAGGACCCTATAGAGG
CCTGGGACAGGAGCTCAATG
AGAAAGG
```

TABLE 29

On-Target Gene Edited Sequences >1% Frequency in At Least One Gene Edited T Cell Donor for the REG1-Z01 gRNA.
Reference on-target sequence[a]:
GATGGGAGCAACG(TGG)CCAT (SEQ ID NO: 104)

| SEQ ID NO: | Gene Edited Sequence[b] | Donor 1 (%) | Donor 2 (%) | Mean (%) | Std. Dev. (%) |
|---|---|---|---|---|---|
| 181 | GATGGGAGCAAACGTGGCCAT | 46.1 | 43.9 | 45.0 | 1.6 |
|  | -----------GTGGCCAT | 6.5 | 4.3 | 5.4 | 1.6 |
| 182 | GATGGGAGC-ACGTGGCCAT | 4.1 | 4.9 | 4.5 | 0.6 |
|  | GA-----------TGGCCAT | 3.5 | 3.9 | 3.7 | 0.3 |
|  | -------------------- | 3.3 | 3.7 | 3.5 | 0.3 |

TABLE 29-continued

On-Target Gene Edited Sequences >1% Frequency in At Least One Gene Edited T Cell Donor for the REG1-Z01 gRNA.
Reference on-target sequence[a]:
GATGGGAGCAACG(TGG)CCAT (SEQ ID NO: 104)

| SEQ ID NO: | Gene Edited Sequence[b] | Donor 1 (%) | Donor 2 (%) | Mean (%) | Std. Dev. (%) |
|---|---|---|---|---|---|
| 183 | GATGGG---AACGTGGCCAT | 2.6 | 3.6 | 3.1 | 0.7 |
| 184 | GATGGGA--------GCCAT | 3.6 | 2.1 | 2.8 | 1.1 |
|  | -----------------CAT | 2.4 | 1.8 | 2.1 | 0.4 |
|  | -----------CGTGGCCAT | 1.4 | 1.2 | 1.3 | 0.1 |
| 185 | GATG----------GGCCAT | 1.1 | 1.3 | 1.2 | 0.1 |
|  | GAT----------------- | 0.9 | 1.1 | 1.0 | 0.1 |
|  | GATGG--------------- | 0.7 | 1.2 | 1.0 | 0.4 |
| 186 | ----------ACGTGGCCAT | 1.1 | 0.5 | 0.8 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 30

On-Target Gene Edited Sequences >1% Frequency in At Least One Gene Edited T Cell Donor for the REG1-Z02 gRNA.
Reference on-target sequence[a]:
CCGCGGGACTAGA(GGG)AGCT (SEQ ID NO: 268)

| SEQ ID NO: | Gene Edited Sequence[b] | Donor 1 (%) | Donor 2 (%) | Mean (%) | Std. Dev. (%) |
|---|---|---|---|---|---|
| 187 | CCGCGGGACTTAGAGGGAGCT | 49.2 | 39.4 | 44.3 | 6.9 |
| 188 | CCGCGGGA---------GCT | 11.9 | 11.5 | 11.7 | 0.3 |
|  | -------------------- | 2.6 | 4.6 | 3.6 | 1.4 |
|  | CCGCGGG------------- | 2.1 | 3.4 | 2.8 | 0.9 |
|  | -------------------T | 2.1 | 2.0 | 2.0 | 0.1 |
| 189 | CCGCGGGA-TAGAGGGAGCT | 1.7 | 1.8 | 1.8 | 0.1 |
| 190 | CCGCGGGACT---------- | 1.8 | 1.3 | 1.6 | 0.4 |
| 191 | CCGCGGG--TAGAGGGAGCT | 1.0 | 1.6 | 1.3 | 0.4 |
| 192 | CCGCGGG--------GAGCT | 1.1 | 1.3 | 1.2 | 0.1 |
| 193 | CCGCGGGAC-AGAGGGAGCT | 1.0 | 1.2 | 1.1 | 0.1 |
| 194 | CCGCGGGACT-GAGGGAGCT | 1.3 | 0.9 | 1.1 | 0.3 |
| 195 | CCG---------AGGGAGCT | 1.2 | 0.9 | 1.0 | 0.2 |
| 196 | CCGCGGGA-----GGGAGCT | 0.8 | 1.1 | 1.0 | 0.2 |
| 197 | CCG------TAGAGGGAGCT | 0.3 | 1.1 | 0.7 | 0.6 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 31

On-Target Gene Edited Sequences >1% Frequency in At Least One Gene Edited T Cell Donor for the REG1-Z03 gRNA.
Reference on-target sequence[a]:
CGCTCCCGCTCGG(TGG)CTGT (SEQ ID NO: 274)

| SEQ ID NO: | Gene Edited Sequence[b] | Donor 1 (%) | Donor 2 (%) | Mean (%) | Std. Dev. (%) |
|---|---|---|---|---|---|
| 198 | CGCTCCCGCTTCGGTGGCTGT | 41.3 | 38.6 | 40.0 | 1.9 |
|  | C----------------TGT | 7.9 | 7.8 | 7.8 | 0.1 |
|  | CGCTCCCG------------ | 7.9 | 7.5 | 7.7 | 0.3 |
| 199 | CGCTCCCGC-CGGTGGCTGT | 3.3 | 3.7 | 3.5 | 0.3 |
|  | -------------------- | 2.7 | 3.7 | 3.2 | 0.7 |
| 200 | CGCTCCCG-TCGGTGGCTGT | 2.8 | 3.7 | 3.2 | 0.6 |
| 201 | CGCTCCCGC--GGTGGCTGT | 2.3 | 2.8 | 2.6 | 0.4 |
|  | -------------------T | 1.7 | 3.0 | 2.4 | 0.9 |
| 202 | CGCTCCCGCT-GGTGGCTGT | 2.2 | 2.4 | 2.3 | 0.1 |
|  | ---------------GCTGT | 2.3 | 1.7 | 2.0 | 0.4 |
| 203 | CGCTCCC--TCGGTGGCTGT | 1.6 | 1.8 | 1.7 | 0.1 |
| 204 | CGCTCCCGCTTTCGGTGGCTGT | 1.1 | 1.4 | 1.2 | 0.2 |
| 205 | CGCTCCCG-----GTGGCTGT | 1.3 | 0.8 | 1.0 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 32

On-Target Gene Edited Sequences >1% Frequency in At Least One Gene Edited T Cell donor for the REG1-Z04 gRNA.
Reference on-target sequence[a]:
CATCACGACGCGT(GGG)TGGC (SEQ ID NO: 280)

| SEQ ID NO: | Gene Edited Sequence[b] | Donor 1 (%) | Donor 2 (%) | Mean (%) | Std. Dev. (%) |
|---|---|---|---|---|---|
| 206 | CATCACGA--CGTGGGTGGC | 34.0 | 32.9 | 33.4 | 0.8 |
| 207 | CATCA-----CGTGGGTGGC | 7.7 | 6.2 | 7.0 | 1.1 |
|  | -------------------- | 2.9 | 3.8 | 3.4 | 0.6 |
| 208 | CATCACGACGCCGTGGGTGGC | 2.5 | 4.2 | 3.4 | 1.2 |
| 209 | CATCACGAC------GTGGC | 3.1 | 3.6 | 3.4 | 0.4 |
| 210 | CATCACGACGGCGTGGGTGGC | 2.3 | 3.4 | 2.8 | 0.8 |
|  | CATCACGA------------ | 2.3 | 2.4 | 2.3 | 0.1 |
| 211 | ----------CGTGGGTGGC | 1.5 | 1.7 | 1.6 | 0.1 |
| 212 | CATCACGACG---TGGTGGC | 1.8 | 1.2 | 1.5 | 0.4 |
| 213 | CATCACGACGTCGTGGGTGGC | 1.5 | 1.2 | 1.4 | 0.2 |
|  | CATCACGAC----------- | 1.7 | 1.1 | 1.4 | 0.4 |
|  | -------------------C | 1.5 | 1.2 | 1.4 | 0.2 |

TABLE 32-continued

On-Target Gene Edited Sequences >1% Frequency in At Least One Gene Edited T Cell donor for the REG1-Z04 gRNA.
Reference on-target sequence[a]:
CATCACGACGCGT(GGG)TGGC (SEQ ID NO: 280)

| SEQ ID NO: | Gene Edited Sequence[b] | Donor 1 (%) | Donor 2 (%) | Mean (%) | Std. Dev. (%) |
|---|---|---|---|---|---|
|  | --------------GGTGGC | 1.1 | 1.3 | 1.2 | 0.1 |
|  | ----------------TGGC | 1.1 | 1.0 | 1.0 | 0.1 |
| 214 | CATCACGAC----GGGTGGC | 0.7 | 1.3 | 1.0 | 0.4 |
|  | CATCA--------------- | 0.9 | 1.1 | 1.0 | 0.1 |
| 215 | CATCACGAC-----GGTGGC | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 33

On-Target Gene Edited Sequences >1% Frequency in At Least One Gene Edited T Cell Donor for the REG1-Z05 gRNA.
Reference on-target sequence[a]:
CACGACGCGTGGG(TGG)CAAG (SEQ ID NO: 286)

| SEQ ID NO: | Gene Edited Sequence[b] | Donor 1 (%) | Donor 2 (%) | Mean (%) | Std. Dev. (%) |
|---|---|---|---|---|---|
| 216 | CACGACGCGTTGGGTGGCAAG | 58.4 | 50.0 | 54.2 | 5.9 |
|  | CACGAC-------------G | 5.5 | 7.8 | 6.6 | 1.6 |
| 217 | CACGACGC--GGGTGGCAAG | 1.7 | 3.7 | 2.7 | 1.4 |
| 218 | CACGAC---------GCAAG | 2.2 | 2.8 | 2.5 | 0.4 |
| 219 | CACGACGC----GTGGCAAG | 2.4 | 1.5 | 2.0 | 0.6 |
| 220 | CACGACGCG-GGGTGGCAAG | 1.6 | 1.9 | 1.8 | 0.2 |
|  | -------------------- | 1.4 | 1.5 | 1.4 | 0.1 |
|  | CACGA--------------- | 1.0 | 1.4 | 1.2 | 0.3 |
|  | CACGACGC------------ | 0.9 | 1.3 | 1.1 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 34

On-Target Gene Edited Sequences >1% Frequency in At Least One Gene Edited T Cell Donor for the REG1-Z06 gRNA.
Reference on-target sequence[a]:
TCTGACGGGATCG(TGG)TTTC (SEQ ID NO: 292)

| SEQ ID NO: | Gene Edited Sequence[b] | Donor 1 (%) | Donor 2 (%) | Mean (%) | Std. Dev. (%) |
|---|---|---|---|---|---|
| 221 | TCTGACGGGAATCGTGGTTTC | 28.1 | 21.9 | 25.0 | 4.4 |
| 222 | TCTGACG-------GGTTTC | 7.0 | 7.4 | 7.2 | 0.3 |
| 223 | TCTGA------CGTGGTTTC | 7.3 | 7.2 | 7.2 | 0.1 |
| 224 | TCTGACGGGATTCGTGGTTTC | 5.4 | 2.6 | 4.0 | 2.0 |
| 225 | TCTGACGGGA-CGTGGTTTC | 4.2 | 2.8 | 3.5 | 1.0 |
| 226 | TCTG------TCGTGGTTTC | 3.5 | 3.1 | 3.3 | 0.3 |
|  | TCTG---------------- | 2.3 | 3.4 | 2.8 | 0.8 |
|  | -------------------- | 2.4 | 3.1 | 2.8 | 0.5 |
|  | ------------------TC | 2.9 | 2.2 | 2.6 | 0.5 |
| 227 | TCTGAC--------GGTTTC | 2.0 | 2.0 | 2.0 | 0.0 |
|  | TCT----------------- | 1.5 | 2.3 | 1.9 | 0.6 |
| 228 | TCTGACGGG-TCGTGGTTTC | 1.7 | 2.1 | 1.9 | 0.3 |
| 229 | TCTGACGGGAGTCGTGGTTTC | 2.4 | 1.3 | 1.8 | 0.8 |
| 230 | TCTGACGGGACTCGTGGTTTC | 1.5 | 1.8 | 1.6 | 0.2 |
| 231 | ----------TCGTGGTTTC | 1.3 | 1.6 | 1.5 | 0.2 |
|  | -------------------C | 1.0 | 1.5 | 1.2 | 0.4 |
| 232 | TCTGACGG--TCGTGGTTTC | 0.6 | 1.4 | 1.0 | 0.6 |
| 233 | TCTGACGGGA--GTGGTTTC | 1.2 | 0.5 | 0.8 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
bDeletions indicated by dashes (-); insertions indicated by bold

TABLE 35

On-Target Gene Edited Sequences >1% Frequency in At Least One Gene Edited T Cell Donor for the REG1-Z07 gRNA.
Reference on-target sequence[a]:
CCACGCGTCGTGA(TGG)TGTG (SEQ ID NO: 298)

| SEQ ID NO: | Gene Edited Sequence[b] | Donor 1 (%) | Donor 2 (%) | Mean (%) | Std. Dev. (%) |
|---|---|---|---|---|---|
| 234 | CCACGCGTCGGTGATGGTGTG | 15.1 | 12.9 | 14.0 | 1.6 |
| 235 | CCACGCGTCGTTGATGGTGTG | 12.3 | 8.5 | 10.4 | 2.7 |
|  | -------------------- | 4.4 | 5.1 | 4.8 | 0.5 |
| 236 | CCACGCGT---------GTG | 4.9 | 4.4 | 4.6 | 0.4 |
|  | CCACGCGT-----------G | 3.6 | 3.0 | 3.3 | 0.4 |
| 237 | CCACGCGTCGATGATGGTGTG | 2.9 | 1.4 | 2.2 | 1.1 |
|  | CCACGCGTC----------- | 1.9 | 2.5 | 2.2 | 0.4 |

TABLE 35-continued

On-Target Gene Edited Sequences >1% Frequency in At Least One Gene Edited T Cell Donor for the REG1-Z07 gRNA.
Reference on-target sequence[a]:
<u>CCACGCGTCGTGA</u>(TGG)TGTG (SEQ ID NO: 298)

| SEQ ID NO: | Gene Edited Sequence[b] | Donor 1 (%) | Donor 2 (%) | Mean (%) | Std. Dev. (%) |
|---|---|---|---|---|---|
| 238 | CCACGCGTCG--ATGGTGTG | 2.2 | 2.1 | 2.2 | 0.1 |
| 239 | CCACGCGTC-TGATGGTGTG | 2.0 | 2.2 | 2.1 | 0.1 |
|  | CCAC---------------- | 1.9 | 2.2 | 2.0 | 0.2 |
|  | C------------------- | 2.2 | 1.9 | 2.0 | 0.2 |
| 240 | CCACGCGTCGCTGATGGTGTG | 1.9 | 1.6 | 1.8 | 0.2 |
| 241 | CCACGCGTCG---------- | 2.0 | 1.7 | 1.8 | 0.2 |
| 242 | CCACGCGTCG-----GTGTG | 1.7 | 1.7 | 1.7 | 0.0 |
| 243 | CCACGCGTGG-----GTGTG | 1.8 | 1.5 | 1.6 | 0.2 |
| 244 | CCACGCGT---GATGGTGTG | 1.4 | 1.3 | 1.4 | 0.1 |
|  | CCA----------------- | 1.1 | 1.7 | 1.4 | 0.4 |
| 245 | CCACGCGTCGTG------TG | 1.4 | 1.1 | 1.2 | 0.2 |
| 246 | CCACGCGTCGTGA------- | 1.2 | 1.1 | 1.2 | 0.1 |
|  | CCACGC-------------- | 0.8 | 1.5 | 1.2 | 0.5 |
|  | CCACGCG------------- | 1.1 | 0.9 | 1.0 | 0.1 |
|  | CCACG-----------TGTG | 0.8 | 1.2 | 1.0 | 0.3 |
| 247 | CCACGCGTGG-------GTG | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 36

On-Target Gene Edited Sequences >1% Frequency in At Least One Gene Edited T Cell Donor for the REG1-Z08 gRNA.
Reference on-target sequence[a]:
<u>CCATCACGACGCG</u>(TGG)GTGG (SEQ ID NO: 304)

| SEQ ID NO: | Gene Edited Sequence[b] | Donor 1 (%) | Donor 2 (%) | Mean (%) | Std. Dev. (%) |
|---|---|---|---|---|---|
| 248 | CCATCACGACCGCGTGGGTGG | 28.0 | 15.4 | 21.7 | 8.9 |
| 249 | CCATCA-----CGTGGGTGG | 8.5 | 3.4 | 6.0 | 3.6 |
| 250 | CCATC---ACGCGTGGGTGG | 4.4 | 2.4 | 3.4 | 1.4 |
|  | -------------------- | 2.3 | 1.8 | 2.0 | 0.4 |
|  | ---------------GGTGG | 1.5 | 0.7 | 1.1 | 0.6 |
| 251 | CCATCACGACAGCGTGGGTGG | 1.3 | 0.2 | 0.8 | 0.8 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 37

On-Target Gene Edited Sequences >1% Frequency in At Least One Gene Edited T Cell Donor for the REG1-Z09 gRNA.
Reference on-target sequence[a]: <u>CCGTCAGACTCGT</u>(AGG)CCAG (SEQ ID NO: 310)

| SEQ ID NO: | Gene Edited Sequence[b] | Donor 1 (%) | Donor 2 (%) | Mean (%) | Std. Dev. (%) |
|---|---|---|---|---|---|
|  | CCGTCAG------------- | 13.5 | 9.9 | 11.7 | 2.5 |
| 252 | CCGTCAGACTTCGTAGGCCAG | 11.3 | 8.5 | 9.9 | 2.0 |
| 253 | CCGT---------AGGCCAG | 7.5 | 8.3 | 7.9 | 0.6 |
| 254 | CCGTCAGACT---------- | 6.9 | 6.1 | 6.5 | 0.6 |
| 255 | CCGTCAGAC--------CAG | 4.2 | 4.3 | 4.2 | 0.1 |
|  | -------------------- | 3.9 | 4.2 | 4.0 | 0.2 |
|  | CCGTCA-------------- | 3.6 | 2.3 | 3.0 | 0.9 |
| 256 | CCGTCAGAC--GTAGGCCAG | 2.5 | 2.4 | 2.4 | 0.1 |
| 257 | CCGTCAG--------GCCAG | 1.9 | 2.4 | 2.2 | 0.4 |
|  | CCG-------------CCAG | 1.2 | 2.2 | 1.7 | 0.7 |
| 258 | CCGTCAGAC-CGTAGGCCAG | 1.7 | 1.4 | 1.5 | 0.2 |
|  | -----------TAGGCCAG | 1.0 | 1.4 | 1.2 | 0.3 |
| 259 | CCGTCAGACT-GTAGGCCAG | 1.5 | 1.0 | 1.2 | 0.4 |
|  | CCGTCAGA------------ | 1.6 | 0.7 | 1.2 | 0.6 |
|  | CCGTCAGAC----------- | 1.2 | 0.6 | 0.9 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 38

On-Target Gene Edited Sequences >1% Frequency in At Least One Gene Edited T Cell Donor for the REG1-Z10 gRNA.
Reference on-target sequence[a]: GTGGGTGGCAAGC(GGG)TGGT (SEQ ID NO: 316)

| SEQ ID NO: | Gene Edited Sequence[b] | Donor 1 (%) | Donor 2 (%) | Mean (%) | Std. Dev. (%) |
|---|---|---|---|---|---|
| 260 | GTGGGTGGCAAAGCGGGTGGT | 23.8 | 21.7 | 22.8 | 1.5 |
|  | GT-----------GGGTGGT | 20.7 | 22.9 | 21.8 | 1.6 |
|  | -----------GCGGGTGGT | 10.4 | 7.7 | 9.0 | 1.9 |
| 261 | GTGGGTGGC-AGCGGGTGGT | 7.0 | 6.5 | 6.8 | 0.4 |
|  | ---------------GTGGT | 3.3 | 4.3 | 3.8 | 0.7 |
|  | GTG-------------GGT | 2.8 | 4.0 | 3.4 | 0.8 |
|  | ------------CGGGTGGT | 2.6 | 3.3 | 3.0 | 0.5 |
|  | -------------------- | 2.0 | 3.5 | 2.8 | 1.1 |
|  | GTGGGTGGC----------- | 2.4 | 1.8 | 2.1 | 0.4 |
| 262 | GTGGGTGGCATAGCGGGTGGT | 1.8 | 1.8 | 1.8 | 0.0 |
|  | GTGGGTG------------ | 1.6 | 1.5 | 1.6 | 0.1 |
|  | GTGG--------------- | 1.5 | 1.8 | 1.6 | 0.2 |
| 263 | GTGGGTGG--AGCGGGTGGT | 0.9 | 1.1 | 1.0 | 0.1 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 39

TGFBRII gRNA Sequences/Targt Sequences

| Name | Unmodified Sequence | Modified Sequence | Target Sequence (PAM) |
|---|---|---|---|
| TGFBRII sgRNA (EX1_T1) | CCGACUUCUGAACGUGCGGUguuuuagagcuagaaauagcaaguuaaaauaaggcuaguccguuaucaacuugaaaaaguggcaccgagucggugcmUUUU (SEQ ID NO: 264) | C*C*G*ACUUCUGAACGUGCGGUGGGguuuuagagcuagaaauagcaaguuaaaauaaggcuaguccguuaucaacuugaaaaaguggcaccgagucggugcU*U*U*U (SEQ ID NO: 265) | CCGACTTCTGAACGTGCGGT (GGG) (SEQ ID NO: 2) CCGACTTCTGAACGTGCGGT (SEQ ID NO: 269) |
| TGFBRII sgRNA (EX1_T1) spacer | CCGACUUCUGAACGUGCGGU (SEQ ID NO: 266) | C*C*C*GACUUCUGAACGUGCGGU (SEQ ID NO: 267) |  |
| TGFBRII sgRNA (EX1_T2) | UGCUGGCGAUACGCGUCCACguuuuagagcuagaaauagcaaguuaaaauaaggcuaguccguuaucaacuugaaaaaguggcaccgagucggugcmUUUU (SEQ ID NO: 270) | U*G*C*UGGCGAUACGCGUCCACguuuuagagcuagaaauagcaaguuaaaauaaggcuaguccguuaucaacuugaaaaaguggcaccgagucggugcU*U*U*U (SEQ ID NO: 271) | TGCTGGCGATACGCGTCCAC (AGG) (SEQ ID NO: 3) TGCTGGCGATACGCGTCCAC (SEQ ID NO: 275) |
| TGFBRII sgRNA (EX1_T2) spacer | UGCUGGCGAUACGCGUCCAC (SEQ ID NO: 272) | U*G*C*UGGCGAUACGCGUCCAC (SEQ ID NO: 273) |  |
| TGFBRII sgRNA (EX1_T3) | UCGGUCUAUGACGAGCAGCGguuuuagagcuagaaauagcaaguuaaaauaaggcuaguccguuaucaacuugaaaaaguggcaccgagucggugcUUUU (SEQ ID NO: 276) | U*C*G*GUCUAUGACGAGCAGCGguuuuagagcuagaaauagcaaguuaaaauaaggcuaguccguuaucaacuugaaaaaguggcaccgagucggugcU*U*U*U (SEQ ID NO: 277) | TCGGTCTATGACGAGCAGCG (GGG) (SEQ ID NO: 4) TCGGTCTATGACGAGCAGCG (SEQ ID NO: 281) |
| TGFBRII sgRNA (EX1_T3) spacer | UCGGUCUAUGACGAGCAGCG (SEQ ID NO: 278) | U*C*G*GUCUAUGACGAGCAGCG (SEQ ID NO: 279) |  |

TABLE 39-continued

TGFBRII gRNA Sequences/Target Sequences

| Name | Unmodified Sequence | Modified Sequence | Target Sequence (PAM) |
|---|---|---|---|
| TGFBRII sgRNA (EX2_T1) | AUGGGCAGUCCUAUUACA GCguuuuagagcuagaaa uagcaaguuaaaauaagg cuaguccguuaucaacuu gaaaaaguggcaccgagu cggugcmUUUU (SEQ ID NO: 282) | A*U*G*GGCAGUCCUAUUA CAGCguuuuagagcuagaa auagcaaguuaaaauaagg cuaguccguuaucaacuug aaaaaguggcaccgagucg gugcU*U*U*U (SEQ ID NO: 283) | ATGGGCAGTCCTATTACAGC (TGG) (SEQ ID NO: 5) ATGGGCAGTCCTATTACAGC (SEQ ID NO: 287) |
| TGFBRII sgRNA (EX2_T1) spacer | AUGGGCAGUCCUAUUACA GC (SEQ ID NO: 284) | A*U*G*GGCAGUCCUAUUA CAGC (SEQ ID NO: 285) | |
| TGFBRII sgRNA (EX3_T1) | AUUGUUCACUUGUUAGCC CCguuuuagagcuagaaa uagcaaguuaaaauaagg cuaguccguuaucaacuu gaaaaaguggcaccgagu cggugcUUUU (SEQ ID NO: 288) | A*U*U*GUUCACUUGUUAG CCCCAGGguuuuagagcua gaaauagcaaguuaaaaua aggcuaguccguuaucaac uugaaaaaguggcaccgag ucggugcU*U*U*U (SEQ ID NO: 289) | ATTGTTCACTTGTTAGCCCC (AGG) (SEQ ID NO: 6) ATTGTTCACTTGTTAGCCCC (SEQ ID NO: 293) |
| TGFBRII sgRNA (EX3_TI) spacer | AUUGUUCACUUGUUAGCC CC (SEQ ID NO: 290) | A*u*U*GUUCACUUGUUAG CCCC (SEQ ID NO: 291) | |
| TGFBRII sgRNA (EX3_T2) | GCUGAAGAACUGCCUCUA UAguuuuagagcuagaaa uagcaaguuaaaauaagg cuaguccguuaucaacuu gaaaaaguggcaccgagu cggugcUUUU (SEQ ID NO: 294) | G*C*U*GAAGAACUGCCUC UAUAguuuuagagcuagaa auagcaaguuaaaauaagg cuaguccguuaucaacuug aaaaaguggcaccgagucg gugcU*U*U*U (SEQ ID NO: 295) | GCTGAAGAACTGCCTCTATA (TGG) (SEQ ID NO: 7) GCTGAAGAACTGCCTCTATA (SEQ ID NO: 299) |
| TGFBRII sgRNA (EX3_T2) spacer | GCUGAAGAACUGCCUCUA UA (SEQ ID NO: 296) | G*C*U*GAAGAACUGCCUC UAUA (SEQ ID NO: 297) | |
| TGFBRII sgRNA (EX4_T1) | GCAGGAUUUCUGGUUGUC ACguuuuagagcuagaaa uagcaaguuaaaauaagg cuaguccguuaucaacuu gaaaaaguggcaccgagu cggugcUUUU (SEQ ID NO: 300) | G*C*A*GGAUUUCUGGUUG UCACguuuuagagcuagaa auagcaaguuaaaauaagg cuaguccguuaucaacuug aaaaaguggcaccgagucg gugcU*U*U*U (SEQ ID NO: 301) | GCAGGATTTCTGGTTGTCAC (AGG) (SEQ ID NO: 8) GCAGGATTTCTGGTTGTCAC (SEQ ID NO: 305) |
| TGFBRII sgRNA (EX4_T1) spacer | GCAGGAUUUCUGGUUGUC AC (SEQ ID NO: 302) | G*C*A*GGAUUUCUGGUUG UCAC (SEQ ID NO: 303) | |
| TGFBRII sgRNA (EX4_T2) | CUCCAUCUGUGAGAAGCC ACguuuuagagcuagaaa uagcaaguuaaaauaagg cuaguccguuaucaacuu gaaaaaguggcaccgagu cggugcUUUU (SEQ ID NO: 306) | C*U*C*CAUCUGUGAGAAG CCACguuuuagagcuagaa auagcaaguuaaaauaagg cuaguccguuaucaacuug aaaaaguggcaccgagucg gugcU*U*U*U (SEQ ID NO: 307) | CTCCATCTGTGAGAAGCCAC (AGG) (SEQ ID NO: 9) CTCCATCTGTGAGAAGCCAC (SEQ ID NO: 311) |
| TGFBRII sgRNA (EX4_T2) spacer | CUCCAUCUGUGAGAAGCC AC (SEQ ID NO: 308) | C*U*C*CAUCUGUGAGAAG CCAC (SEQ ID NO: 309) | |
| TGFBRII sgRNA (EX5_T1) | CCCCUACCAUGACUUUAU UCguuuuagagcuagaaa uagcaaguuaaaauaagg cuaguccguuaucaacuu gaaaaaguggcaccgagu cggugcUUUU (SEQ ID NO: 312) | C*C*C*CUACCAUGACUUU AUUCguuuuagagcuagaa auagcaaguuaaaauaagg cuaguccguuaucaacuug aaaaaguggcaccgagucg gugcU*U*U*U (SEQ ID NO: 313) | CCCCTACCATGACTTTATTC (TGG) (SEQ ID NO: 10) CCCCTACCATGACTTTATTC (SEQ ID NO: 317) |

TABLE 39-continued

TGFBRII gRNA Sequences/Target Sequences

| Name | Unmodified Sequence | Modified Sequence | Target Sequence (PAM) |
|---|---|---|---|
| TGFBRII sgRNA (EX5_T1) spacer | CCCCUACCAUGACUUUAU UCUGG (SEQ ID NO: 314) | C*C*C*CUACCAUGACUUU AUUC (SEQ ID NO: 315) | |

*2'-O-methyl phosphorothioate residue

TABLE 40

On-Target Gene Edited Sequences >%1 Frequency in At Least One Gene Edited T Cell Donor for the TGFBRII-Ex1-T1 gRNA.
Reference on-target sequence[a]:
<u>CTGAACGTGCGGT</u>(GGG)ATCG (SEQ ID NO: 360)

| SEQ ID NO: | Gene Edited Sequence[b] | Donor 1 (%) | Donor 2 (%) | Mean (%) | Std. Dev. (%) |
|---|---|---|---|---|---|
| 361 | CTGAACGTGC---------- | 28.7 | 29.8 | 29.2 | 0.8 |
| 362 | CTGAACGTG-----GGATCG | 10.7 | 12 | 11.4 | 0.9 |
| | CTGA-------------TCG | 9.8 | 9.3 | 9.6 | 0.4 |
| | -------------------- | 3.7 | 1.3 | 2.5 | 1.7 |
| 363 | CTGAACGTGCCGGTGGGATCG | 1.2 | 3.2 | 2.2 | 1.4 |
| | CTG---------------- | 2.8 | 1.1 | 2 | 1.2 |
| 364 | CTGAACGTG-GGTGGGATCG | 0.8 | 2.1 | 1.5 | 0.9 |
| 365 | ----------GGTGGGATCG | 2.2 | 0.8 | 1.5 | 1 |
| 366 | CTGAACGTG--GTGGGATCG | 1 | 1.6 | 1.3 | 0.4 |
| 367 | CTGAACG----GTGGGATCG | 1.5 | 0.8 | 1.2 | 0.5 |
| | CTGAACG------------- | 1.3 | 1 | 1.2 | 0.2 |
| 368 | CTG--------GTGGGATCG | 1.3 | 0.4 | 0.8 | 0.6 |
| 369 | CTGAACGTGCAGGTGGGATCG | 1.3 | 0.3 | 0.8 | 0.7 |
| 370 | CTGAACGTGCGT--GGATCG | 0 | 1.1 | 0.6 | 0.8 |
| | -----------------TCG | 0 | 1.1 | 0.6 | 0.8 |

[a]On-target sequence centered on cleavage site, with 10 bp in either direction. For comparison, the portion of gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 41

On-Target Gene Edited Sequences >1% Frequency in At Least One Gene Edited T Cell Donor for the TGFBR11-Ex1-T2 gRNA.
Reference on-target sequence[a]:
<u>GATACGCGTCCAC</u>(AGG)ACGA (SEQ ID NO: 371)

| SEQ ID NO: | Gene Edited Sequence[b] | Donor 1 (%) | Donor 2 (%) | Mean (%) | Std. Dev. (%) |
|---|---|---|---|---|---|
| 372 | GATACGCGTC-ACAGGACGA | 15.2 | 15.3 | 15.2 | 0.1 |
| | GAT----------------- | 8.5 | 10.3 | 9.4 | 1.3 |
| | GATACGC------------- | 6.7 | 5.9 | 6.3 | 0.6 |
| 373 | GATACGCGTCCCACAGGACGA | 3.7 | 6.1 | 4.9 | 1.7 |
| | GATACG-------------A | 4.3 | 5.6 | 4.9 | 0.9 |
| | | 5.4 | 3.5 | 4.4 | 1.3 |
| | ----------------ACGA | 3.4 | 3.9 | 3.6 | 0.4 |
| | -------------AGGACGA | 3.7 | 2.2 | 3 | 1.1 |
| 374 | GATACGCGTCCA--GGACGA | 2.2 | 3.2 | 2.7 | 0.7 |
| 375 | GATACGC----ACAGGACGA | 2.3 | 2.8 | 2.6 | 0.4 |
| 376 | GATAC------ACAGGACGA | 2.8 | 1.7 | 2.2 | 0.8 |
| | ----------ACAGGACGA | 1.4 | 2.5 | 2 | 0.8 |
| | GATACGCG-----------A | 2.5 | 1.4 | 2 | 0.8 |
| 377 | GATACGCGTCC-------GA | 1.9 | 1.7 | 1.8 | 0.1 |
| 378 | GATACGCGTC--------GA | 1.1 | 2 | 1.6 | 0.6 |
| 379 | GATACGCGTC---AGGACGA | 1.9 | 1.1 | 1.5 | 0.6 |
| 380 | GATAC--------AGGACGA | 1.2 | 1.5 | 1.4 | 0.2 |
| 381 | GATACGC---CACAGGACGA | 1.5 | 0.8 | 1.2 | 0.5 |
| 382 | GATACGCGTC---------- | 1 | 1.3 | 1.2 | 0.2 |
| 383 | GATACGCGTCACACAGGACGA | 1.4 | 0.8 | 1.1 | 0.4 |
| 384 | GATACGC-TGCACAGGACGA | 1.1 | 0.8 | 1 | 0.2 |

TABLE 41-continued

On-Target Gene Edited Sequences >1% Frequency in At Least One Gene Edited T Cell Donor for the TGFBR11-Ex1-T2 gRNA.
Reference on-target sequence[a]:
GATACGCGTCCAC(AGG)ACGA (SEQ ID NO: 371)

| SEQ ID NO: | Gene Edited Sequence[b] | Donor 1 (%) | Donor 2 (%) | Mean (%) | Std. Dev. (%) |
|---|---|---|---|---|---|
| 385 | GATACGC------AGGACGA | 0.8 | 1.3 | 1 | 0.4 |
|  | GATACGCG------------ | 0.6 | 1.1 | 0.8 | 0.4 |
|  | GATACGCGT----------- | 0.6 | 1.1 | 0.8 | 0.4 |
|  | ------------------A | 1.1 | 0.3 | 0.7 | 0.6 |
| 386 | ---ACGC----ACAGGACGA | 1.2 | 0 | 0.6 | 0.8 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 42

On-Target Gene Edited Sequences >1% Frequency in At Least One Gene Edited T Cell Donor for the TGFBRII-Ex1-T3 gRNA.
Reference on-target sequence[a]:
ATGACGAGCAGCG(GGG)TCTG (SEQ ID NO: 387)

| SEQ ID NO: | Gene Edited Sequence[b] | Donor 1 (%) | Donor 2 (%) | Mean (%) | Std. Dev. (%) |
|---|---|---|---|---|---|
| 388 | ATGACGAGCAAGCGGGGTCTG | 66.7 | 65.9 | 66.3 | 0.6 |
| 389 | ATGACG---AGCGGGGTCTG | 4.5 | 5.8 | 5.2 | 0.9 |
|  | ---------------GGTCTG | 2.2 | 2.5 | 2.4 | 0.2 |
| 390 | ATGACGA--AGCGGGGTCTG | 1.9 | 1.9 | 1.9 | 0 |
|  | -------------------- | 2.1 | 1.4 | 1.8 | 0.5 |
|  | ------------GGGGTCTG | 1 | 1.7 | 1.4 | 0.5 |
| 391 | ATG------AGCGGGGTCTG | 1.6 | 1.1 | 1.4 | 0.4 |
| 392 | ATGACGAGCAAAGCGGGGTCTG | 1.8 | 0.6 | 1.2 | 0.8 |
| 393 | ATGA-------CGGGGTCTG | 0.7 | 1.5 | 1.1 | 0.6 |
|  | A----------------TG | 1.2 | 0.5 | 0.8 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 43

On-Target Gene Edited Sequences >1% Frequency in At Least One Gene Edited T Cell Donor for the TGFBRII-Ex5-T1 gRNA.
Reference on-target sequence[a]:
CATGACTTTATTC(TGG)AAGA (SEQ ID NO: 394)

| SEQ ID NO: | Gene Edited Sequence[b] | Donor 1 (%) | Donor 2 (%) | Mean (%) | Std. Dev. (%) |
|---|---|---|---|---|---|
| 395 | CATGA-------CTGGAAGA | 10.6 | 12.4 | 11.5 | 1.3 |
| 396 | CATGAC----TTCTGGAAGA | 8.8 | 8.9 | 8.9 | 0.1 |
| 397 | CATGACT---TTCTGGAAGA | 7 | 5.4 | 6.2 | 1.1 |
| 398 | CATGACTTTATTTCTGGAAGA | 5 | 6.2 | 5.6 | 0.8 |
| 399 | CATGACTTTAATTCTGGAAGA | 5.1 | 6.2 | 5.6 | 0.8 |
|  | CA-----------TGGAAGA | 3.7 | 3.8 | 3.8 | 0.1 |
| 400 | CATGACTT--TTCTGGAAGA | 3.6 | 3 | 3.3 | 0.4 |
|  | CAT------------GAAGA | 2.2 | 3.2 | 2.7 | 0.7 |
|  | C------------------A | 2.5 | 2.1 | 2.3 | 0.3 |
|  | -------------------- | 2.5 | 1.9 | 2.2 | 0.4 |
|  | CATGA--------------- | 2.6 | 1.8 | 2.2 | 0.6 |
|  | CAT---------------GA | 2 | 2 | 2 | 0 |
| 401 | CA---------TCTGGAAGA | 2 | 2.1 | 2 | 0.1 |
| 402 | CATGACTTT-TTCTGGAAGA | 1.6 | 2.3 | 2 | 0.5 |
| 403 | CATGACTTTA-TCTGGAAGA | 2.1 | 1.4 | 1.8 | 0.5 |
| 404 | CATGACTTT-------AAGA | 1.1 | 1 | 1 | 0.1 |
| 405 | ----------TTCTGGAAGA | 1.2 | 0.9 | 1 | 0.2 |
| 406 | CATGACTTTA--CTGGAAGA | 1.1 | 0.9 | 1 | 0.1 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 44

On-Target Gene Edited Sequences >1% Frequency in At Least One Gene Edited T Cell Donor for the TGFBRII-Ex2-T1 gRNA.
Reference on-target sequence[a]: GTCCTATTACAGC(TGG)GGCA
(SEQ ID NO: 407)

| SEQ ID NO: | Gene Edited Sequence[b] | Donor 1 (%) | Donor 2 (%) | Mean (%) | Std. Dev. (%) |
|---|---|---|---|---|---|
|  | G------------------- | 18.4 | 17.4 | 17.9 | 0.7 |
| 408 | GTCCTATTA--GCTGGGGCA | 6.4 | 13 | 9.7 | 4.7 |
|  | -----------------GCA | 9.2 | 5.7 | 7.4 | 2.5 |
| 409 | GTCCTATTA-AGCTGGGGCA | 7.5 | 7.1 | 7.3 | 0.3 |
| 410 | GTCCTAT---AGCTGGGGCA | 6.8 | 7.5 | 7.2 | 0.5 |
| 411 | GTCCTA----AGCTGGGGCA | 7.3 | 4.6 | 5.9 | 1.9 |
| 412 | GTCCTA-----GCTGGGGCA | 7.5 | 4.2 | 5.8 | 2.3 |
|  | -------------------- | 2.8 | 2.2 | 2.5 | 0.4 |
| 413 | GTCCTATTAC---TGGGGCA | 2 | 1.7 | 1.8 | 0.2 |
|  | G-----------CTGGGGCA | 1 | 2 | 1.5 | 0.7 |
| 414 | GTCC------AGCTGGGGCA | 1 | 1.7 | 1.4 | 0.5 |
| 415 | GTCCTATTACCAGCTGGGGCA | 1.2 | 1.3 | 1.2 | 0.1 |
|  | GTCCTAT------------- | 1.4 | 0.8 | 1.1 | 0.4 |
| 416 | GTCCTATT---GCTGGGGCA | 1.1 | 1.1 | 1.1 | 0 |
| 417 | GTCCTATTAC-GCTGGGGCA | 0.7 | 1.2 | 1 | 0.4 |
| 418 | GTCCT-------- GGGGCA | 1.6 | 0.3 | 1 | 0.9 |
|  | GT------------------ | 1.1 | 0.1 | 0.6 | 0.7 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 45

On-Target Gene Edited Sequences >1% Frequency in At Least One Gene Edited T Cell Donor for the TGFBRII-Ex3-T1 gRNA.
Reference on-target sequence[a]: ACTTGTTAGCCCC(AGG)GCCA
(SEQ ID NO: 419)

| SEQ ID NO: | Gene Edited Sequence | Donor 1 (%) | Donor 2 (%) | Mean (%) | Std. Dev. (%) |
|---|---|---|---|---|---|
| 420 | ACTTGTTAG--CCAGGGCCA | 26.7 | 22.6 | 24.6 | 2.9 |
| 421 | ACTTGTTAG-CCCAGGGCCA | 5.1 | 9.1 | 7.1 | 2.8 |
|  | -------------------- | 6 | 4.1 | 5 | 1.3 |
| 422 | ACTTGTTAG---CAGGGCCA | 4.9 | 3.7 | 4.3 | 0.8 |
| 423 | ACTTGTTA--------GCCA | 4.6 | 3.1 | 3.8 | 1.1 |
|  | ------------CAGGGCCA | 4.1 | 2.7 | 3.4 | 1 |
| 424 | ACTTGTT------AGGGCCA | 2.1 | 3.3 | 2.7 | 0.8 |
|  | ------------------CA | 3.6 | 1.6 | 2.6 | 1.4 |

TABLE 45-continued

On-Target Gene Edited Sequences >1% Frequency in At Least One Gene Edited T Cell Donor for the TGFBRII-Ex3-T1 gRNA. Reference on-target sequence[a]: ACTTGTTAGCCCC(AGG)GCCA (SEQ ID NO: 419)

| SEQ ID NO: | Gene Edited Sequence | Donor 1 (%) | Donor 2 (%) | Mean (%) | Std. Dev. (%) |
|---|---|---|---|---|---|
| 425 | ACTTGTTAGCCCCCAGGGCCA | 2 | 3.3 | 2.6 | 0.9 |
| 426 | ACTTGTT---CCCAGGGCCA | 1.3 | 3 | 2.2 | 1.2 |
| 427 | ----------CCCAGGGCCA | 2.3 | 1.7 | 2 | 0.4 |
| 428 | ACTTGTTA--CCCAGGGCCA | 2 | 1.8 | 1.9 | 0.1 |
| 429 | ACTTG-----CCCAGGGCCA | 2 | 1.7 | 1.8 | 0.2 |
|  | ACT----------------- | 1.3 | 1.3 | 1.3 | 0 |
| 430 | ACTTGT----CCCAGGGCCA | 0.8 | 1.5 | 1.2 | 0.5 |
| 431 | A-----------CAGGGCCA | 1.6 | 0.7 | 1.2 | 0.6 |
|  | ---------------GGCCA | 1.1 | 1.1 | 1.1 | 0 |
|  | A-----------CAGGGCCA | 0.5 | 1.1 | 0.8 | 0.4 |
| 432 | ACTTG-------CAGGGCCA | 0.2 | 1.2 | 0.7 | 0.7 |
| 433 | ACTTGTTAGC-------CCA | 0.3 | 1.1 | 0.7 | 0.6 |

[a]On-target sequence centered on cleavage site with 10 bp in either direction For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 46

On-Target Gene Edited Sequences >1% Frequency in At Least One Gene Edited T Cell Donor for the TGFBRII-Ex3-T2 gRNA. Reference on-target sequence[a]: AACTGCCTCTATA(TGG)TGTG (SEQ ID NO: 434)

| SEQ ID NO: | Gene Edited Sequence | Donor 1 (%) | Donor 2 (%) | Mean (%) | Std. Dev. (%) |
|---|---|---|---|---|---|
| 435 | AACTGCCTCTTTATATGGTGTG | 37.1 | 41.7 | 39.4 | 3.3 |
|  | AAC----------------- | 7 | 6 | 6.5 | 0.7 |
|  | -------------------- | 7.2 | 5 | 6.1 | 1.6 |
| 436 | AACTGCCT--ATATGGTGTG | 2.9 | 4.1 | 3.5 | 0.8 |
| 437 | AACTGCCTCTAT--GGTGTG | 3 | 3 | 3 | 0 |
|  | AACTG--------------- | 2.7 | 2.3 | 2.5 | 0.3 |
| 438 | AACTGCCTC-ATATGGTGTG | 2 | 2.4 | 2.2 | 0.3 |
| 439 | AACTG----TATATGGTGTG | 1.6 | 2.4 | 2 | 0.6 |
| 440 | AACTGC---TATATGGTGTG | 1.6 | 1.8 | 1.7 | 0.1 |
| 441 | AACT------ATATGGTGTG | 1.1 | 1.8 | 1.5 | 0.5 |
|  | AACTGCC------------- | 1.2 | 1.5 | 1.4 | 0.2 |
|  | A------------------- | 1.8 | 0.9 | 1.4 | 0.6 |
| 442 | AACTGCCT-TATATGGTGTG | 1.1 | 1.3 | 1.2 | 0.1 |

TABLE 46-continued

On-Target Gene Edited Sequences >1% Frequency in At Least One Gene Edited T Cell Donor for the TGFBRII-Ex3-T2 gRNA. Reference on-target sequence[a]: <u>AACTGCCTCTATA</u>(TGG)TGTG (SEQ ID NO: 434)

| SEQ ID NO: | Gene Edited Sequence | Donor 1 (%) | Donor 2 (%) | Mean (%) | Std. Dev. (%) |
|---|---|---|---|---|---|
| 443 | AACTGCCTCT---------- | 1.5 | 1 | 1.2 | 0.4 |
| 444 | ---------TATATGGTGTG | 1.1 | 0.9 | 1 | 0.1 |
|  | AACTG-------------TG | 0.8 | 1.1 | 1 | 0.2 |
|  | AACTGCCTC----------- | 0.6 | 1.4 | 1 | 0.6 |
|  | AACT---------------- | 1.1 | 1 | 1 | 0.1 |
| 445 | AACTGCCTCTA--------- | 1.1 | 0.7 | 0.9 | 0.3 |
| 446 | AACTGCCTCT-TATGGTGTG | 0.7 | 1.1 | 0.9 | 0.3 |
| 447 | AACTG---------GTGTG | 1.1 | 0.7 | 0.9 | 0.3 |

[a]On-target sequence centered on cleavage site with 10 bp in either direction For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 47

On-Target Gene Edited Sequences >1% Frequency in At Least One Gene Edited T Cell Donor for the TGFBRII-Ex4-T1 gRNA. Reference on-target sequence[a]: <u>TTCTGGTTGTCAC</u>(AGG)TGGA (SEQ ID NO: 448)

| SEQ ID NO: | Gene Edited Sequence | Donor 1 (%) | Donor 2 (%) | Mean (%) | Std. Dev. (%) |
|---|---|---|---|---|---|
| 449 | TTCTGGTTGTTCACAGGTGGA | 31.3 | 33.1 | 32.2 | 1.3 |
| 450 | TTCTGGT----------GGA | 11.2 | 11.5 | 11.4 | 0.2 |
| 451 | TTC----------AGGTGGA | 5.2 | 4 | 4.6 | 0.8 |
|  | ----------------TGGA | 4.2 | 3.7 | 4 | 0.4 |
| 452 | TTCTGGTT--CACAGGTGGA | 3.5 | 3.5 | 3.5 | 0 |
| 453 | TTCTGGTTGTTTCACAGGTGGA | 2.1 | 2.7 | 2.4 | 0.4 |
| 454 | TTCTGGTTG---------GA | 2.3 | 2.2 | 2.2 | 0.1 |
|  | TTCTGG------------A | 1.9 | 1.6 | 1.8 | 0.2 |
| 455 | TTCTGGTTGTCCACAGGTGGA | 1.6 | 1.9 | 1.8 | 0.2 |
| 456 | TTC-------CACAGGTGGA | 1.4 | 2.1 | 1.8 | 0.5 |
| 457 | TTCTGGTT-TCACAGGTGGA | 1.4 | 2 | 1.7 | 0.4 |
|  | -------------------- | 2 | 1.1 | 1.6 | 0.6 |
| 458 | TTCTGGTTG-CACAGGTGGA | 1.1 | 1.4 | 1.2 | 0.2 |
| 459 | TTCTGGTTGTACACAGGTGGA | 1.1 | 1.2 | 1.2 | 0.1 |
|  | TTCT---------------- | 1.4 | 0.7 | 1 | 0.5 |

TABLE 47-continued

On-Target Gene Edited Sequences >1% Frequency in At Least One Gene Edited T Cell Donor for the TGFBRII-Ex4-T1 gRNA.
Reference on-target sequence[a]: TTCTGGTTGTCAC(AGG)TGGA (SEQ ID NO: 448)

| SEQ ID NO: | Gene Edited Sequence | Donor 1 (%) | Donor 2 (%) | Mean (%) | Std. Dev. (%) |
|---|---|---|---|---|---|
| 460 | TTCTGGTTG----------A | 1.1 | 1 | 1 | 0.1 |
| 461 | TTCTGGTTGT-ACAGGTGGA | 0.7 | 1.2 | 1 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 48

On-Target Gene Edited Sequences >1% Frequency in At Least One Gene Edited T Cell Donor for the TGFBRII-Ex4-T2 gRNA.
Reference on-target sequence[a]: TGTGAGAAGCCAC(AGG)AAGT (SEQ ID NO: 462)

| SEQ ID NO: | Gene Edited Sequence | Donor 1 (%) | Donor 2 (%) | Mean (%) | Std. Dev. (%) |
|---|---|---|---|---|---|
| 463 | TGTGA----------GAAGT | 22.3 | 17.3 | 19.8 | 3.5 |
| 464 | TGTGAGAAG-CACAGGAAGT | 9.9 | 12.7 | 11.3 | 2 |
|  | -------------------T | 11.8 | 8.2 | 10 | 2.5 |
| 465 | TGTGAGAAGCCCACAGGAAGT | 4.8 | 8.1 | 6.4 | 2.3 |
| 466 | TGTG---------AGGAAGT | 3.1 | 3.5 | 3.3 | 0.3 |
| 467 | TGTGAGAAGC--CAGGAAGT | 3 | 3.1 | 3 | 0.1 |
| 468 | TGTGAGA------AGGAAGT | 3 | 2.8 | 2.9 | 0.1 |
| 469 | ----------CACAGGAAGT | 2.5 | 2.7 | 2.6 | 0.1 |
| 470 | TGTGAGAAGCACACAGGAAGT | 1.2 | 2.3 | 1.8 | 0.8 |
| 471 | TGTGAGAAG---CAGGAAGT | 1.6 | 1.6 | 1.6 | 0 |
|  | ------------CAGGAAGT | 1.3 | 1.8 | 1.6 | 0.4 |
| 472 | TGTG------CACAGGAAGT | 1.2 | 1.8 | 1.5 | 0.4 |
|  | -------------------- | 1.7 | 1 | 1.4 | 0.5 |
| 473 | ---------CCACAGGAAGT | 1.5 | 1.4 | 1.4 | 0.1 |
| 474 | TGTGAGA---CACAGGAAGT | 0.7 | 1.4 | 1 | 0.5 |
| 475 | TGTGAG-----ACAGGAAGT | 1.2 | 0.8 | 1 | 0.3 |
|  | TGT-----------GAAGT | 1.2 | 0.7 | 1 | 0.4 |
| 476 | TGTGAGAA--CACAGGAAGT | 0.6 | 1.4 | 1 | 0.6 |
| 477 | TGTGAGAAGC---------- | 0.8 | 1.1 | 1 | 0.2 |
| 478 | TGTGAGAAGCCACACAG-GAAGT | 1.4 | 0.7 | 1 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The term "about" as used herein means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Where particular values are described in the application and claims, unless otherwise stated, the term "about" is implicit and in this context means within an acceptable error range for the particular value.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for treating cancer, the method comprising administering to a subject in need thereof a population of genetically engineered T cells, wherein the genetically engineered T cells comprise:
   (i) a disrupted Regnase-1 (Reg1) gene;
   (ii) a disrupted Transforming Growth Factor Beta Receptor II (TGFBRII) gene; and
   (iii) a nucleic acid encoding a chimeric antigen receptor (CAR) that binds a tumor antigen.

2. The method of claim 1, wherein the disrupted Reg1 gene is genetically edited in exon 2 and/or exon 4; and/or wherein the disrupted TGFBRII gene is genetically edited in exon 4 or exon 5.

3. The method of claim 1, wherein the disrupted Reg1 gene, the disrupted TGFBRII gene, or both are genetically edited by a CRISPR/Cas-mediated gene editing system.

4. The method of claim 3,
   wherein the CRISPR/Cas-mediated gene editing comprises a guide RNA (gRNA) targeting a site in the Reg1 gene, wherein the target site comprises a nucleotide selected from the group consisting of SEQ ID NO: SEQ ID NO: 320, 322, 323, and 327; and/or
   wherein the CRISPR/Cas-mediated gene editing system comprises a guide RNA (gRNA) targeting a site in the TGFBRII gene that comprises a nucleotide sequence selected from the group consisting of SEQ ID NOs: 275, 305, 311, and 317.

5. The method of claim 4,
   wherein the gRNA targeting the Reg1 gene comprises the nucleotide sequence selected from the group consisting of SEQ ID NO: 22, 30, 34, and 50; and/or wherein the gRNA targeting the TGFBRII gene comprises a nucleotide sequence selected from the group consisting of SEQ ID NOs: 270, 300, 306, and 312.

6. The method of claim 1, wherein the genetically engineered T cells further comprise:
   (iv) a disrupted T cell receptor alpha chain constant region (TRAC) gene,
   (v) a disrupted beta-2-microglobulin (β2M) gene,
   (vi) a disrupted CD70 gene, or
   (vii) a combination of any of (iv)-(vi).

7. The method of claim 6, wherein the genetically engineered T cells comprise a disrupted T cell receptor alpha chain constant region (TRAC) gene and a disrupted beta-2-microglobulin (β2M) gene.

8. The method of claim 7, wherein the nucleic acid encoding the CAR is inserted in the disrupted TRAC gene.

9. The method of claim 7, the CAR binds CD19 and comprises an extracellular antigen binding domain specific to CD19, wherein the extracellular antigen binding domain comprises a single chain variable fragment (scFv) that comprises the amino acid sequence of SEQ ID NO: 120.

10. The method of claim 9, wherein the CAR that binds CD19 comprises the amino acid sequence of SEQ ID NO: 117 or SEQ ID NO:353.

11. The method of claim 9, wherein the subject is a human patient having a CD19+ cancer.

12. The method of claim 11, wherein the CD19+ cancer is a hematologic cancer.

13. The method of claim 7, wherein the genetically engineered T cells further comprise a disrupted CD70 gene.

14. The method of claim 13, wherein the CAR is specific to CD70 and comprises an extracellular antigen binding domain that binds CD70, wherein the extracellular antigen binding domain comprises a single chain variable fragment (scFv) that comprises the amino acid sequence of SEQ ID NO: 140 or 142.

15. The method of claim 14, wherein the CAR specific to CD70 comprises the amino acid sequence of SEQ ID NO:138 or SEQ ID NO:354.

16. The method of claim 14, wherein the subject is a human patient having a CD70+ cancer.

17. The method of claim 16, wherein the CD70+ cancer is a hematopoietic cancer or a solid cancer.

18. The method of claim 1, wherein the tumor antigen is CD19, BCMA, CD70, CD33, or PTK7.

19. The method of claim 1, wherein the genetically engineered T cells are prepared from immune cells of one or more human donors.

20. The method of claim 1, wherein the genetically engineered T cells are allogeneic to the subject.

* * * * *